US006545108B1

(12) United States Patent
Moody et al.

(10) Patent No.: US 6,545,108 B1
(45) Date of Patent: *Apr. 8, 2003

(54) CATALYSTS CONTAINING N-PYRROLYL SUBSTITUTED NITROGEN DONORS

(75) Inventors: Leslie Shane Moody, Johnson City, TN (US); Peter Borden Mackenzie, Kingsport, TN (US); Christopher Moore Killian, Gray, TN (US); Gino Georges Lavoie, Kingsport, TN (US); James Allen Ponasik, Jr., Blountville, TN (US); Thomas William Smith, Kingsport, TN (US); Jason Clay Pearson, Kingsport, TN (US); Anthony Gerard Martin Barrett, Chiswick (GB); Geoffrey William Coates, Ithaca, NY (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/563,812

(22) Filed: May 3, 2000

Related U.S. Application Data

(63) Continuation-in-part of application No. 09/507,492, filed on Feb. 18, 2000
(60) Provisional application No. 60/121,135, filed on Feb. 22, 1999, provisional application No. 60/123,385, filed on Mar. 8, 1999, provisional application No. 60/123,276, filed on Mar. 8, 1999, provisional application No. 60/130,503, filed on Apr. 23, 1999, and provisional application No. 60/145,277, filed on Jul. 26, 1999.

(51) Int. Cl.$^7$ .............................. C08F 4/06; C08F 4/44; B01J 31/00
(52) U.S. Cl. ...................... 526/161; 526/132; 526/134; 526/172; 502/167
(58) Field of Search ................................ 526/132, 134, 526/161, 172; 502/167

(56) References Cited

U.S. PATENT DOCUMENTS

| | | | |
|---|---|---|---|
| 4,564,647 A | 1/1986 | Hayashi et al. | |
| 4,724,273 A | 2/1988 | Fink et al. | |
| 4,752,597 A | 6/1988 | Turner | |
| 5,106,804 A | 4/1992 | Bailly et al. | |
| 5,132,380 A | 7/1992 | Stevens et al. | |
| 5,227,440 A | 7/1993 | Canich et al. | |
| 5,296,565 A | 3/1994 | Ueda et al. | |
| 5,324,800 A | 6/1994 | Welborn, Jr. et al. | |
| 5,331,071 A | 7/1994 | Kataoka et al. | |
| 5,332,706 A | 7/1994 | Nowlin et al. | |

(List continued on next page.)

FOREIGN PATENT DOCUMENTS

| | | |
|---|---|---|
| DE | 19707236 A1 | 8/1998 |
| DE | 19944993 A1 | 7/1999 |
| DE | 19959251 A1 | 12/1999 |
| EP | 0 381 495 A2 | 8/1990 |
| EP | 0 416 815 A2 | 3/1991 |
| EP | 0 420 436 A1 | 4/1991 |
| EP | 0 532 098 A1 | 3/1993 |
| EP | 0 641 804 A2 | 3/1995 |
| EP | 0 816 384 A2 | 1/1998 |
| EP | 0 874 005 A1 | 10/1998 |

(List continued on next page.)

OTHER PUBLICATIONS

U.S. 2002/0147286 A1, U.S. Pre–Grant publication to Resconi et al., published Oct. 2002.*
U.S. 2001/0044510 A1, U.S. Pre–Grant Publication to Arthur et al., Nov. 2001.*
U.S. 2002/0049135 A1, U.S. Pre–Grant Publication to Moody et al., Apr. 2002.*
U.S. 2002/0058769 A1, U.S. Pre–Grant Publication to Killian et al., May 2002.*
U.S. 2002/0065192 A1, U.S. Pre–Grant Publication to Mackenzie et al., May 2002.*
U.S. 2002/0082366 A1, U.S. Pre–Grant Publication to Johnson et al., Jun. 2002.
U.S. 2002/0091210 A1, U.S. Pre–Grant Publication to Lavoie et al., Jul. 2002.
M.G. Gardiner et al., J. Organomet. Chem., vol. 572, pp. 239–247 (1999).*
S. D. Ittel et al., "Late–Metal Catalysts for Ethylene Homo– and Copolymerization,"*Chem. Rev.*, 2000, pp. 1169–1203, 100.
M. Schmid et al., "New $C_{2v}$ and Chiral $C_2$–Symmetric Olefin Polymerization Catalysts Based on Nickel (II) and Palladium (II) Diimine Complexes Bearing 2,6–Diphenyl Aniline Moieties: Synthesis, Structural Characterization, and First Insight into Polymerization Properties," *Organometallics*, 2001, 20(11), 2321.
Timo Repo, et al., "Ethylenebis(Salicylidenetiminato)zirconium Dichloride: Crystal Structure and Use as a Heterogeneous Catalyst in the Polymerization of Ethylene," *Maromolecules*, (1997), 171–175, 30.
Oleg V. Mikhailov, "From Novel Complexing Conditions to Novel Coordination of Nickel (II) with Dithiooxamide and its Bulky Analogues," *Transition Met. Chem.*, (1996), 363–369, 21.
D. H. McConville et al., *J. Am. Chem. Soc.*, 1996, 118, pp. 10008–10009.

(List continued on next page.)

Primary Examiner—Mark L. Bell
Assistant Examiner—J. Pasterczyk
(74) Attorney, Agent, or Firm—Jonathan D. Wood, Esq.; Bernard J. Graves, Jr., Esq.

(57) ABSTRACT

Catalyst compositions useful for the polymerization or oligomerization of olefins are disclosed. Certain of the catalyst compositions comprise metal complexes of mono through tetradentate ligands comprising N-pyrrolyl substituted nitrogen donors bonded to the metal. Also disclosed are processes for the polymerization or oligomerization of olefins using the catalyst compositions.

5 Claims, No Drawings

U.S. PATENT DOCUMENTS

| | | | |
|---|---|---|---|
| 5,350,723 A | | 9/1994 | Neithamer et al. |
| 5,399,635 A | | 3/1995 | Neithamer et al. |
| 5,466,766 A | | 11/1995 | Patsidis et al. |
| 5,468,702 A | | 11/1995 | Jejelowo |
| 5,474,962 A | | 12/1995 | Takahashi et al. |
| 5,578,537 A | | 11/1996 | Herrmann et al. |
| 5,863,853 A | | 1/1999 | Vaughan et al. |
| 5,866,663 A | | 2/1999 | Brookhart et al. |
| 5,880,241 A | | 3/1999 | Brookhart et al. |
| 5,880,323 A | | 3/1999 | Brookhart, III et al. |
| 5,886,224 A | | 3/1999 | Brookhart et al. |
| 5,891,963 A | | 4/1999 | Brookhart et al. |
| 5,955,555 A | * | 9/1999 | Bennett ...................... 526/133 |
| 6,197,715 B1 | * | 3/2001 | Bansleben et al. .......... 526/172 |
| 6,403,738 B1 | * | 6/2002 | Johnson et al. ............. 502/167 |

FOREIGN PATENT DOCUMENTS

| | | |
|---|---|---|
| EP | 0 884 331 A2 | 12/1998 |
| EP | 0 893 455 A1 | 1/1999 |
| EP | 1 099 714 A1 | 11/1999 |
| JP | 10-324709 | 3/1997 |
| JP | Hei 9-255712 | 9/1997 |
| JP | Hei 9-272709 | 10/1997 |
| JP | Hei 9-272713 | 10/1997 |
| WO | WO 94/01471 | 1/1994 |
| WO | WO 94/11410 | 5/1994 |
| WO | WO 94/14854 | 7/1994 |
| WO | WO 96/23010 | 8/1996 |
| WO | WO 97/02298 | 1/1997 |
| WO | WO 97/17380 | 5/1997 |
| WO | WO 97/38024 | 10/1997 |
| WO | WO 97/48735 | 12/1997 |
| WO | WO 97/48736 | 12/1997 |
| WO | WO 97/48737 | 12/1997 |
| WO | WO 97/48739 | 12/1997 |
| WO | WO 97/48740 | 12/1997 |
| WO | WO 97/48742 | 12/1997 |
| WO | WO 97/48777 | 12/1997 |
| WO | 98/03521 A | 1/1998 |
| WO | WO 98/03559 | 1/1998 |
| WO | WO 98/11144 | 3/1998 |
| WO | WO 98/27124 | 6/1998 |
| WO | WO 98/30609 | 7/1998 |
| WO | WO 98/30610 | 7/1998 |
| WO | WO 98/37110 | 8/1998 |
| WO | WO 98/40374 | 9/1998 |
| WO | WO 98/40420 | 9/1998 |
| WO | WO 98/40421 | 9/1998 |
| WO | WO 98/41529 | 9/1998 |
| WO | WO 98/42664 | 10/1998 |
| WO | WO 98/42665 | 10/1998 |
| WO | WO 98/47933 | 10/1998 |
| WO | WO 98/47934 | 10/1998 |
| WO | WO 98/56832 | 12/1998 |
| WO | WO 99/02472 | 1/1999 |
| WO | WO 99/02570 | 1/1999 |
| WO | 00/47592 A1 | 2/1999 |
| WO | WO 99/05189 | 2/1999 |
| WO | WO 99/09078 | 2/1999 |
| WO | 00/58320 A1 | 3/1999 |
| WO | 99/10391 | 3/1999 |
| WO | WO 99/10391 | 3/1999 |
| WO | WO 99/12981 | 3/1999 |
| WO | 01/07491 A1 | 7/1999 |
| WO | 01/12684 A1 | 8/1999 |
| WO | 01/07492 A1 | 9/1999 |
| WO | 01/14391 A1 | 9/1999 |
| WO | 01/21586 A1 | 9/1999 |
| WO | 01/23396 A1 | 9/1999 |
| WO | 01/42257 A1 | 12/1999 |
| WO | 99/62968 A | 12/1999 |
| WO | WO 00/04057 | 1/2000 |
| WO | 01/55231 A1 | 1/2000 |
| WO | 00/50470 A | 8/2000 |
| WO | 01/92342 A | 12/2001 |

OTHER PUBLICATIONS

R. R. Schrock et al., *J. Am. Chem. Soc.*, 1997, 119, pp. 3830–3831.
R. R. Schrock et al., *J. Am. Chem. Soc.*, 1999, 121, pp. 5797–5798.
M. Peuckert et al., *Organometallics*, 1983, 2, pp. 594–597.
W. Keim et al., *Angew Chem. Int. Ed. Engl.*, 1981, 20, pp. 116–117.
V. M. Mohring et al., *Angew. Chem. Int. Ed. Engl.*, 1985, 24, pp. 1001–1003.
M. Brookhart et al., *J. Am. Chem. Soc.*, 1995, 117, pp. 6414–6415.
V. C. Gibson et al., *Chem. Commun.*, 1998, pp. 313–314.
S. H. Strauss, *Chem. Rev.*, 1993, 93, pp. 927–942.
S. B. Roscoe et al., "Polyolefin Spheres from Metallocenes Supported on Noninteracting Polystyrene," *Science*, 1998, 280, pp. 270–273.
Buelow, "Chemische Berichte", *Berichte Der Deutschen Chemischen Gesellschaft, DE, Verlag Chemie. Weinheim*, 1905, pp. 3915, 3917, vol. 38.
Bach, A., et al., "Metal Chelates of N–(1–Pyrrolyl)salicylaldimines and Their Structure Determination by X–Ray Structure Analysis and X–Ray Absorption Spectroscopy (XANES)", *Z. Naturforsch., Chem. Sci.*, 1966, pp. 757–764, vol. 51(6).
Narang, K.K., et al., "Synthesis, Characterization, Thermal Studies and Biological Activity of Iron (III) Complexes with Some Acylhydrazines", *Synth. React. Inorg. Met.–Org. Chem.*, 1993, pp. 971–989, vol. 23(6).
Fritsky, I.O., et al., "Template Synthesis of Square–Planar Nickel (II) and Copper (III) Complexes Based on Hydrazide Ligands", *J. Chem. Soc., Dalton Trans.*, 1998, pp. 3269–3274, vol. 19.
Rosenberg, L., et al., "Binuclear Nickel (II) and Cobalt (II) Complexes of the Novel Binucleating Ligand 3,–Bis(1'–pyrazolyl)pyridazine. Crystal and Molecular Structure and Magnetism of Bis[$\mu$–3,6–bis(1'–pyrazolyl)pyridazine–$N^1$ ($Ni^1$)$N^{2'}$($Ni^1$)$N^{2'}$($Ni^1$) $N^2$($Ni^2$) $N^{2''}$($Ni^2$)]–bis[diaquanickel (II)]Tetrachloride Dihydrate", *J. Chem. Soc., Dalton Trans.*, 1986, pp. 625–631, vol. 3.
Watson, A.A., et al., "Chiral Heterocyclic Ligands. VIII. Syntheses and Complexes of New Chelating Ligands Derived from Camphor", *Aust. J. Chem.*, 1995, pp. 1549–1572, vol. 48, No. 9.
Claramunt, R.M., et al., "Rhodium (I) Complexes with the Polydentate Ligand 3,5–bis(4–methylpyrazol–1–yl)–4–methylpyrazole", *Journal Organometallic Chemistry*, 1991, pp. 259–271, vol. 412, No. 1–2.
Neugebauer, F.A., "ESR Studies of 1,2,4,5–Tetraazapentenyls", *Chem. Ber.*, 1973, pp. 1716–1723, vol. 106(6).
Narang, K.K., et al., Glyoxal–Aroyl Hydrazone (Schiff Base) Complexes of Nickel (II), Copper (II) & Zinc (II), *Indian J. Chem., Sect. A.*, 1982, pp. 830–832, vol. 21A(8).
Bordunov, A.V., et al., "Azacrown Ethers Containing Oximic and Schiff Base Sidearms—Potential Heteronuclear Metal Ion Receptors", *Tetrahedron*, NL, Dec. 29, 1997, pp. 17595–17606, vol. 53, No. 52, Elsevier Science Publishers, Amsterdam.

* cited by examiner

CATALYSTS CONTAINING N-PYRROLYL SUBSTITUTED NITROGEN DONORS

CROSS REFERENCE TO RELATED APPLICATIONS

This application is a continuation-in-part of U.S. patent application Ser. No. 09/507,492, filed on Feb. 18, 2000; which is a non-provisional of Provisional Application Ser. Nos. 60/121,135, filed on Feb. 22, 1999; 60/123,276, filed on Mar. 8, 1999; 60/123,385, filed on Mar. 8, 1999; 60/130,503, filed on Apr. 23, 1999; and 60/145,277, filed on Jul. 26, 1999.

FIELD OF THE INVENTION

The present invention generally relates to catalyst compositions useful for the polymerization or oligomerization of olefins, and to processes using the catalyst compositions. Certain of these catalyst compositions comprise N-pyrrolyl substituted nitrogen donors.

BACKGROUND OF THE INVENTION

Olefin polymers are used in a wide variety of products, from sheathing for wire and cable to film. Olefin polymers are used, for instance, in injection or compression molding applications, in extruded films or sheeting, as extrusion coatings on paper, for example photographic paper and digital recording paper, and the like. Improvements in catalysts have made it possible to better control polymerization processes and, thus, influence the properties of the bulk material. Increasingly, efforts are being made to tune the physical properties of plastics for lightness, strength, resistance to corrosion, permeability, optical properties, and the like, for particular uses. Chain length, polymer branching and functionality have a significant impact on the physical properties of the polymer. Accordingly, novel catalysts are constantly being sought in attempts to obtain a catalytic process for polymerizing olefins which permits more efficient and better-controlled polymerization of olefins.

Conventional polyolefins are prepared by a variety of polymerization techniques, including homogeneous liquid phase, gas phase, and slurry polymerization. Certain transition metal catalysts, such as those based on titanium compounds (e.g. $TiCl_3$ or $TiCl_4$) in combination with organoaluminium cocatalysts, are used to make linear and linear low-density polyethylenes as well as poly-$\alpha$-olefins such as polypropylene. These so-called "Ziegler-Natta" catalysts are quite sensitive to oxygen and are ineffective for the copolymerization of nonpolar and polar monomers. Following the early discovery of Ziegler-Natta catalysts, there has been intense recent interest in the development and study of homogeneous early transition metal (Group 4–6) catalysts for the polymerization of olefins. These well-defined catalysts, which were first viewed as mechanistic models for heterogeneous Ziegler-Natta catalysts, are receiving increasing commercial attention. Recent advances in Group 4–6 single-site olefin polymerization catalysis include the following.

The following documents describe the use of monocyclopentadienyl amido titanium complexes for the polymerization of olefins as described by J. M. Canich, EP 420,436 (1991) and Stevens et al., EP 416,815 (1991). Waymouth et al., Science, 1995, 267, 217, disclose the use of oscillating catalysts based on unbridged substituted indenyl complexes of zirconium. Mitsui Chemicals Inc. disclose the use of nitrogen/oxygen chelate ligands on Group 4–6 transition metals as catalysts for the polymerization of olefins, EP 874,005 (1998). McConville et al., *J. Am. Chem. Soc.*, 1996, 118, 10008–10009, describe the living polymerization of olefins with chelating diamido complexes of Ti and Zr. Schrock et al., *J. Am. Chem. Soc.*, 1997, 119, 3830, *J. Am. Chem. Soc.*, 1999, 121, 5797, also describe catalysts comprising chelating diamido complexes of Ti and Zr. DSM (WO 94/14854 and EP 0 532 098 A1), BP (EP 0 641 804 A2 and EP 0 816 384 A2), Chevron (WO 94/11410), and Exxon (WO 94/01471) describe the use of Group 4–6 imido catalysts for the polymerization of olefins. Jordan et al., WO 98/40421, disclose the use of novel cationic Group 13 complexes incorporating bidentate ligands as olefin polymerization catalysts.

Recent advances in Group 8–10 catalysts for the polymerization of olefins include the following.

European Patent Application No. 381,495 describes the polymerization of olefins using palladium and nickel catalysts, which contain selected bidentate phosphorous containing ligands.

U. Klabunde, U.S. Pat. Nos. 4,906,754, 4,716,205, 5,030,606, and 5,175,326, describes the conversion of ethylene to polyethylene using anionic phosphorous, oxygen donors ligated to Ni(II). The polymerization reactions were run between 25 and 100° C. with modest yields, producing linear polyethylene having a weight-average molecular weight ranging between 8K and 350 K. In addition, Klabunde describes the preparation of copolymers of ethylene and functional group containing monomers.

M. Peuckert et al., *Organomet.* 1983, 2(5), 594, disclose the oligomerization of ethylene using phosphine/carboxylate donors ligated to Ni(II), which showed modest catalytic activity (0.14 to 1.83 TO/s). The oligomerizations were carried out at 60 to 95° C. and 10 to 80 bar ethylene in toluene, to produce $\alpha$-olefins.

R. E. Murray, U.S. Pat. Nos. 4,689,437 and 4,716,138, describes the oligomerization of ethylene using phosphine, sulfonate donors ligated to Ni(II). These complexes show catalyst activities approximately 15 times greater than those reported with phosphine, carboxylate analogs.

W. Keim et al., *Angew. Chem. Int. Ed. Eng.*, 1981, 20, 116, and V. M. Mohring et al., *Angew. Chem. Int. Ed. Eng.*, 1985, 24, 1001, disclose the polymerization of ethylene and the oligomerization of $\alpha$-olefins with aminobis(imino) phosphorane nickel catalysts.

Wilke, *Angew. Chem. Int. Ed. Engl.*, 1988, 27, 185, describes a nickel allyl phosphine complex for the polymerization of ethylene.

K. A. O. Starzewski et al., *Angew. Chem. Int. Ed. Engl.*, 1987, 26, 63, and U.S. Pat. No. 4,691,036, describe a series of bis(ylide) nickel complexes, used to polymerize ethylene to provide high molecular weight linear polyethylene.

L. K. Johnson et al., WO 96/23010; U.S. Pat. Nos. 5,866,663; 5,886,224; 5,891,963; 5,880,323; and 5,880,241; disclose the polymerization of olefins using cationic nickel, palladium, iron, and cobalt complexes containing diimine and bisoxazoline ligands. This document also describes the polymerization of ethylene, acyclic olefins, and/or selected cyclic olefins and optionally selected unsaturated acids or esters such as acrylic acid or alkyl acrylates to provide olefin homopolymers or copolymers. L. K. Johnson et al., *J. Am. Chem. Soc.*, 1995, 117, 6414, describe the polymerization of olefins such as ethylene, propylene, and 1-hexene using cationic $\alpha$-diimine-based nickel and palladium complexes. These catalysts have been described to polymerize ethylene to high molecular weight branched polyethylene. In addition to polymerizing ethylene, the Pd complexes act as catalysts for the polymerization and copolymerization of olefins and methyl acrylate.

WO 97/02298 discloses the polymerization of olefins using a variety of neutral N, O, P, or S donor ligands, in combination with a nickel(0) compound and an acid.

Eastman Chemical Company has recently described in a series of patent applications (WO 98/40374, WO 98/37110, WO 98/47933, and WO 98/40420) several new classes of Group 8–10 transition metal catalysts for the polymerization of olefins. Also described are several new polymer compositions derived from epoxybutene and derivatives thereof.

Brown et al., WO 97/17380, WO 97/48777, WO 97/48739, and WO 97/48740, describe the use of Pd α-diimine catalysts for the polymerization of olefins including ethylene in the presence of air and water.

Fink et al., U.S. Pat. No. 4,724,273, describe the polymerization of α-olefins using aminobis(imino)phosphorane nickel catalysts and the compositions of the resulting poly (α-olefins).

Recently, Vaughan et al., WO 97/48736, Denton et al., WO 97/48742, and Sugimura et al., WO 97/38024, describe the polymerization of ethylene using silica supported α-diimine nickel catalysts.

Phillips, EP 884,331, discloses the use of nickel α-diimine catalysts for the polymerization of ethylene in their slurry loop process.

Neutral nickel catalysts for the polymerization of olefins are described in WO 98/30610; WO 98/30609; WO 98/42665; and WO 98/42664.

Highly active iron and cobalt catalysts ligated by pyridine bis(imines) for the polymerization and oligomerization of ethylene have been independently described by the University of North Carolina-Chapel Hill (WO 99/02472), DuPont (WO 98/27124), BP Chemical and Imperial College (WO 99/12981).

Also recently, Canich et al., WO 97/48735, and Mecking, DE 19707236 A1, describe the use of mixed α-diimine catalysts with Group 4 transition metal catalysts for the polymerization of olefins. Additional recent developments are described by Sugimura et al. in JP 96-84344 and JP 96-84343, by Yorisue et al. in JP 96-70332, by McLain et al. in WO 98/03559, by Weinberg et al. in WO 98/03521, by Wang et al. in WO 99/09078, by Coughlin in WO 99/10391, and by Matsunaga et al. in WO 97/48737.

Notwithstanding these advances in non-Ziegler-Natta catalysis, there remains a need for new transition metal catalysts, particularly those which are more thermally stable, allow for new polymer microstructures, or are more functional group tolerant. In addition, there is a need for novel methods of polymerizing olefins employing such catalysts, and for the novel polymers which result.

SUMMARY OF THE INVENTION

A number of transition metal complexes containing nitrogen donor ligands have proven valuable as catalysts for olefin polymerization. A key feature of many of these catalysts is the introduction of steric hindrance through the use of a substituted aryl group on the ligated nitrogen. The steric bulk associated with such fragments tends to suppress premature chain transfer and may, in some cases, stabilize the catalyst towards decomposition, increase the catalyst activity, act to modify the polymer microstructure, or otherwise have beneficial effects.

We have found that catalysts comprising 1-pyrrolyl or substituted 1-pyrrolyl substituted N-donor ligands represent a highly effective and versatile new class of olefin polymerization catalysts. Indeed, we have discovered that the use of such fragments represents a new polyolefin catalyst design principle, wherein aryl substituted nitrogen donors of existing polyolefin catalysts are replaced by 1-pyrrolyl substituted nitrogen donors, as shown in Scheme I, where M is Sc, a Group 4–10 transition metal, Al or Ga, and $R^{3a-i}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro, and where any two of $R^{3a-i}$ may be linked by a bridging group.

Scheme I

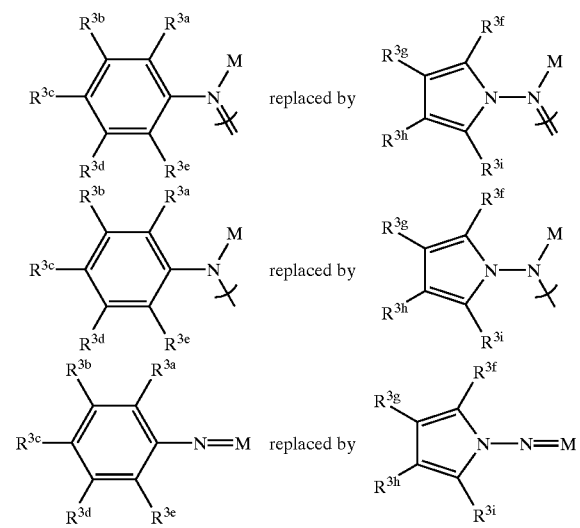

This strategy is expected to apply to essentially all previously reported olefin polymerization and oligomerization catalysts incorporating an aryl-substituted nitrogen donor ligand. Thus, catalysts reported in U.S. Pat. Nos. 5,866,663; 5,886,224; 5,891,963; 5,880,323; 5,880,241, and in WO 96/23010, WO 99/10391, WO 99/05189, WO 98/56832, WO 98/03559, WO 98/47934, WO97/02298, WO 98/30609, WO 98/42665, WO 98/42664, WO 98/47933, WO 98/40420, WO 98/40374, EP 420,436 (1991), EP 416,815 (1991), *Science*, 1995, 267, 217, EP 874,005(1998), *J. Am. Chem. Soc.*, 1996, 118, 10008–10009, WO 94/14854, EP 0 532 098 A1, EP 0 641 804 A2, EP 0 816 384 A2, WO 94/11410, WO 94/01471, WO 98/40421, and Chem. Commun., 1998, 313, which have their aryl substituted nitrogen donor fragment or fragments replaced by a N-pyrrol-1-yl or substituted N-pyrrol-1-yl nitrogen donor fragment or fragments are all contemplated to be within the scope of our invention. All U.S. Patents referred to herein are incorporated by reference. Also provided are certain ligands, as depicted in Sets 1–17 below, which are useful as intermediates in the preparation of the polyolefin polymerization and oligomerization catalyst compositions of the present invention.

While catalysts containing N-donors substituted by pyrrol-1-yl or substituted pyrrol-1-yl groups represent a preferred class, N-donor ligands substituted by other types of $-NR^{2a}R^{2b}$ groups, where $R^{2a}$ and $R^{2b}$ are each independently H, hydrocarbyl, substituted hydrocarbyl, silyl, boryl, or ferrocenyl, and where $R^{2a}$ and $R^{2b}$ may be connected to form a ring, are also expected to be useful in constituting olefin polymerization catalysts. Examples of cyclic —NR$^{2a}$R$^{2b}$ groups are shown in Scheme X, wherein R$^{3a-d}$ are as defined above, and include 2,6-dialkyl-4-oxo-4H-pyridin-1-yl, 2,5-dialkyl-1-imidazolyl, and 2,6-dimethyl-3-methoxycarbonyl-4-oxo-4H-pyridin-1-yl groups.

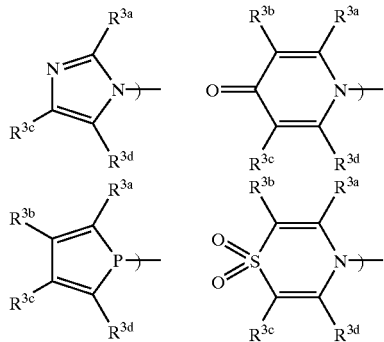

It is expected that those cyclic —NR$^{2a}$R$^{2b}$ groups wherein the electronic characteristics of the nitrogen of the —NR$^{2a}$R$^{2b}$ group are similar to those of a 1-pyrrolyl nitrogen will be especially useful. Catalysts containing N-donors substituted by cyclic —PR$^{4a}$R$^{4b}$ groups (wherein R$^{4a}$ and R$^{4b}$ are each independently hydrocarbyl, substituted hydrocarbyl, heteroatom connected hydrocarbyl, or heteroatom connected substituted hydrocarbyl, and wherein R$^{4a}$ and R$^{4b}$ may be linked by a bridging group), including especially 1-phospholyl or substituted 1-phospholyl groups, are similarly expected to be useful in constituting olefin polymerization catalysts.

DETAILED DESCRIPTION OF THE INVENTION

Thus, in a first aspect, this invention relates to a catalyst composition for the polymerization or oligomerization of olefins, comprising a metal complex ligated by a monodentate, bidentate, tridentate, or tetradentate ligand, wherein at least one of the donor atoms of the ligand is a nitrogen atom substituted by a 1-pyrrolyl or substituted 1-pyrrolyl group; wherein:
the remaining donor atoms of the ligand are selected from the group consisting of C, N, P, As, O, S, and Se; and wherein
said metal of said metal complex is selected from the group consisting of Sc, Ta, Ti, Zr, Hf, V, Nb, Cr, Mo, W, Mn, Re, Fe, Ru, Os, Co, Rh, Ir, Ni, Cu, Pd, Pt, Al, and Ga.

Preferred catalyst compositions in this first aspect are those comprising a bidentate or tridentate ligand. Numerous examples of such catalyst compositions are contained herein.

In a second aspect, this invention relates to a process for the polymerization or oligomerization of olefins, which comprises contacting one or more olefins with the catalyst composition of the first aspect. Polymerization reaction temperatures of between about 20 and about 160° C. are preferred, with temperatures between about 60 and about 100° C. being especially preferred. Ethylene, propylene, 1-butene, 1-hexene and 1-octene are preferred olefin monomers. When ethylene is used as the primary or predominant olefin monomer, pressures between about 1 and about 100 atm are preferred.

In a third aspect, this invention relates to a catalyst composition for the polymerization or oligomerization of olefins, comprising a catalyst composition of the first aspect, wherein the metal is selected from the group consisting of Co, Fe, Ni, and Pd, and the ligand is a neutral bidentate ligand.

A first preferred embodiment of this third aspect are those catalyst compositions wherein the metal complex is either (i) a compound of formula XIa, or (ii) the reaction product of Ni(1,5-cyclooctadiene)$_2$, B(C$_6$F$_5$)$_3$, one or more olefins, and said neutral bidentate ligand:

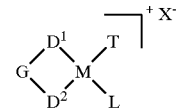

XIa wherein:
M is Fe, Co, Ni or Pd;
D$^1$, D$^2$, and G collectively comprise the neutral bidentate ligand;
D$^1$ and D$^2$ are monodentate donors linked by a bridging group G, wherein at least one of D$^1$ and D$^2$ is ligated to the metal M by a nitrogen atom substituted by a 1-pyrrolyl or a substituted 1-pyrrolyl group;
T is H, hydrocarbyl, substituted hydrocarbyl, or other group capable of inserting an olefin;
L is an olefin or a neutral donor group capable of being displaced by an olefin; in addition, T and L may be taken together to form a π-allyl or π-benzyl group; and
X$^-$ is a weakly coordinating anion.

A second preferred embodiment in this third aspect are those catalyst compositions wherein the metal complex is the reaction product of a compound of formula XIb and a second compound Y$^2$.

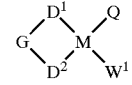

XIb wherein:
M is Fe, Co, Ni or Pd;
D$^1$, D$^2$, and G collectively comprise the neutral bidentate ligand;
D$^1$ and D$^2$ are monodentate donors linked by a bridging group G, wherein at least one of D$^1$ and D$^2$ is ligated to the metal M by a nitrogen atom substituted by a 1-pyrrolyl or a substituted 1-pyrrolyl group;
Q and W$^1$ are each independently fluoro, chloro, bromo or iodo, hydrocarbyl, substituted hydrocarbyl, heteroatom connected hydrocarbyl, heteroatom connected substituted hydrocarbyl, or collectively sulfate, or may be taken together to form a π-allyl, π-benzyl, or acetylacetonate group, in which case a weakly coordinating counteranion X$^-$ is also present; and
Y$^2$ is a neutral Lewis acid capable of abstracting Q$^-$ or W$^{1-}$ to form a weakly coordinating anion, a cationic Lewis acid whose counterion is a weakly coordinating anion, or a Bronsted acid whose conjugate base is a weakly coordinating anion.

A third, more preferred, embodiment in this third aspect are those catalyst compositions of the first or second embodiments in which the metal M in formulas XIa or XIb is Ni and the neutral bidentate ligand is selected from Set 1:

Set 1

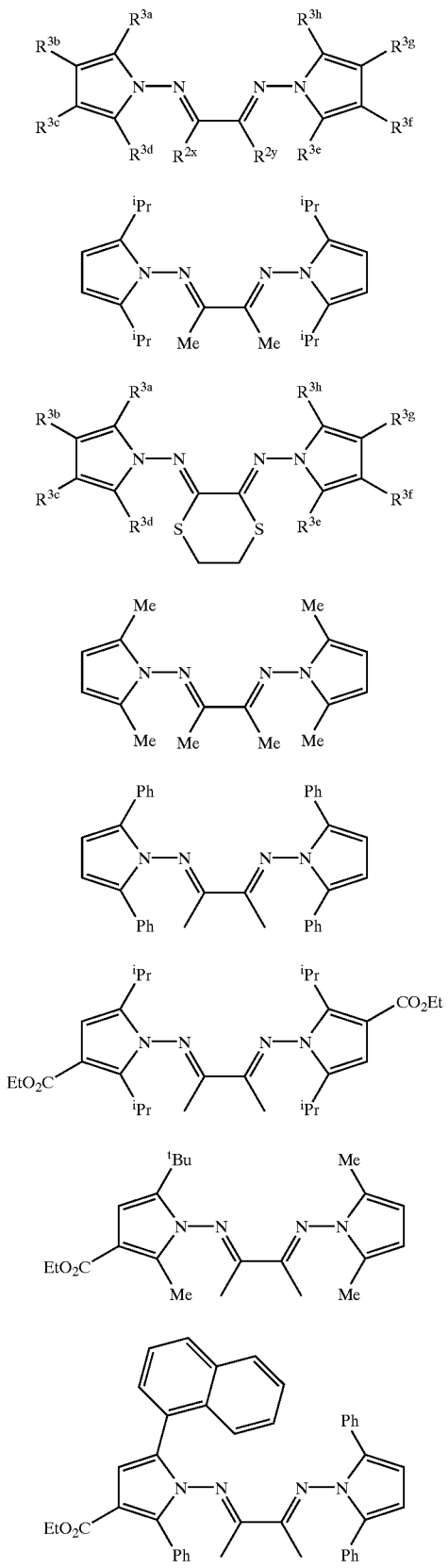

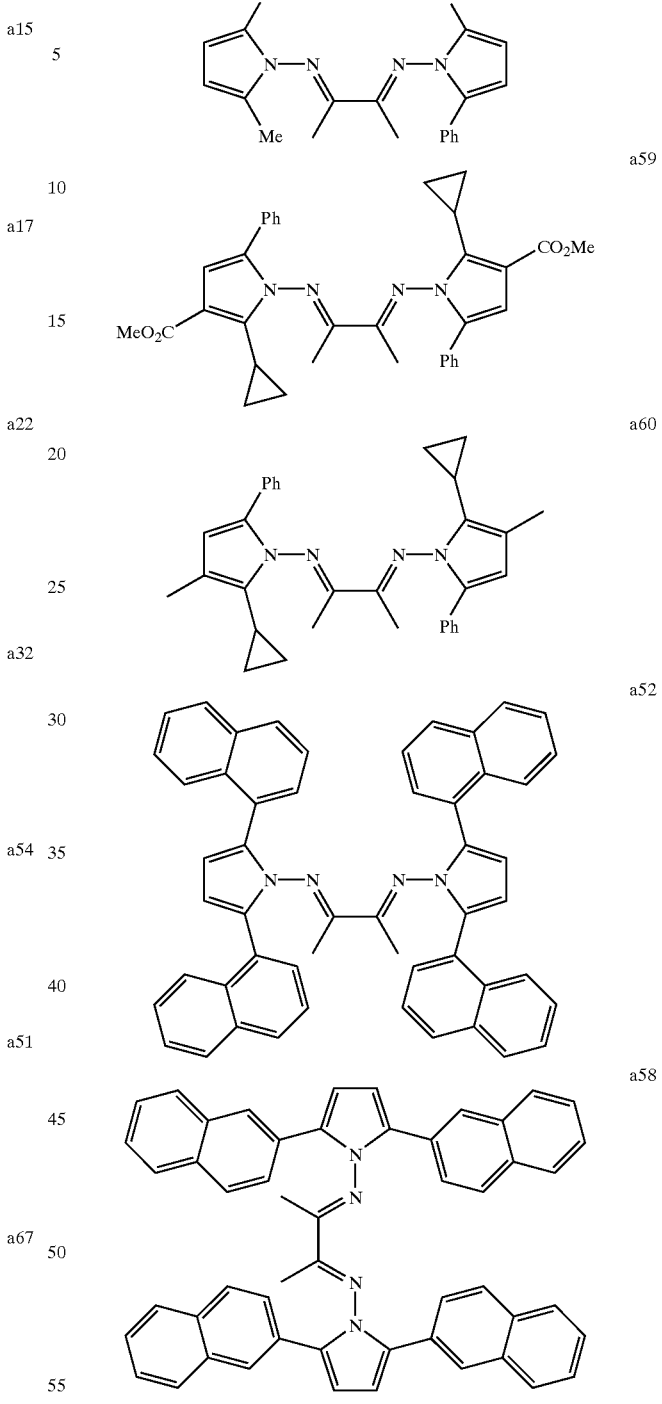

wherein:
  $R^{2x,y}$ are each independently H, hydrocarbyl, substituted hydrocarbyl, heteroatom connected hydrocarbyl, heteroatom connected substituted hydrocarbyl; silyl, boryl, or ferrocenyl; in addition, $R^{2x}$ and $R^{2y}$ may be linked by a bridging group; and
  $R^{3a-h}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two of $R^{3a-h}$ may be linked by a bridging group.

In a fourth preferred embodiment, the catalyst compositions of the third aspect are attached to a solid support, with those catalyst compositions wherein the metal is nickel and the solid support is silica representing an especially preferred, fifth embodiment.

In a fourth aspect, this invention relates to a process for the polymerization or oligomerization of olefins, which comprises contacting one or more olefins with the catalyst composition of the third aspect.

A first preferred embodiment of this fourth aspect is the process wherein linear α-olefins are obtained.

A second preferred embodiment of this fourth aspect is the process wherein a polyolefin wax is obtained.

In a fifth aspect, this invention relates to a process for the polymerization of olefins, which comprises contacting one or more olefins with a catalyst composition of the fourth or fifth embodiment of the third aspect. A first preferred embodiment of this fifth aspect is the process wherein the metal is Ni, the solid support is silica, and the catalyst is activated by treatment with an alkylaluminum in a gas phase, fluidized bed, olefin polymerization reactor, or in an inlet stream thereof. A second, more preferred, embodiment of this fifth aspect is the process wherein the alkylaluminum is trimethylaluminum.

The in situ catalyst activation protocol described as a first preferred embobiment of the fifth aspect represents a significant process breakthrough. The in situ catalyst activation allows for the addition to a gas phase reactor of an inactive or passivated catalyst that is activated in the reactor, and catalyst activity increases as additional sites become activated. This process allows for more convenient catalyst handling as well as improved control and stability of the gas phase process.

In a sixth aspect, this invention relates to a compound selected from Set 2.

Set 2

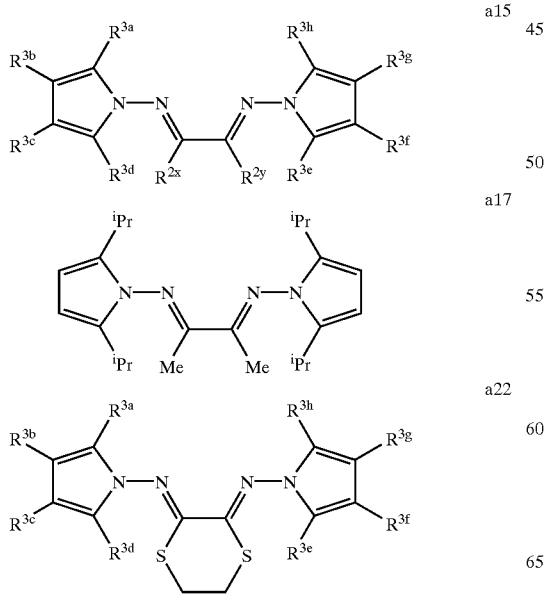

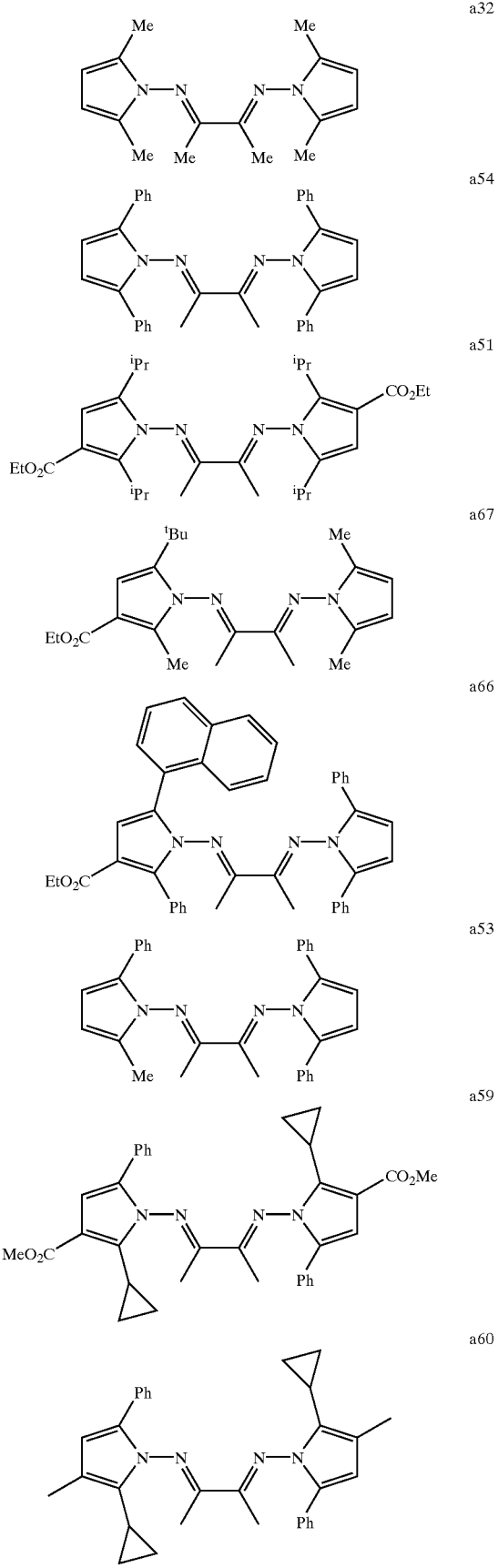

-continued

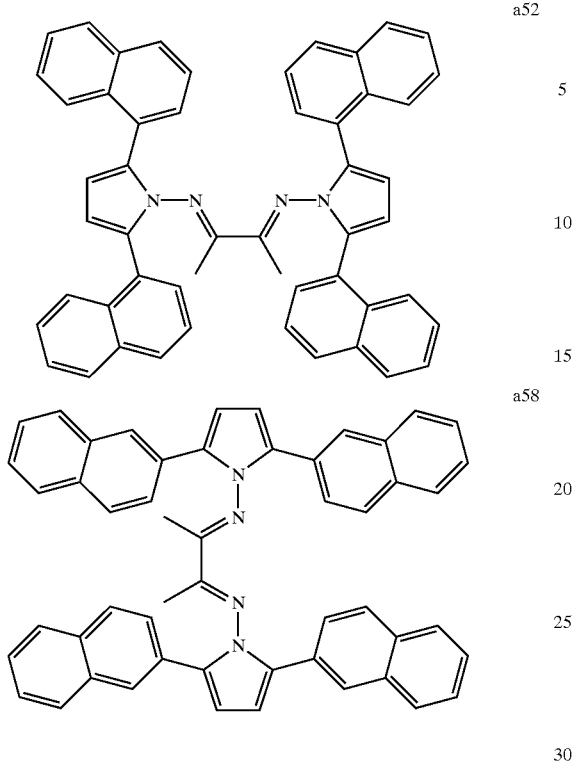

a52 a58 wherein:

R$^{2x,y}$ are each independently H, hydrocarbyl, substituted hydrocarbyl, heteroatom connected hydrocarbyl, heteroatom connected substituted hydrocarbyl; silyl, boryl, or ferrocenyl; in addition, R$^{2x}$ and R$^{2y}$ may be linked by a bridging group;

R$^{3a-h}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two of R$^{3a-h}$ may be linked by a bridging group.

In a seventh aspect, this invention relates to a catalyst composition for the polymerization or oligomerization of olefins, comprising either (i) a cationic Group 8–10 transition metal complex of a neutral bidentate ligand selected from Set 3, or a tautomer thereof, and a weakly coordinating anion X$^-$, or (ii) the reaction product of Ni(1,5-cyclooctadiene)$_2$, B(C$_6$F$_5$)$_3$, one or more olefin monomers, and a neutral bidentate ligand selected from Set 3:

Set 3

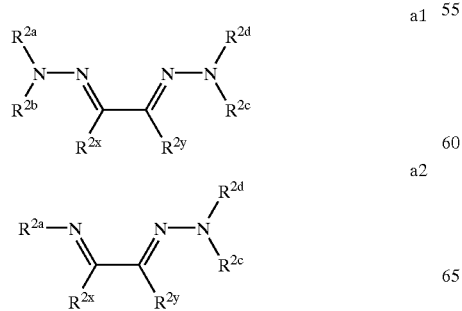

a1 a2

-continued

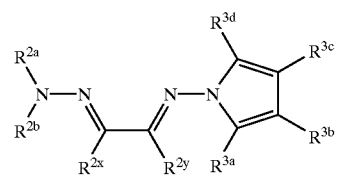

a3

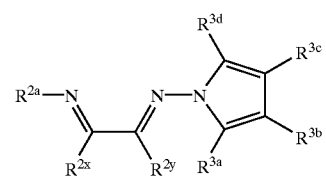

a4

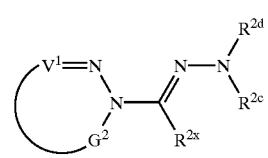

a5

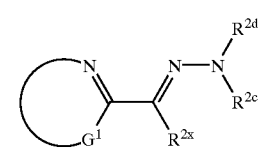

a6

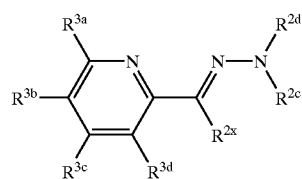

a7

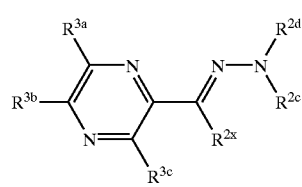

a8

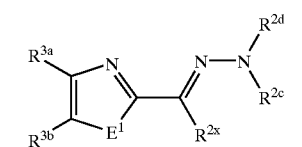

a9

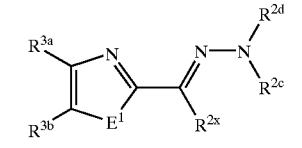

a10

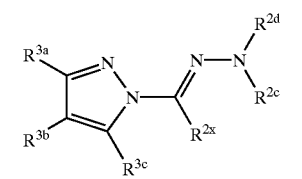

a11

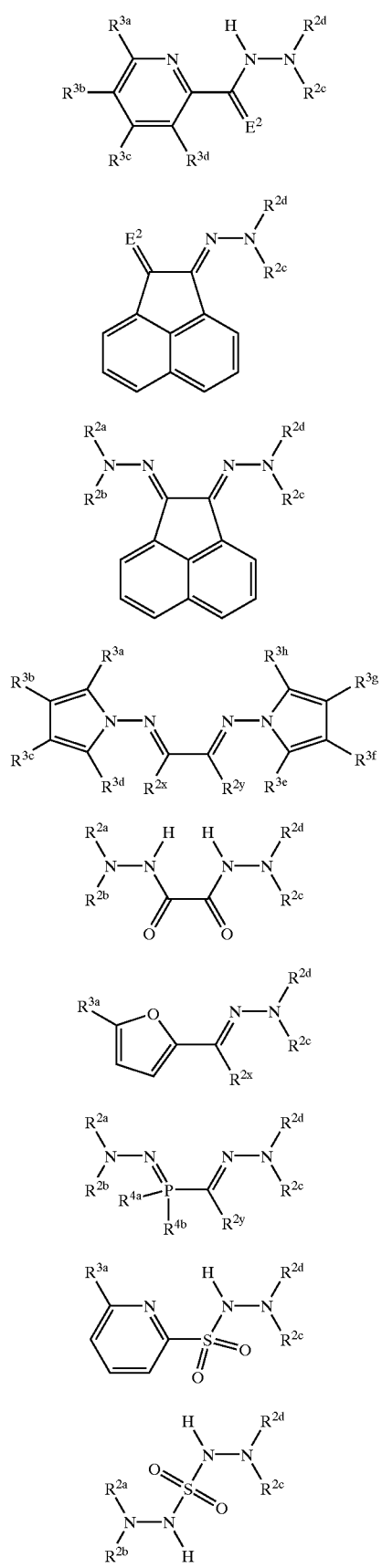
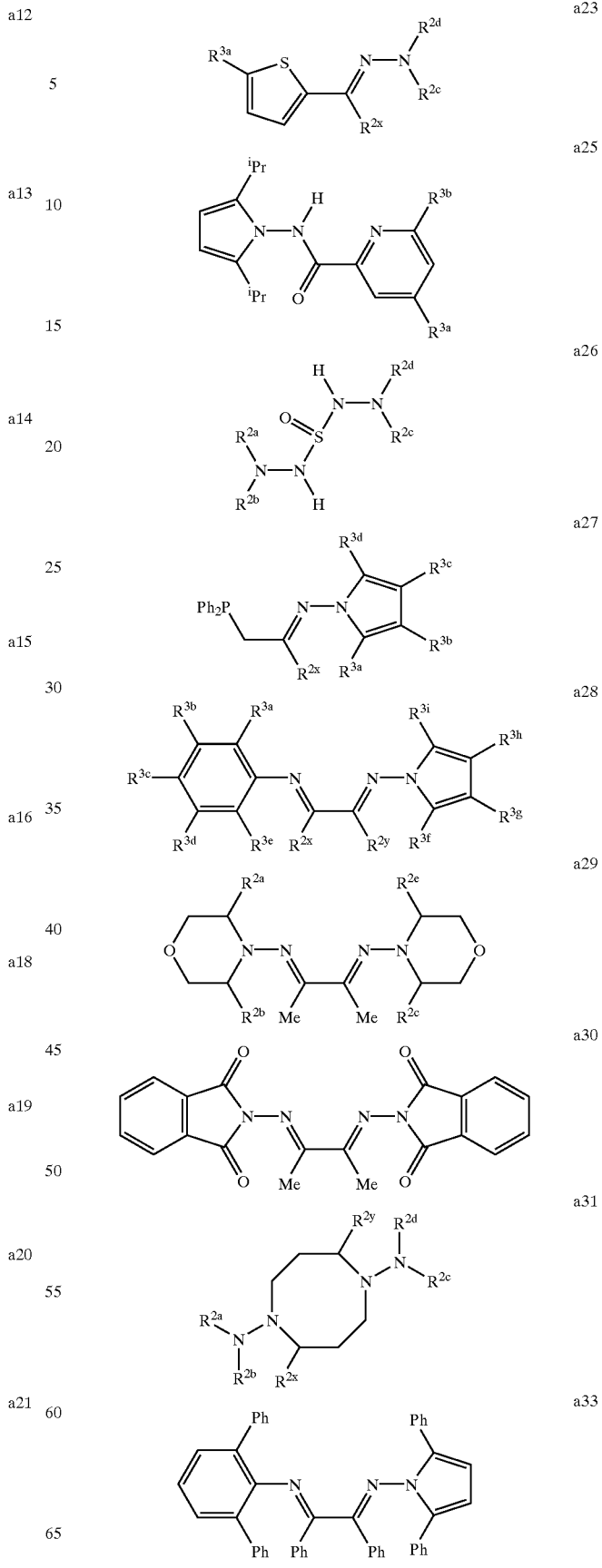

-continued
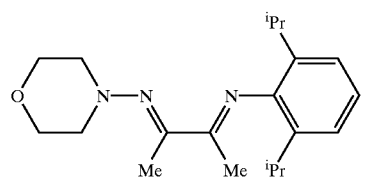 a34
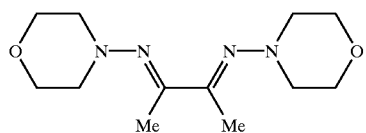 a35
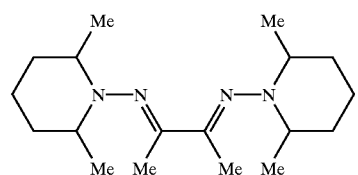 a36
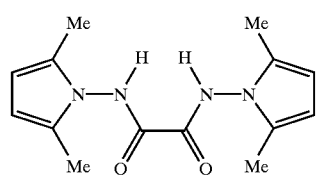 a37
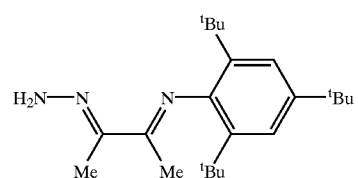 a38
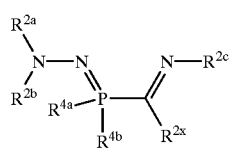 a39
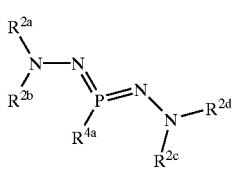 a40
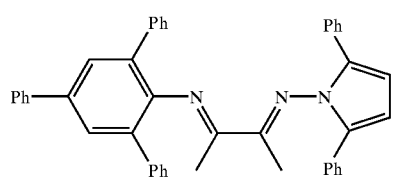 a41
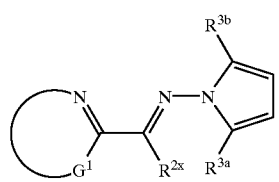 a43
-continued
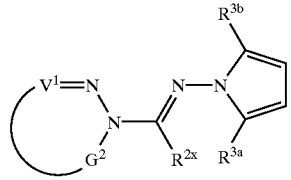 a44
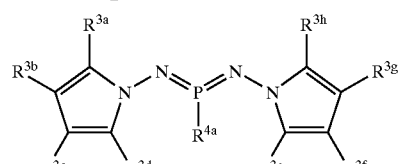 a45
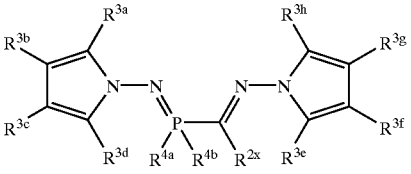 a46
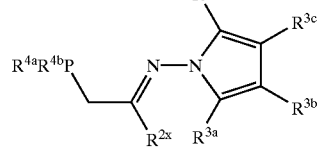 a47
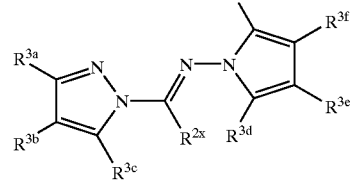 a48
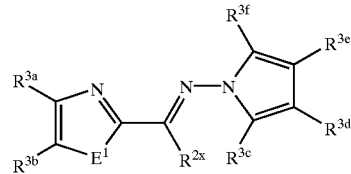 a49
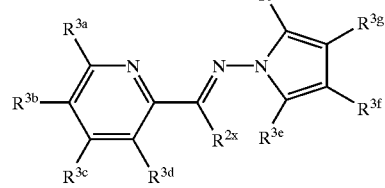 a55
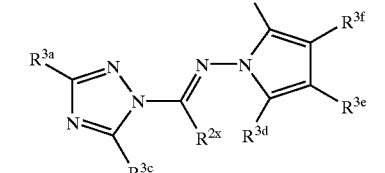 a56
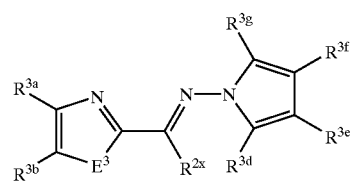 a57

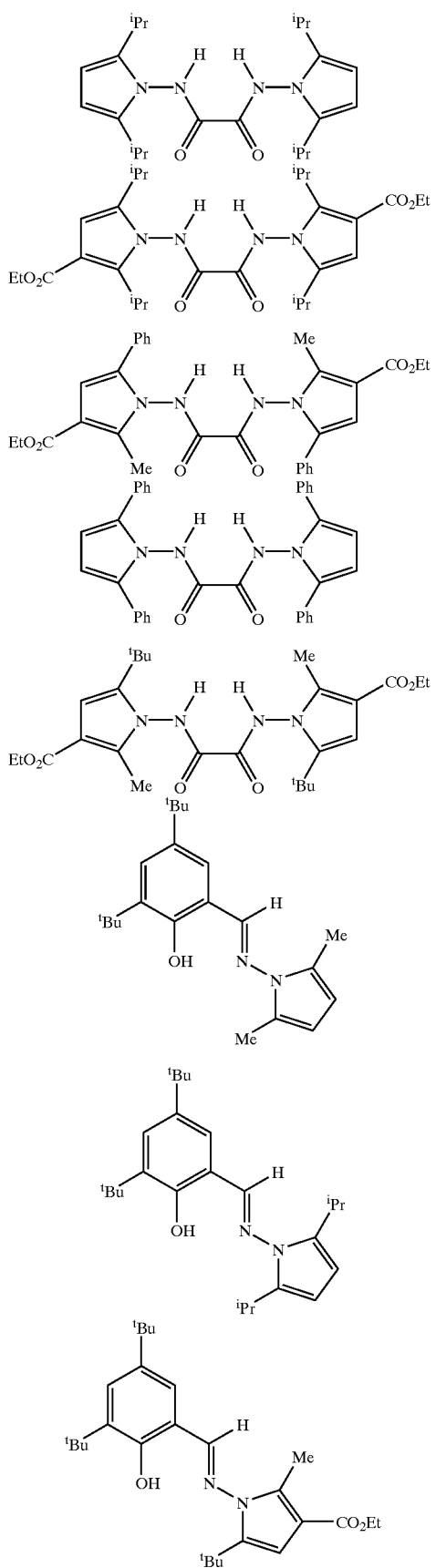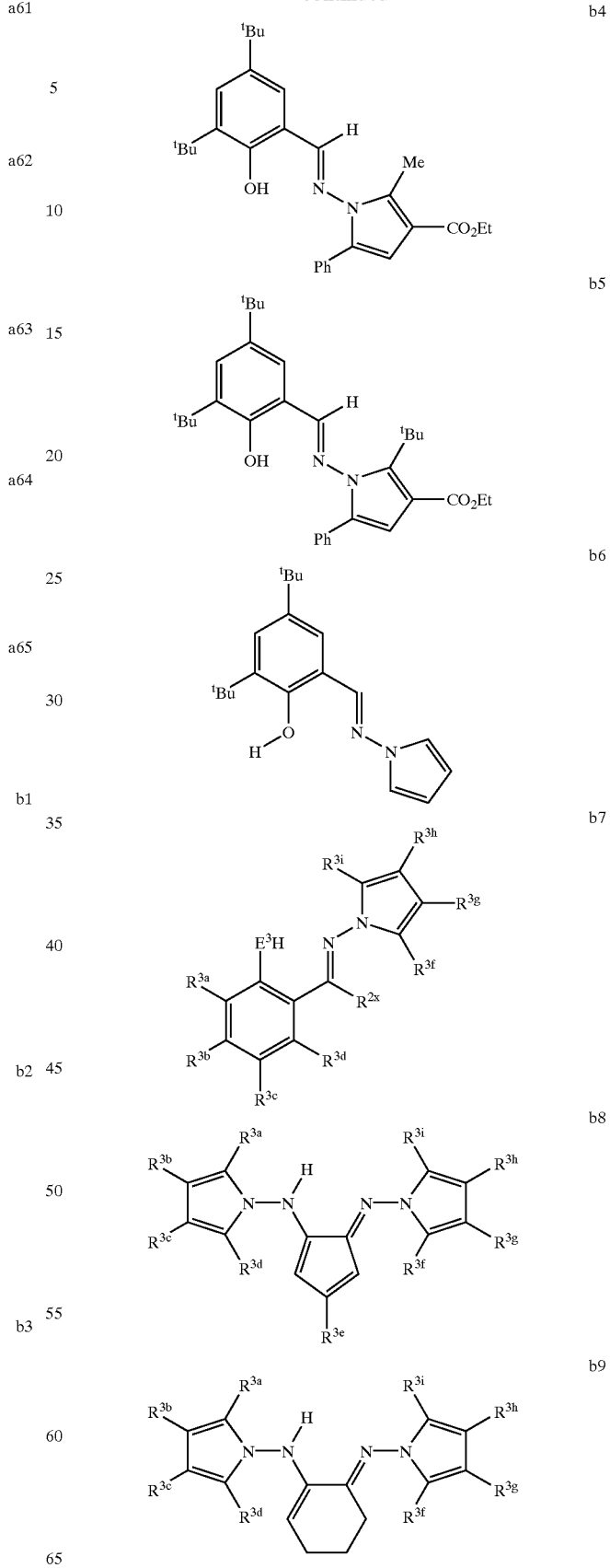

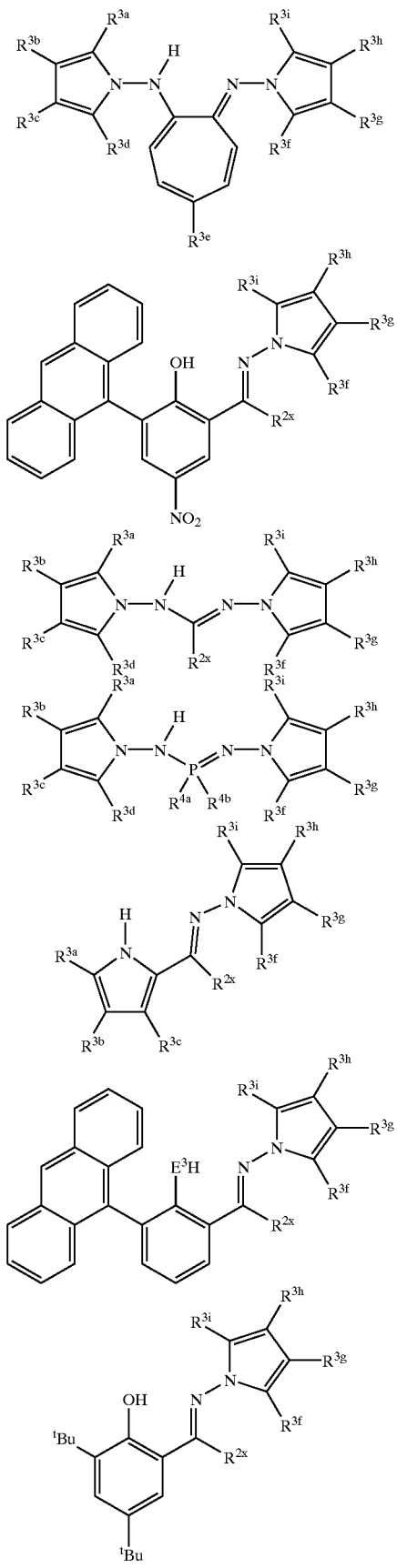

-continued

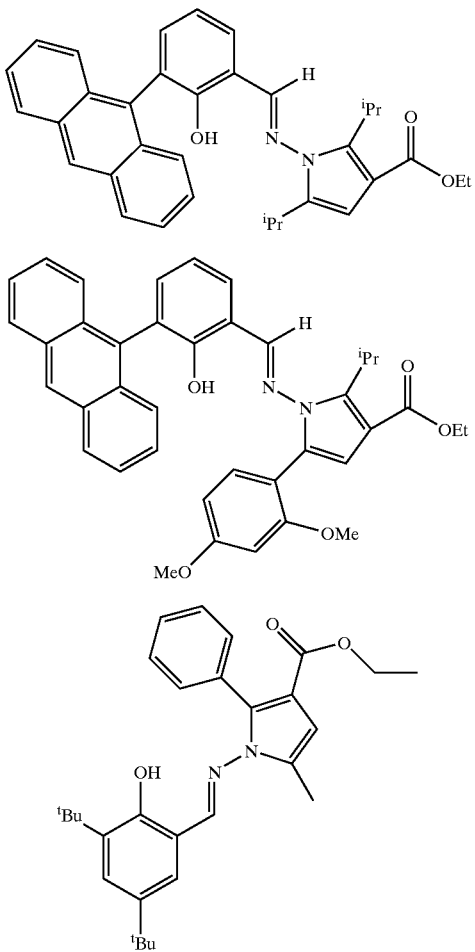

wherein:
R$^{2a\text{-}f,x\text{-}z}$ are each independently H, hydrocarbyl, substituted hydrocarbyl, heteroatom connected hydrocarbyl, or heteroatom connected substituted hydrocarbyl; R$^{2a\text{-}f}$ may also be silyl, boryl, or ferrocenyl; in addition, any two of R$^{2a\text{-}d}$, or R$^{2x}$ and R$^{2y}$, may be linked by a bridging group;

R$^{3a\text{-}j}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two of R$^{3a\text{-}j}$ may be linked by a bridging group;

R$^{4a}$ and R$^{4b}$ are each independently hydrocarbyl, substituted hydrocarbyl, heteroatom connected hydrocarbyl, or heteroatom connected substituted hydrocarbyl; in addition, R$^{4a}$ and R$^{4b}$ may be linked by a bridging group;

G$^1$ is hydrocarbyl, substituted hydrocarbyl, heteroatom connected hydrocarbyl, or heteroatom connected substituted hydrocarbyl;

G$^1$, C, and N collectively comprise a 5- or 6-membered heterocyclic ring;

G$^2$ is hydrocarbyl, substituted hydrocarbyl, heteroatom connected hydrocarbyl, or hetero atom connected substituted hydrocarbyl;

G$^2$, V$^1$, N, and N collectively comprise a 5- or 6-membered heterocyclic ring;

V$^1$ is CR$^{3j}$, N, or PR$^{4a}$R$^{4b}$;
E$^1$ is O, S, Se, or NR$^{2e}$;
E$^2$ and E$^3$ are O, S, or NR$^{2e}$; and
Q$^1$ is C—R$^{3j}$, PR$^{4a}$R$^{4b}$, S(E$^2$)(NR$^{2e}$R$^{2f}$), or S(E$^2$)(E$^3$R$^{2e}$); provided that the ligand is not of the formula a15, which has been previously described in the third embodiment of the third aspect of the present invention.

In an eighth aspect, this invention relates to a process for the polymerization or oligomerization of olefins, which comprises contacting one or more olefins with the catalyst composition of the seventh aspect. Polymerization reaction temperatures between about 20 and about 160° C. are preferred, with temperatures between about 60 and about 100° C. being more preferred. Ethylene, propylene, 1-butene, 1-hexene and 1-octene are preferred olefin monomers. When ethylene is used as the primary or predominant olefin monomer, pressures between about 1 and about 100 atm are preferred.

In a ninth aspect, this invention relates to a ligand selected from Set 4:

Set 4

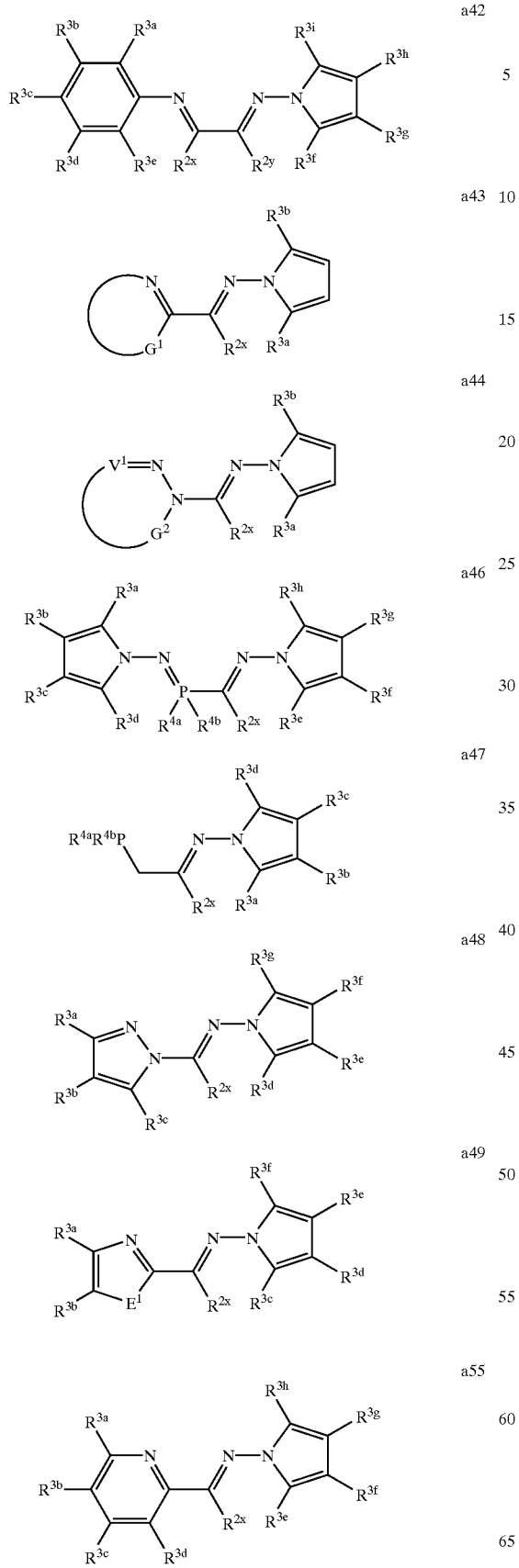
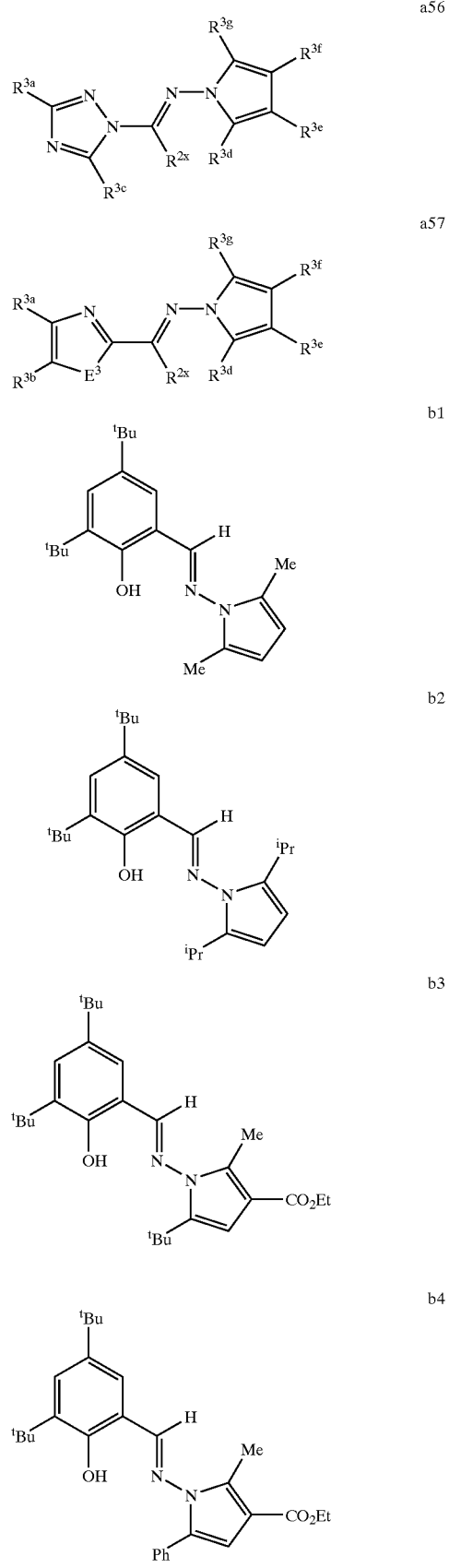

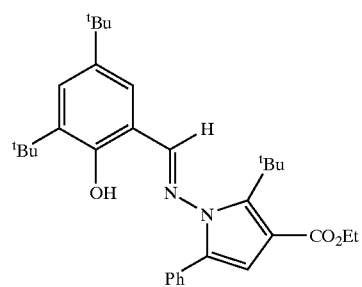
b5
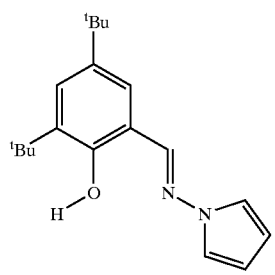
b6
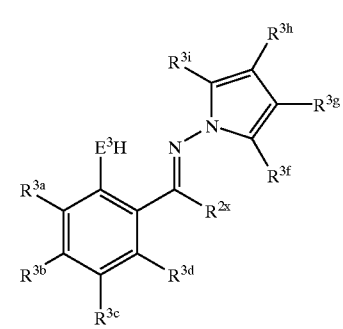
b7
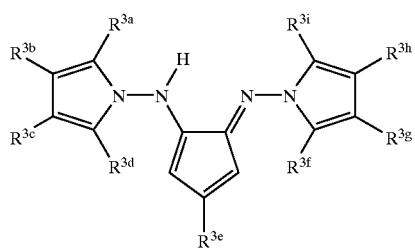
b8
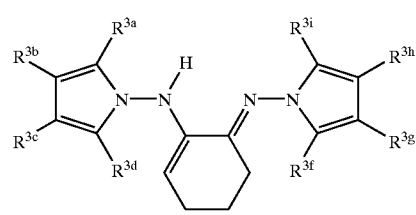
b9
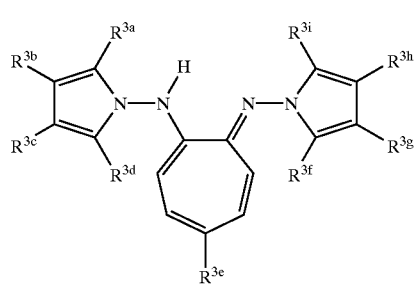
b10
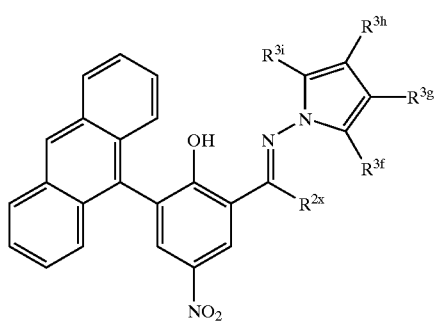
b11
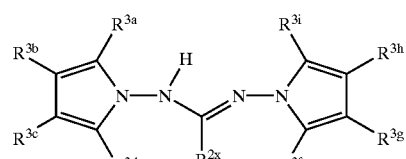
b12
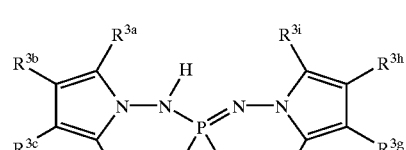
b13
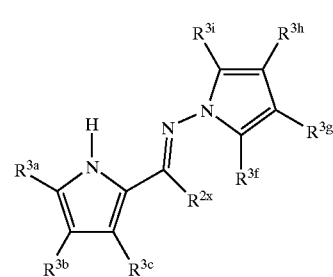
b14
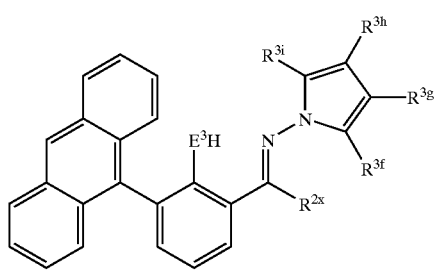
b15
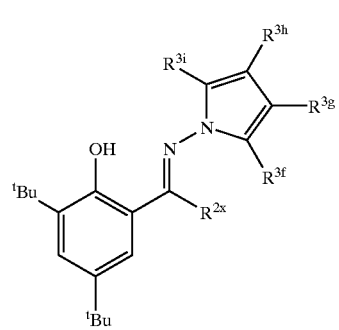
b16

-continued

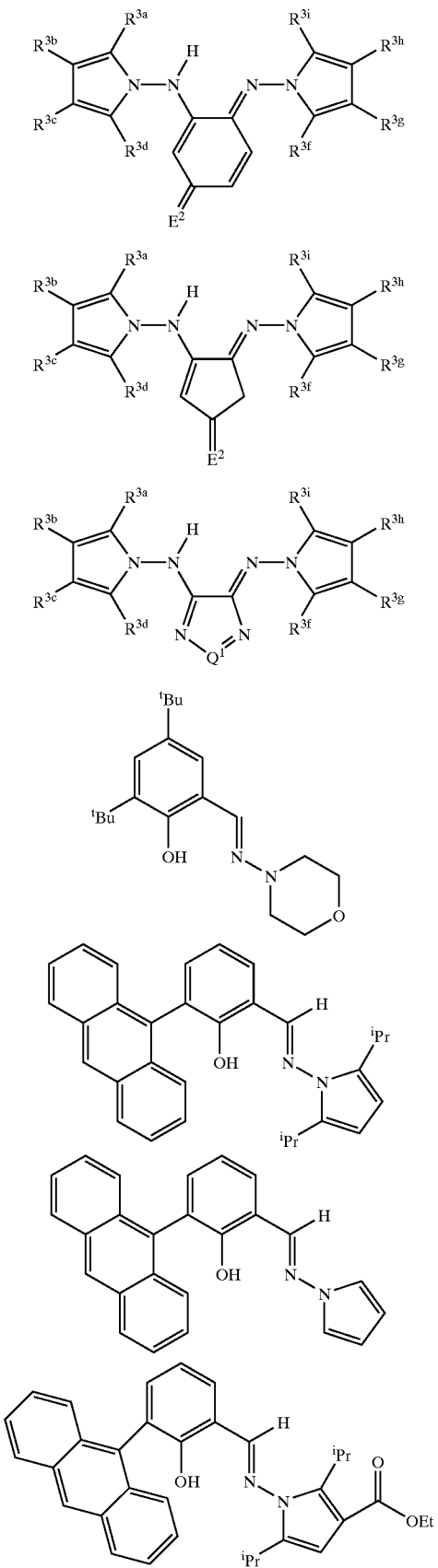

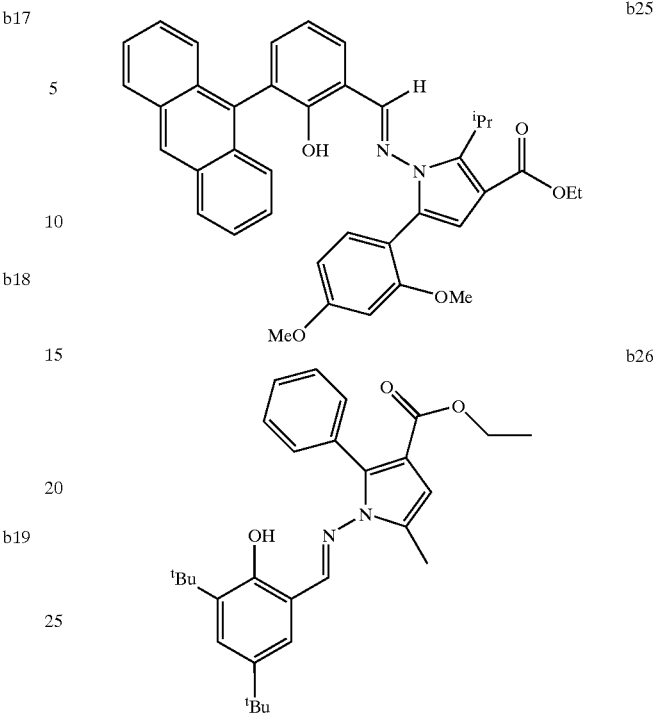

wherein:
R²ᵃ⁻ᶠ,ˣ⁻ᶻ are each independently H, hydrocarbyl, substituted hydrocarbyl, heteroatom connected hydrocarbyl, or heteroatom connected substituted hydrocarbyl; R²ᵃ⁻ᶠ may also be silyl, boryl, or ferrocenyl; in addition, any two of R²ᵃ⁻ᵈ, or R²ˣ and R²ʸ, may be linked by a bridging group;

R³ᵃ⁻ʲ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two of R³ᵃ⁻ʲ may be linked by a bridging group;

R⁴ᵃ and R⁴ᵇ are each independently hydrocarbyl, substituted hydrocarbyl, heteroatom connected hydrocarbyl, or heteroatom connected substituted hydrocarbyl; in addition, R⁴ᵃ and R⁴ᵇ may be linked by a bridging group;

G¹ is hydrocarbyl, substituted hydrocarbyl, heteroatom connected hydrocarbyl, or heteroatom connected substituted hydrocarbyl;

G¹, C, and N collectively comprise a 5- or 6-membered heterocyclic ring;

G² is hydrocarbyl, substituted hydrocarbyl, heteroatom connected hydrocarbyl, or heteroatom connected substituted hydrocarbyl;

G², V¹, N, and N collectively comprise a 5- or 6-membered heterocyclic ring;

V¹ is CR³ʲ, N, or PR⁴ᵃR⁴ᵇ;

E¹ is O, S, Se, or NR²ᵉ;

E² and E³ are O, S, or NR²ᵉ; and

Q¹ is C—R³ʲ, PR⁴ᵃR⁴ᵇ, S(E²)(NR²ᵉR²ᶠ), or S(E²)(E³R²ᵉ);

provided that (i) the ligand is not of the formula a15, which has been previously described in the sixth aspect, (ii) when the ligand is of the formula b7, and E³ is O, R³ᵃ⁻ᵈ are H, and R²ˣ is H, the pyrrol-1-yl group is other than carbazol-9-yl, 3-phenylinden-1-yl or unsubstituted pyrrol-1-yl, and (iii) when the ligand is of formula a55, it is other than carbazol-9-yl-quinolin-2-ylmethylene-amine.

In a tenth aspect, this invention relates to a catalyst composition for the polymerization or oligomerization of olefins, comprising a catalyst composition of the first aspect, wherein the metal is selected from the group consisting of Co, Ni, and Pd, and the ligand is a monoanionic bidentate ligand. Preferred catalyst compositions in this tenth aspect are those wherein the metal is nickel; more preferred are those catalyst compositions wherein the metal complex is of formula XII:

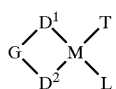

XII wherein:
  M is nickel;
  $D^1$, $D^2$, and G collectively comprise the monoanionic bidentate ligand;
  $D^1$ and $D^2$ are monodentate donors linked by a bridging group G, wherein at least one of $D^1$ and $D^2$ is ligated to the metal M by a nitrogen atom substituted by a 1-pyrrolyl or a substituted 1-pyrrolyl group;
  T is H, hydrocarbyl, substituted hydrocarbyl, or other group capable of inserting an olefin; and
  L is an olefin or a neutral donor group capable of being displaced by an olefin; in addition, T and L may be taken together to form a π-allyl or π-benzyl group.

Even more preferred catalyst compositions in this tenth aspect are those wherein the monoanionic bidentate ligand is selected from Set 5, or a tautomer thereof:

Set 5 c1

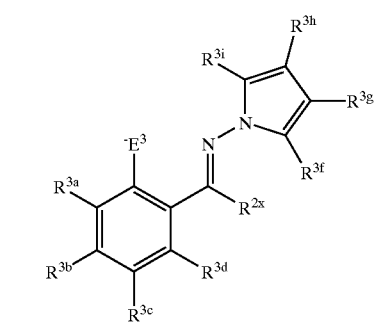

c2 c3

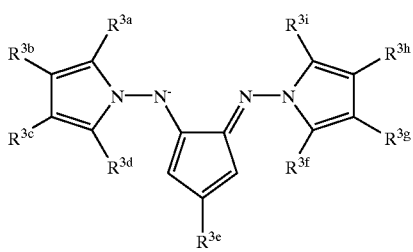

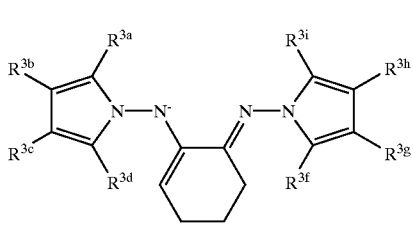

-continued c4

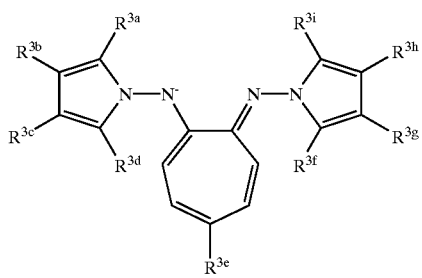

c5

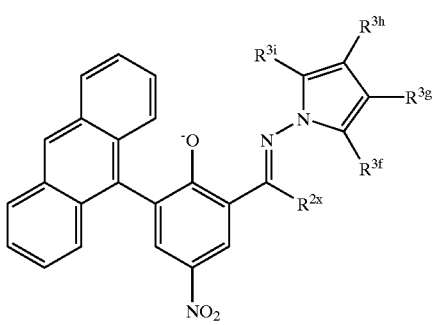

c6

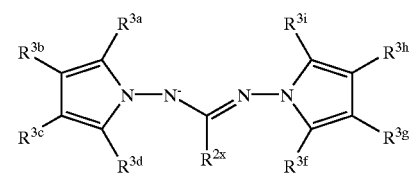

c7

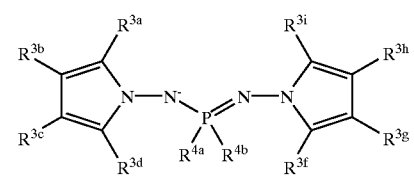

c8

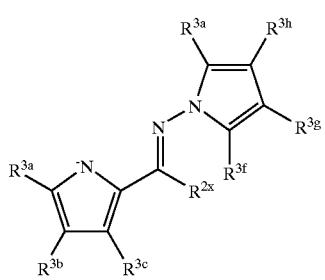

c9

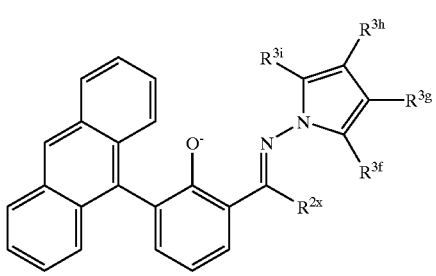

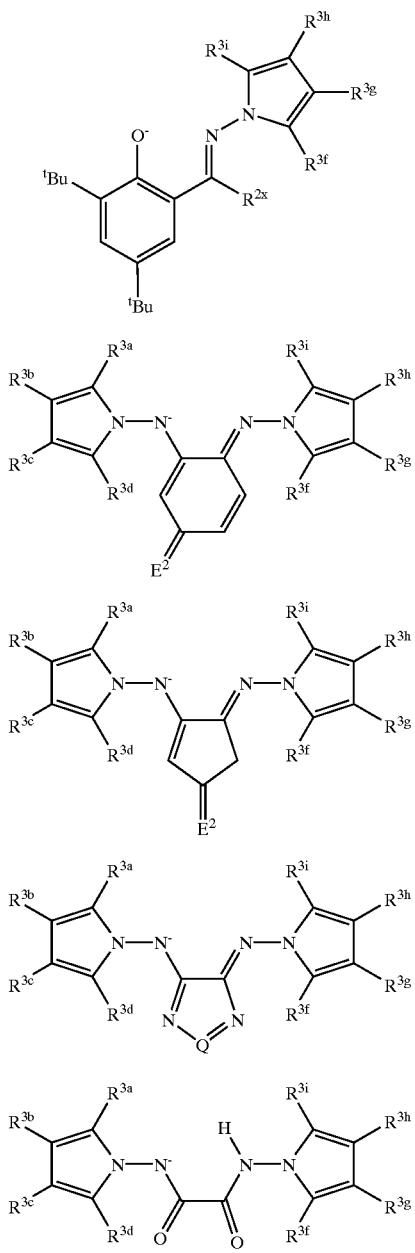

wherein:
- $R^{2x-z}$ are each independently H, hydrocarbyl, substituted hydrocarbyl, heteroatom connected hydrocarbyl, or heteroatom connected substituted hydrocarbyl;
- $R^{3a-j}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two of $R^{3a-j}$ may be linked by a bridging group;
- $R^{4a}$ and $R^{4b}$ are each independently hydrocarbyl, substituted hydrocarbyl, heteroatom connected hydrocarbyl, or heteroatom connected substituted hydrocarbyl; in addition, $R^{4a}$ and $R^{4b}$ may be linked by a bridging group;
- $E^2$ and $E^3$ are O, S, or $NR^{2x}$; and
- Q is $C-R^{3j}$, $PR^{4a}R^{4b}$, $S(E^2)(NR^{2y}R^{2z})$, or $S(E^2)(E^3R^{2x})$.

Also preferred in this tenth aspect are those catalyst compositions wherein the metal complex is attached to a solid support, with silica being an especially preferred support.

In an eleventh aspect, this invention relates to a process for the polymerization or oligomerization of olefins, which comprises contacting one or more olefins with the catalyst composition of the tenth aspect. Polymerization reaction temperatures between about 20 and about 160° C. are preferred, with temperatures between about 60 and about 100° C. being more preferred. Ethylene, propylene, 1-butene, 1-hexene, 1-octene, norbornene and substituted norbornenes are preferred olefin monomers. When ethylene is used as the primary or predominant olefin monomer, pressures between about 1 and about 100 atm are preferred.

In a twelfth aspect, this invention relates to a catalyst composition for the polymerization or oligomerization of olefins, comprising a catalyst composition of the first aspect, wherein the metal is selected from the group consisting of Mn, Fe, Ru, and Co, and the ligand is a neutral tridentate ligand. Preferred catalyst compositions in this twelfth aspect are those wherein the metals are Fe and Co; more preferred are those catalyst compositions comprising a compound of formula XIII:

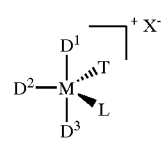

XIII wherein:
M is Co or Fe;
$D^{1-3}$ are monodentate donors which are linked by a bridging group(s) to collectively comprise the neutral tridentate ligand, wherein at least one of $D^1$, $D^2$, and $D^3$ is ligated to the metal M by a nitrogen atom substituted by a 1-pyrrolyl or a substituted 1-pyrrolyl group;

T is H, hydrocarbyl, substituted hydrocarbyl or other group capable of inserting an olefin;

L is an olefin or a neutral donor group capable of being displaced by an olefin; in addition, T and L may be taken together to form a π-allyl or π-benzyl group; and $X^-$ is a weakly coordinating anion.

Even more preferred catalyst compositions in this twelfth aspect are those wherein the neutral tridentate ligand is selected from Set 6, or a tautomer thereof:

Set 6

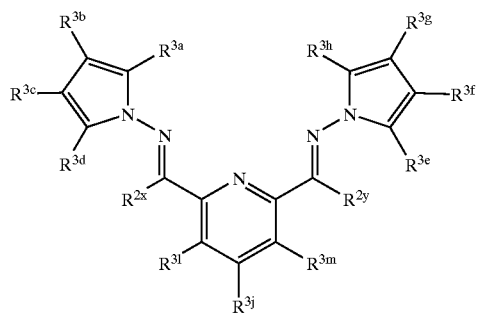

h1

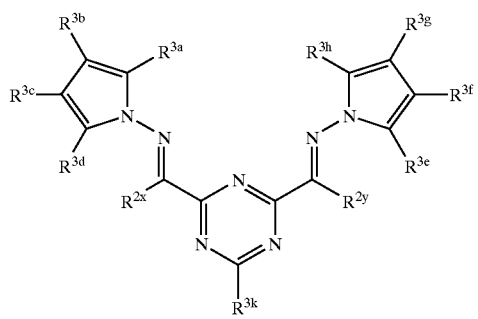 h2
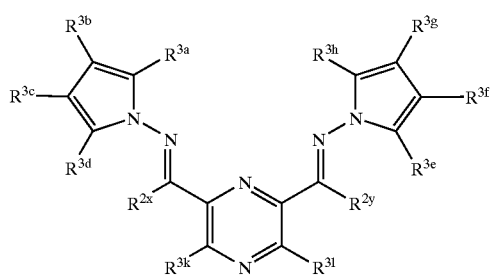 h3
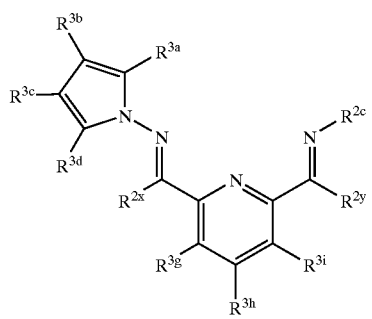 h4
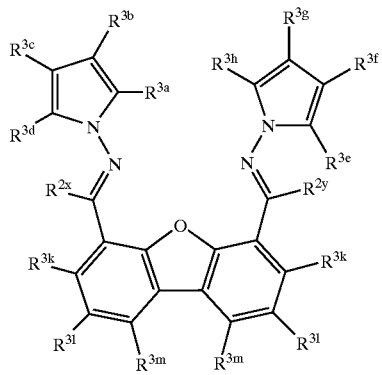 h5
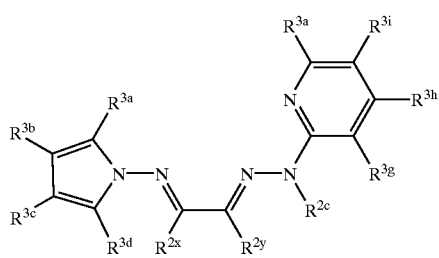 h6
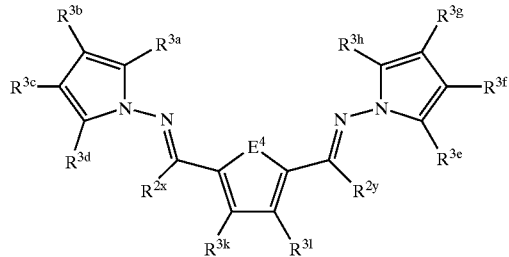 h7
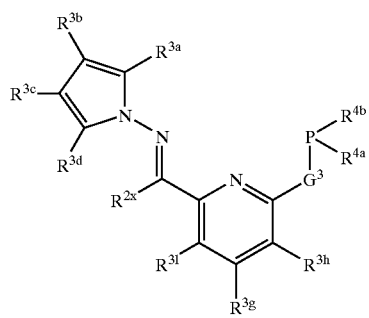 h8
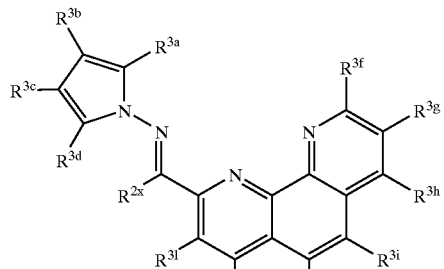 h9
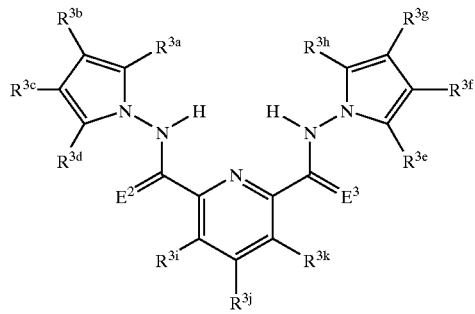 h10
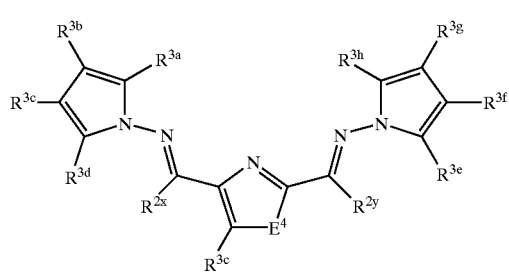 h11

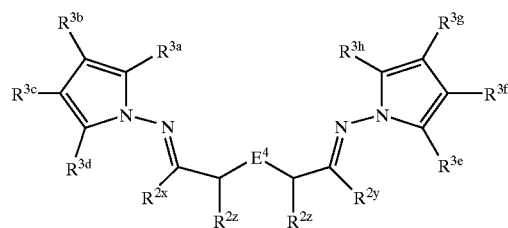
h12
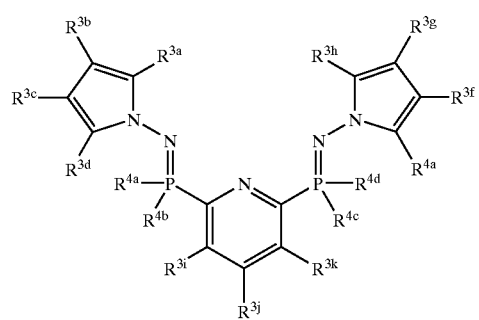
h13
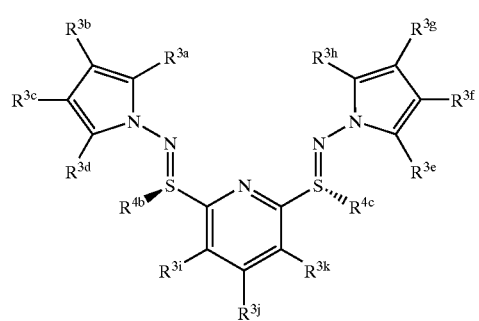
h14
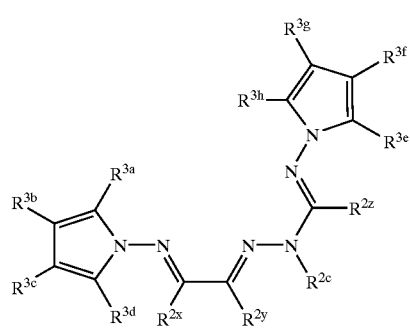
h15
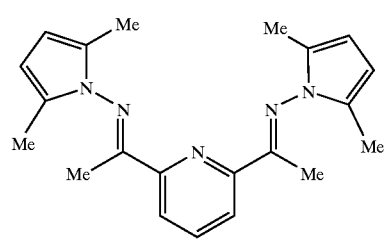
h16
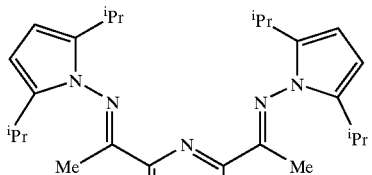
h17
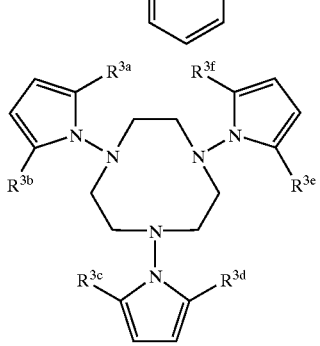
h18
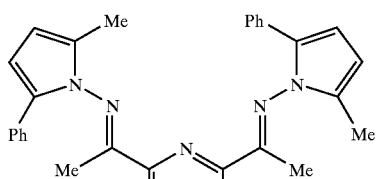
h19
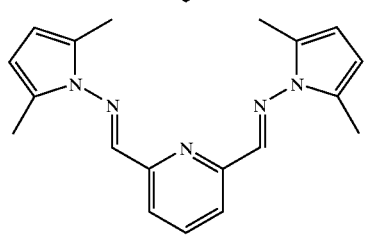
h20
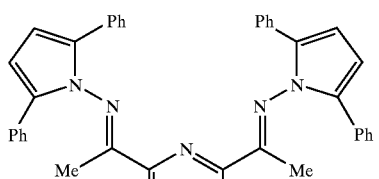
h21
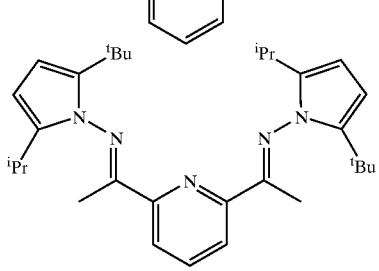
h22
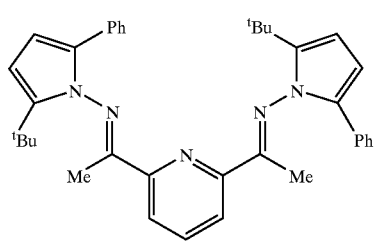
h23

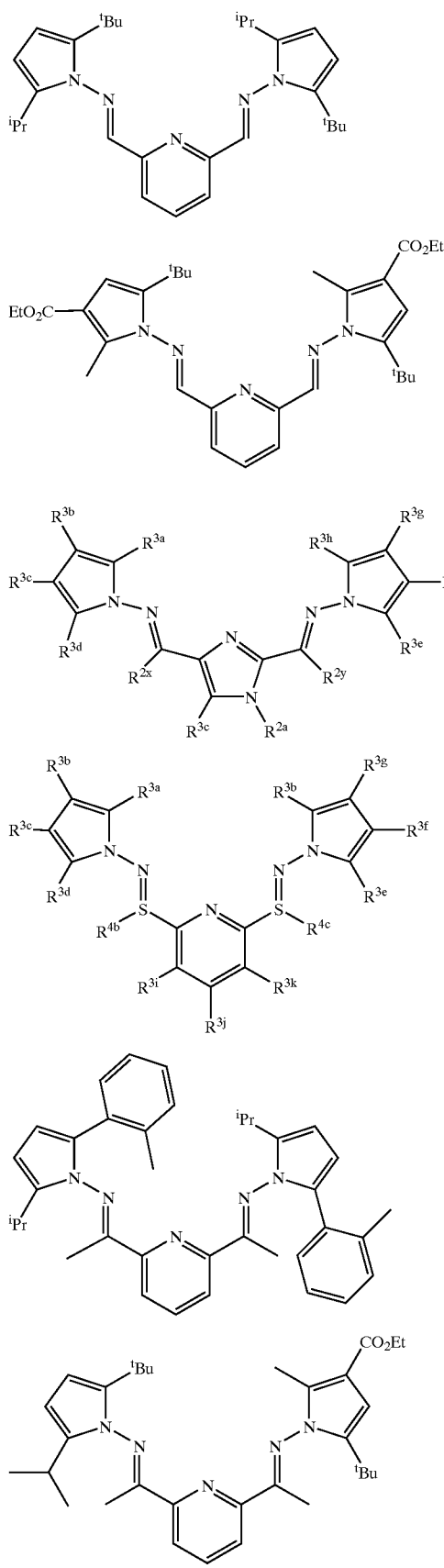

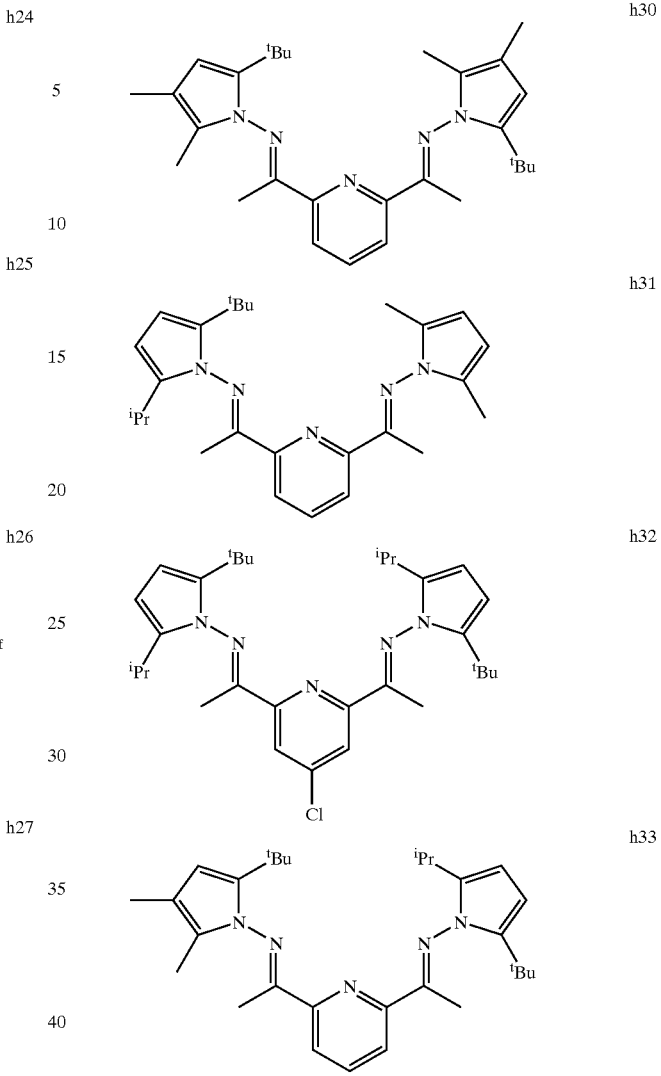

wherein:

$R^{2c,x-z}$ are each independently H, hydrocarbyl, substituted hydrocarbyl, heteroatom connected hydrocarbyl, or heteroatom connected substituted hydrocarbyl; in addition, $R^{2x}$ and $R^{2y}$ may be linked by a bridging group in the ligand of formula h6;

$R^{3a-m}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two of $R^{3a-m}$ may be linked by a bridging group;

$R^{4a-d}$ are each independently hydrocarbyl, substituted hydrocarbyl, heteroatom connected hydrocarbyl, or heteroatom connected substituted hydrocarbyl; in addition, any two of $R^{4a-z}$ may be linked by a bridging group or groups;

$G^3$ is hydrocarbyl or substituted hydrocarbyl;

$E^2$ and $E^3$ are O, S, or Se; and $E^4$ is O, S, or Se.

Also preferred in this twelfth aspect are those catalyst compositions wherein the metal complex is attached to a solid support, with silica being an especially preferred support.

In a thirteenth aspect, this invention also relates to a process for the polymerization or oligomerization of olefins, which comprises contacting one or more olefins with a catalyst composition of the twelfth aspect. Polymerization reaction temperatures between about 20 and about 160° C. are preferred, with temperatures between about 60 and about 100° C. being more preferred. Ethylene, propylene, 1-butene, 1-hexene and 1-octene are preferred olefin monomers. When ethylene is used, pressures between about 1 and about 100 atm are preferred. Also preferred are those embodiments wherein non-supported catalysts are used to produce linear α-olefins or polyolefin waxes.

In a fourteenth aspect, this invention relates to a catalyst composition for the polymerization of olefins, comprising a Ti, Zr, or Hf complex of a dianionic bidentate ligand, wherein at least one of the donor atoms of the ligand is a nitrogen atom substituted by a 1-pyrrolyl or substituted 1-pyrrolyl group; wherein the remaining donor atoms of the ligand are selected from the group consisting of C, N, P, As, O, S, and Se. Preferred catalyst compositions in this fourteenth aspect are those wherein the metal complex is a compound of formula XIV:

XIV

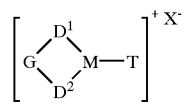

wherein:

M is Zr or Ti;

$D^1$, $D^2$, and G collectively comprise the dianionic bidentate ligand;

$D^1$ and $D^2$ are monodentate donors linked by a bridging group G, wherein at least one of $D^1$ and $D^2$ is ligated to the metal M by a nitrogen atom substituted by a 1-pyrrolyl or a substituted 1-pyrrolyl group;

T is H, hydrocarbyl, substituted hydrocarbyl, or other group capable of inserting an olefin; and $X^-$ is a weakly coordinating anion.

More preferred catalyst compositions in this fourteenth aspect are those wherein the dianionic bidentate ligand is selected from Set 7, or a tautomer thereof:

Set 7

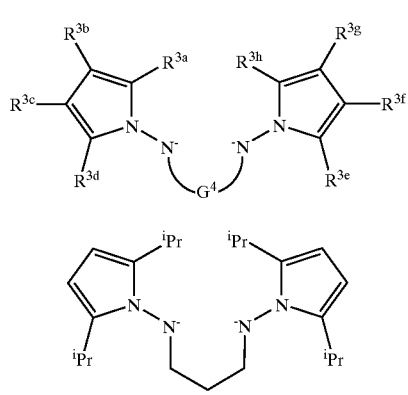

-continued

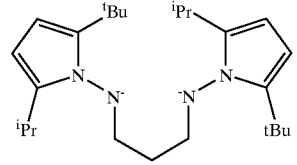

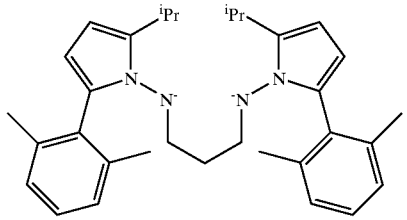

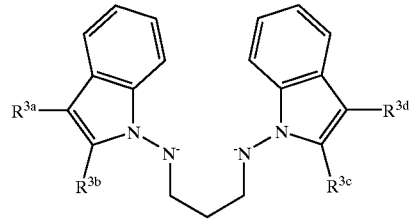

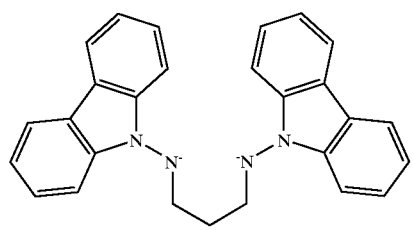

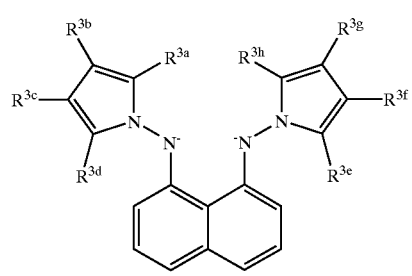

wherein:

$R^{3a-h}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two of $R^{3a-h}$ may be linked by a bridging group; and $G^4$ is a divalent bridging hydrocarbyl, substituted hydrocarbyl, heteroatom connected hydrocarbyl, or heteroatom connected substituted hydrocarbyl.

Also preferred in this fourteenth aspect are those catalyst compositions which are attached to a solid support.

In a fifteenth aspect, this invention relates to a process for the polymerization of olefins, comprising contacting one or more olefins with the catalyst composition of the fourteenth aspect, and optionally an aluminum or boron-centered Lewis acid. Examples of aluminum or boron-centered Lewis acids include MAO, $B(C_6F_5)_3$, triisobutylaluminum modified MAO, and $B(C_{12}F_9)_3$. Polymerization reaction temperatures between about 20 and about 1 60° C. are preferred, with temperatures between about 60 and about 100° C. being more preferred. Ethylene, proplene, 1-butene, 1-hexene and 1-octene are preferred olefin monomers. When ethylene is used, pressures between about 1 and about 100 atm are preferred.

In a sixteenth aspect, this invention relates to a catalyst composition for the polymerization of olefins, comprising a Ti, Zr, or Hf complex of a monoanionic bidentate ligand, wherein at least one of the donor atoms of the ligand is a nitrogen atom substituted by a 1-pyrrolyl or substituted 1-pyrrolyl group; wherein the remaining donor atoms of the ligand are selected from the group consisting of C, N, P, As, O, S, and Se.

Preferred catalyst compositions in the sixteenth aspect are those which optionally further comprise a second compound $Y^2$, wherein the metal complex is a compound of formula XV:

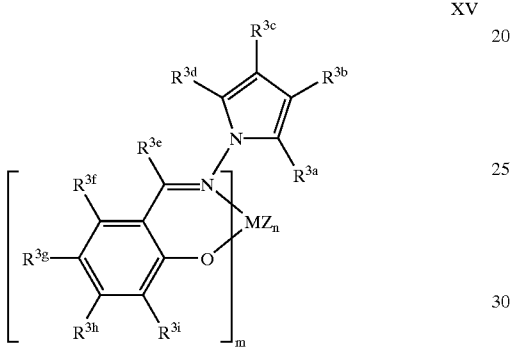

wherein:
  M is Ti, Zr, or Hf;
  m and n are integers, defined as follows: when M is Ti and m is 1, n is 2 or 3; when M is Ti and m is 2, n is 1 or 2; when M is Zr and m is 1, n is 3; when M is Zr and m is 2, n is 2; when M is Hf, m is 2 and n is 2;
  $R^{3a-i}$ are each independently H, hydrocarbyl, substituted hydrocarbyl, heteroatom connected hydrocarbyl, heteroatom connected substituted hydrocarbyl, silyl, boryl, fluoro, chloro, bromo, or nitro, with the proviso that $R^{3e}$ is other than halogen or nitro; in addition, any two of $R^{3a-i}$ on the same or different N-pyrrol-1-yliminophenoxide ligand may be linked by a bridging group;
  Z is H, halogen, hydrocarbyl, substituted hydrocarbyl, heteroatom connected hydrocarbyl, heteroatom connected substituted hydrocarbyl, silyl, allyl, benzyl, alkoxy, carboxylate, amido, nitro, or trifluoromethane sulfonyl; each Z may be the same or different and plural Z may be taken together to form sulfate, oxalate, or another divalent group;
  $Y^2$ is selected from the group consisting of a neutral Lewis acid capable of abstracting $Z^-$ to form a weakly coordinating anion, a cationic Lewis acid whose counterion is a weakly coordinating anion, and a Bronsted acid whose conjugate base is a weakly coordinating anion; and
  when n is 2 or 3, the metal complex may be a salt, comprising a Ti, Zr, or Hf centered cation with one of the groups $Z^-$ being a weakly coordinating anion.

Even more preferred catalyst compositions in this sixteenth aspect are those wherein the monoanionic bidentate ligand is selected from Set 8, or a tautomer thereof:

Set 8

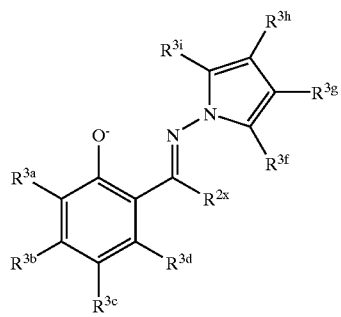
k1

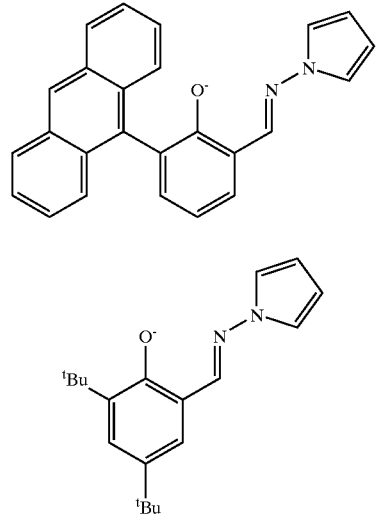
k2

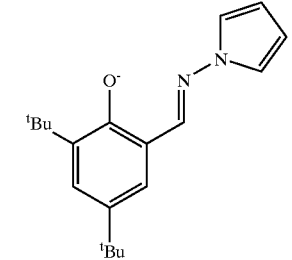
k3

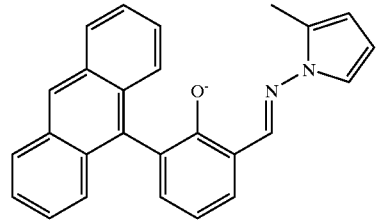
k4

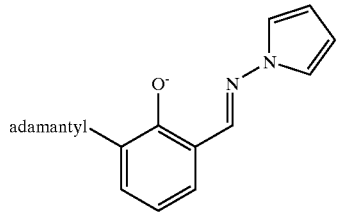
k5

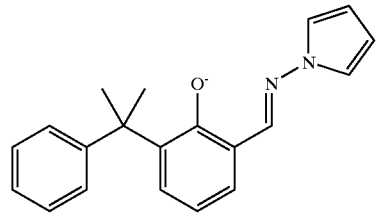
k6

-continued

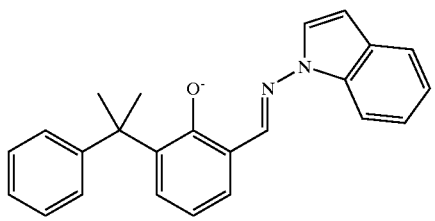

k7 wherein:
R$^{2x}$ is H, hydrocarbyl, substituted hydrocarbyl, heteroatom connected hydrocarbyl, or heteroatom connected substituted hydrocarbyl; and
R$^{3a-d,f-i}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two of R$^{3a-d,f-i}$ may be linked by a bridging group.

Also preferred catalyst compositions in this sixteenth aspect are those catalyst compositions which are attached to a solid support, with silica being an especially preferred solid support.

In a seventeenth aspect, this invention also relates to a process for the polymerization of olefins, which comprises contacting one or more olefins with the catalyst composition of the sixteenth aspect, and optionally a second compound Y$^2$; wherein Y$^2$ is selected from the group consisting of (i) a neutral Lewis acid which is capable of reacting with said Ti, Zr, or Hf complex to form a salt comprising a weakly coordinating anion, (ii) a cationic Lewis acid whose counterion is a weakly coordinating anion, and (iii) a Bronsted acid whose conjugate base is a weakly coordinating anion. Polymerization reaction temperatures between about 20 and about 160° C. are preferred, with temperatures between about 60 and about 100° C. being more preferred. Ethylene, propylene, 1-butene, 1-hexene and 1-octene are preferred olefin monomers. When ethylene is used, pressures between about 1 and about 100 atm are preferred.

In an eighteenth aspect, this invention relates to a catalyst composition for the polymerization of olefins, comprising a Cr, Mo, or W complex of a monodentate dianionic ligand, wherein at least one of the donor atoms of the ligand is a nitrogen atom substituted by a 1-pyrrolyl or substituted 1-pyrrolyl group; wherein the remaining donor atoms of the ligand are selected from the group consisting of C, N, P, As, O, S, and Se. Preferred catalyst compositions in this eighteenth aspect are those which optionally further comprise a second compound Y$^2$, wherein the metal complex is a compound of formula XVI:

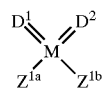

XVI wherein:
M is Cr, Mo, or W;
D$^1$ and D$^2$ are monodentate dianionic ligands that may be linked by a bridging group to collectively comprise a bidentate tetraanionic ligand;
Z$^{1a}$ and Z$^{1b}$ are each, independently, H, halogen, hydrocarbyl, substituted hydrocarbyl, heteroatom connected hydrocarbyl, heteroatom connected substituted hydrocarbyl, silyl, allyl, benzyl, alkoxy, carboxylate, amido, nitro, trifluoromethanesulfonyl, or may be taken together to form sulfate, oxalate, or another divalent group;
Y$^2$ is selected from the group consisting of a neutral Lewis acid capable of abstracting (Z$^{1a}$)$^-$ or (Z$^{1b}$)$^-$ to form a weakly coordinating anion, a cationic Lewis acid whose counterion is a weakly coordinating anion, and a Bronsted acid whose conjugate base is a weakly coordinating anion; and wherein the metal complex may be a salt, comprising a Cr, Mo, or W centered cation with one of (Z$^{1a}$)$^-$ or (Z$^{1b}$)$^-$ being a weakly coordinating anion.

Even more preferred catalyst compositions in this eighteenth aspect are those wherein the metal is Cr and the monodentate dianionic ligand is selected from Set 9, or a tautomer thereof:

Set 9

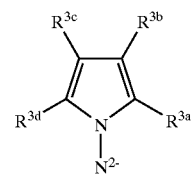

11

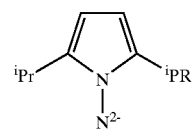

12

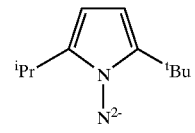

13

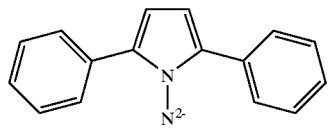

14

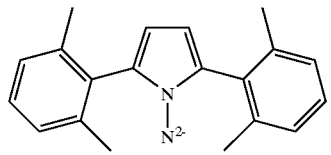

15

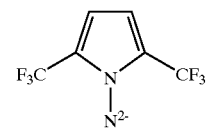

16

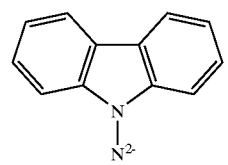

17

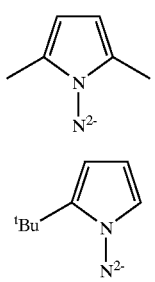

18

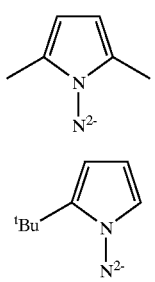

19 wherein:

$R^{3a-d}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two of $R^{3a-d}$ may be linked by a bridging group.

Also preferred in this eighteenth aspect are those catalyst compositions which are attached to a solid support, with silica being an especially preferred solid support.

In a nineteenth aspect, this invention also relates to a process for the polymerization of olefins, which comprises contacting one or more olefins with the catalyst composition of the eighteenth aspect, and optionally a second compound $Y^2$; wherein $Y^2$ is selected from the group consisting of (i) a neutral Lewis acid which is capable of reacting with said Cr, Mo, or W complex to form a salt comprising a weakly coordinating anion, (ii) a cationic Lewis acid whose counterion is a weakly coordinating anion, and (iii) a Bronsted acid whose conjugate base is a weakly coordinating anion. Polymerization reaction temperatures between about 20 and about 160° C. are preferred, with temperatures between about 60 and about 100° C. being more preferred. Ethylene, propylene, 1-butene, 1-hexene and 1-octene are preferred olefin monomers. When ethylene is used, pressures between about 1 and about 100 atm are preferred.

In a twentieth aspect, this invention relates to a catalyst composition for the polymerization of olefins, comprising a V, Nb, or Ta complex of a monodentate dianionic ligand, wherein at least one of the donor atoms of the ligand is a nitrogen atom substituted by a 1-pyrrolyl or substituted 1-pyrrolyl group; wherein the remaining donor atoms of the ligand are selected from the group consisting of C, N, P, As, O, S, and Se.

Preferred catalyst compositions in this twentieth aspect are those which optionally further comprise a second compound $Y^2$, wherein the metal complex is a compound of formula XVII:

XVII

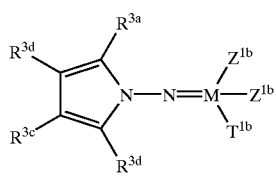

wherein:

M is V, Nb, or Ta;

$R^{3a-d}$ are each independently H, hydrocarbyl, substituted hydrocarbyl, heteroatom connected hydrocarbyl, heteroatom connected substituted hydrocarbyl, silyl, boryl, fluoro, chloro, bromo, or nitro; in addition, any two of $R^{3a-d}$ may be linked by a bridging group;

$T^{1b}$ is hydrocarbyl, substituted hydrocarbyl, heteroatom connected hydrocarbyl, heteroatom connected substituted hydrocarbyl, cyclopentadienyl, substituted cyclopentadienyl, N(hydrocarbyl)$_2$, O(hydrocarbyl), or halide;

$Z^{1a}$ and $Z^{1b}$ are each, independently, H, halogen, hydrocarbyl, substituted hydrocarbyl, heteroatom connected hydrocarbyl, heteroatom connected substituted hydrocarbyl, silyl, allyl, benzyl, alkoxy, carboxylate, amido, nitro, trifluoromethane sulfonyl, or may be taken together to form sulfate, oxalate, or another divalent group;

$Y^2$ is selected from the group consisting of a neutral Lewis acid capable of abstracting $(Z^{1a})^-$ or $(Z^{1b})^-$ to form a weakly coordinating anion, a cationic Lewis acid whose counterion is a weakly coordinating anion, and a Bronsted acid whose conjugate base is a weakly coordinating anion; and wherein the metal complex may be a salt, comprising a V, Nb, or Ta centered cation with one of $(Z^{1a})^-$ or $(Z^{1b})^-$ being a weakly coordinating anion.

More preferred catalyst compositions in this twentieth aspect are those wherein the monodentate dianionic ligand is selected from Set 10, or a tautomer thereof, and $T^{1b}$ is a N(hydrocarbyl)$_2$ group:

Set 10

I1

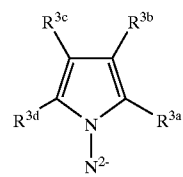

I2

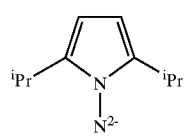

I3

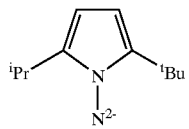

I4

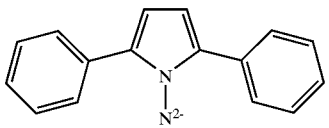

I5

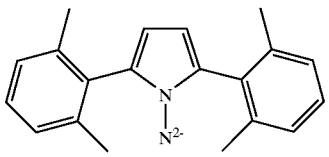

I6

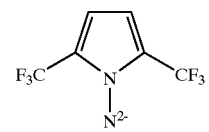

I7

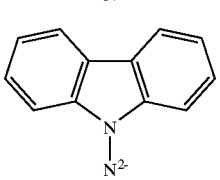

I8

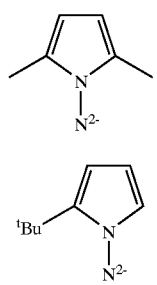

I9

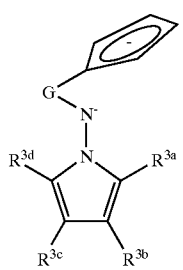

wherein:

R$^{3a-d}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two of R$^{3a-d}$ may be linked by a bridging group.

Even more preferred catalyst compositions in this twentieth aspect are those wherein the metal is V and the metal complex is attached to a solid support.

In a twenty-first aspect, this invention also relates to a process for the polymerization of olefins, which comprises contacting one or more olefins with the catalyst composition of the twentieth aspect, and optionally a second compound Y$^2$; wherein Y$^2$ is selected from the group consisting of (i) a neutral Lewis acid which is capable of reacting with said V, Nb, or Ta complex to form a salt comprising a weakly coordinating anion, (ii) a cationic Lewis acid whose counterion is a weakly coordinating anion, and (iii) a Bronsted acid whose conjugate base is a weakly coordinating anion.

In a twenty-second aspect, this invention relates to a catalyst composition for the polymerization olefins, comprising (i) a cationic Ti, Zr or Hf complex of a mono- or dianionic, nitrogen donor ligand, wherein said nitrogen donor is substituted by a 1-pyrrolyl or substituted 1-pyrrolyl group and is linked by a bridging group to a cyclopentadienyl, phosphacyclopentadienyl, pentadienyl, 6-oxacyclohexadienyl, or borataaryl group which is also ligated to said metal, and optionally, (ii) an aluminum or boron-centered Lewis acid. Preferred catalyst compositions within this twenty-second aspect are those wherein the mono- or dianionic, nitrogen donor ligand is selected from Set 11, or a tautomer thereof:

Set 11 n1

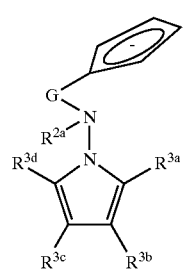

n2

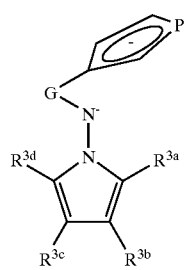

n3 n4

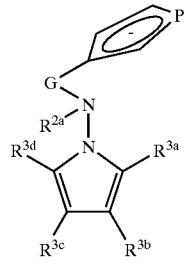

n5

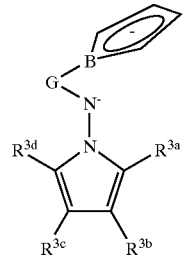

n6

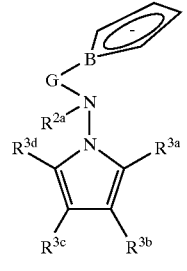

n7

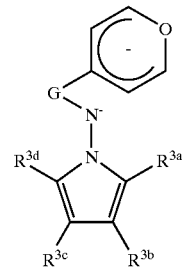

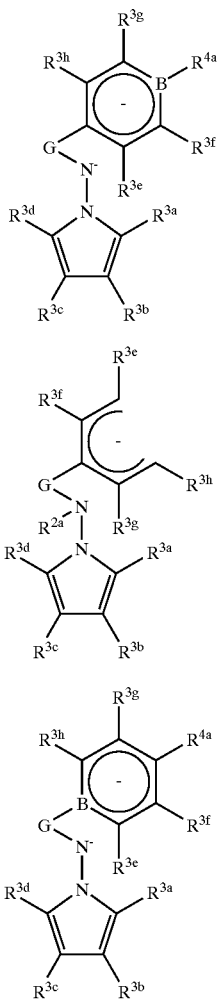

wherein:
- $R^{2a}$ is H, hydrocarbyl, substituted hydrocarbyl, heteroatom connected hydrocarbyl, heteroatom connected substituted hydrocarbyl, silyl, boryl, or ferrocenyl;
- $R^{3a-h}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two of $R^{3a-h}$ may be linked by a bridging group;
- $R^{4a}$ is hydrocarbyl, substituted hydrocarbyl, heteroatom connected hydrocarbyl, or heteroatom connected substituted hydrocarbyl; and
- G is a divalent bridging hydrocarbyl, substituted hydrocarbyl, silyl, heteroatom connected hydrocarbyl, or heteroatom connected substituted hydrocarbyl.

Also preferred catalyst compositions in this twenty-second aspect are those wherein the metal complex is attached to a solid support.

In a twenty-third aspect, this invention also relates to a process for the polymerization of olefins, which comprises contacting one or more olefins with the catalyst composition of the twenty-second aspect. Polymerization reaction temperatures between about 20 and about 160° C. are preferred, with temperatures between about 60 and about 100° C. being more preferred. Ethylene, propylene, 1-butene, 1-hexene and 1-octene are preferred olefin monomers. When ethylene is used, pressures between about 1 and about 100 atm are preferred.

Notwithstanding the above-noted advances in polyolefin catalysis, set forth in the Background of the Invention section, there remains a need for new catalysts which can not only produce novel polyolefin microstructures or incorporate functional co-monomers, but also possess sufficient thermal stability to be used in existing production reactors, and exhibit an appropriate response to hydrogen under such conditions, so as to allow for control of molecular weight without an unacceptable loss of catalyst productivity. This is particularly true in the case of nickel catalysts comprising bidentate N,N-donor ligands, which typically exhibit very short lifetimes ($t_{1/2}$ ca. 2–4 min) at 60° C., and are generally so severely inhibited by hydrogen that when enough hydrogen is added to bring the molecular weight down to that of a typical commercial linear low density polyethylene (LLDPE), the catalyst productivities at elevated temperature are so low as to be impractical. A common structural feature of these catalysts is that they contain a nitrogen donor substituted by an aromatic or heteroaromatic ring, wherein the substituents ortho to the point of attachment to the ligated nitrogen are alkyl groups, as exemplified by complex XXI.

We have discovered that both the thermal stability and the catalyst productivity in the presence of hydrogen are dramatically improved if the ortho substituents are aryl groups, as exemplified by complex XXII. Productivity improvements of about an order of magnitude, or more, are observed when the ortho-alkyl groups are replaced by ortho-aryl groups.

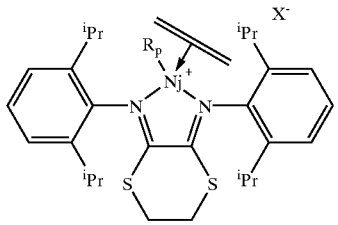

XXI

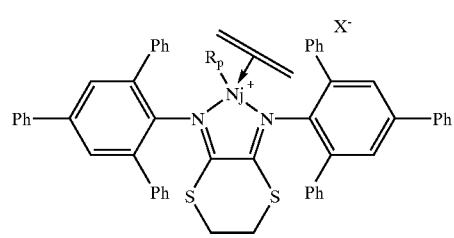

XXII

Whereas the half-life for catalyst deactivation for complex XXI is about 2–4 minutes at 60° C., 200 psig ethylene, the half-life for catalyst deactivation for complex XXII is at least about 32 minutes at 200 psig ethylene, and even at 1 atm ethylene, detectable activity is still observed after 16 hours at 60° C.

Without wishing to be bound by theory, the inventors attribute the improved stability to the reversible formation of agostic aryl intermediates in the catalytic chemistry (c.f. structure XXIII, wherein $R_p$ represents the growing polymer chain, $X^-$ is a weakly coordinating anion, and no specific bonding mode is implied for the interaction of the agostic phenyl group with the nickel center).

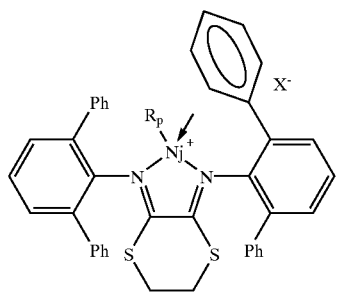

XXIII

As such, the catalysis no longer involves a strictly bidentate ligand, but rather a variable denticity ligand, whereby the ability of the ligand to donate additional electron density (and possibly also accept π-electron density from the nickel) is believed to stabilize low coordinate intermediates (e.g. three-coordinate cationic nickel hydride species), which otherwise would rapidly decompose to catalytically inactive species. When ortho-alkyl groups are present, it is believed that rapid cyclometallation occurs to give species which are either permanently deactivated, or which are so slowly reactivated as to render them much less attractive for commercial polyolefin production. Deactivation reactions of this general type have been discussed by Brookhart et al. (*J. Am. Chem. Soc.*, 117, 6414, 1995).

Ligands wherein some, but not all, of the ortho positions are substituted by bromo groups also give rise to catalysts which exhibit enhanced thermal stability and stability towards hydrogen. In contrast, when even one of four ortho substituents in a catalyst of this invention is alkyl, and the rest are aryl, poor thermal stabilities are observed (u2, $R^{7a-c}$=Ph; $R^{7d}$=Me or cyclopropyl; $R2^{x,y}$=Me). Similarly, when all four of the ortho positions are bromo (u4, $R^{7a-d}$=Br; $R^{2x,y}$ collectively $OCH_2CH_2O$), poor thermal stability is also observed. Without wishing to be bound by theory, the inventors believe that catalysts wherein the ortho positions are substituted by groups other than alkyl will exhibit enhanced thermal stability and stability towards hydrogen, provided that at least one of the ortho positions of one of said aromatic or heteroaromatic rings is an aryl or heteroaryl group.

Therefore, although the pro-catalyst may comprise, for example, a bidentate N,N—N,O— or N,P-donor ligand, it is a novel feature of these ortho-aryl substituted ligands that they can reversibly form an additional bonding interaction, thereby helping to stabilize catalytic intermediates under polymerization conditions.

Thus, in a twenty-fourth aspect, this invention relates to a process for the polymerization or oligomerization of olefins, comprising contacting one or more olefins with a catalyst composition comprising a Group 8–10 transition metal complex, wherein said catalyst composition exhibits improved thermal stability, and wherein said metal complex comprises a bidentate or variable denticity ligand comprising one or two nitrogen donor atom or atoms independently substituted by an aromatic or heteroaromatic ring, wherein the ortho positions of said ring(s) are substituted by groups other than H or alkyl; provided that at least one of the ortho positions of at least one of said aromatic or heteroaromatic rings is substituted by an aryl or heteroaryl group.

As used herein, examples of groups other than H or alkyl include aryl, heteroaryl, bromo, fluoroalkyl and cyano.

In a twenty-fifth aspect, this invention also relates to a process for the polymerization or oligomerization of olefins, comprising contacting one or more olefins with a catalyst composition comprising a Group 8–10 transition metal complex, wherein said catalyst composition exhibits improved stability in the presence of an amount of hydrogen effective to achieve chain transfer, and wherein said metal complex comprises a bidentate or variable denticity ligand comprising one or two nitrogen donor atom or atoms independently substituted by an aromatic or heteroaromatic ring, wherein the ortho positions of said ring(s) are substituted by groups other than H or alkyl; provided that at least one of the ortho positions of at least one of said aromatic or heteroaromatic rings is substituted by an aryl or heteroaryl group.

In a twenty-sixth aspect, this invention also relates to a process for the polymerization or oligomerization of olefins, comprising contacting one or more olefins with a catalyst composition comprising a Group 8–10 transition metal complex, wherein said catalyst composition exhibits either improved thermal stability, or exhibits improved stability in the presence of an amount of hydrogen effective to achieve chain transfer, or both, wherein said metal complex comprises a bidentate or variable denticity ligand comprising one or two nitrogen donor atom or atoms independently substituted by an aromatic or heteroaromatic ring, wherein at least one of the ortho positions of at least one of said aromatic or heteroaromatic rings is substituted by an aryl or heteroaryl group which is capable of reversibly forming an agostic bond to said Group 8–10 transition metal under olefin polymerization reaction conditions.

In a twenty-seventh aspect, this invention also relates to a process for the polymerization or oligomerization of olefins, comprising contacting one or more olefins with a catalyst composition comprising a Group 8–10 transition metal complex, wherein said catalyst composition exhibits either improved thermal stability, or exhibits improved stability in the presence of an amount of hydrogen effective to achieve chain transfer, or both, wherein said composition comprises a bidentate or variable denticity ligand comprising one or two nitrogen donor atom or atoms independently substituted by an aromatic or heteroaromatic ring, wherein the ortho positions of said ring(s) are substituted by groups other than H or alkyl; provided that at least one of the ortho positions of at least one of said aromatic or heteroaromatic rings is substituted by an aryl or heteroaryl group.

In a twenty-eighth aspect, the ortho positions of the aromatic or heteroaromatic ring(s) of the twenty-fourth, twenty-fifth, twenty-sixth, or twenty-seventh aspect are substituted by aryl or heteroaryl groups.

In a first preferred embodiment of the twenty-fourth, twenty-fifth, twenty-sixth, twenty-seventh or twenty-eighth aspect, the half-life for thermal decomposition is greater than 10 min in solution at 60° C., 200 psig ethylene, and the average apparent catalyst activity of said catalyst is greater than 100,000 mol $C_2H_4$/mol catalyst/h. In a second, more preferred embodiment of these aspects, the half-life for thermal decomposition is greater than 20 minutes, and the average apparent catalyst activity of said catalyst is greater than 1,000,000 mol $C_2H_4$/mol catalyst/h. In a third, also more preferred embodiment of these aspects, the half-life for thermal decomposition of said catalyst is greater than 30 min. In a fourth, especially preferred embodiment of the first, second, and third embodiments of these aspects, the Group 8–10 metal is Ni. In a fifth preferred embodiment of these aspects, the process temperature is between about 60 and about 150° C., more preferably between about 100 and about 150° C. In a sixth, more preferred embodiment of these aspects, the bidentate or variable denticity ligand is selected from Set 12:

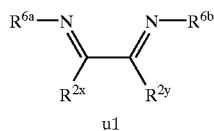

Set 12 wherein:
R$^{6a}$ and R$^{6b}$ are each independently an aromatic or heteroaromatic ring wherein the ortho positions of said ring(s) are substituted by groups other than H or alkyl; provided that at least one of the ortho positions of at least one of said aromatic or heteroaromatic rings is substituted by an aryl or heteroaryl group;
and R$^{2x}$ and R$^{2y}$ are each independently H, hydrocarbyl, substituted hydrocarbyl, heteroatom connected hydrocarbyl, or heteroatom connected substituted hydrocarbyl, and may be linked by a bridging group.

In a seventh, especially preferred embodiment of the twenty-fourth, twenty-fifth, twenty-sixth, twenty-seventh or twenty-eighth aspect, the Group 8–10 transition metal is nickel and the bidentate or variable denticity ligand is selected from Set 13:

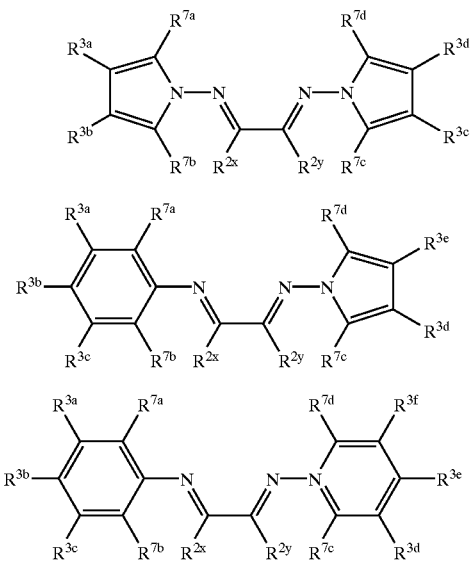

Set 13 wherein:
R$^{7a\text{-}d}$ are groups other than H or alkyl; provided that at least one of R$^{7a\text{-}d}$ is an aryl or heteroaryl group;
R$_{2x}$ and R$^{2y}$ are each independently H, hydrocarbyl, substituted hydrocarbyl, heteroatom connected hydrocarbyl, or heteroatom connected substituted hydrocarbyl, and may be linked by a bridging group; and
R$^{3a\text{-}f}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two of R$^{3a\text{-}f}$ may be linked by a bridging group.

In an eighth, also especially preferred embodiment of the twenty-fourth, twenty-fifth, twenty-sixth, twenty-seventh or twenty-eighth aspect, the composition is attached to a solid support, with silica being an especially preferred solid support and reaction temperatures between about 60 and about 100° C. also being especially preferred in this embodiment.

In the case of gas phase olefin polymerization reactions, it can sometimes be advantageous if the catalyst can be introduced into the olefin polymerization reactor in an inactive form, and subsequently activated. When the catalyst is introduced in a fully activated form, there are sometimes problems with overheating of the supported catalyst particle, which initially has a very high rate of heat generation per unit volume. Overheating can result in catalyst deactivation, or excessive agglomeration of the polymer particles, or both. In addition, unfavorable static charge behavior may be observed, causing the freshly introduced particles to migrate to the reactor walls and give rise to deleterious sheeting phenomena. It is therefore another object of the current invention to describe methods of activating the catalyst in the gas phase olefin polymerization reactor itself.

Thus, in a twenty-ninth aspect, this invention also relates to a process for olefin polymerization comprising: contacting one or more olefin monomers with a single site catalyst attached to a solid support, wherein said catalyst comprises a cationic Group 4–11 transition metal complex and a weakly coordinating counteranion, and wherein said catalyst is introduced into a gas phase olefin polymerization reactor in an inactive form which is subsequently activated by reaction with a second compound Y$^1$ to form said catalyst in said reactor.

Preferred Group 4–11 transition metals in this twenty-ninth aspect include Ti, Zr, Hf, Ni, Co, and Fe. Preferred second compounds Y$^1$ in this aspect include trialkylaluminum or dialkylzinc compounds, with trimethylaluminum being especially preferred. In a more preferred embodiment, said inactive form of said catalyst is selected from Set 14, said weakly coordinating counteranion is either formed by reaction of said inactive form of said catalyst with Y$^1$, or is selected from the group consisting of B(C$_6$F$_5$)$_4$$^-$, B(3,5-bis (trifluoromethyl)phenyl)$_4$$^-$[(C$_6$F$_5$)$_3$B-(imidazole)-B(C$_6$F$_5$)$_3$]$^-$, BF$_4$$^-$, and [(C$_6$F$_5$)$_3$B-CN-B(C$_6$F$_5$)$_3$]$^-$, and Y$^1$ is trimethylaluminum;

Set 14

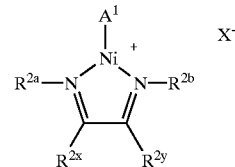

bb1

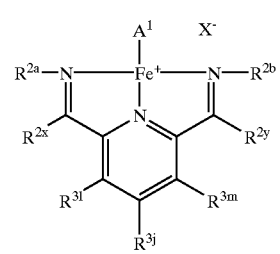

bb2

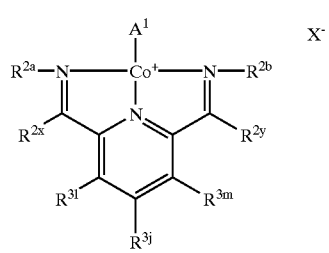

bb3

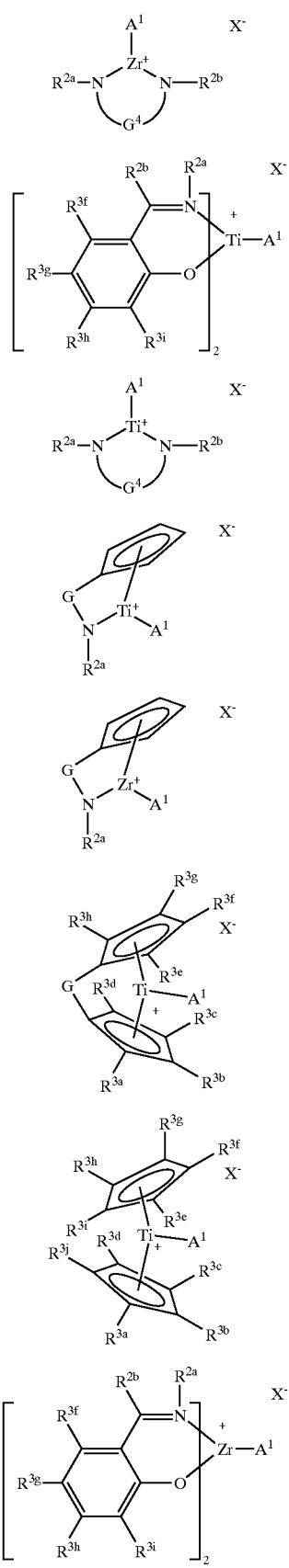
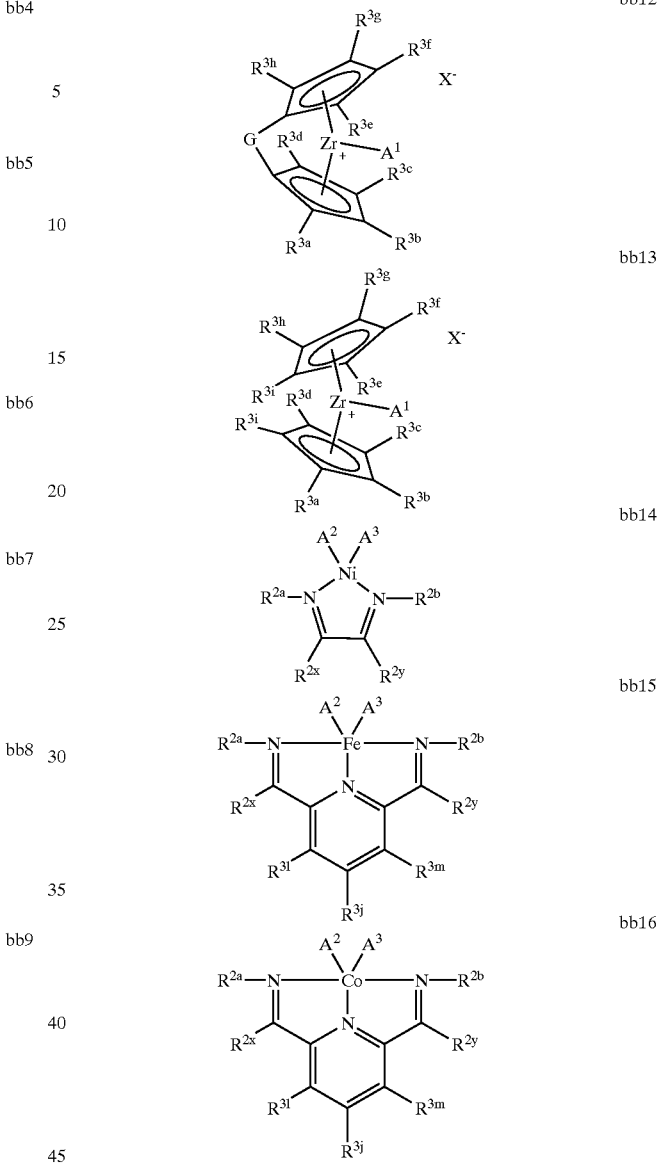

wherein:

$R^{2a,b,x,y}$ are each independently H, hydrocarbyl, substituted hydrocarbyl, heteroatom connected hydrocarbyl, heteroatom connected substituted hydrocarbyl, silyl, boryl, or ferrocenyl; in addition, any two of $R^{2a,b,x,y}$ may be linked by a bridging group;

$R^{3a-m}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two of $R^{3a-m}$ may be linked by a bridging group;

$A^1$ is halide or a monoanionic group which is capable of reacting with $Y^1$ to generate an active olefin polymerization catalyst, provided that in the absence of $Y^1$, $A^1$ is such that said inactive form of said single site catalyst is at least 10 times less active as a catalyst for olefin polymerization than said active olefin polymerization catalyst;

$A^2$ and $A^3$ are each independently hydrocarbyl, halide, O(hydrocarbyl) or O(substituted hydrocarbyl), provided that at least one of $A^2$ and $A^3$ is capable of being abstracted by $Y^1$ to form a weakly coordinating counteranion, and the other is either capable of inserting an olefin to initiate polymer chain growth, or is capable of being exchanged with a group on $Y^1$ which can then initiate chain growth;

G and $G^4$ are divalent bridging hydrocarbyl, substituted hydrocarbyl, silyl, heteroatom connected hydrocarbyl, or heteroatom connected substituted hydrocarbyl; and $X^-$ is a weakly coordinating anion.

In a thirtieth aspect, this invention also relates to a process wherein the catalyst of the twenty-fourth, twenty-fifth, twenty-sixth, twenty-seventh or twenty-eighth aspect is introduced into a gas phase olefin polymerization reactor in an inactive form attached to a solid support, and wherein said catalyst is subsequently activated by a second compound $Y^1$ in said reactor. In a first preferred embodiment of this thirtieth aspect, the bidentate or variable denticity ligand is selected from Set 15:

Set 15

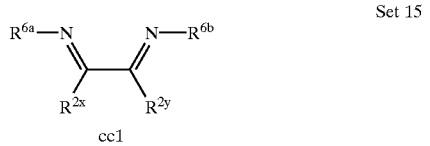

cc1 wherein:

$R^{6a}$ and $R^{6b}$ are each independently an aromatic or heteroaromatic ring wherein the ortho positions of said ring(s) are substituted by groups other than H or alkyl; provided that at least one of the ortho positions of at least one of said aromatic or heteroaromatic rings is substituted by an aryl or heteroaryl group;

and $R^{2x}$ and $R^{2y}$ are each independently H, hydrocarbyl, substituted hydrocarbyl, heteroatom connected hydrocarbyl, or heteroatom connected substituted hydrocarbyl, and may be linked by a bridging group.

In a second, more preferred embodiment of the thirtieth aspect, (i) the Group 8–10 transition metal is nickel, (ii) the weakly coordinating counteranion is either formed by reaction of said inactive form of said catalyst with a volatile second compound $Y^1$, or is selected from the group consisting of $B(C_6F_5)_4^-$, $B(3,5\text{-bis(trifluoromethyl)phenyl})_4^-$, $[(C_6F_5)_3B\text{-(imidazole)-}B(C_6F_5)_3]^-$, $BF_4^-$, and $[(C_6F_5)_3B\text{—CN—}B(C_6F_5)_3]^-$, (iii) $Y^1$ is trimethylaluminum, and (iv) the bidentate or variable denticity ligand is selected from Set 16;

Set 16

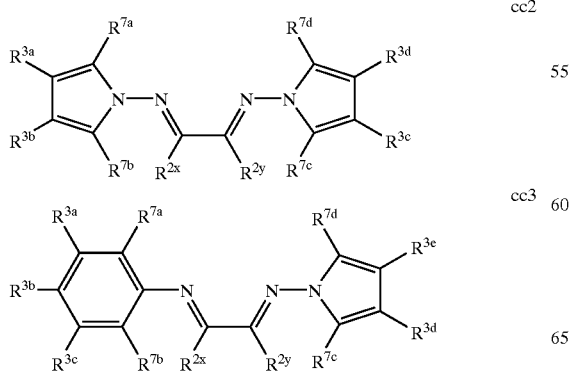

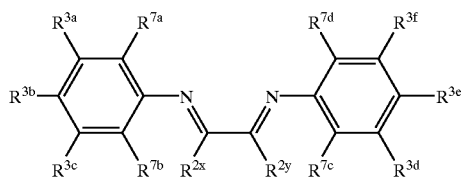

wherein:

$R^{7a-d}$ are groups other than H or alkyl; provided that at least one of $R^{7a-d}$ is an aryl or heteroaryl group;

$R^{2x}$ and $R^{2y}$ are each independently H, hydrocarbyl, substituted hydrocarbyl, heteroatom connected hydrocarbyl, or heteroatom connected substituted hydrocarbyl, and may be linked by a bridging group; and $R^{3a-f}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two of $R^{3a-f}$ may be linked by a bridging group.

In a thirty-first aspect, this invention also relates to a process wherein said aromatic or heteroaromatic rings of the catalyst of the twenty-fourth, twenty-fifth, twenty-sixth, twenty-seventh or twenty-eighth aspect is selected from Set 17;

Set 17

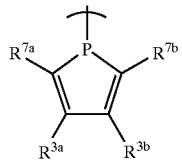

dd1

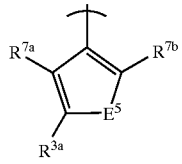

dd2

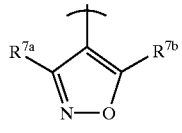

dd3

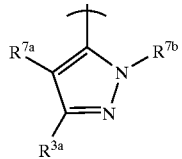

dd4

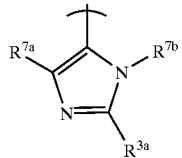

dd5

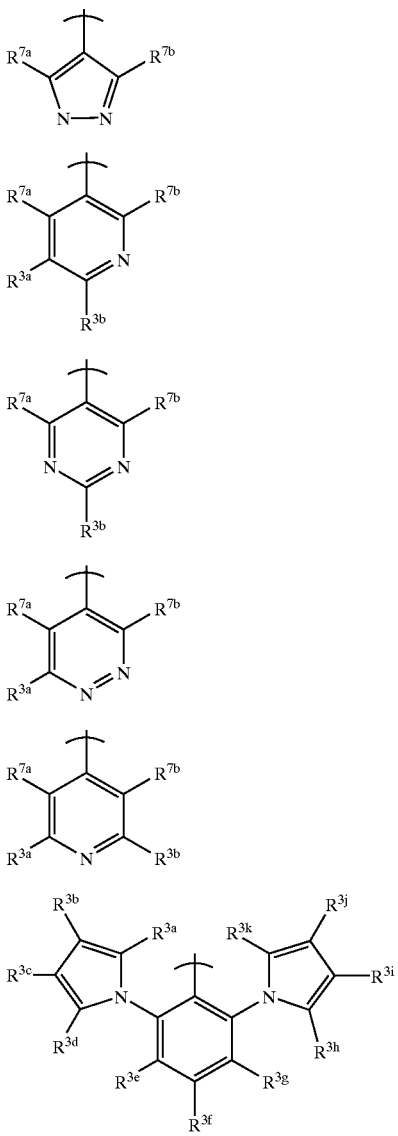

wherein:
R$^{7a,b}$ are groups other than H or alkyl; provided that at least one of R$^{7a,b}$ is an aryl or heteroaryl group;
R$^{3a-k}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two of R$^{3a-k}$ may be linked by a bridging group; and
E$^5$ is O, S, Se, or NR$^{3b}$.

In this disclosure, symbols ordinarily used to denote elements in the Periodic Table and commonly abbreviated groups, take their ordinary meaning, unless otherwise specified. Thus, N, O, S, P, and Si stand for nitrogen, oxygen, sulfur, phosphorus, and silicon, respectively, while Me, Et, Pr, $^i$Pr, Bu, $^t$Bu and Ph stand for methyl, ethyl, propyl, iso-propyl, butyl, tert-butyl and phenyl, respectively.

A "1-pyrrolyl or substituted 1-pyrrolyl" group refers to a group of formula II below:

wherein R$^{3a-d}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two or more of R$^{3a-d}$ may be linked by a bridging group or groupsto form bicyclic or polycyclic ring systems including carbazol-9-yl and indol-1-yl.

A "hydrocarbyl" group means a monovalent or divalent, linear, branched or cyclic group which contains only carbon and hydrogen atoms. Examples of monovalent hydrocarbyls include the following: C$_1$–C$_{20}$ alkyl; C$_1$–C$_{20}$ alkyl substituted with one or more groups selected from C$_1$–C$_{20}$ alkyl, C$_3$–C$_8$ cycloalkyl, and aryl; C$_3$–C$_8$ cycloalkyl; C$_3$–C$_8$ cycloalkyl substituted with one or more groups selected from C$_1$–C$_{20}$ alkyl, C$_3$–C$_8$ cycloalkyl, and aryl; C$_6$–C$_{14}$ aryl; and C$_6$–C$_{14}$ aryl substituted with one or more groups selected from C$_1$–C$_{20}$ alkyl, C$_3$–C$_8$ cycloalkyl, and aryl. Examples of divalent (bridging) hydrocarbyls include: —CH$_2$—, —CH$_2$CH$_2$—, —CH$_2$CH$_2$CH$_2$—, and 1,2-phenylene.

The term "aryl" refers to an aromatic carbocyclic monoradical, which may be substituted or unsubstituted, wherein the substituents are halo, hydrocarbyl, substituted hydrocarbyl, heteroatom attached hydrocarbyl, heteroatom attached substituted hydrocarbyl, nitro, cyano, fluoroalkyl, sulfonyl, and the like. Examples include: phenyl, naphthyl, anthracenyl, phenanthracenyl, 2,6-diphenylphenyl, 3,5-dimethylphenyl, 4-nitrophenyl, 3-nitrophenyl, 4-methoxyphenyl, 4-dimethylaminophenyl, and the like.

A "heterocyclic ring" refers to a carbocyclic ring wherein one or more of the carbon atoms has been replaced by an atom selected from the group consisting of O, N, S, P, Se, As, Si, B, and the like.

A "heteroaromatic ring" refers to an aromatic heterocycle; examples include pyrrole, furan, thiophene, indene, imidazole, oxazole, isoxazole, carbazole, thiazole, pyrimidine, pyridine, pyridazine, pyrazine, benzothiophene, and the like.

A "heteroaryl" refers to a heterocyclic monoradical which is aromatic; examples include 1-pyrrolyl, 2-pyrrolyl, 3-pyrrolyl, furyl, thienyl, indenyl, imidazolyl, oxazolyl, isoxazolyl, carbazolyl, thiazolyl, pyrimidinyl, pyridyl, pyridazinyl, pyrazinyl, benzothienyl, and the like, and substituted derivatives thereof.

A "silyl" group refers to a SiR$_3$ group wherein Si is silicon and R is hydrocarbyl or substituted hydrocarbyl or silyl, as in Si(SiR$_3$)$_3$.

A "boryl" group refers to a BR$_2$ or B(OR)$_2$ group, wherein R is hydrocarbyl or substituted hydrocarbyl.

A "heteroatom" refers to an atom other than carbon or hydrogen. Preferred heteroatoms include oxygen, nitrogen, phosphorus, sulfur, selenium, arsenic, chlorine, bromine, silicon, and fluorine.

A "substituted hydrocarbyl" refers to a monovalent, divalent, or trivalent hydrocarbyl substituted with one or more heteroatoms. Examples of monovalent substituted hydrocarbyls include: 2,6-dimethyl-4-methoxyphenyl, 2,6-diisopropyl-4-methoxyphenyl, 4-cyano-2,6- dimethylphenyl, 2,6-dimethyl-4-nitrophenyl, 2,6-difluorophenyl, 2,6-dibromophenyl, 2,6-dichlorophenyl, 4-methoxycarbonyl-2,6-dimethylphenyl, 2-tert-butyl-6-chlorophenyl, 2,6-dimethyl-4-phenylsulfonylphenyl, 2,6-dimethyl-4-trifluoromethylphenyl, 2,6-dimethyl-4-trimethylammoniumphenyl (associated with a weakly coordinated anion), 2,6-dimethyl-4-hydroxyphenyl, 9-hydroxyanthr-10-yl, 2-chloronapth-1-yl, 4-methoxyphenyl, 4-nitrophenyl, 9-nitroanthr-10-yl, -CH$_2$OCH$_3$, cyano, trifluoromethyl, and fluoroalkyl. Examples of divalent (bridging) substituted hydrocarbyls include: 4-methoxy-1,2-phenylene, 1-methoxymethyl-1,2-ethanediyl, 1,2-bis(benzyloxymethyl)-1,2-ethanediyl, and 1-(4-methoxyphenyl)-1,2-ethanediyl.

A "heteroatom connected hydrocarbyl" refers to a group of the type $E^{10}$(hydrocarbyl), $E^{20}$H(hydrocarbyl), or $E^{20}$(hydrocarbyl)$_2$, where $E^{10}$ is an atom selected from Group 16 and $E^{20}$ is an atom selected from Group 15.

A "heteroatom connected substituted hydrocarbyl" refers to a group of the type $E^{10}$(substituted hydrocarbyl), $E^{20}$H (substituted hydrocarbyl), or $E^{20}$(substituted hydrocarbyl)$_2$, where $E^{10}$ is an atom selected from Group 16 and $E^{20}$ is an atom selected from Group 15.

The term "fluoroalkyl" as used herein refers to a $C_1$–$C_{20}$ alkyl group substituted by one or more fluorine atoms.

An "olefin" refers to a compound of the formula $R^{1a}CH=CHR^{1b}$, where $R^{1a}$ and $R^{1b}$ may independently be H, hydrocarbyl, substituted hydrocarbyl, fluoroalkyl, silyl, O(hydrocarbyl), or O(substituted hydrocarbyl), and where $R^{1a}$ and $R^{1b}$ may be connected to form a cyclic olefin, provided that in all cases, the substituents $R^{1a}$ and $R^{1b}$ are compatible with the catalyst. In the case of most Group 4–7 catalysts, this will generally mean that the olefin should not contain good Lewis base donors, since this will tend to severely inhibit catalysis. Preferred olefins for such catalysts include ethylene, propylene, butene, hexene, octene, cyclopentene, norbornene, and styrene.

In the case of the Group 8–10 catalysts, Lewis basic substituents on the olefin will tend to reduce the rate of catalysis in most cases; however, useful rates of homopolymerization or copolymerization can nonetheless be achieved with some of those olefins. Preferred olefins for such catalysts include ethylene, propylene, butene, hexene, octene, and fluoroalkyl substituted olefins, but may also include, in the case of palladium and some of the more functional group tolerant nickel catalysts, norbornene, substituted norbornenes (e.g., norbornenes substituted at the 5-position with halide, siloxy, silane, halo carbon, ester, acetyl, alcohol, or amino groups), cyclopentene, ethyl undecenoate, acrylates, vinyl ethylene carbonate, 4-vinyl-2, 2-dimethyl- 1,3-dioxolane, and vinyl acetate.

In some cases, the Group 8–10 catalysts can be inhibited by olefins which contain additional olefinic or acetylenic functionality. This is especially likely if the catalyst is prone to "chain-running" wherein the catalyst can migrate up and down the polymer chain between insertions, since this can lead to the formation of relatively unreactive π-allylic intermediates when the olefin monomer contains additional unsaturation. Such effects are best determined on a case-by-case basis, but may be predicted to some extent through knowledge of how much branching is observed with a given catalyst in ethylene homopolymerizations; those catalysts which tend to give relatively high levels of branching with ethylene will tend to exhibit lower rates when short chain diene co-monomers are used under the same conditions. Longer chain dienes tend to be less inhibitory than shorter chain dienes, when other factors are kept constant, since the catalyst has farther to migrate to form the π-allyl, and another insertion may intervene first.

Similar considerations apply to unsaturated esters which are capable of inserting and chain-running to form relatively stable intramolecular chelate structures wherein the Lewis basic ester functionality occupies a coordination site on the catalyst. In such cases, short chain unsaturated esters, such as methyl acrylate, tend to be more inhibitory than long chain esters, such as ethyl undecenoate, if all other factors are kept constant.

The term "α-olefin" as used herein is a 1-alkene with from 3 to 40 carbon atoms.

A "π-allyl" group refers to a monoanionic group with three sp$^2$ carbon atoms bound to a metal center in a η$^3$-fashion. Any of the three sp$^2$ carbon atoms may be substituted with a hydrocarbyl, substituted hydrocarbyl, heteroatom connected hydrocarbyl, heteroatom connected substituted hydrocarbyl, or O-silyl group.

Examples of π-allyl groups include:

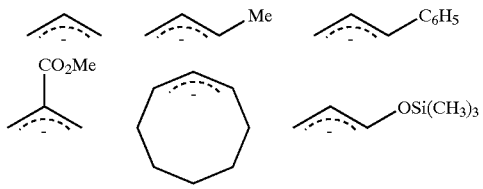

The term π-benzyl group denotes an π-allyl group where two of the sp$^2$ carbon atoms are part of an aromatic ring. Examples of π-benzyl groups include:

A "bridging group" refers to an atom or group which links two or more groups, which has an appropriate valency to satisfy its requirements as a bridging group, and which is compatible with the desired catalysis. Suitable examples include divalent or trivalent hydrocarbyl, substituted hydrocarbyl, heteroatom connected hydrocarbyl, heteroatom connected substituted hydrocarbyl, substituted silicon (IV), boron(III), N(III), P(III), and P(V), —C(O)—, —SO$_2$—, —C(S)—, —B(OMe)—, —C(O)C(O)—, O, S, and Se. In some cases, the groups which are said to be "linked by a bridging group" are directly bonded to one another, in which case the term "bridging group" is meant to refer to that bond. By "compatible with the desired catalysis," we mean the bridging group either does not interfere with the desired catalysis, or acts to usefully modify the catalyst activity or selectivity.

The term "weakly coordinating anion" is well known in the art per se and generally refers to a large bulky anion capable of delocalization of the negative charge of the anion. The importance of such delocalization depends to some extent on the nature of the transition metal comprising the cationic active species, with the Group 4–6 transition metals requiring less coordinating anions, such as B(C$_6$F$_5$)$_4^-$, than many Group 8–10 transition metal based catalysts, which can in some cases give active catalysts with BF$_4^-$ counteranions. Weakly coordinating anions, not all of which would be considered bulky, include, but are not limited to: B(C$_6$F$_5$)$_4^-$, PF$_6^-$, BF$_4^-$, SbF$_6^-$, (Ph)$_4$B$^-$ wherein Ph=phenyl, and Ar$_4$B$^-$ wherein Ar$_4$B$^-$=tetrakis[3,5-bis(trifluoromethyl)

phenyl]-borate. The weakly coordinating nature of such anions is known and described in the literature (S. Strauss et al., *Chem. Rev.*, 1993, 93, 927).

The term "agostic" is known to those skilled in the art, and is generally used to refer to a weak bonding interaction between a C—H bond and a coordinatively unsaturated transition metal. It is used herein to denote a weak bonding interaction between any or all of the atoms of the ortho-aryl or ortho-heteroaryl groups of the ligands described in the twenty-fourth and higher aspects of the present invention, and a coordinatively unsaturated Group 8–10 transition metal center to which said ligands are complexed. By "weak bonding interaction" we mean a bond that is sufficiently weak that it is formed reversibly under olefin polymerization reaction conditions, so that it does not, for example, preclude the binding and insertion of olefin monomer.

The term "ortho" is used herein in the context of the ligands of the twenty-fourth and higher aspects to denote the positions which are adjacent to the point of attachment of said aromatic or heteroaromatic ring to the ligated nitrogen (s). In the case of a 1-attached, 6-membered ring, we mean the 2- and 6-positions. In the case of a 1-attached, 5-membered ring, we mean the 2- and 5-positions. In the case of 1-attached, fused ring aromatic or heteroaromatic rings, we mean the first positions which can be substituted; for example, in the case of 1-naphthyl, these would be the 2- and 8-positions; in the case of 9-anthracenyl, these would be the 1- and 8-positions.

The term "variable denticity" is used herein in the context of otherwise bidentate ligands to refer to the reversible formation of a third binding interaction between the ligand and the Group 8–10 transition metal center to which it is complexed.

The abbreviation "acac" refers to acetylacetonate. In general, substituted acetylacetonates, wherein one or more hydrogens in the parent structure have been replaced by a hydrocarbyl, substituted hydrocarbyl, or fluoroalkyl, may be used in place of the "acac". Hydrocarbyl substituted acetylacetonates may be preferred in some cases when it is important, for example, to improve the solubility of a (ligand)Ni(acac)BF$_4$ salt in mineral spirits.

The term "half-life for thermal decomposition" refers to the time required for the catalyst to lose half of its activity, as determined under substantially non-mass transport limited conditions.

The phrase "substantially non-mass transport limited conditions" refers to the fact that when an ethylene polymerization reaction is conducted in solution using gaseous ethylene as the monomer or co-monomer, the rate of dissolution of ethylene in the liquid phase can often be the turnover-limiting step of the catalytic cycle, so that the apparent catalyst activity is less than would be observed under improved mass transport conditions. Mass transport limitations may typically be reduced by either increasing the partial pressure of ethylene, improving the agitation and mixing of the gaseous phase with the liquid phase, or decreasing the catalyst loading, to the point where the polymerization reaction rate exhibits a first order dependence on the amount of catalyst charged to the reactor, and the reaction can then be considered to be substantially non-mass transport limited.

The phrase "apparent catalyst activity" refers to the moles of monomer consumed per mole of catalyst per unit time, without consideration of the impact of mass transport limitations.

The phrase "wherein said catalyst composition exhibits improved thermal stability" refers to a catalyst composition which has a half-life for thermal decomposition which is at least 2 times, preferably 5 times, and most preferably 10 times longer than that observed under substantially non-mass transport limited conditions for an otherwise structurally identical catalyst composition lacking the novel ortho-aryl substitution pattern of the catalysts of the current invention, described in the twenty-fourth, twenty-fifth, twenty-sixth, twenty-seventh and twenty-eighth aspects of the current invention.

The phrase "an amount of hydrogen effective to achieve chain transfer" refers to the ability of hydrogen to react with an olefin polymerization catalyst to cleave off a growing polymer chain and initiate a new chain. In most cases, this is believed to involve hydrogenolysis of the metal-carbon bond of the growing polymer chain, to form a metal hydride catalytic intermediate, which can then react with the olefin monomer to initiate a new chain. In the context of the current invention, an effective amount is considered to be that amount of hydrogen which reduces both the number average molecular weight and the weight average molecular weight of the polymer by at least 10%, relative to an otherwise similar reaction conducted in the absence of hydrogen. In this context, "otherwise similar" denotes that the catalyst, catalyst loading, solvent, solvent volume, agitation, ethylene pressure, co-monomer concentration, reaction time, and other process relevant parameters are sufficiently similar that a valid comparison can be made.

In general, previously reported catalysts lacking the novel ortho-aryl substitution pattern of the current invention are far less productive in the presence of an amount of hydrogen effective to achieve chain transfer than they are under otherwise similar conditions without hydrogen. In order to quantify this effect, the following terms are defined.

The productivity P is defined as the grams of polymer produced per mole of catalyst; over a given period of time. The productivity $P_{hydrogen}$ is define as the grams of polymer produced per mole of catalyst in the presence of an amount of hydrogen effective to achieve chain transfer, in an otherwise similar reaction conducted for the same period of time. Catalysts lacking the novel ortho-aryl substitution pattern of the catalyst compositions of the current invention typically exhibit ratios $P_{hydrogen}/P$ less than or equal to 0.05 under substantially non-mass transport limited conditions.

The phrase "improved stability in the presence of an amount of hydrogen effective to achieve chain transfer" means that the ratio $P_{hydrogen}/P$ is at least 0.1 under substantially non-mass transport limited conditions. Preferred catalysts of the present invention exhibit a ratio $P^{hydrogen}/P$ greater than or equal to 0.2 under substantially non-mass transport limited conditions. Especially preferred catalysts of the present invention exhibit a ratio $P_{hydrogen}/P$ greater than or equal to 0.5 under substantially non-mass transport limited conditions.

The phrase "one or more olefins" refers to the use of one or more chemically different olefin monomer feedstocks, for example, ethylene and propylene.

The term "single site catalyst" is used as commonly defined, and preferably refers to an olefin polymerization catalyst which can be dissolved and activated to form a single active species, capable of reacting with one or more olefin monomers to form a polymer having a narrow molecular weight distribution, typically characterized by a $M_w/M_n < 4$. Many examples of such catalysts are illustrated herein; additional specific examples are given in the following references: EP 420,436 (1991); EP 416,815 (1991); *Science*, 1995, 267, 217; EP 874,005 (1998); *J. Am. Chem. Soc.*, 1996, 118, 10008; *J. Am. Chem. Soc.*, 1997, 119, 3830, J. Am. Chem. Soc., 1999, 121, 5797; WO 94/14854, EP 0 532 098 A1; EP 0 641 804 A2, EP 0 816 384 A2; WO 94/11410; WO 94/0147; WO 96/23010, U.S. Pat. No. 5,866, 663, U.S. Pat. Nos. 5,886,224, 5,891,963, 5,880,323, 5,880, 241, J. Am. Chem. Soc., 1995, 117, 6414; WO 97/02298; WO 98/40374, WO 98/37110, WO 98/47933, WO 98/40420; WO 97/17380, WO 97/48777, WO 97/48739, WO 97/48740; WO 99/02472; WO 98/27124; WO 99/12981; WO 98/30610, WO 98/30609, WO 98/42665, WO 98/42664; U.S. Pat. Nos. 4,564,647,; 4,752,597; 5,106, 804; 5,132,380; 5,227,440; 5,296,565; 5,324,800; 5,331, 071; 5,332,706; 5,350,723; 5,399,635; 5,466,766; 5,468, 702; 5,474,962; 5,578,537 and 5,863,853. The entire contents of these patents are incorporated herein by reference.

The term "inactive form" is used to refer to a transition metal complex which serves as a precursor to the active olefin polymerization catalyst, and has either no polymerization activity prior to activation by the second compound $Y^1$, or is at least 10 times less active than the product of activation.

Compound $Y^1$ is a compound which is capable of reacting with said inactive form of said catalyst to generate an active olefin polymerization catalyst composition, and which also has a volatility effective to activate said inactive form of said catalyst under the conditions of a gas phase olefin polymerization reactor. Examples include trimethylaluminum, dimethylzinc, $Me_nEt_{3-n}Al$ (n=0–3), diethylzinc, and $Et_2AlCl$.

The phrase "capable of inserting an olefin" refers to a group Z bonded to the transition metal M, which can insert an olefin monomer of the type $R^{1a}CH=CHR^{1b}$ to form a moiety of the type $M$—$CHR^{1a}$—$CHR^{1b}$—Z, which can subsequently undergo further olefin insertion to form a polymer chain; wherein $R^{1a}$ and $R^{1b}$ may independently be H, hydrocarbyl, substituted hydrocarbyl, fluoroalkyl, silyl, O(hydrocarbyl), or O(substituted hydrocarbyl), and wherein $R^{1a}$ and $R^{1b}$ may be connected to form a cyclic olefin, provided that in all cases, the substituents $R^{1a}$ and $R^{1b}$ are compatible with the desired catalysis; wherein additional groups will be bound to the transition metal M to comprise the actual catalyst, as discussed in more detail below.

The phrase "capable of being exchanged with a group on said volatile second compound $Y^1$" refers to the ability of some activators to transfer a group which will be capable of inserting an olefin to the transition metal, in exchange for a group which is not capable of inserting an olefin.

The term "borataaryl" is used to refer to a monoanionic heterocyclic group of formula XXX:

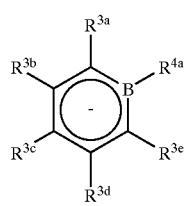

XXX wherein:
$R^{3a-e}$ are each independently H, hydrocarbyl, substituted hydrocarbyl, heteroatom connected hydrocarbyl, hetero atom connected substituted hydrocarbyl, fluoroalkyl, silyl, boryl, fluoro, chloro, bromo, cyano, or nitro; in addition, any two of $R^{3a-e}$ may be linked by a bridging group;
$R^{4a}$ is hydrocarbyl, substituted hydrocarbyl, heteroatom connected hydrocarbyl, or heteroatom connected substituted hydrocarbyl; and wherein any one of $R^{3a-e}$ or $R^{4a}$ may function as a divalent bridging group to connect the borataaryl to the remainder of the ligand.

In general, the catalysts of the present invention can be made sufficiently sterically hindered that chain transfer is slow with respect to chain propagation so that a chain of degree of polymerization (DP) of 10 or more results. For example, in the case of a catalyst system comprising a catalyst of the type $[(ligand)Fe(T^{1a})(L)]^+X^-$, where $T^{1a}$ is a hydrogen atom, hydrocarbyl, or other group capable of inserting an olefin, L is an olefin or neutral donor group capable of being displaced by an olefin, $X^-$ is a weakly coordinating anion, and ligand is a compound of formula h17, the catalyst system reacts with ethylene to form low molecular weight polymer. However, it is to be understood that less hindered forms of these catalysts, for example those derived from h19, generally comprising ligands which do not contain bulky substituents, can also be used as dimerization or oligomerization catalysts.

The degree of steric hindrance at the active catalyst site required to give slow chain transfer, and thus form polymer, depends on a number of factors and is often best determined by experimentation. These factors include: the exact structure of the catalyst, the monomer or monomers being polymerized, whether the catalyst is in solution or attached to a solid support, and the temperature and pressure. Polymer is defined herein as corresponding to a degree of polymerization, DP, of about 10 or more; oligomer is defined as corresponding to a DP of 2 to about 10.

A variety of protocols may be used to generate active polymerization catalysts comprising transition metal complexes of various nitrogen, phosphorous, oxygen and sulfur donor ligands. Examples include (i) the reaction of a Group 4 metallocene dichloride with MAO, (ii) the reaction of a Group 4 metallocene dimethyl complex with N,N-diethylanilinium tetrakis(pentafluorophenyl)borate, (iii) the reaction of a Group 8 or 9 metal dihalide complex of a tridentate N-donor ligand with an alkylaluminum reagent, (iv) the reaction of a Group 8 or 9 metal dialkyl complex of a tridentate N-donor ligand with MAO or $HB(3,5-bis(trifluoromethyl)phenyl)_4$, (v) the reaction of $(Me_2N)_4Zr$ with 2 equivalents of an N-pyrrol-1-ylsalicylimine, followed by treatment of the product of that reaction with $Me_3SiCl$ and then a triisobutylaluminum-modified methylaluminoxane, and (vi) the reaction of a nickel or palladium dihalide complex of a bidentate N-donor ligand with an alkylaluminum reagent. Additional methods described herein include the reaction of (tridentate N-donor ligand)$M(acac)B(C_6F_5)_4$ salts with an alkylaluminum reagent, where M is Fe(II) or Co(II), and the reaction of (bidentate N-donor ligand)Ni(acac)X salts with an alkylaluminum reagent, where X is a weakly coordinating anion, such as $B(C_6F_5)_4^-$, $BF^{4-}$, $PF_6^-$, $SbF_6^-$ and $OS(O)_2CF_3^-$. Cationic $[(ligand)M(\pi-allyl)]^+$ complexes with weakly coordinating counteranions, where M is a Group 10 transition metal, are often also suitable catalyst precursors, requiring only exposure to olefin monomer and in some cases elevated temperatures (40–100 ° C.) or added Lewis acid, or both, to form an active polymerization catalyst.

More generally, a variety of $(ligand)_nM(Z^{1a})(Z^{1b})$ complexes, where "ligand" refers to a compound of the present invention, and comprises at least one nitrogen donor wherein the nitrogen ligated to the metal M is substituted by a 1-pyrrolyl or substituted 1-pyrrolyl group, n is 1 or 2, M is a Group 4–10 transition metal, and $Z^{1a}$ and $Z^{1b}$ are univalent groups, or may be taken together to form a divalent group, may be reacted with one or more compounds, collectively referred to as compound $Y^2$, which function as co-catalysts or activators, to generate an active catalyst of the form $[(ligand)_nM(T^{1a})(L)]^+X^-$, where n is 1 or 2, $T^{1a}$ is a hydrogen atom or hydrocarbyl, L is an olefin or neutral donor group capable of being displaced by an olefin, M is a Group 4–10 transition metal, and $X^-$ is a weakly coordinating anion. When $Z^{1a}$ and $Z^{1b}$ are both halide, examples of suitable compound $Y^2$ include: methylaluminoxane (hereinafter MAO) and other aluminum sesquioxides, $R_3Al$, $R_2AlCl$, and $RAlCl_2$ (wherein R is alkyl, and plural groups R may be the same or different). When $Z^{1a}$ and $Z^{1b}$ are both alkyl, examples of suitable compound $Y^2$ include: MAO and other aluminum sesquioxides, $R_3Al$, $R_2AlCl$, $RAlCl_2$ (wherein R is alkyl, and plural groups R may be the same or different), $B(C_6F_5)_3$, $R^0{}_3Sn[BF_4]$ (wherein $R^0$ is hydrocarbyl or substituted hydrocarbyl and plural groups $R^0$ may be the same or different), $H^+X^-$, wherein $X^-$ is a weakly coordinating anion, for example, tetrakis[3,5-bis(trifluoromethyl)phenyl]borate, and Lewis acidic or Bronsted acidic metal oxides, for example, montmorillonite clay. In some cases, for example, when $Z^{1a}$ and $Z^{1b}$ are both halide or carboxylate, sequential treatment with a metal hydrocarbyl, followed by reaction with a Lewis acid, may be required to generate an active catalyst. Suitable examples of metal hydrocarbyls include: MAO, other aluminum sesquioxides, $R_3Al$, $R_2AlCl$, $RAlCl_2$ (wherein R is alkyl, and plural groups R may be the same or different), Grignard reagents, organolithium reagents, and diorganozinc reagents. Examples of suitable Lewis acids include: MAO, other aluminum sesquioxides, $R_3Al$, $R_2AlCl$, $RAlCl_2$ (wherein R is alkyl, and plural groups R may be the same or different), $B(C_6F_5)_3$, $R^0{}_3Sn[BF_4]$ (wherein $R^0$ is hydrocarbyl or substituted hydrocarbyl and plural groups $R^0$ may be the same or different), and Lewis acidic metal oxides.

The term "alkylaluminum" is used to refer to compounds containing at least one alkyl group bonded to Al (III), which are capable of reacting with a metal complex of the present invention to generate an active olefin polymerization catalyst. In general, this will involve exchanging one or more alkyl groups from the aluminum with a monoanionic atom or group on the metal complex pro-catalyst. In some cases, a hydride may be directly transferred from the β-carbon of the aluminum alkyl to said metal complex. Subsequent abstraction of a second monoanionic atom or group from the metal complex may also be required to generate a cationic active catalyst. When the pro-catalyst is already a cationic metal complex, the role of the alkylaluminum may simply be to exchange an alkyl or hydride from the aluminum with a monoanionic group, such as acetylacetonate, attached to the metal complex. In the case of a cationic π-allyl or π-benzyl pro-catalyst, the alkylaluminum reagent may, in some cases, simply act as a Lewis acid, to promote conversion of the π-allyl or π-benzyl to a σ-allyl or σ-benzyl bonding mode, thereby facilitating binding and insertion of the olefin monomer. When a cationic pro-catalyst is used with an alkylaluminum activator or co-catalyst, it should also be recognized that the starting counteranion (e.g. $BF_4^-$) may react with the alkylaluminum reagent to generate a new counteranion (or a mixture of several different counteranions) under olefin polymerization reaction conditions. Examples of alkylaluminum reagents include: MAO, other aluminum sesquioxides, $Me_3Al$, $EtAlCl_2$, $Et_2AlCl$, $R_3Al$, $R_2AlCl$, $RAlCl_2$ (wherein R is alkyl, and plural groups R may be the same or different), and the like.

The foregoing discussion is intended to illustrate that there are frequently many ways to generate an active catalyst, and that in some cases the structure of the active species has not been fully elucidated. It is, however, an object of this disclosure to teach that there are a variety of methods wherein the ligands of the present invention can be reacted with a suitable metal precursor, and optionally a co-catalyst, to generate an active olefin polymerization catalyst. Without wishing to be bound by theory, the inventors also believe that the active catalyst typically comprises the catalytically active metal, one or more ligands of the present invention, the growing polymer chain (or a hydride capable of initiating a new chain), and a site on the metal adjacent to the metal-alkyl bond of said chain where ethylene can coordinate, or at least closely approach, prior to insertion. Where specific structures for active catalysts have been implied herein, it should be understood that an object of this invention is to teach and claim that active catalysts comprising the ligands of the present invention are formed as the reaction products of the catalyst activation reactions disclosed herein, regardless of the detailed structures of those active species.

Active catalysts may, in some cases, be generated from more than one oxidation state of a given metal. For example, the present invention describes the use of both Co(III) and Co(II) catalyst precursors to effect olefin polymerization using MAO or other alkylaluminum co-catalysts. In some cases, the oxidation state of the active catalyst has not been unambiguously established, so that it is not known if the same metal can give rise to active catalysts with different oxidation states, or if different oxidation state precursors all give rise to the same oxidation state catalyst under polymerization conditions. The latter could arise, for example, by reduction of a Co(III) catalyst precursor to a Co(II) compound under reaction conditions. Where only one oxidation state of a given metal has been specified herein, it is therefore to be understood that other oxidation states of the same metal, complexed by the ligands of the present invention, can serve as catalyst precursors or active catalysts. When different oxidation state complexes of said ligands are used, appropriate changes in the ancillary ligands or the counteranion must obviously accompany any change in oxidation level to balance the charge. Examples where multiple oxidation state precurors are especially likely to be encountered include, but are not limited to, Ti(III)/Ti(IV), Fe(III)/Fe(II), and Co(III)/Co(II).

The catalysts of the present invention may be used in batch and continuous processes, in solution or slurry or gas phase processes.

In some cases, it is advantageous to attach the catalyst to a solid support. Examples of useful solid supports include: inorganic oxides, such as talcs, silicas, titania, silica/chromia, silica/chromia/titania, silica/alumina, zirconia, aluminum phosphate gels, silanized silica, silica hydrogels, silica xerogels, silica aerogels, montmorillonite clay and silica co-gels, as well as organic support materials such as polystyrene and functionalized polystyrene. (See, for example, S. B. Roscoe et al., "Polyolefin Spheres from Metallocenes Supported on Non-Interacting Polystyrene," 1998, *Science*, 280, 270–273 (1998)).

Thus, in a preferred embodiment, the catalysts of the present invention are attached to a solid support (by "attached to a solid support" is meant ion paired with a component on the surface, adsorbed to the surface or covalently attached to the surface) that has been pre-treated with a compound $Y^2$. More generally, the compound $Y^2$ and the solid support can be combined in any order and any number of compound(s) $Y^2$ can be utilized. In addition, the supported catalyst thus formed may be treated with additional quantities of compound $Y^2$. In another preferred embodiment, the compounds of the present invention are attached to silica that has been pre-treated with an alkylaluminum compound $Y^2$, for example, MAO, $Et_3Al$, $^iBu_3Al$, $Et_2AlCl$, or $Me_3Al$.

Such supported catalysts are prepared by contacting the transition metal compound, in a substantially inert solvent (by which is meant a solvent which is either unreactive under the conditions of catalyst preparation, or if reactive, acts to usefully modify the catalyst activity or selectivity) with MAO-treated silica for a sufficient period of time to generate the supported catalyst. Examples of substantially inert solvents include toluene, o-difluorobenzene, mineral spirits, hexane, $CH_2Cl_2$, and $CHCl_3$.

In another preferred embodiment, the catalysts of the present invention are activated in solution under an inert atmosphere, and then adsorbed onto a silica support which has been pre-treated with a silylating agent to replace surface silanols by trialkylsilyl groups. Methods to pre-treat silicas in this way are known to those skilled in the art and may be achieved, for example, by heating the silica with hexamethyldisilazane and then removing the volatiles under vacuum. A variety of precurors and procedures may be used to generate the activated catalyst prior to said adsorption, including, for example, reaction of a (ligand)Ni(acac)B $(C_6F_5)_4$ complex with $Et_2AlCl$ in a toluene/hexane mixture under nitrogen; where "ligand" refers to a compound of the present invention.

In several cases, metal complexes are depicted herein with square planar, trigonal bipyramidal, or other coordination, however, it is to be understood that no specific geometry is implied.

The polymerizations may be conducted as solution polymerizations, as non-solvent slurry type polymerizations, as slurry polymerizations using one or more of the olefins or other solvent as the polymerization medium, or in the gas phase. One of ordinary skill in the art, with the present disclosure, would understand that the catalyst could be supported using a suitable catalyst support and methods known in the art. Substantially inert solvents, such as toluene, hydrocarbons, methylene chloride and the like, may be used. Propylene and 1-butene are excellent monomers for use in slurry-type copolymerizations and unused monomer can be flashed off and reused.

Temperature and olefin pressure have significant effects on polymer structure, composition, and molecular weight. Suitable polymerization temperatures are preferably from about 20° C. to about 160° C., more preferably 60° C. to about 100° C.

The catalysts of the present invention may be used alone, or in combination with one or more other Group 3–10 olefin polymerization or oligomerization catalysts, in solution, slurry, or gas phase processes. Such mixed catalysts systems are sometimes useful for the production of bimodal or multimodal molecular weight or compositional distributions, which may facilitate polymer processing or final product properties.

After the reaction has proceeded for a time sufficient to produce the desired polymers, the polymer can be recovered from the reaction mixture by routine methods of isolation and/or purification.

In general, the polymers of the present invention are useful as components of thermoset materials, as elastomers, as packaging materials, films, compatibilizing agents for polyesters and polyolefins, as a component of tackifying compositions, and as a component of adhesive materials.

High molecular weight resins are readily processed using conventional extrusion, injection molding, compression molding, and vacuum forming techniques well known in the art. Useful articles made from them include films, fibers, bottles and other containers, sheeting, molded objects and the like.

Low molecular weight resins are useful, for example, as synthetic waxes and they may be used in various wax coatings or in emulsion form. They are also particularly useful in blends with ethylene/vinyl acetate or ethylene/methyl acrylate-type copolymers in paper coating or in adhesive applications.

Although not required, typical additives used in olefin or vinyl polymers may be used in the new homopolymers and copolymers of this invention. Typical additives include pigments, colorants, titanium dioxide, carbon black, antioxidants, stabilizers, slip agents, flame retarding agents, and the like. These additives and their use in polymer systems are known per se in the art.

The ligands of the present invention may be prepared by methods known to those skilled in the art, wherein a substituted 1-aminopyrrole is condensed with a di-aldehyde or di-ketone to afford the desired ligands (Scheme II). The requisite substituted 1-aminopyrroles may be prepared by any of a variety of methods, including those shown in Scheme III.

Scheme II

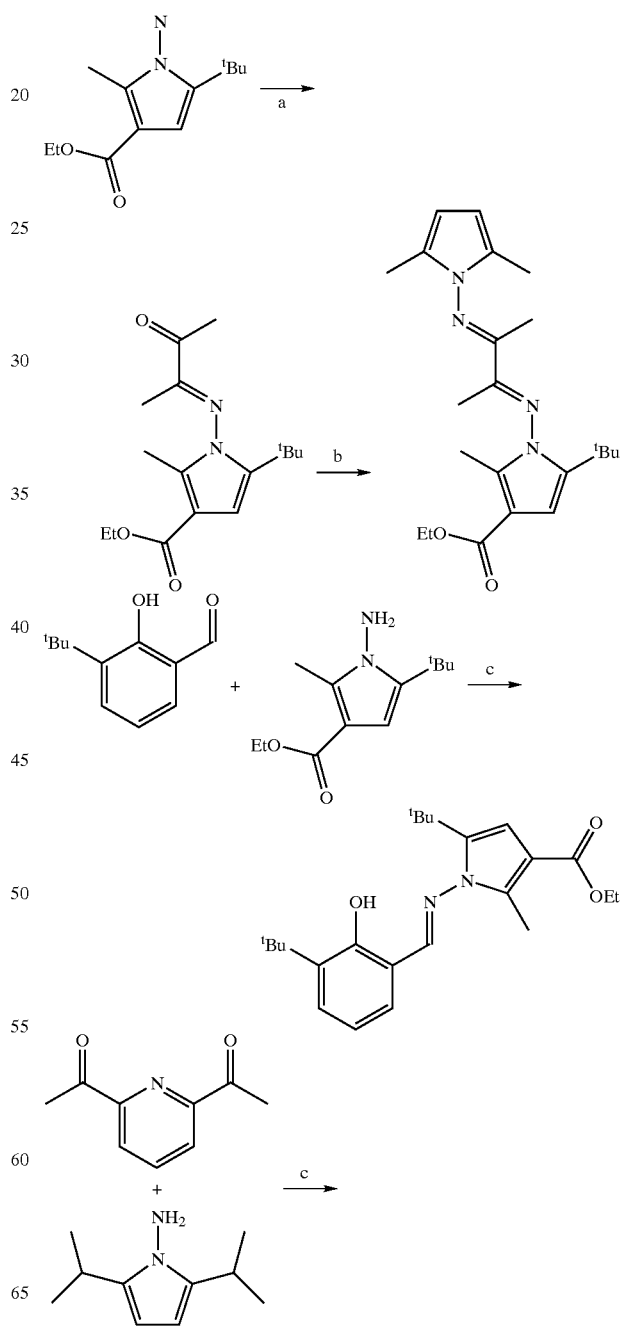

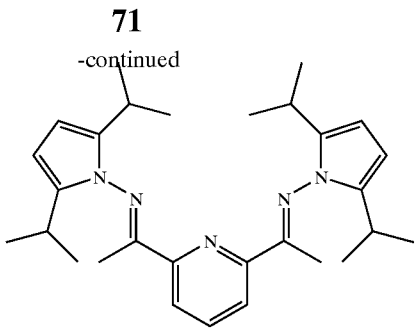

Scheme III

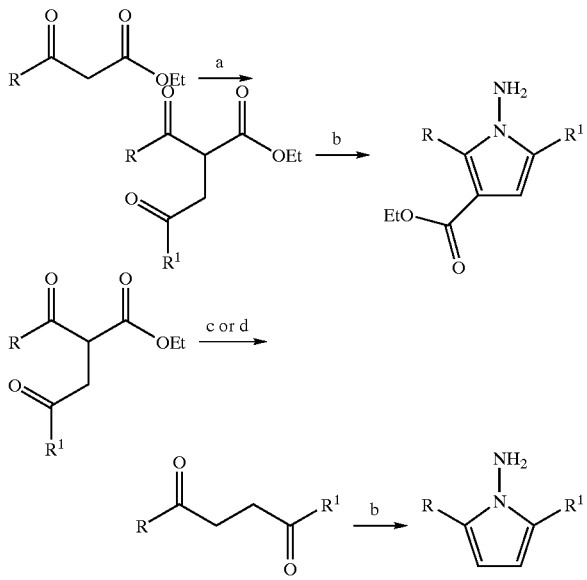

Other features of the invention will become apparent in the following description of working examples, which have been provided for illustration of the invention and are not intended to be limiting thereof.

The molecular weight data presented in the following examples is determined at 135° C. in 1,2,4-trichlorobenzene using refractive index detection, calibrated using narrow molecular weight distribution poly(styrene) standards.

EXAMPLES

Example 1

Preparation of a32

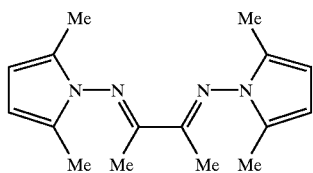

a32

A 50 mL round bottom flask was charged with 2,5-dimethyl-pyrrol-1-ylamine (400 mg), 2,3-butanedione (146 mg), ethanol (10 mL), and 1 drop of formic acid. The mixture was allowed to stand for 16 h at 22° C.; upon subsequent agitation the product crystallized and was isolated by vacuum filtration, washed with cold ethanol and dried to obtain 100 mg of the desired product as bright yellow rhombic platelets. The combined filtrate and washings were concentrated and the residue subjected to flash chromatography ($SiO_2$, 2.4 vol % Ethyl Acetate (EtOAc)/hexane) to obtain an additional 172 mg of product. $^1$H NMR ($CDCl_3$, chemical shifts in ppm relative to tetramethyl silane (TMS)): 2.075 (12p, s); 0.211 (6p, s); 5.912 (4p, s). Field Desorption Mass Spectrometry: m/z 270.

Example 2

Preparation of the Nickel Dibromide Complex of a32

A 50 mL flame-dried Schlenk flask equipped with a magnetic stir bar and capped by a septum was charged with 92 mg of a32, and 85 mg of (1,2-dimethoxyethane)nickel(II) dibromide in the drybox, under nitrogen. On the Schlenk line, 6 mL dry, deoxygenated dichloromethane was added by syringe, and the mixture was stirred under nitrogen for 3.25 h at 23° C. to afford a dark brown mixture. This mixture was diluted with 10 mL of dry, deoxygenated hexane and stirred for 15 min to precipitate the product, after which the supernatant was removed via a filter paper-tipped cannula. The brown powdery residue was dried in vacuo to obtain 73.5 mg (54%) of the nickel dibromide complex of a32.

Example 3

Polymerization of Ethylene with the Nickel Dibromide Complex of a32 in the Presence of MMAO (Modified Methylalumoxane; 23% iso-Butylaluminoxane in Heptane; 6.42% Al)

A 250 mL round bottom Schlenk flask equipped with a magnetic stir bar and capped with a septum was evacuated and refilled with ethylene, then charged with 100 mL of dry, deoxygenated toluene and 4.0 mL of a MMAO in toluene (6.42% Al) and stirred under 1 atm ethylene at 0° C. for 15 min. A 2 mL aliquot of a mixture of 3.5 mg of the nickel dibromide complex of a32 in 3.5 mL dry, deoxygenated dihioromethane was injected, and the mixture was stirred under 1 atm ethylene at 0° C. A white polyethylene precipitate was observed within minutes. After 10 minutes, the mixture was quenched by the addition of acetone (50 mL), methanol (50 mL) and 6 N aqueous HCl (100 mL). The swollen polyethylene which separated was isolated by vacuum filtration and washed with water, methanol and acetone, then dried under reduced pressure (200 mm Hg) at 80° C. for 16 h to obtain 3.95 g of a white polyethylene. $^1$H NMR: 3.7 branches/1000 carbon atoms; $M_n$=8563. GPC: $M_n$=9,190; $M_w/M_n$=3.48.

Example 4

Ethylene polymerization with a37, bis(1,5-cyclooctadiene)nickel(0) and $B(C_6F_5)_3$.

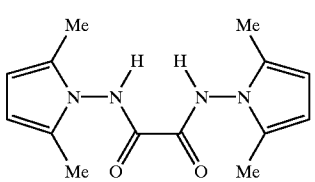

a37

A 200 mL septum-capped Schlenk flask was charged with 12 mg of N,N'-bis(2,5-dimethylpyrrol-1-yl)oxalamide (a37), 109 mg of tris(pentafluorophenyl)boron, and 7 mg of bis(1, 5-cyclooctadiene)nickel(0) under an Ar atmosphere. On the Schlenk line, the flask was evacuated and refilled with ethylene. 100 mL of dry, deoxygenated toluene were added with rapid magnetic stirring at room temperature. Polyethylene precipitated from the golden-yellow solution. After 11 minutes, the reaction was quenched by the addition of methanol. The polymer was collected by vacuum filtration, washed with methanol, and dried in vacuo (200 mm Hg) at 80° C. overnight to yield 0.14 g. $^1$H NMR: 8.6 branchpoints/1000 carbon atoms; $M_n$=17,106 g/mol.

Example 5

Ethylene Polymerization with a37, bis(1,5-Cyclooctadiene)nickel(0) and $B(C_6F_5)_3$. 10 mg of N,N'-bis(2,5-dimethylpyrrol-1-yl)oxalamide, 132 mg of tris(pentafluorophenyl)boron, and 4.7 mg of bis(1,5-cyclooctadiene)nickel(0) were weighed to 500 mL septum-capped Schlenk flask under an Ar atmosphere. On the Schlenk line, the flask was evacuated, then provided an ethylene atmosphere. 200 mL of dry, deoxygenated toluene were added with rapid magnetic stirring at room temperature. Polyethylene precipitated from the golden-yellow solution. After 70 minutes, the reaction was quenched by the addition of methanol. The polymer was collected by vacuum filtration, washed with methanol, and dried in vacuo (200 mm Hg) at 80° C. overnight to yield 1.1 g. $^1$H NMR: 5.8 branchpoints/1000 carbon atoms. GPC: $M_n$=24,400 g/mol; $M_w/M_n$=8.3.

Example 6

Ethylene polymerization with a34, bis(1,5-cyclooctadiene)nickel(0) and $B(C_6F_5)_3$.

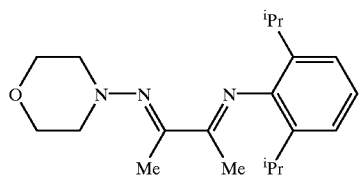

a34

10 mg of compound a34, 65 mg of tris(pentafluorophenyl)boron, and 5 mg of bis(1,5-cyclooctadiene)nickel(0) were weighed to 20 mL septum-capped vial under an Ar atmosphere. On the Schlenk line, the vial was provided an ethylene atmosphere. 10 mL of dry, deoxygenated toluene were added with rapid magnetic stirring at room temperature to give a brown mixture. After 20 minutes, the reaction was quenched by the addition of methanol. The polymer was collected by vacuum filtration, washed with methanol, and dried in vacuo (200 mm Hg) at 80° C. overnight to yield 30 mg. $^1$H NMR: 27.5 branchpoints/1000 carbon atoms; $M_n$=2319 g/mol. GPC: $M_n$=1760 g/mol; $M_w/M_n$=5.03.

Example 7

Ethylene Polymerization with a32, bis(1,5-Cyclooctadiene)nickel(0) and $B(C_6F_5)_3$ 10 mg of compound a32, 65 mg of tris(pentafluorophenyl)boron, and 4.2 mg of bis(1,5-cyclooctadiene)nickel(0) were weighed to 20 mL septum-capped vial under an Ar atmosphere. On the Schlenk line, the vial was provided an ethylene atmosphere. 10 mL of dry, deoxygenated toluene were added with rapid magnetic stirring at room temperature to give a brown mixture. After 20 minutes, the reaction was quenched by the addition of methanol. The polymer was collected by vacuum filtration, washed with methanol, and dried in vacuo (200 mm Hg) at 80° C. overnight to yield 847 mg. $^1$H NMR: 46.8 branchpoints/1000 carbon atoms; $M_n$=2347 g/mol. GPC: $M_n$=1220 g/mol; $M_w/M_n$=4.84.

Example 8

1-Hexene Polymerization with a32, bis(1,5-Cyclooctadiene)nickel(0) and $B(C_6F_5)_3$ 6 mg of compound a32, 24 mg of tris(pentafluorophenyl)boron, and 3.6 mg of bis(1,5-cyclooctadiene)nickel(0) were weighed to 20 mL septum-capped vial under an Ar atmosphere. On the Schlenk line, the vial was provided a nitrogen atmosphere. 10 mL of dry 1-hexene were added with rapid magnetic stirring at room temperature to give a brown mixture. After 120 minutes, the reaction was quenched by the addition of methanol. The oily polymer was stirred with methanol, and then the methanol was decanted away. The polymer was dried in vacuo (200 mm Hg) at 80° C. overnight to yield 350 mg. $^1$H NMR: 157.5 branchpoints/1000 carbon atoms; $M_n$=2220 g/mol. GPC: $M_n$=1480 g/mol; $M_w/M_n$=2.22.

Example 9

1-Hexene Polymerization with a32, bis(1,5-Cyclooctadiene)nickel(0) and $B(C_6E_5)_3$ 4.2 mg of compound a32, 28 mg of tris(pentafluorophenyl)boron, and 2.2 mg of bis(1,5-cyclooctadiene)nickel(0) were weighed to 20 mL septum-capped vial under an Ar atmosphere. On the Schlenk line, the vial was provided an ethylene atmosphere. 10 mL of dry toluene was added with rapid magnetic stirring at room temperature to give a brown mixture. 5 mL of 1-hexene were immediately added, and the ethylene supply replaced with nitrogen. After 120 minutes, the reaction was quenched by the addition of methanol. The oily polymer was stirred with methanol, and then the methanol was decanted away. The polymer was dried in vacuo (200 mm Hg) overnight to yield 2 g. $^1$H NMR: 142.9 branchpoints/1000 carbon atoms; $M_n$=1952 g/mol. GPC: $M_n$=1200 g/mol; $M_w/M_n$=3.79.

Example 10

Polymerization of Ethylene with the Nickel Dibromide Complex of a32 in the Presence of MMAO (Methylaluminoxane Modified with 23% iso-Butylaluminoxane in Heptane; 6.42% Al)

A 600 mL Parr® autoclave was first heated to about 100° C. under high vacuum to ensure the reactor was dry. The reactor was cooled and purged with argon. Under an argon atmosphere, the autoclave was charged with 150 mL of toluene. The reactor was pressurized to 200 psig with ethylene and then relieved to ambient pressure (2×). 3 mL of MMAO solution were added. With stirring and with the ethylene pressure rising to 200 psig, 2.0 mL of a stock solution (4.30 mg in 17.2 mL $CH_2Cl_2$) of the nickel dibromide complex of a32 were injected. The pressure was maintained at 200 psig. The autoclave temperature was controlled at 30° C. After 10 minutes, the reaction was quenched by the addition of methanol and the pressure relieved. The swollen polyethylene which separated was stirred with a mixture of acetone and aqueous HCl. The polymer was isolated by filtration, washed with acetone and dried in vacuo (200 mm Hg) overnight to yield 8.3 g. GPC: $M_n$=1370; $M_w/M_n$=18.88.

Example 11

Preparation of a34.

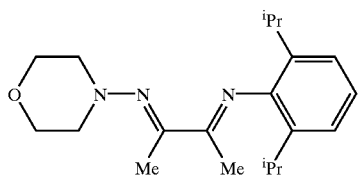

a34

A 100 mL round bottom flask was charged with 2,6-diisopopylaniline (10 g) and 2,3-butanedione (4.87 g). After 6 days, the volatiles were removed in vacuo to give an amber oil (13 g). This oil (5.13 g) was treated with methanol (25 mL), 4-amino morpholine (1 mL), and 8 drops of formic acid. The mixture was allowed to stand for 16 h at 22° C. The mixture was concentrated, and the residue was subjected to flash chromatography ($SiO_2$, 8 vol % of EtOAc/hexane) to obtain a34 as a pale yellow oil (2.5 g) which crystallized upon exposure to methanol. Field Desorption Mass Spectrometry: m/z 329.

Example 12

Preparation of a35

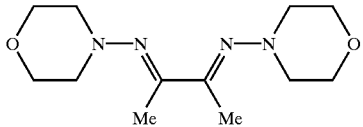

a35

A 100 mL round bottom flask was charged with methanol (20 mL), 4-amino morpholine (5 mL), 2,3-butanedione (1.95 mL), and formic acid (0.2 mL). A precipitate separated almost immediately. After 3 days, the product was collected by vacuum filtration as pale green-yellow crystals.

Example 13

Preparation of a36

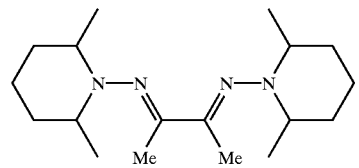

a36

A 50 mL round bottom flask was charged with methanol (10 mL), 1-amino-2,6-dimethylpiperidine (2.0 mL), 2,3-butanedione (0.54 mL), and formic acid (0.2 mL). The mixture was stirred at 22° C. for 3 days, and the yellow crystals that separated were isolated by filtration. Field Desorption Mass Spectrometry: m/z 306.

Preparation of a30

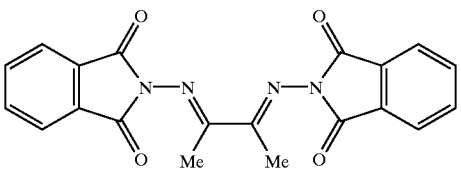

a30

A 100 mL round bottom flask was provided a nitrogen atmosphere, a magnetic stirrer, and a reflux condenser, and was charged with toluene (16 mL), N-aminophthalimide (4.5 g), 2,3-butanedione (1 mL), and formic acid (0.25 mL). The mixture was heated to and maintained at reflux for 1 hour, then allowed to cool to room temperature overnight. The white crystals that separated were isolated by filtration and washed with methanol. Field Desorption Mass Spectrometry: m/z 374.

Example 15

Preparation of the Nickel Dibromide Complex of a36

A 50 mL flame-dried Schlenk flask equipped with a magnetic stir bar and capped by a septum was charged with 100 mg of a36, and 92 mg of (1,2-dimethoxyethane)nickel (II) dibromide in the drybox, under nitrogen. On the Schlenk line, 6 mL of dry, deoxygenated dichloromethane were added by syringe to quickly give a dark brown mixture. The mixture was stirred under nitrogen for overnight at 23° C. The mixture was then diluted with 10 mL of dry, deoxygenated hexane, then 28 mg more of a36 were added, and the mixture was stirred for 1 h more. Some $CH_2Cl_2$ was evaporated under a stream of nitrogen to completely precipitate the product, after which the supernatant was removed via a filter paper-tipped cannula. The brown powdery residue was dried in vacuo.

Example 16

Preparation of the Cobalt Dichloride Complex of a36

A 50 mL flame-dried Schlenk flask equipped with a magnetic stir bar and capped by a septum was charged with 100 mg of a36, and 44 mg of cobalt dichoride in the drybox, under nitrogen. On the Schlenk line, 9 mL of dry, deoxygenated dichloromethane were added by syringe to slowly give a green supernatant. The mixture was stirred under nitrogen for overnight at 23° C. The mixture was then diluted with 10 mL of dry, deoxygenated hexane, then some $CH_2Cl_2$ was evaporated under a stream of nitrogen to completely precipitate the product as green crystals. The supernatant was removed via a filter paper-tipped cannula, and the crystals were dried in vacuo to afford the desired complex.

Example 17

Oligomerization of Ethylene with the Cobalt Dichloride Complex of a36 in the Presence of MAO (Methylaluminoxane; 10% Solution in Toluene)

A 200 mL round bottom Schlenk flask equipped with a magnetic stir bar and capped with a septum was charged with 9.8 mg of the cobalt dichloride complex of a36, then evacuated and refilled with ethylene. The flask was then charged with 50 mL of dry, deoxygenated toluene and stirred under 1 atm of ethylene at 0° C. for 24 min. 4 mL of MAO (methylaluminoxane; 10% solution in toluene) were added, and the ethylene was rapidly consumed to form ethylene oligomers. After 62 minutes, the mixture was quenched by the addition of acetone (50 mL), methanol (50 mL), and 6 N aqueous HCl (100 mL).

Example 18

Preparation of the Nickel Dibromide Complex of a35

A 200 mL flame-dried Schlenk flask equipped with a magnetic stir bar and capped by a septum was charged with 103 mg of a35, and 109 mg of (1,2-dimethoxyethane)nickel (II) dibromide in the drybox, under nitrogen. On the Schlenk line, 5 mL of dry, deoxygenated dichloromethane were added by syringe to quickly give a dark brown mixture. The mixture was stirred under nitrogen for overnight at 23° C. This mixture was diluted with 10 mL of dry, deoxygenated hexane to completely precipitate the product, after which the supernatant was removed via a filter paper-tipped cannula. The brown powdery residue was dried in vacuo.

Example 19

Oligomerization of Ethylene with the Nickel Dibromide Complex of a35 in the Presence of MAO (Methylaluminoxane; 10% Solution in Toluene)

A 500 mL round bottom Schlenk flask equipped with a magnetic stir bar and capped with a septum was charged with 19.5 mg of the nickel dibromide complex of a35, then evacuated and refilled with ethylene. The flask was then charged with 50 mL of dry, deoxygenated toluene and stirred under 1 atm of ethylene at 0° C. for 3 min. 4 mL of MAO (methylaluminoxane; 10% solution in toluene) were added, and the ethylene was rapidly consumed. After 130 minutes, the mixture was quenched by the addition of acetone (50 mL), methanol (50 mL), and 6 N aqueous HCl (100 mL). A small amount of polyethylene precipitated and, as evidenced by gas chromatography, a distribution of higher olefins was produced.

Example 20

Preparation of a38

In a 500 mL round bottom flask, 2,4,6-tri-tert-butylaniline (2.0 g) and 2.6 mL triethylamine were dissolved in dichloromethane (50 mL) and cooled to 0° C. A mixture of ethyl chloroglyoxylate (0.85 mL) and dichloromethane (33 mL) was slowly added via dropping funnel, after which the mixture was stirred at 0° C. for 1 h, and then at 25° C. for 3 h. The resultant mixture was quenched with 100 mL of water. The aqueous layer was extracted with 100 mL of dichloromethane. The combined organic layers were dried over sodium sulfate, filtered, and concentrated under reduced pressure (20 mm Hg). The residue was purified by flash chromatography (silica; hexane/EtOAc; linear gradient). The N-(2,4,6-tri-tert-butylphenyl)oxalamic acid ethyl ester so obtained (201.5 mg) was reacted with excess hydrazine hydrate (81 μL) in 5 mL of EtOH at 50° C. for 14 h. The resultant solid was isolated by filtration and washed with EtOH to obtain compound a38.

Example 21

Ethylene Polymerization with a38, bis(1,5-Cyclooctadiene)nickel(0), and B($C_6F_5$)$_3$ 8.9 mg of compound a38, 85 mg of tris (pentafluorophenyl)boron, and 4.2 mg of bis(1,5-cyclooctadiene)nickel(0) were weighed to 20 mL septum-capped vial under an Ar atmosphere. On the Schlenk line, the vial was provided an ethylene atmosphere. 10 mL of dry, deoxygenated toluene were added with rapid magnetic stirring at room temperature to give a brown mixture. After 61 minutes, the reaction was quenched by the addition of methanol. The polymer was collected by vacuum filtration, washed with methanol, and dried in vacuo (200 mm Hg) at 80° C. overnight to yield 147 mg. $^1$H NMR: 74.8 branchpoints/1000 carbon atoms; $M_n$=8423 g/mol. GPC: $M_n$=35700 g/mol; $M_w/M_n$=1.21.

Example 22

Ethylene Polymerization with a17, bis(1,5-Cyclooctadiene)nickel(0), and B($C_6F_5$)$_3$ 6.2 mg of compound a17, 30 mg of tris (pentafluorophenyl)boron, and 1.9 mg of bis(1,5-cyclooctadiene)nickel(0) were weighed to 20 mL septum-capped vial under an Ar atmosphere. On the Schlenk line, the vial was provided an ethylene atmosphere. 10 mL of dry, deoxygenated toluene were added with rapid magnetic stirring at room temperature to give a brown mixture. After 15 minutes, the reaction was quenched by the addition of methanol. The polymer was collected by vacuum filtration, washed with methanol, and dried in vacuo (200 mm Hg) at 80° C. overnight to yield 370 mg.

Example 23

Synthesis of a50

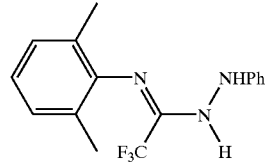

a50

Phenylhydrazine (0.551 mL, 5.6 mmol) was added to a solution of N-(2,6-dimethylphenyl)-2,2,2-trifluoro-acetimidoyl chloride (263.4 mg, 1.12 mmol) (prepared from TFA, 2,6-dimethyl aniline, Ph$_3$P, CCl$_4$, and Et$_3$N according to the procedure of Tamura, K., et al., J. Org. Chem. 1993, 58, 32–35) in toluene (8.0 mL). The resulting solution was heated at reflux for 2 days, cooled to room temperature and concentrated in vacuo. The residue was partitioned between H$_2$O (3 mL) and CH$_2$Cl$_2$ (3 mL). The aqueous layer was further extracted with CH$_2$Cl$_2$ (3×2 mL). The combined organic layers were dried over Na$_2$SO$_4$, filtered and concentrated in vacuo. The residue was purified by flash chromatography (SiO$_2$, 4% EtOAc/Hex) to afford amidrazone a50 (182 mg, 53%); R$_f$ 0.27 (5% EtOAc/Hex); $^1$H NMR (300 MHz, CD$_3$OD) δ 7.09–7.14 (m, 5H), 6.79–6.82 (m, 3H), 2.26 (s, 6H); IR (CDCl$_3$ Film) cm$^{-1}$ 3383, 3360, 1661, 1604, 1496, 1226, 1164, 1119; FDMS m/z 307 (M$^+$, 100%).

Example 24

Polymerization of Ethylene Ni(COD)$_2$/a50/HB(3,5-CF$_3$C$_6$H$_3$)$_4$ (Et$_2$O)$_2$ In an inert atmosphere glove box, a flame dried Schlenk flask equipped with a magnetic stir bar and a rubber septum was charged with 20 mg (0.073 mmol) of bis(1,5-cyclooctadiene) nickel(0) and 22 mg of the ligand of formula CI. The flask was removed from the box and backfilled with ethylene. Toluene (50 ml) was added resulting in a yellow solution. After 15 minutes, H$^+$ B(3,5-CF$_3$C$_6$H$_3$)$_4$ (Et$_2$O)$_2$ was added as a solid resulting in an orange solution with modest ethylene uptake rates. After 1 hour methanol was added to quench the polymerization. The solvent was removed in vacuo resulting in a free flowing oil. The $^1$H NMR is consistent with branched polyethylene.

Example 25

Synthesis of the Nickel(II) Dibromide Complex of a50 and Test for Ethylene Polymerization To a flame dried Schlenk flask equipped with a rubber septum and a stir bar was added 10 mg (0.0325 mmol) of a50 and 9 mg (0.03 mmol) of (DME)NiBr$_2$. To the solid mixture, 10 ml of CH$_2$Cl$_2$ was added and the reaction left to stir under an argon atmosphere for 16 hours. The solvent was removed in vacuo resulting in a powder. The powder was then taken up in 50 ml of toluene and the flask backfilled with ethylene. MAO (1.5 ml, 10-wt % solution in toluene) was added resulting in a purple solution. After 30 minutes of vigorous stirring at 23° C. and 1 atmosphere ethylene, methanol, acetone and 6M HCl were added to quench the reaction. The organic layer was isolated and the solvent removed in vacuo giving an oily solid. $^1$H NMR confirms the preparation of a highly branched ethylene homopolymer (M$_n$=870).

Example 26

Polymerization of ethylene with Ni(COD)$_2$/b1/B(C$_6$F$_5$)$_3$.

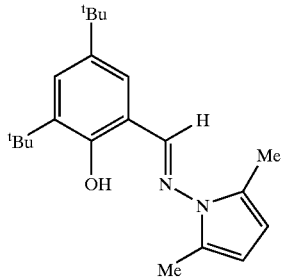

b1

In an inert atmosphere glove box, a flame dried Schlenk flask equipped with a magnetic stir bar and a rubber septum was charged with 10 mg (0.036 mmol) of bis(1,5-cyclooctadiene)nickel(0), 18.4 mg (0.036 mmol) of tris(pentafluorophenyl)borane, and 12 mg (0.036 mmol) of b1. The flask was removed from the box and evacuated and refilled with ethylene. Toluene (50 ml) was added, resulting in a orange solution. The polymerization mixture was allowed to stir at room temperature for 15 hours. After 15 hours, methanol and acetone were added to quench the reaction and a white flocculent polyethylene precipitated from solution. The polymer was collected by suction filtration and dried in the vacuum oven overnight at ~100° C. resulting in 1.1 grams of polyethylene. DSC T$_m$=41° C.; GPC M$_n$=3,500, M$_w$/M$_n$=1.76; $^1$H NMR 65 branches/1000 carbon atoms.

Example 27

Synthesis of b2

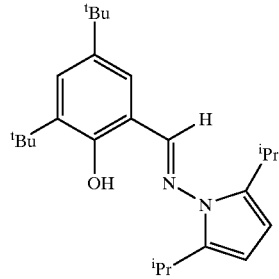

b2

1-Amino-2,5-diisopropylpyrrole (100 mg) and 3,5-di-tert-butyl-2-hydroxybenzaldehyde (126 mg) were weighed to a septum capped scintillation vial. The vial was well purged with dry nitrogen gas, then methanol (1 ml) was added. All solids dissolved after a few minutes, then 4 drops of a solution of formic acid in methanol (2drops formic acid in 1-ml methanol) was added. The reaction was allowed to stand at room temperature for 16 h. The light yellow crystalline product that separated was collected by vacuum filtration. The crystals were washed with methanol on the filter and then dried several hours in vacuo to yield 160 mg.

Example 28

Representative Ligand Synthesis

1-Amino-2-phenyl-5-methylpyrrole (174 mg) and 3,5-di-tert-butyl-2-hydroxybenzaldehyde (236 mg) were weighed to a scintillation vial then dissolved methanol (2 ml). Formic acid (1 drop) was added. The reaction was allowed to stand at room temperature for 16 h. The light yellow crystalline product that separated was collected by vacuum filtration. The crystals were washed with methanol on the filter and then dried several hours in vacuo to yield 254 mg.

Example 29

Polymerization of Ethylene Ni(COD)$_2$/b2/B(C$_6$F$_5$)$_3$

In an inert atmosphere glove box, a flame dried Schlenk flask equipped with a magnetic stir bar and a rubber septum was charged with 10 mg (0.036 mmol) of bis(1,5-cyclooctadiene)nickel(0), 18.4 mg (0.036 mmol) of tris(pentafluorophenyl)borane, and 13.75 mg (0.036 mmol) of the ligand of formula b2. The flask was removed from the box and evacuated and refilled with ethylene. Toluene (50 ml) was added, resulting in a orange solution. The polymerization mixture was allowed to stir at room temperature for 15 hours. After 15 hours, methanol and acetone were added to quench the reaction and a white flocculent polyethylene precipitated from solution. The polymer was collected by suction filtration and dried in the vacuum oven overnight at ~100° C. resulting in 3.8 grams of polyethylene. DSC T$_m$=41° C.; GPC M$_n$=12,400, M$_w$/M$_n$=1.96; $^1$H NMR 67 ranches/1000 carbon atoms.

Example 30

Polymerization of Ethylene Ni(COD)$_2$/b2/B(C$_6$F$_5$)$_3$

A Parr® stirred autoclave (600-ml) was heated to 100° C. under dynamic vacuum to completely dry the reactor. The reactor was cooled and charged with 150 ml of dry toluene. In an inert atmosphere glove box, a flame dried Schlenk flask equipped with a magnetic stir bar and a rubber septum was charged with 10 mg (0.036 mmol) of bis(1,5-cyclooctadiene)nickel(0), 18.4 mg (0.036 mmol) of tris(pentafluorophenyl)borane, and 13.75 mg (0.036 mmol) of the ligand of formula b2. The flask was removed from the box and evacuated and refilled with ethylene. Toluene (50 ml) was added resulting in a orange solution. After 15 minutes, the contents of the reaction flask were transferred via SS cannula to the autoclave. The reactor was sealed and pressurized up to 400-psig ethylene and left to stir at room temperature for 5 hours. After 5 hours, the reactor was vented and the contents poured into a beaker containing a methanol acetone/mixture. The polymer was collected by suction filtration and dried in the vacuum oven overnight at ~100° C. resulting in 9 grams of polyethylene. DSC $T_m=111°$ C.; GPC $M_n=39,000$, $M_w/M_n=2.23$; $^1$H NMR 25 branches/1000 carbon atoms.

Example 31

Ethylene Polymerization with d1

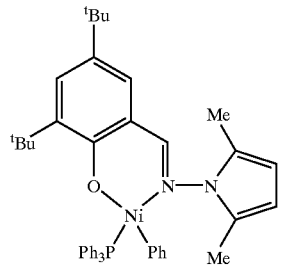

d1

A Parr® stirred autoclave (600-ml) was heated to 100° C. under dynamic vacuum to completely dry the reactor. The reactor was cooled and charged with 200 ml of dry toluene and a 5-ml solution of tris(pentafluorophenyl)borane (20 mg) in toluene. The reactor was pressurized to 200-psig ethylene and vented. The catalyst solution (7.5 mg of d1 in 2 ml of toluene) was added to the reactor and the autoclave was sealed and pressurized to 200-psig ethylene. After 30 minutes, the reactor was vented and the contents poured into a beaker containing a methanol/acetone mixture. The polymer was collected by suction filtration and dried in the vacuum oven overnight at ~100° C. resulting in 0.1 grams of polyethylene. $^1$H NMR branched polyethylene with a $M_n=3600$.

Example 32

Ethylene Polymerization with d2

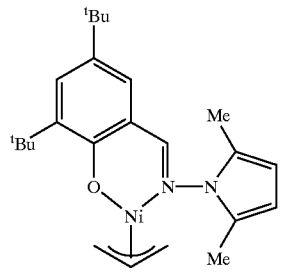

d2

A Parr® stirred autoclave (600-ml) was heated to 100° C. under dynamic vacuum to completely dry the reactor. The reactor was cooled and charged with 200 ml of dry toluene and a 5 ml solution of tris(pentafluorophenyl)borane (6.5 mg, 0.027mmol) in toluene. The reactor was pressurized to 200-psig ethylene and vented. The catalyst solution (5.25 mg of d2 in 3 ml of toluene) was added to the reactor and the autoclave was sealed and pressurized to 200-psig ethylene. After 60 minutes at 35° C., the reactor was vented and the contents poured into a beaker containing a methanol acetone/mixture. The polymer was collected by suction filtration and dried in the vacuum oven overnight at ~100° C. resulting in 0.13 grams of polyethylene. $^1$H NMR is consistent with branched polyethylene.

Example 33 to Example 36

Polymerization of ethylene with Ni(COD)$_2$/ligand/B(C$_6$F$_5$)$_3$

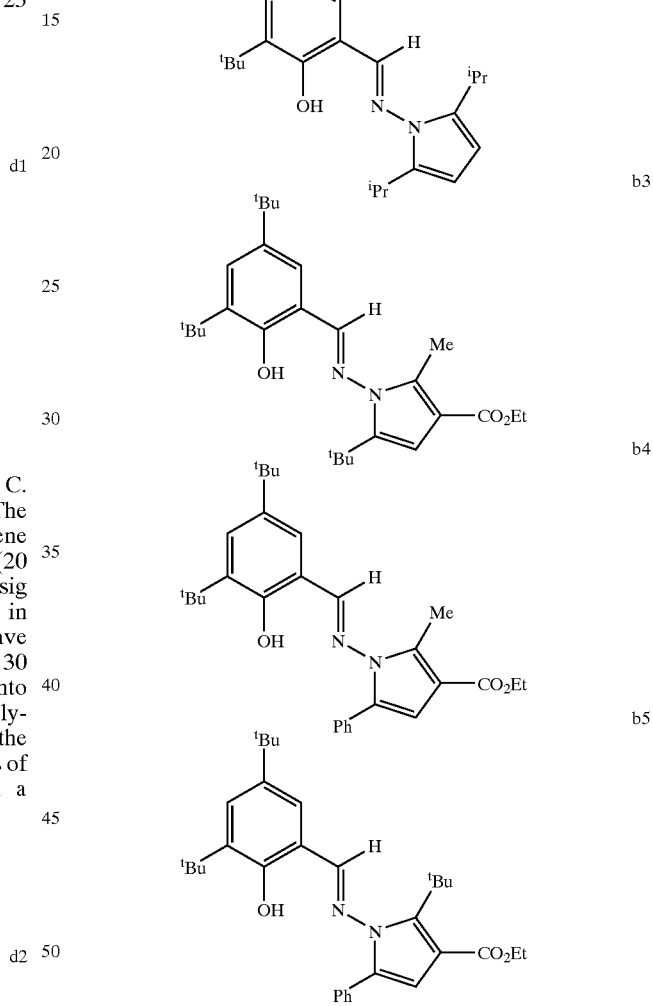

A Parr® stirred autoclave (600-ml) was heated to 100° C. under dynamic vacuum to completely dry the reactor. The reactor was cooled and charged with 150 ml of dry toluene. In an inert atmosphere glove box, a flame dried Schlenk flask equipped with a magnetic stir bar and a rubber septum was charged with between 0.018 mmol and 0.036 mmol of bis(1,5-cyclooctadiene)nickel(0), between 0.018 mmol and 0.036 mmol of tris(pentafluorophenyl)borane, and between 0.018 mmol and 0.036 mmol of the ligand in a 1:1:1 ratio. The flask was removed from the box and evacuated and refilled with ethylene. Toluene (50 ml) was added. After 10–15 minutes, the contents of the reaction flask were transferred via SS cannula to the autoclave. The reactor was sealed and pressurized up to 400-psig ethylene and left to stir at room temperature for 2–3 hours at 30° C. After the desired reaction time, the reactor was vented and the contents poured into a beaker containing a methanol acetone/mixture. The polymer was collected by suction filtration and dried in the vacuum oven overnight at ~100° C.

| Example | Ligand | mmol cat | Rxn time (minutes) | PE yield (g) | Mw (× $10^{-3}$) | Branching/ 1000 C ($^1$H NMR) | $T_m$ (° C.) |
|---|---|---|---|---|---|---|---|
| 33 | b3 | 0.036 | 180 | 2.4 | 1,254 | 20 | 128 |
| 34 | b4 | 0.036 | 120 | 8.2 | 4.5 | 64 | 76 |
| 35 | b2 | 0.018 | 120 | 2.2 | 71 | 33 | 108 |
| 36 | b5 | 0.036 | 120 | 0.22 | 610 | 10 | 128 |

Example 37

Polymerization of norbornene with Ni(COD)$_2$/b1/B(C$_6$F$_5$)$_3$

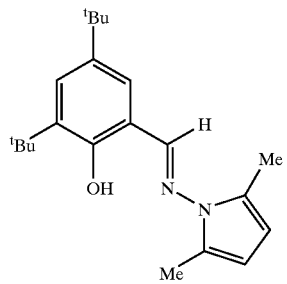

b1

In an inert atmosphere glove box, a flame dried Schlenk flask equipped with a magnetic stir bar and a rubber septum was charged with 10 mg (0.036 mmol) of bis(1,5-cyclooctadiene)nickel(0), 18.4 mg (0.036 mmol) of tris (pentafluorophenyl)borane, and 12 mg (0.036 mmol) of the ligand of formula b1. The flask was removed from the box and evacuated and refilled with argon. Toluene (50 ml) was added, resulting in a orange solution. To the polymerization mixture was added a toluene solution containing 3 g of norbornene. After 1 hour, methanol and acetone were added to quench the reaction and a white flocculent polynorbornene precipitated from solution. The polymer was collected by suction filtration and dried in the vacuum oven overnight at ~100° C. resulting in 2.3 grams of polynorbornene.

Example 38

Synthesis of d3

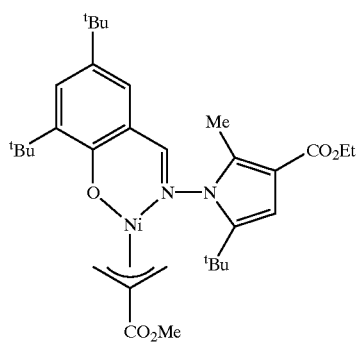

d3

A flame dried Schlenk flask equipped with a stir bar and a rubber septum was charged in the inert atmosphere glove box with 50 mg (0.10 mmol) [(H$_2$CC(CO$_2$Me)CH$_2$)Ni($\mu$-Br)] and 100 mg of the sodium salt of ligand b3. The flask was removed from the glove box attached to the Schlenk line and evacuated and refilled with argon. Diethyl ether (10-ml) was then added and the mixture was stirred for 2–3 hours. The reaction mixture was transferred via cannula through a pad of celite to remove the NaBr. The pad of celite and SS cannula was rinsed with an additional 10-ml of ether. The solvent was removed in vacuo giving 65 mg of the desired product d3. [(H$_2$CC(CO$_2$Me)CH$_2$)Ni($\mu$-Br)] was prepared by the procedure described in Angew. Chem., Int. Ed. Eng. 1966, 5, 151.

Example 39

Ethylene Polymerization with d3

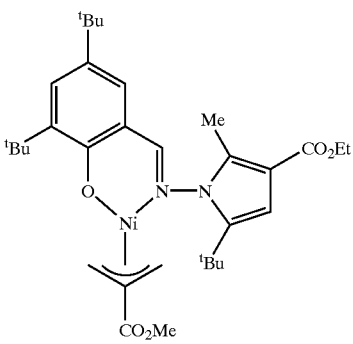

d3

A Parr® stirred autoclave (600-ml) was heated to 100° C. under dynamic vacuum to completely dry the reactor. The reactor was cooled and charged with 150 ml of dry toluene and a 5-ml catalyst solution (5 mg of d3 in 5 ml of toluene). The reactor was pressurized to 200 psig ethylene and tri(phenyl)borane (4 mg, 0.017 mmol) in toluene was added to the reactor via the high-pressure sample loop while the reactor was being pressurized to 400 psig. After 120 minutes at 30° C., the reactor was vented and the contents poured into a beaker containing a methanol acetone/mixture. The polymer was collected by suction filtration and dried in the vacuum oven overnight at ~100° C. resulting in 0.350 grams of polyethylene. $^1$H NMR is consistent with branched polyethylene (7 branches/1000 carbon atoms and $M_n$=97,000).

Example 40 to Example 42

Polymerization of ethylene Zr(Me$_2$)$_4$/b6/Cocatalyst

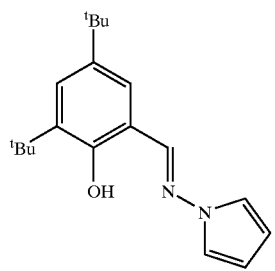

b6

In an inert atmosphere glove box, a flame dried Schlenk flask equipped with a magnetic stir bar and a rubber septum was charged with 5 mg (1.9×10$^{-5}$ mol) of tetrakis (dimethylamino) zirconium and 11 mg (3.7×10$^{-5}$mol) of the ligand of formula b6. The flask was removed from the box and evacuat ed and refilled with ethylene. Toluene (50 ml) was added followed by the addition of the desired amount of cocatalyst(s) (see table for details). The polymerization mixture was allowed to stir at room temperature and 1 atmosphere ethylene for 30 minutes. After 30 minutes, methanol, 6 M HCl and acetone were added to quench the reaction and a white flocculent polyethylene precipitated from solution. The polymer was collected by suction filtration and dried in the vacuum oven overnight at ~100° C.

| Ex. | Cocatalysts | mmol Zr(Me$_2$)$_4$ | Rxn time (minutes) | PE yield (g) | M$_w$ | T$_m$(° C.) |
|---|---|---|---|---|---|---|
| 40 | TMA (0.18 mmol)/ MAO (5.2 mmol) | 0.019 | 30 | 0.13 | 2300 | 122 |
| 41 | mMAO$^a$ (3.2 mmol) | 0.019 | 30 | 0.25 | 1400 | 118 |
| 42 | TMA (0.18 mmol)/ mMAO$^a$ (3.2 mmol) | 0.019 | 30 | 0.24 | 1700 | 123 |

$^a$mMAO-3A from Akzo Nobel.

Example 43

Polymerization of Ethylene Zr(Me$_2$)$_4$/b6/mMAO

A Parr® stirred autoclave (600-ml) was heated to 100° C. under dynamic vacuum to completely dry the reactor. The reactor was cooled and charged with 150 ml of dry toluene and 3-ml of mMAO-3A (Akzo Nobel). In an inert atmosphere glove box, 5 mg (0.019 mmol) of Zr(Me$_2$)$_4$ and 11 mg (0.037 mmol) of the ligand of formula b6 were weighed into a septum-capped vial. To the vial was added 4-ml of toluene. The resulting solution (2-ml of it) was added to the autoclave at pressure using a sample loop. The reactor was pressurized up to 400 psig ethylene and left to stir at room temperature for 15 minutes. After 15 minutes, the reaction was quenched by addition of methanol via the sample loop and the reactor was vented and the contents poured into a beaker containing a methanol/acetone/6M HCl mixture. The polymer was collected by suction filtration and dried in the vacuum oven overnight at ~100° C. resulting in 8.9 grams of polyethylene. DSC T$_m$=125° C.; GPC M$_w$=36,000.

Example 44

Synthesis of i1

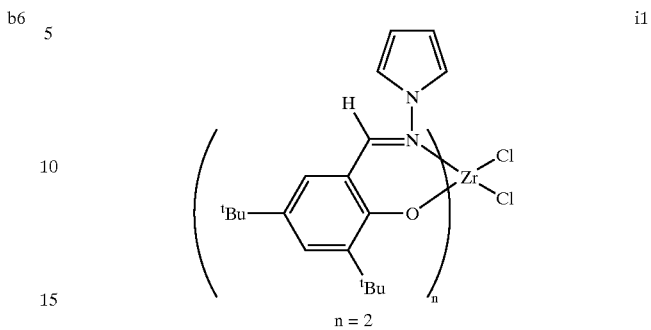

i1

A flame dried reaction flask equipped with a rubber septum and a stir bar was charged in the glove box with the ligand b6. Diethyl ether (10-ml) was added to the flask and the solution was cooled to −78° C. using a dry ice/acetone bath. To the solution was added 0.58-ml of n-BuLi resulting in a bright yellow solution. The mixture was stirred as the flask was warmed to room temperature over the period of 1 hour. The solution containing the lithium salt of the ligand was transferred via a SS cannula to another Schlenk flask that contained a suspension of ZrCl$_4$. The mixture was stirred for 3 hours and the solvent was removed in vacuo. Methylene Chloride (5-ml) was added to solubilize the resulting Zr-complex and leave the LiCl undissolved. The mixture was transferred via SS cannula through a pad celite to a new Schlenk flask. The solvent was again removed in vacuo leaving a glassy yellow solid that was then recrystallized from hexane. The $^1$H NMR is consistent with the desired procatalyst i1.

Example 45 to Example 50

Polymerization of Ethylene using Ligand i1 and mMAO-3A (Akzo Nobel)

A Parr® stirred autoclave (600-ml) was heated to 100° C. under dynamic vacuum to completely dry the reactor. The reactor was cooled and charged with 150 ml of dry toluene and mMAO-3A (Akzo Nobel). In an inert atmosphere glove box, a septum-capped vial was charged with ligand i1. To the vial was added 4-ml of toluene. The resulting solution (2-ml of it) was added to the autoclave at pressure using a sample loop (initial pressure 200 psig ramped up to 400 psig). The reactor was left to stir for 15 minutes at the appropriate temperature. After 15 minutes, the reaction was quenched by addition of methanol via the sample loop. The reactor was vented and the contents poured into a beaker containing a methanol/acetone/6M HCl mixture. The polymer was collected by suction filtration and dried in the vacuum oven overnight.

| Ex. | Eq (mMAO) | mmol i1 | T (° C.) | PE yield (g) | kg PE per mmol i1 | $M_w$ | $T_m$ (° C.) |
|---|---|---|---|---|---|---|---|
| 45 | 9400 | 0.00033 | 70 | 5.2 | 15 | 98,000 | 132 |
| 46 | 3100 | 0.00033 | 70 | 4 | 12 | 195,000 | 132 |
| 47 | 1000 | 0.00033 | 70 | 4 | 12 | 190,000 | 135 |
| 48 | 667 | 0.00033 | 70 | 4.2 | 13 | 65,000 | 136 |
| 49 | 300 | 0.00033 | 70 | 4.9 | 15 | — | 135 |
| 50 | 1000 | 0.00017 | 50 | 6.5 | 38 | 934,000 | 131 |

Example 51

Preparation of h17. Reaction of 2,6-Diacetylpyridine and 1-amino-2,5-diisopropylpyrrole to Afford the Corresponding bis (Hydrazone)

A 65 mL round bottom flask equipped with a magnetic stir bar was sequentially charged with 2,6-diacetylpyridine (50 mg), 1-amino-2,5-diisopropylpyrrole (115 mg) and ethanol (1 mL). Upon addition of formic acid (1 drop), the product began to crystallize, however, TLC analysis indicated both these crystals, and a second crop isolated from the filtrate, to contain a second compound, presumed to be the mono (hydrazone). The crystals and filtrate were therefore recombined and heated at reflux under nitrogen for 2 h, then let stand at 23 C for 6 days, after which time no mono (hydrazone) was detected by TLC analysis. The volatiles were removed in vacuo, and the residue was passed through silica using 4 vol % ethyl acetate in hexane as eluent to afford the bis(hydrazone) as a yellow powder (67 mg). Field desorption mass spectrometry: 459 m/z.

Example 52

Preparation of h16. Reaction of 2,6-Diacetylpyridine and 1-amino-2,5-dimethylpyrrole to Afford the Corresponding bis(Hydrazone)

A 250 mL round bottom flask was sequentially charged with 2,6-diacetylpyridine (427 mg), 1-amino-2,5-dimethylpyrrole (668 mg), ethanol (10 mL), and formic acid (2 drops), then concentrated to a volume of ca. 3 mL under a stream of dry nitrogen and stand at 23 C for 16 h. The yellow crystals that separated were collected by vacuum filtration, washed with cold ethanol (3×5 mL), and dried in vacuo to yield 740 mg (81%). Field desorption mass spectrometry: 347 m/z.

Example 53

Preparation of g18. Reaction of 2,6-Diacetylpyridine and 4-aminomorpholine to Afford the Corresponding bis(Hydrazone)

A 2 drain vial was sequentially charged with 2,6-diacetylpyridine (0.810 g), 4-aminomorpholine (1.22 g), ethanol (1 mL), and formic acid (1 drop) and agitated to afford a crusty yellow mass. The mixture was triturated with an additional 5 mL ethanol and then allowed to stand at 23 C for 16 h. The yellow crystals that separated were collected by vacuum filtration, washed with ethanol and dried on the filter for several hours to give 1.6 g product.

Example 54

Preparation of g19. Reaction of 2,6-Diacetylpyridine and 1-amino-4-methylpiperazine to Afford the Corresponding bis(Hydrazone)

A 2 dram vial was sequentially charged with 2,6-diacetylpyridine (0.830 g), 1-amino-4-methylpiperazine (1.28 g), ethanol (4 mL), and formic acid (1 drop). After 1 h, the mixture was briefly concentrated under a flow of nitrogen gas until the product began to crystallize, then let stand at 23 C for 16 h. The yellow crystals that separated were collected by vacuum filtration, washed with ethanol, and dried in vacuo for several hours to obtain 1.2 g of the bis(Hydrazone).

Example 55

Preparation of g17. Reaction of 2,6-Diacetylpyridine and 1-amino-2,6-dimethylpiperidine to Afford the Corresponding bis (Hydrazone)

A 2 dram vial was sequentially charged with 2,6-diacetylpyridine (0.248 g), 1-amino-2,6-dimethylpiperidine (0.525 g), ethanol (4 drops), and formic acid (1 drop) to afford a viscous mixture. After 2 h, 0.6 g ethanol was added to obtain a homogeneous mixture, which was allowed to stand at 23 C for 16 h. The yellow crystals that separated were collected by vacuum filtration, washed with etanol (2×2 mL) and dried to obtain 0.366 g of the bis(Hydrazone).

Example 56

Preparation of the Iron Dichloride Complex of g17

Under an inert nitrogen atmosphere, a solution of g17 (95.4 mg; 0.249 mmol) in 4 mL THF (tetrahydrofuran) was added dropwise to a suspension of $FeCl_2$ in 2 mL THF. Upon addition the yellow drops immediately turned dark green. The mixture was agitated at room temperature for 24 h. Hexanes (12 mL) was then added. The precipitate was allowed to settle and the supernatant removed. The residue was washed with hexane (2×20 mL) and dried in vacuo to give 87.6 mg of a dark green solid.

Example 57

Ethylene Polymerization using the Iron Dichloride Complex of g17

Under nitrogen, a 1000-mL Parr® reactor was charged with 300 mL toluene and heated to 35° C. MMAO in toluene (Akzo Nobel, 7.12 wt % Al; 2 mL) was added, followed by the title complex (3.0 mL; 1.18 mM in toluene/$CH_2Cl_2$ 1:1). The vessel was pressurized to 200 psig and agitated for 54 min. The reaction was then quenched at elevated pressure with methanol. The reaction mixture was agitated in the presence of 6M HCl and then filtered. The collected solid was dried in vacuo to give 21.8 mg polymer. ($T_m$=124° C., $M_n$=330,000, $M_w$=675,000, 11 branches/1000 C by $^1$H NMR).

Example 58

Preparation of the Iron Dichloride Complex of h16

Under an inert nitrogen atmosphere, a solution of h16 (93.8 mg; 0.270 mmol) in 8 mL THF was added dropwise to a suspension of FeCl$_2$ (33.2 mg; 0.262 mmol) in 2 mL THF. Addition of the ligand caused an immediate color change to dark green. The suspension was stirred at room temperature for 5 days. Hexane (15 mL) was then added and the solid allowed to settle. The supernatant was then removed and the solid residue washed twice with 15 mL hexane. The green solid was dried in vacuo to yield 122 mg.

Example 59

Polymerization of Ethylene with the Iron Dichloride Complex of h16

A 300-mL pear-shaped flask was charged with the title complex (5.0 mg; 10.5 μmol) under nitrogen. The flask was placed in a room-temperature water bath and the atmosphere replaced with ethylene. MMAO in toluene (Akzo Nobel, 7.12 wt % Al; 2 mL) was added under vigorous stirring. No significant color change was observed. The reaction was quenched after 3.5 min by addition of methanol and 6M HCl. The slurry was filtered and the cake dried in a vacuum oven to give 1.37 g ($M_n$ (NMR)=1154, $T_m$=93° C., 11 branches/1000 C by $^1$H NMR). The filtrate was recovered and extraction with toluene. The combined organic fractions were dried and the volatiles removed under reduced pressure to give 1.73 g. Combined yield of both fractions: 3.10 g (180,000 TO h$^{-1}$).

Example 60

Polymerization of Ethylene with the Iron Dichloride Complex of h16 at Elevated Pressure (200 psig)

Under nitrogen, a 1000-mL Parr® reactor was charged with 300 mL toluene and heated to 45° C. A solution of the title complex (2.0 mL; 0.749 mM in toluene) was added, followed by MMAO in toluene (Akzo Nobel, 7.12 wt % Al; 2 mL). The vessel was pressurized to 200 psig and agitated for 15 min. The reaction was then quenched at elevated pressure with methanol. The reaction mixture was agitated in the presence of 6M HCl and then filtered. The collected solid was dried in a vacuum oven to give 28.62 g of polymer. The filtrate was recovered and extracted with toluene. The combined organic fractions were dried over sodium sulfate and the volatiles removed in vacuo, yielding 14.90 g additional material. The combined yield of the reaction was 43.52 g (4.14×10$^6$ TO h$^{-1}$).

Example 61

Preparation of the Supported Iron Dichloride Complex of h16

A 50-mL pear-shaped flask, previously heated to 200° C. for several hours and allowed to cool to room temperature under vacuum, was charged with 1.70 g MAO-treated silica (purchased from Witco TA 02794/HL/04) and the iron dichloride complex of h16 (8.0 mg; 17 μmol) under a nitrogen inert atmosphere. The flask was equipped with a magnetic stirring bar and a septum cap. The solid was cooled to 0 ° C. and dichloromethane (15 mL) was added under vigorous stirring. After 1 hour, the volatiles were removed in vacuo. The resulting solid was stored at −30° C. Yield: 1.57 g. Loading of Fe complex/g support: 15.2 μmol/g (based on Fe-content analysis).

Example 62

Polymerization of Ethylene with the Supported Iron Dichloride Complex of h16

A 300-mL pear-shaped flask, previously heated to 200° C. for several hours and allowed to cool to room temperature under vacuum, was charged with 227 mg of the title catalyst under nitrogen. Toluene (100 mL) was then added and the atmosphere immediately replaced with ethylene. The suspension was agitated for 90 min, at room temperature, under 1 atm ethylene. The reaction was then quenched with methanol and 6M HCl. The mixture was filtered, the solid collected and dried in a vacuum oven (133 mg; GPC $M_n$=810, $M_w/M_n$=6.4; NMR $M_n$=1379 (77% terminal olefin); Tm=119° C.). The filtrate was also recovered and extracted with toluene. The organic layers were combined and the volatiles removed under reduced pressure. The residue was dried in a vacuum oven (0.07 g; GPC $M_n$=380, $M_w/M_n$=20; NMR $M_n$=531 (98% terminal olefin); Tm=63° C.).

Example 63

Preparation of the Cobalt Dichloride Complex of h16

Under an inert nitrogen atmosphere, h16 (107.7 mg; 0.310 mmol) in 10 mL THF was added dropwise to a suspension of CoCl$_2$ (39.1 mg; 0.301 mmol) in 2 mL THF. No color change was observed. The suspension was agitated for 5 days. Hexane (15 mL) was added and the solid allowed to settle. The supernatant was removed and the solid subsequently washed with 2×15 mL hexane. The solid residue was dried in vacuo and a mustard yellow solid was collected.

Example 64

Polymerization of Ethylene with the Cobalt Dichloride Complex of h16

Under nitrogen, a 300-mL pear-shaped flask was charged with the title complex (8.9 mg; 19 μmol) and 100 mL toluene. The flask was placed in a room-temperature water bath and the atmosphere replaced with ethylene. MMAO in toluene (Akzo Nobel, 7.12 wt % Al; 2 mL) was added under vigorous stirring, leading to an immediate color change to purple. The reaction was quenched after 3.5 min by addition of methanol and 6M HCl. The slurry was filtered and the cake dried in a vacuum oven to give 823 mg ($M_n$ (NMR)= 948, $T_m$=97° C.). The filtrate was recovered and extraction with toluene. The combined organic fractions were dried and the volatiles removed under reduced pressure to give 0.91 g. Combined yield of both fractions: 1.73 g (56,900 TO h$^{-1}$).

Example 65

Preparation of the Iron Dichloride Complex of g18

Under an inert nitrogen atmosphere, g18 (96.6 mg; 0.291 mmol) in 5mL THF was added to a suspension of FeCl$_2$ (35.2 mg; 0.278 mmol) in 2 mL THF. The suspension was agitated for 4 days. Hexane (15 mL) was added and the solid allowed to settle. The supernatant was removed and the solid subsequently washed with 2×20 mL hexane. The solid residue was dried in vacuo and a dark green solid was collected (101 mg).

Example 66

Polymerization of Ethylene with the Iron Dichloride Complex of g18

A 300-mL pear-shaped flask was charged with the title complex (2.7 mg; 5.9 μmol) under nitrogen. The atmosphere was replaced with ethylene. MMAO in toluene (Akzo Nobel, 7.12 wt % Al; 2 mL) was subsequently added under vigorous stirring. No ethylene uptake was apparent. The reaction was quenched after 20 min by addition of methanol and 6M HCl.

Example 67

Preparation of the Cobalt Dichloride Complex of g18

Under an inert nitrogen atmosphere, g 18 (91.8 mg; 0.277 mmol) in 5 mL THF was added to a suspension of $CoCl_2$ (34.9 mg; 0.277 mmol) in 2 mL THF. The suspension was agitated for 4 days. Hexane (15 mL) was added and the solid allowed to settle. The supernatant was removed and the solid subsequently washed with 2×20 mL hexane. The solid residue was dried in vacuo and an orange solid was collected (119 mg).

Example 68

Polymerization of Ethylene with the Cobalt Dichloride Complex of g18

A 300-mL pear-shaped flask was charged with the title complex (4.5 mg; 9.8 µmol) under nitrogen. The atmosphere was replaced with ethylene. MMAO in toluene (Akzo Nobel, 7.12 wt % Al; 2 mL) was subsequently added under vigorous stirring. The solution immediately turned purple. The reaction was quenched after 60 min by addition of methanol and 6M HCl. An organic extraction with toluene was performed on the reaction mixture. The organic fractions were combined and the volatiles removed in vacuo. The residue was heated and dried in vacuo to give 0.09 g polymer (327 TO $h^{-1}$).

Example 69

Preparation of the Iron Dichloride Complex of g19

Under an inert nitrogen atmosphere, g19 (83.8 mg; 0.234 mmol) in 5 mL THF was added to a suspension of $FeCl_2$ (28.2 mg; 0.222 mmol) in 2 mL THF. An immediate color change to green was observed. The suspension was agitated for 24 hours. Hexane (15 mL) was added and the solid allowed to settle. The supernatant was removed and the solid subsequently washed with 2×20 mL hexane. The solid residue was dried in vacuo and a dark green solid was collected (96.5 mg).

Example 70

Polymerization of Ethylene with the Iron Dichloride Complex of g19

A 300-mL pear-shaped flask was charged with the title complex (5.9 mg; 12 µmol) under nitrogen. The atmosphere was replaced with ethylene. MMAO in toluene (Akzo Nobel, 7.12 wt % Al; 2 mL) was subsequently added under vigorous stirring. No ethylene uptake was apparent. The reaction was quenched by addition of methanol and 6M HCl.

Example 71

Preparation of the Cobalt Dichloride Complex of g19

Under an inert nitrogen atmosphere, g19 (42.3 mg; 0.118 mmol) in 5 mL THF was added to a suspension of $CoCl_2$ (14.9 mg; 0.115 mmol) in 2 mL THF. The suspension was agitated for 24 hours. Hexane (15 mL) was added and the solid allowed to settle. The supernatant was removed and the solid subsequently washed with 2×20 mL hexane. The solid residue was dried in vacuo and an orange-brown solid was collected (48.6 mg).

Example 72

Polymerization of Ethylene with the Cobalt Dichloride Complex of g19

A 300-mL pear-shaped flask was charged with the title complex (7.2 mg; 15 µmol) under nitrogen. The atmosphere was replaced with ethylene. MMAO in toluene (Akzo Nobel, 7.12 wt % Al; 2 mL) was subsequently added under vigorous stirring. The solution immediately turned purple. The reaction was quenched after 20 min by addition of methanol and 6M HCl. An organic extraction with toluene was performed on the reaction mixture. The organic fractions were combined and the volatiles removed in vacuo. The residue was heated and dried in vacuo to give 0.06 g polymer (433 TO $h^{-1}$).

Example 73

Preparation of the Iron Dichloride Complex of h17

Under an inert nitrogen atmosphere, a solution of h17 (26.6 mg; 57.9 µmol) in 5 mL THF was added dropwise to a suspension of $FeCl_2$ (7.2 mg; 57 µmol) in 2 mL THF. The solution gradually turned green over 12 hours. Addition of hexane (15 mL) presumably led to decomposition of the complex, as evidenced by the resulting white solid suspended in a yellow solution. THF (10 mL) was then added to the mixture that was subsequently pumped to dryness under a reduced atmosphere. The solid was then suspended in THF (10 mL) and the suspension allowed to stir at room temperature for 18 hours. The volatiles were then removed in vacuo to give a green solid.

Example 74

Polymerization of Ethylene with the Iron Dichloride complex of h17

Under nitrogen, a 1000-mL Parr® reactor was charged with 300 mL toluene and 0.45 mL of MMAO (Akzo Nobel, 7.12 wt % Al) and heated to 50° C. A solution of the title complex (2.0 mL; 0.17 mM in toluene:dichloromethane 1:1) was introduced via an injection loop as the vessel was being pressurized. The solution was vigorously agitated for 30 min. The reaction was then quenched at elevated pressure with methanol. The solution was then transferred to a beaker and stirred with 6M HCl. The solution was extracted with toluene. The organic layers were combined and the volatiles removed on a rotary evaporator to give, after drying in an oven, 0.83 g of product (174,000 TO/h).

Example 75

Preparation of the Cobalt Dichloride Complex of h17

Under an inert nitrogen atmosphere, a solution of h17 (19.3 mg; 42.0 µmol) in 7 mL THF was added to a suspension of $CoCl_2$ (5.3 mg; 41 µmol) in 2 mL THF. The solution gradually turned amber and within 45 min, had evolved to an olive-green color. The mixture was stirred at room temperature for about 18 h after which, the volatiles were removed in vacuo.

Example 76

Polymerization of Ethylene with the Cobalt Dichloride Complex of h17

Under nitrogen, a 300-mL pear-shaped flask was charged with the title complex (3.5 mg; 5.9 µmol) and 100 mL toluene. The atmosphere was then replaced with ethylene. The flask was placed in a room temperature water bath and MMAO in toluene (Akzo Nobel, 7.12 wt % Al; 2 mL) was added under vigorous stirring, leading to an immediate color change to purple. The reaction medium rapidly turned cloudy. The reaction was quenched after 4 min by addition of methanol and 6M HCl. The slurry was filtered and the cake dried in a vacuum oven to give 628 mg polymer. The filtrate was recovered and extracted with toluene. The combined organic fractions were dried and the volatiles removed under reduced pressure to give 335 mg. Combined yield of both fractions: 963 mg (87,300 TO h$^{-1}$).

Example 77

Synthesis of b4

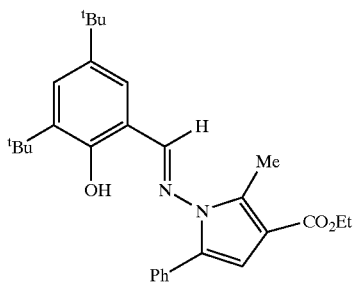

b4

A solution of 1-Amino-2-methyl-5-phenyl-1H-pyrrole-3-carboxylic acid ethyl ester (208 mg, 0.89 mmol) in toluene (17.6 mL) was treated with pyridinium p-toluenesulfonate (2.4 mg) and 3,5-di-tert-butyl-2-hydroxy-benzaldehyde (238 mg, 0.975 mmol) at room temperature. The resulting solution was immersed in a 130° C. oil bath, and stirred vigorously under Ar for 1.5 h. The solution was cooled to room temperature, and concentrated in vacuo. The residue was purified by flash chromatography (SiO$_2$, 30%–60% CH$_2$Cl$_2$/Hex) to afford b4 (190 mg, 46%).

Example 78

Synthesis of b5

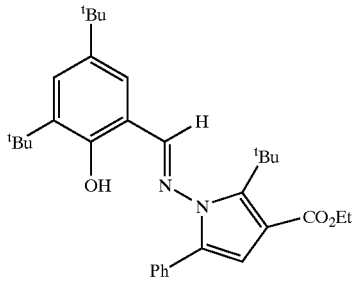

b5

A solution of 1-Amino-5-tert-butyl-2-phenyl-1H-pyrrole-3-carboxylic acid ethyl ester (240 mg, 0.79 mmol) in toluene (14.2 mL) was treated with pyridinium p-toluenesulfonate (1.7 mg) and 3,5-di-tert-butyl-2-hydroxy-benzaldehyde (160 mg, 0.69 mmol) at room temperature. The resulting solution was immersed in a 130° C. oil bath, and stirred vigorously under Ar for 6 h. The reaction was cooled to room temperature and allowed to stand under Ar overnight. A second portion of 3,5-di-tert-butyl-2-hydroxy-benzaldehyde (65 mg, 0.28 mmol) was added and the reaction heated at reflux for 3 h, cooled to room temperature and concentrated in vacuo. The residue was purified by flash chromatography (SiO$_2$, 2%–15% EtOAc/Hex, where EtOAc and Hex refer to ethyl acetate and hexane, respectively) to afford b5 (230 mg, 58%).

Example 79

Synthesis of b3

A solution of 1-Amino-5-tert-butyl-2-methyl-1H-pyrrole-3-carboxylic acid ethyl ester (258 mg, 1.15 mmol) in toluene (20.8 mL) was treated with pyridinium p-toluenesulfonate (2.5 mg) and 3,5-di-tert-butyl-2-hydroxy-benzaldehyde (234 mg, 1.0 mmol) at room temperature. The flask was fitted with a Dean Stark trap, and immersed in a 150° C. oil bath for 6h, after which the temperature was raised to 170° C. for one hour. The reaction was cooled to room temperature and allowed to stand under Ar overnight, then treated with a second portion of 3,5-di-tert-butyl-2-hydroxy-benzaldehyde (70 mg, 0.30 mmol) and heated to 150° C. in an oil bath for 2.5 h. The solution was cooled to room temperature, and concentrated in vacuo. The residue was purified by flash chromatography (SiO$_2$, 2%–15% EtOAc/Hex) to afford b3 (325.5 mg, 74%).

Example 80

Preparation of the Iron Dichloride Complex of h19

A solution of h19 (129.7 mg; 0.275 mmol) in 6 mL THF was added to a suspension of FeCl$_2$ (33.4 mg; 0.264 mmol) at room temperature. The color of the supernatant immediately turned emerald-green. The suspension was agitated for 5 days. The volatiles were removed in vacuo to give a dark green solid.

Example 81

Preparation of the Cobalt Dichloride Complex of h19

A solution of h19 (96.2 mg; 0.204 mmol) in 6 mL THF was added to a suspension of CoCl$_2$ (25.5 mg; 0.196 mmol) at room temperature. The color of the supernatant turned amber/orange within 30 min. The suspension was agitated for 6 days. The solid was then allowed to settle and the supernatant removed. The residual solid was dried in vacuo to give a brownish solid.

Example 82

Preparation of the Iron Dichloride Complex of h20

A solution of h20 (86.2 mg; 0.270 mmol) in 8 mL THF was added to a suspension of FeCl$_2$ (33.0 mg; 0.260 mmol) at room temperature. The suspension was agitated for 8 days. The volatiles were removed in vacuo to give a brownish solid.

Example 83

Preparation of the Cobalt Dichloride Complex of h20

A solution of h20 (40.6 mg; 0.127 mmol) in 6 mL THF was added to a suspension of CoCl$_2$ (15.8 mg; 0.122 mmol) at room temperature. The suspension was agitated for 8 days. The volatiles were removed in vacuo and the residual solid dried in vacuo.

Example 84

Preparation of the Iron Dichloride Complex of h21

A solution of h21 (77.4 mg; 0.130 mmol) in 8 mL THF was added to a suspension of $FeCl_2$ (15.8 mg; 0.125 mmol) at room temperature. The suspension was agitated for 8 days. The volatiles were removed in vacuo to give a brownish solid.

Example 85

Preparation of a Stock Solution of the Iron Dichloride Complex of h21

A solution of h21 (4.8 mg; 20 µmol) in 5 mL $CH_2Cl_2$ was added to a suspension of FeCl2.x THF (12.2 mg; 20.4 µmol) at room temperature. The suspension was agitated for 8 days. Dichloromethane was added to give a total volume of 10 mL (2.04 mM).

Example 86

Preparation of a Stock Solution of the Iron Complex of h21

A solution of h21 (8.7 mg; 15 µmol) in 5 mL $CH_2Cl_2$ was added to a suspension of bis(acetylacetonato)iron (3.7 mg; 15 µmol) at room temperature. The suspension was agitated for 8 days. Dichloromethane was added to give a total volume of 20 mL (0.75 mM).

Example 87

Preparation of the Cobalt Dichloride Complex of h21

A solution of h21 (89.4 mg; 0.150 mmol) in 6 mL THF was added to a suspension of $CoCl_2$ (18.7 mg; 0.144 mmol) at room temperature. The suspension was agitated for 8 days. The volatiles were removed in vacuo and the residual solid dried in vacuo.

Example 88

Preparation of a Stock Solution of the Cobalt Complex of h21

A solution of h21 (4.1 mg; 6.9 µmol) in 5 mL $CH_2Cl_2$ was added to bis(1,1,1,5,5,5,-hexafluoroacetylacetonato) cobalt.2.5 $H_2O$ (3.6 mg; 6.9 µmol) in 3 mL $CH_2Cl_2$ at room temperature. The purple solution readily turned orange. Dichloromethane was added to give a total volume of 20 mL (0.35 mM).

Example 89

Preparation of a Cobalt Complex of h22

A solution of h22 (8.1 mg; 16 µmol) in 5 mL n-butanol was added to bis(acetylacetonato)cobalt (4.1 mg; 16 µmol) in 3 mL n-butanol at room temperature. The suspension gradually turned homogeneous. The volatiles were removed in vacuo.

Example 90

Preparation of an Iron Complex of h23

A solution of h23 (21.4 mg; 33.3 µmol) in 2 mL THF was added to $FeCl_2$ (4.2 mg; 33 µmol) in 4 mL THF at room temperature. After 1 day, n-butanol (10 mL) was added and the resulting mixture heated with a constant flow of nitrogen to strip off any volatiles. The residue was redispersed in n-butanol and a suspension $TlPF_6$ (11.6 mg; 33.3 µmol) in 5 mL n-butanol was added. The suspension was stirred for 1 day and the volatiles then removed under reduced pressure.

Example 91

Preparation of a Stock Solution of the Iron Complex of h23

A solution of h23 (11.7 mg; 20.2 µmol) in 5 mL $CH_2Cl_2$ was added to bis(acetylacetonato)iron (4.9 mg; 19 µmol) in 3 mL $CH_2Cl_2$ at room temperature. The purple solution readily turned orange. Dichloromethane was added to give a total volume of 15 mL (1.29 mM).

Example 92

Preparation of a Stock Solution of the Cobalt Complex of h23

A solution of h23 (9.6 mg; 17 µmol) in 3 mL $CH_2Cl_2$ was added to bis(1,1,1,5,5,5,-hexafluoroacetylacetonato)cobalt (8.5 mg; 16 µmol) in 2 mL $CH_2Cl_2$ at room temperature. The purple solution readily turned orange. Dichloromethane was added to give a total volume of 10 mL (1.7 mM).

Example 93

Preparation of a Stock Solution of the Iron Dichloride Complex of h24

A solution of h24 (10.0 mg; 20.9 µmol) in 4 mL $CH_2Cl_2$ was added to FeCl2.x THF (4.9 mg; 21 µmol) in 2 mL $CH_2Cl_2$ at room temperature. The suspension slowly turned orange. Dichloromethane was added to give a total volume of 20 mL (1.0 mM).

Example 94

Preparation of a Stock Solution of the Iron Complex of h24

A solution of h24 (44.8 mg; 93.0 µmol) in 10 mL $CH_2Cl_2$ was added to bis(acetylacetonato)iron (23.3 mg; 91.7 µmol) in 10 mL $CH_2Cl_2$ at room temperature. The purple solution readily turned orange and was used as a stock solution for polymerization (4.59 mM).

Example 95

Preparation of a Stock Solution of the Iron Complex of h24

A solution of h24 (4.0 mg; 8.3 µmol) in 5 mL $CH_2Cl_2$ was added to bis(1,1,1,5,5,5,-hexafluoroacetylacetonato)iron (3.4 mg; 7.2 µmol) (prepared as described in J. Chem. Soc. (A) 1970, 3153 by F. G. A. Stone et al.) in 3 mL $CH_2Cl_2$ at room temperature. The purple solution readily turned orange. Dichloromethane was added to give a total volume of 10 mL (0.72 mM).

Example 96

Preparation of a Stock Solution of the Cobalt Complex of h24

A solution of h24 (4.0 mg; 8.3 µmol) in 5 mL $CH_2Cl_2$ was added to bis(1,1,1,5,5,5,-hexafluoroacetylacetonato)

cobalt.2.5 H$_2$O (4.4 mg; 8.5 μmol) in 4 mL CH$_2$Cl$_2$ at room temperature. Dichloromethane was added to give a total volume of 20 mL (0.42 mM).

Example 97

Preparation of a Stock Solution of the Iron Complex of h25

A solution of h25 (4.3 mg; 18 μmol) in 5 mL CH$_2$Cl$_2$ was added to a suspension of FeCl$_2$.x THF (11.1 mg; 20.3 μmol) at room temperature. The suspension was agitated for 8 days. Dichloromethane was added to give a total volume of 10 mL (1.83 mM).

Example 98

Preparation of a Stock Solution of the Cobalt Complex of h25

A solution of h25 (6.5 mg; 12 μmol) in 5 mL CH$_2$Cl$_2$ was added to bis(1,1,1,5,5,5,-hexafluoroacetylacetonato) cobalt.2.5 H$_2$O (5.5 mg; 11 μmol) in 3 mL CH$_2$Cl$_2$ at room temperature. The purple solution readily turned orange. Dichloromethane was added to give a total volume of 15 mL (0.71 mM).

Example 99

High-pressure Polymerization of Ethylene using a Catalyst Prepared as in Example 91

A 1000-mL Parr® reactor was charged with 300 mL toluene and 2.0 mL MAO (10 wt % in toluene). The resulting solution was heated to 44° C. and then pressurized to 200 psi with vigorous stirring. A solution of an iron complex prepared as in Example 91 (0.68 μmol total Fe) was added under pressure through an injection loop by slightly depressurizing the reactor. Upon injection, the internal temperature rose to 47° C. The reaction mixture was agitated under 200 psi ethylene for 5 min and then quenched with MeOH under elevated pressure. The reactor was vented and the mixture further treated with 6M HCl. A liquid-liquid extraction was performed on the slurry. The organic layers were combined and the volatiles removed on a rotary evaporator. The solid residue was further dried in a vacuum oven to give 4.26 g polyethylene. GPC: $M_n$=29,500; $M_w/M_n$=2.4.

Example 100 to Example 125

High Pressure Polymerization of Ethylene using pro-catalysts Prepared as in Examples 80–98

The examples summarized in Table I were generated following the procedure of Example 99.

TABLE 1

| Example # | Catalyst Prepared as in Example # | Qty of metal used (μmol) | Pressure (psi); Temperature (° C.) | Time (min) | Total yield (g) | GPC Mn | Toluene-insoluble Fraction NMR Mn | Toluene-insoluble Fraction % terminal olefin | Toluene soluble Fraction: Tm | Toluene soluble Fraction: NMR Mn; % terminal olefin |
|---|---|---|---|---|---|---|---|---|---|---|
| 100 | 56[f] | 3.5 | 200; 35 | 54 | 0.022 | 330K | — | | 124 | — |
| 101 | 58[g] | 0.016 | 200; 60 | 60 | 12.22 | 590 | 655; | >99% | 89 | 362; >99% |
| 102 | 63[g] | 0.21 | 200; 62 | 60 | 44.85 | 660 | 585; | >99% | 89 | 355; 98% |
| 103 | 67[f] | 9.8 | 15; RT | 60 | 0.09 | — | — | | — | 400[GPC Mn] |
| 104 | 71[f] | 15 | 15; RT | 20 | 0.06 | 460 | — | | — | 666 |
| 105 | 73[f] | 0.68 | 200; 50 | 15 | 14.78 | 600 | 1694; | 99% | 127 | — |
| 106 | 75[f] | 42 | 15; RT | 4 | 0.96 | 2960 | 3374; | 83% | 132 | 869; >99% |
| 107 | 80[f] | 3.8 | 15; RT | 3 | 0.57 | — | — | | — | 830; 97% |
| 108 | 81[f] | 3.5 | 15; RT | 3 | 10.63 | — | — | | — | 209; 93% |
| 109 | 82[f] | 7.2 | 15; RT | 10 | 3.26[†] | — | — | | — | 175; 93% |
| 110 | 83[f] | 7.6 | 15; RT | 10 | 2.08[‡] | — | — | | — | 183; 93% |
| 111 | 84[f] | 7.9 | 15; RT | 10 | 0.21 | 3220 | 1362; | >99% | — | |
| 112 | 85[g] | 1.4 | 200; 59 | 5 | 1.23 | 1270 | 2848; | >99% | 131 | — |
| 113 | 86[g] | 1.5 | 200; 59 | 60 | 3.77 | 3890 | 3281; | 90% | 132 | 360; >99% |
| 114 | 87[f] | 3.7 | 15; RT | 10 | 0.01 | — | 472; | 93% | — | — |
| 115 | 88[g] | 0.70 | 200; 60 | 60 | 0.14 | 110 | 292; | >99% | — | — |
| 116 | 89[g] | 16 | 15; RT | 15 | 0.23 | 74.3K | 28.0K; | 93% | 138 | 1968; 83% |
| 117 | 90[g] | 33 | 15; RT | 15 | 0.59 | 23.4K | — | | 137 | — |
| 118 | 91[g] | 0.68 | 200; 47 | 5 | 4.26 | 61.8K | >75K | | 136 | — |
| 119 | 92[g] | 5.8 | 15; RT | 15 | 0.097 | 15.4K | — | | 138 | — |

TABLE 1-continued

| | Catalyst | | | | | | Toluene-insoluble Fraction | Toluene soluble Fraction: |
|---|---|---|---|---|---|---|---|---|
| Example # | Prepared as in Example # | Qty of metal used (μmol) | Pressure (psi); Temperature (° C.) | Time (min) | Total yield (g) | GPC Mn | NMR Mn % terminal olefin | NMR Mn; Tm % terminal olefin |
| 120 | 93$^\pounds$ | 0.85 | 200; 57 | 5 | 2.65 | 6320 | 15.8K; 90% | 134 5105; >99% |
| 121 | 94$^\pounds$ | 0.46 | 600; 58 | 60 | 2.99 | 800 | 2873; >99% | 132 414; 17% |
| 122 | 95$^\pounds$ | 1.44 | 200; 58 | 58 | 1.21 | 4240 | 10.2K; 67% | 132 500; 99% |
| 123 | 96$^\pounds$ | 0.21 | 200; 47 | 60 | 7.10 | 5160 | 4838; 99% | 133 1229; 99% |
| 124 | 97$^\pounds$ | 3.6 | 200; 43 | 60 | 0.25 | 36.4K | >75K | 139 — |
| 125 | 98$^\pounds$ | 2.1 | 15; RT | 6 | 0.22 | 300 | 4624; 10% | 133 — |

$^\pounds$MAO (10 wt % Al in toluene) was used as cocatalyst.
$^f$MMAO (modified methylalumoxane; 23% iso-butylaluminoxane in heptane; 6.4% Al) was used as cocatalyst.
$^s$Total calculated yield from the isolated yield using GC analysis. Schultz-Flory constant = 0.52.
$^\dagger$Total calculated yield from the isolated yield using GC analysis. Schultz-Flory constant = 0.61.
$^\ddagger$Total calculated yield from the isolated yield using GC analysis. Schultz-Flory constant = 0.61.

Example 126

Preparation of the Supported Cobalt Dichloride Complex of h17

A 50-mL pear-shaped flask, previously heated to 200° C. for several hours and allowed to cool to room temperature under vacuum, was charged with 2.05 g MAO-treated silica (purchased from Witco TA 02794/HL/04) and the iron dichloride complex of h17 (17.1 mg; 29.0 μmol) under a nitrogen inert atmosphere. The flask was equipped with a magnetic stirring bar and a septum cap. The solid was cooled to 0° C. and dichloromethane (20 mL) was added under vigorous stirring. After 1 hour, the volatiles were removed in vacuo. The resulting solid was stored at −30° C. Yield: 2.05 g.

Example 127

Polymerization of Ethylene with the Supported Cobalt Dichloride Complex of h17

A 300-mL pear-shaped flask, previously heated to 200° C. for several hours and allowed to cool to room temperature under vacuum, was charged with 184 mg of the title catalyst under nitrogen. Toluene (100 mL) was then added and the atmosphere immediately replaced with ethylene. The suspension was agitated for 4 hours, at room temperature, under 1 atm ethylene. The reaction was then quenched with methanol and 6M HCl. The mixture was filtered, the solid collected and dried in a vacuum oven (86 mg). NMR $M_n$=5510 (100% terminal olefin); $T_m$=127° C.

Example 128

Polymerization of Ethylene Using the Iron Dichloride Complex of h16

1000-mL Parr® reactor was charged with 300 mL toluene and 2.0 mL MAO (10 wt % in toluene). The resulting solution was heated to 60° C. and then pressurized to 200 psi with vigorous stirring. A solution of the iron dichloride complex of h16 (11 nmol Fe) was added under pressure through an injection loop. The reaction mixture was agitated under 200 psi ethylene for 60 min and then quenched with MeOH under elevated pressure. The reactor was vented and the mixture further treated with 6M HCl. Solid material was isolated by filtration (3.44 g; $^1$H NMR: $M_n$=5090, 21 BP/1000 C, where BP/1000C refers to branch points per 1000 carbons, >99% terminal olefin; GPC: $M_n$=580, $M_w/M_n$=1.5; $T_m$=89° C.). Additional material was isolated by performing a liquid-liquid extraction on the filtrate using toluene. The organic layers were combined and the volatiles removed on a rotary evaporator. The solid residue was further dried in a vacuum oven to give 14.46 g polyethylene ($^1$H NMR: $M_n$=4118, 64 BP/1000C, 99% terminal olefin; GPC: $M_n$=130, $M_w/M_n$=1.8; $T_m$=55° C.), for a total combined yield of 13.50 g (1.4M TO, where TO refers to mol olefin monomer/mol metal). The combined fractions was further analyzed by NMR to give an $M_n$ value of 477 (99% terminal olefin) with 4 BP/1000 C.

Example 129

Copolymerization of Ethylene and 1-Hexene Using the Iron Dichloride Complex of h16

A 1000-mL Parr® reactor was charged with 270 mL toluene, 30 mL 1-hexene and 2.0 mL MAO (10 wt % in toluene). The resulting solution was heated to 60° C. and then pressurized to 200 psi with vigorous stirring. A solution of the iron dichloride complex of h16 (6.0 nmol Fe) was added under pressure through an injection loop.

The reaction mixture was agitated under 200 psi ethylene for 60 min and then quenched with MeOH under elevated pressure. The reactor was vented and the mixture further treated with 6M HCl. Solid material was isolated by filtration (7.62 g; $^1$H NMR: $M_n$=1590, 2 BP/1000 C, 98% terminal olefin; GPC: $M_n$=540, $M_w/M_n$=1.8; $T_m$=91° C.). Additional material was isolated by performing a liquid-liquid extraction on the filtrate using toluene. The organic layers were combined and the volatiles removed on a rotary evaporator. The solid residue was further dried in a vacuum oven to give 6.92 g polyethylene ($^1$H NMR: $M_n$=364, 20 BP/1000C, >99% terminal olefin; GPC: $M_n$=210, $M_w/M_n$=1.2; $T_m$=55° C.), for a total combined yield of 14.54 g (86M TO). $^{13}$C NMR showed poor incorporation of 1-hexene.

Example 130

Preparation of the Iron Dichloride Complex of h21

A solution of h21 (3.7 mg; 6.2 μmol) in 5 mL dichloromethane was added to a suspension of FeCl$_2$.THF (1.4 mg; 6.0 μmol) in 1 mL CH$_2$Cl$_2$. The solution gradually turned green and then back to yellow after 7 hours. Additional dichloromethane was added to reach an iron concentration of 0.31 μmol/mL. This solution was used as is for Example 131.

Example 131

Polymerization of Ethylene Using the Dichloride Complex Prepared in Example 130

A 1000-mL Parr® reactor was charged with 300 mL toluene and 2.0 mL MAO (10 wt % in toluene). The resulting solution was heated to 45° C. and then pressurized to 200 psi with vigorous stirring. A solution of the iron complex as prepared in Example 130 (0.62 μmol Fe) was added under pressure through an injection loop. The reaction mixture was agitated under 200 psi ethylene for 60 min and then quenched with MeOH under elevated pressure. The reactor was vented and the mixture further treated with 6M HCl. The product was isolated by performing a liquid-liquid extraction on the reaction mixture. The organic layers were combined and the volatiles removed on a rotary evaporator. The solid residue was further dried in a vacuum oven to give 0.22 g (12,600 TO) polyethylene ($^1$H NMR: M$_n$=597, <1 BP/1000 C, 74% terminal olefin; GPC: M$_n$=300, M$_w$/M$_n$=6.7; T$_m$=119° C.).

Example 132

Preparation of the Iron Dichloride Complex of Ligand h28

To a suspension of FeCl$_2$.xTHF (2.2 mg; 9.4 μmol) in ca. 2 mL dichloromethane was added a solution of h28 (5.4 mg; 9.7 μmol) in 4 mL CH$_2$Cl$_2$. The yellow solution turned green within 30 min. Additional CH$_2$Cl$_2$ was added to reach a concentration of 0.53 μmol/mL.

Example 133

Polymerization of Ethylene Using the Iron Dichloride Complex of h28 Prepared in Example 132

A 1000-mL Parr® reactor was charged with 300 mL toluene and 2.0 mL MAO (10 wt % in toluene). The resulting solution was heated to 45° C. and then pressurized to 200 psi with vigorous stirring. A solution of the iron complex as prepared in Example 132 (1.1 μmol Fe) was added under pressure through an injection loop. The reaction mixture was agitated under 200 psi ethylene for 60 min and then quenched with MeOH under elevated pressure. The reactor was vented and the mixture further treated with 6M HCl. The product was isolated by performing a liquid-liquid extraction on the reaction mixture with toluene. The organic layers were combined and the volatiles removed on a rotary evaporator. The solid residue was further dried in a vacuum oven to give 3.56 g (120K TO) polyethylene ($^1$H NMR: M$_n$=2082, <1 BP/1000 C, 78% terminal olefin; GPC: M$_n$=1800, M$_w$/M$_n$=1.6; T$_m$=128° C.).

Example 134

Preparation of the Iron Trichloride Complex of h17

Under an inert nitrogen atmosphere, a solution of h17 (5.6 mg; 0.016 mmol) in 2 mL dichloromethane was added to a suspension of FeCl$_3$.6H$_2$O (4.5 mg; 0.017 mmol) in dichloromethane, leading to an immediate color change from yellow to dark brown. The solution was stirred at room temperature for about 18 hours before use as polymerization catalyst.

Example 135

Ethylene Polymerization Using the Iron Trichloride Complex of h17 Generated as in Example 134

Under nitrogen, a 300-mL pear-shaped flask was charged with 100 mL toluene. MAO (Aldrich, 10 wt % in toluene; 1.0 mL) was added to the solvent. The flask was evacuated and backfilled with ethylene. The iron complex (0.014 mmol) was added with vigorous stirring. The solution was agitated for 15 min and the reaction was then quenched by addition of methanol and 6M HCl. The product was extracted with toluene. The volatiles were then removed to give 0.03 g (76 TO) solid material. $^1$H NMR: M$_n$=653; 63 BP/1000C; >99% terminal olefin.

Example 136

Preparation of the Iron Bis(tetrafluoroborate) Complex of h17

To a suspension of iron(II) bis(tetrafluoroborate) hexahydrate (4.9 mg; 15 μmol) in dichloromethane was added a solution of h17 (5.0 mg; 14 μmol) in a few milliliters of dichloromethane. The solution turned from light yellow to dark orange with time within 18 hours. The solution was used as is in further polymerization study.

Example 137

Ethylene Polymerization Using the Iron Bis (tetrafluoroborate) Complex of h17 as Prepared in Example 136

Under nitrogen, a 300-mL pear-shaped flask was charged with 100 mL toluene. MAO (Aldrich, 10 wt % in toluene; 1.0 mL) was added to the solvent. The flask was evacuated and backfilled with ethylene. The iron complex (0.014 mmol) was added with vigorous stirring. The solution was agitated for 7 min and the reaction was then quenched by addition of methanol and 6M HCl. The product was isolated by performing a liquid extraction with toluene. The organic layers were combined and the volatiles removed in vacuo to give 2.17 g (119,000 TO); $^1$H NMR: M$_n$=993, 4 BP/1000 C, >99% terminal olefin; GPC: M$_n$=630, M$_w$/M$_n$=7.7; T$_m$=124° C.).

Example 138

Preparation of an Iron Complex of h17

To a solution of h17 (5.0 mg; 0.014 mmol) in dichloromethane was added tris(pentafluorophenyl)borane (72.1 mg; 0.141 mmol) in dichloromethane, with subsequent addition of FeCl$_3$ (2.3 mg; 0.014 mmol). The solution was stirred at room temperature for about 18 hours before being used in the polymerization of ethylene.

Example 139

Preparation of an Iron Complex of h25

To a suspension of FeCl$_3$ (2.6 mg; 16 μmol) in dichloromethane was added tris(pentafluorophenyl)borane (71.6 mg; 0.140 mmol), with subsequent addition of a solution of h25 (8.0 mg; 13 μmol) in dichloromethane. The solution was

Example 140

Ethylene Polymerization Using the Iron Complex of h25 as Prepared in Example 139

A 1000-mL Parr® reactor was charged with 300 mL toluene and 2.0 mL MAO (10 wt % in toluene). The resulting solution was heated to 60° C. and then pressurized to 600 psi with vigorous stirring. A solution of the iron complex as prepared in Example 139 (0.34 µmol Fe) was added under pressure through an injection loop. The reaction mixture was agitated under 600 psi ethylene for 60 min and then quenched with MeOH under elevated pressure. The reactor was vented and the mixture further treated with 6M HCl. Solid material was isolated by filtration (5.88 g; polymer could not be analyzed by GPC; $T_m$=91° C.). Additional material was isolated by performing a liquid-liquid extraction on the filtrate using toluene. The organic layers were combined and the volatiles removed on a rotary evaporator. The solid residue was further dried in a vacuum oven to give 7.62 g polyethylene (GPC: $M_n$=170, $M_w/M_n$=1.2; $T_m$=53° C.), for a total combined yield of 13.50 g (1.4M TO). The combined fractions were further analyzed by NMR to give an $M_n$ value of 477 (99% terminal olefin) with 4 BP/1000 C.

Example 141

Preparation of a Cobalt Complex of h25

To a solution of ca. 3 mL dichloromethane containing $Ph_3CB(C_6F_5)_4$ (15.4 mg; 16.7 µmol) and $Co(acac)_2$ (4.2 mg; 16.3 µmol) was added h25 (9.5 mg; 16.5 µmol) in dichloromethane (ca. 2 mL). The resulting solution was used as is in Example 142.

Example 142

Polymerization of Ethylene Using the Cobalt Complex of h25 Prepared in Example 141

A 300-mL oven-dried flask was charged with toluene (100 mL) under ethylene. MAO (Aldrich, 10 wt % in toluene; 1.0 mL) was added to the solution, followed by addition of a dichloromethane solution of the cobalt complex of h25 (16.3 µmol) prepared in Example 141. The reaction solution was stirred at room temperature for 3 min and then quenched with 6M HCl. The product was isolated by extraction with toluene (296 mg, 640 TO; NMR: $M_n$>50,000, <1 BP/1000 C; $T_m$=141° C.).

Example 143

Preparation of the Iron Bis(tetrafluoroborate) Complex of h25

A solution of h25 (5.1 mg; 8.9 µmol) in about 2 mL dichloromethane was added to a suspension of iron bis (tetrafluoroborate) hexahydrate (3.0 mg; 8.9 µmol) in dichloromethane. The mixture was stirred at room temperature for about 18 hours before being used in the polymerization of ethylene.

Example 144

Polymerization of Ethylene Using the Iron Complex of h25 as Prepared in Example 143

A 300-mL oven-dried flask was charged with toluene (100 mL) under ethylene. MAO (Aldrich, 10 wt % in toluene; 1.0 mL) was added to the solution, followed by addition of a dichloromethane solution of the iron complex of h25 (1.1 µmol), as prepared in Example 143. The reaction solution was stirred at room temperature for 10 min and then quenched with 6M HCl. The product was isolated by extraction with toluene (1.78 g, 7160 TO; NMR: $M_n$=786, 4 BP/1000 C, 94% thermal olefin; GPC: $M_n$=440, $M_w/M_n$=1.8; $T_m$=122° C.).

Example 145

Polymerization of Ethylene and 1-Hexene Using the Iron Dichloride Complex of h16

A 300-mL oven-dried flask was charged with toluene (90 mL) and 1-hexene (10 mL) under ethylene. MAO (Aldrich, 10 wt % in toluene; 2.0 mL) was added to the solution, followed by addition of a dichloromethane solution of iron dichloride complex of h16 (1.1 µmol). The reaction solution was stirred at room temperature or 20 min and then quenched with 6M HCl. The product was isolated by extraction with toluene (5.2 g; NMR: $M_n$=472, 48 BP/1000 C, 85% terminal olefin; GPC: $M_n$=330, $M_w/M_n$=2.1; $T_m$=88° C.). Analysis of NMR data suggests 18 mol % incorporation of 1-hexene.

Example 146

Polymerization of Ethylene and 1-Hexene Using the Iron Dichloride Complex of h16

A 1000-mL Parr® reactor was charged with 270 mL toluene and 2.0 mL MAO (10 wt % in toluene). The resulting solution was heated to 60° C. and then pressurized to 200 psi with vigorous stirring. A solution of the iron dichloride complex of h16 (6.0 nmol Fe) was added under pressure through an injection loop by slightly depressurizing the reactor. Upon injection, the internal temperature rose to 69° C. The reaction mixture was agitated under 200 psi ethylene for 60 min and then quenched with MeOH under elevated pressure. The reactor was vented and the mixture further treated with 6M HCl. Solid material was isolated by filtration (7.62 g; NMR: $M_n$=1590, 2 BP/1000 C, 98% terminal olefin; GPC: $M_n$=540, $M_w/M_n$=1.8; $T_m$=91° C.). Additional material was isolated by performing a liquid-liquid extraction on the filtrate using toluene. The organic layers were combined and the volatiles removed on a rotary evaporator. The solid residue was further dried in a vacuum oven to give 6.92 g polyethylene (NMR: $M_n$=364, 20 BP/1000C, >99% terminal olefin; GPC: $M_n$=210, $M_w/M_n$=1.2; $T_m$=55° C.), for a total combined yield of 14.54 g (86M TO).

Example 147

Polymerization of 1-Hexene Using the Iron Dichloride Complex of h16

A 300-mL oven-dried flask was charged with toluene (90 mL) and 1-hexene (10 mL) under nitrogen. MAO (Aldrich, 10 wt % in toluene; 2.0 mL) was added to the solution, followed by addition of a dichloromethane solution of iron dichloride complex of h16 (0.28 µmol). The reaction solution was stirred at room temperature for 24 min and then quenched with methanol and 6M HCl. The product was isolated by extraction with toluene (0.07 g; $M_n$=408, 137 BP/1000C, >99% terminal olefin; $M_n$ (GPC)=240, $M_w/M_n$=1.3).

Example 148

Polymerization of Ethylene Using the Iron Dichloride Complex of h16 in the Presence of Dichlorophenyl Ethyl Acetate ($PhCl_2CCO_2Et$)

A 1000-mL Parr® reactor was charged with 300 mL toluene and 2.0 mL MAO (10 wt % in toluene). The resulting solution was heated to 60° C. and then pressurized to 200 psi with vigorous stirring. A solution of the iron dichloride complex of h16 (6.0 nmol Fe) was added under pressure through an injection loop by slightly depressurizing the reactor. The reaction mixture was agitated under 200 psi ethylene for 5 min and then quenched with MeOH under elevated pressure. The reactor was vented and the mixture further treated with 6M HCl. Solid material was isolated by filtration (12.58 g; NMR: $M_n$=804, 2 BP/1000 C, 98% terminal olefin; GPC: $M_n$=650, $M_w/M_n$=1.5; $T_m$=92° C.). Additional material was isolated by performing a liquid-liquid extraction on the filtrate using toluene. The organic layers were combined and the volatiles removed on a rotary evaporator. The solid residue was further dried in a vacuum oven to give 5.73 g polyethylene (NMR: $M_n$=390, 5 BP/1000 C, >99% terminal olefin; GPC: $M_n$=9000, $M_w/M_n$=1.2; $T_m$=60° C.), for a total combined yield of 18.31 g (75M TO).

Example 149

Polymerization of Ethylene Using the Iron Dichloride Complex of h16

A 1000-mL Parr® reactor was charged with 270 mL toluene and 0.5 mL triisobutylaluminum (25 wt % in toluene). The resulting solution was heated to 60° C. and then pressurized to 200 psi with vigorous stirring. A solution of the iron dichloride complex of h16 (77 nmol Fe) was added under pressure through an injection loop by slightly depressurizing the reactor. A solution of trityl tetrakis (perfluorophenyl)borate (0.46 µmol) in dichloromethane was subsequently added under pressure. Upon injection, the internal temperature rose to 73° C. The reaction mixture was agitated under 200 psi ethylene for 60 min and then quenched with MeOH under elevated pressure. The reactor was vented and the mixture further treated with 6M HCl. Solid material was isolated by filtration (43.38 g; NMR: $M_n$=697, 3 BP/1000 C, >99% terminal olefin; GPC: $M_n$=360, $M_w/M_n$=1.9; $T_m$=101° C.). Additional material was isolated by performing a liquid-liquid extraction on the filtrate using toluene. The organic layers were combined and the volatiles removed on a rotary evaporator. The solid residue was further dried in a vacuum oven to give 2.72 g polyethylene (NMR: $M_n$=263, 2 BP/1000 C, >99% terminal olefin; GPC: $M_n$=110, $M_w/M_n$=1.1; $T_m$=35° C.), for a total combined yield of 46.10 g (21M TO).

Example 150

Polymerization of Ethylene Using the Iron Dichloride Complex of h16

A 1000-mL Parr® reactor was charged with 300 mL toluene and 1.7 mL diethylaluminum chloride (25 wt % in toluene). The resulting solution was heated to 60° C. and then pressurized to 200 psi with vigorous stirring. A solution of the iron dichloride complex of h16 (1.0 nmol Fe) was added under pressure through an injection loop by slightly depressurizing the reactor. The reaction mixture was agitated under 200 psi ethylene for 60 min and then quenched with MeOH under elevated pressure. The reactor was vented and the mixture further treated with 6M HCl. Solid material was isolated by performing a liquid-liquid extraction on the reaction mixture, using toluene. The organic layers were combined and the volatiles removed on a rotary evaporator. The solid residue was further dried in a vacuum oven to give 0.05 g polyethylene (NMR: $M_n$=876, 95 BP/1000 C, 69% terminal olefin; $T_m$=138° C.).

Example 151

Polymerization of Ethylene Using the Iron Dichloride Complex of h16

A 1000-mL Parr® reactor was charged with 300 mL toluene and 0.22 mL triisobutylaluminum (25 wt % in toluene). The resulting solution was heated to 60° C. and then pressurized to 200 psi with vigorous stirring. A solution of the iron dichloride complex of h16 (1.34 µmol Fe) was added under pressure through an injection loop by slightly depressurizing the reactor. The reaction mixture was agitated under 200 psi ethylene for 60 min and then quenched with MeOH under elevated pressure. The reactor was vented and the mixture further treated with 6M HCl. The mixture was filtered to give 5.37 g (NMR: $M_n$=935, 2 BP/1000 C, >99% terminal olefin; GPC: $M_n$=580, $M_w/M_n$=1.4; $T_m$=98° C.) of white solid. Additional solid material was isolated by performing a liquid-liquid extraction on the filtrate, using toluene. The organic layers were combined and the volatiles removed on a rotary evaporator. The solid residue was further dried in a vacuum oven to give 10.8 g (430K TO) polyethylene (NMR: $M_n$=329, 5 BP/1000 C, >99% terminal olefin; GPC: $M_n$=120, $M_w/M_n$=1.6; $T_m$=60° C.).

Example 152

Polymerization of Ethylene Using the Iron Dichloride Complex of h16

A 1000-mL Parr® reactor was charged with 300 mL toluene and a solution of solid MAO (3.0 mmol) in 2.0 mL toluene. The resulting solution was heated to 60° C. and then pressurized to 200 psi with vigorous stirring. A solution of the iron dichloride complex of h16 (0.011 µmol Fe) was added under pressure through an injection loop by slightly depressurizing the reactor. The reaction mixture was agitated under 200 psi ethylene for 60 min and then quenched with MeOH under elevated pressure. The reactor was vented and the mixture further treated with 6M HCl. The mixture was filtered to give 3.44 g (NMR: $M_n$=5090, 21 BP/1000 C, >99% terminal olefin; GPC: $M_n$=580, $M_w/M_n$=1.5; $T_m$=89°C.) of white solid. Additional solid material was isolated by performing a liquid-liquid extraction on the filtrate, using toluene. The organic layers were combined and the volatiles removed on a rotary evaporator. The solid residue was further dried in a vacuum oven to give 14.46 g (58M TO) polyethylene (NMR: $M_n$=5118, 64 BP/1000 C, 99% terminal olefin; GPC: $M_n$=130, $M_w/M_n$=1.8; $T_m$=55°C.).

Example 153

Polymerization of Ethylene Using the Iron Dichloride Complex of h16

A 1000-mL Parr® reactor was charged with 300 mL toluene and modified MAO (Akzo Nobel, —[(CH$_3$)$_{0.7}$(i-C$_4$H$_9$)$_{0.3}$AlO]—, 7.18 wt % Al). The resulting solution was heated to 60° C. and then pressurized to 200 psi with vigorous stirring. A solution of the iron dichloride complex of h16 (0.011 µmol Fe) was added under pressure through an injection loop by slightly depressurizing the reactor. The reaction mixture was agitated under 200 psi ethylene for 60 min and then quenched with MeOH under elevated pressure. The reactor was vented and the mixture further treated with 6M HCl. The mixture was filtered to give 7.97 g (NMR: $M_n$=664, 2 BP/1000 C, 99% terminal olefin; GPC: $M_n$=370, $M_w/M_n$=1.7; $T_m$=88° C.) of white solid. Additional solid material was isolated by performing a liquid-liquid extraction on the filtrate, using toluene. The organic layers were combined and the volatiles removed on a rotary evaporator. The solid residue was further dried in a vacuum oven to give 7.49 g polyethylene (GPC: $M_n$=150, $M_w/M_n$=1.3; $T_m$=55° C.). Total yield: 15.46 g (50×10$^6$ TO).

Example 154

Preparation of a Cobalt Complex of h29

A solution of ligand h29 (3.1 mg; 5.8 μmol) in dichloromethane was added to a suspension of Co(acac)$_2$ (1.7 mg; 6.6 μmol). Ph$_3$CB(C$_6$F$_5$)$_4$ (5.7 mg; 6.2 μmol) was subsequently added, followed by dichloromethane to reach a total volume of 3.0 mL.

Example 155

Ethylene Polymerization Using the Cobalt Complex of h29 as Prepared in Example 154

A 1000-mL Parr® reactor was charged with 300 mL toluene and 2.0 mL MAO (10 wt % in toluene). The resulting solution was heated to 60° C. and then pressurized to 200 psi with vigorous stirring. A solution of the cobalt complex as prepared in Example 154 (0.20 μmol Co) was added under pressure through an injection loop. The reaction mixture was agitated under 200 psi ethylene for 60 min and then quenched with MeOH under elevated pressure. The reactor was vented and the mixture further treated with 6M HCl. Solid material was isolated by filtration (8.77 g; GPC: $M_n$=323,000; $M_w$=953,000; $^1$H NMR: $M_n$=15,251, <1 BP/1000 C, 17% terminal olefin; $T_m$=91° C.).

Example 156

Preparation of a Cobalt Complex of h30

A solution of ligand h30 (3.5 mg; 7.6 μmol) in dichloromethane was added to Co(acac)$_3$ (2.9 mg; 8.1 μmol). Trityl tetrakis(pentafluorophenyl)borate (15.0 mg; 16.3 μmol) in dichloromethane was then added to the solution. The resulting solution was further diluted with dichloromethane to give a concentration of 88 nmol/mL.

Example 157

Ethylene Polymerization Using the Cobalt Complex of h30 as Prepared in Example 156

A 1000-mL Parr® reactor was charged with 300 mL toluene and 2.0 mL MAO (10 wt % in toluene). The resulting solution was heated to 60° C. and then pressurized to 200 psi with vigorous stirring. A solution of the cobalt complex as prepared in Example 156 (0.18 μmol Co) was added under pressure through an injection loop. The reaction mixture was agitated under 200 psi ethylene for 60 min and then quenched with MeOH under elevated pressure. The reactor was vented and the mixture further treated with 6M HCl. Solid material was isolated by filtration (7.38 g; 1.5M TO; $^1$H NMR: $M_n$>50K, <1 BP/1000C; $T_m$=138° C. GPC: $M_n$=346,000; $M_w$=978,000).

Example 158

Ethylene Polymerization in the Presence of Hydrogen Using the Cobalt Complex of h30 as Prepared in Example 156

A 1000-mL Parr® reactor was charged with 300 mL toluene, 50 mL hydrogen and 2.0 mL MAO (10 wt % in toluene). The resulting solution was heated to 60° C. and then pressurized to 200 psi with vigorous stirring. A solution of the cobalt complex as prepared in Example 156 (0.17 μmol Co) was added under pressure through an injection loop. The reaction mixture was agitated under 200 psi ethylene for 60 min and then quenched with MeOH under elevated pressure. The reactor was vented and the mixture further treated with 6M HCl. Solid material was isolated by filtration (1.51 g; $^1$H NMR: $M_n$=51K, 2 BP/1000 C, 83% terminal olefin; GPC: $M_n$=22.600; $M_w$=60,600; $T_m$=139° C.). A second fraction was isolated by performing an organic extraction on the filtrate. The combined organic fractions were dried over sodium sulfate and the volatiles were then removed in vacuo. The residue was further dried in a vacuum oven at 100° C. to give 0.13 g. The combined isolated yield amounted to 1.64 g (3.51×10$^5$ TO).

Example 159

Preparation of a Cobalt Complex of h22

A solution of ligand h22 (6.3 mg; 13 μmol) and Ph$_3$CB(C$_6$F$_5$)$_4$ (13.0 mg; 14.1 μmol) in dichloromethane was added to a solution of Co(acac)$_2$ (3.4 mg; 14 μmol) in dichloromethane to give a resulting concentration of 4.3 μmol/mL.

Example 160

Ethylene Polymerization Using the Cobalt Complex of h22 as Prepared in Example 159

A 1000-mL Parr® reactor was charged with 300 mL toluene and 2.0 mL MAO (10 wt % in toluene). The resulting solution was heated to 60° C. and then pressurized to 600 psi with vigorous stirring. A solution of the cobalt complex as prepared in Example 159 (0.17 μmol Co) was added under pressure through an injection loop. The reaction mixture was agitated under 600 psi ethylene for 60 min and then quenched with MeOH under elevated pressure. The reactor was vented and the mixture further treated with 6M HCl. Solid material was isolated by filtration (3.44 g; 710K TO; NMR: $M_n$>50,000, <1 BP/1000C, 51% terminal olefin; $T_m$=139° C.; GPC: $M_n$=372,000; $M_w$=859,000).

Example 161

Preparation of an Iron Complex of h22

A solution of ligand h22 (3.7 mg; 7.6 μmol) and Ph$_3$CB(C$_6$F$_5$)$_4$ (7.5 mg; 8.13 μmol) in dichloromethane was added to a solution of Fe(acac)$_2$ (2.0 mg; 7.9 μmol) in dichloromethane to give a resulting concentration of 1.7 μmol/mL.

Example 162

Ethylene Polymerization Using the Cobalt Complex of h22 as Prepared in Example 161

A 1000-mL Parr® reactor was charged with 300 mL toluene and 2.0 mL MAO (10 wt % in toluene). The resulting solution was heated to 60° C. and then pressurized to 200 psi with vigorous stirring. A solution of the cobalt complex as prepared in Example 161 (0.17 μmol Fe) was added under pressure through an injection loop. The reaction mixture was agitated under 200 psi ethylene for 60 min and then quenched with MeOH under elevated pressure. The reactor was vented and the mixture further treated with 6M HCl. Solid material was isolated by filtration (2.22 g; 645K TO; $^1$H NMR: $M_n$>50K, 1 BP/1000 C; $T_m$=140° C.; GPC: $M_n$=24,600; $M_w$=96,700).

Example 163

Preparation of Stock Solution of the Iron Complex of h31

A solution of ligand h31 (3.8 mg; 9.1 μmol) in dichloromethane was added to Fe(acac)$_2$ (2.3 mg; 9.1 μmol) and Ph$_3$CB(C$_6$F$_5$)$_4$ (8.5 mg; 9.2 μmol). The resulting solution was used in Example 164.

Example 164

Ethylene Polymerization Using the Iron Complex of h31 as Prepared in Example 163

A 300-mL oven-dried flask was charged with toluene (100 mL) under ethylene. MAO (Aldrich, 10 wt % in toluene; 1.0 mL) was added to the solution, followed by addition of a dichloromethane solution of the iron complex of h31 (9.1 μmol), as prepared in Example 163. The reaction solution was stirred at room temperature for 2 min and then quenched with 6M HCl. The product was isolated by extraction with toluene (2.70 g, 11,000 TO; $T_m$=132° C.; $^1$H NMR: $M_n$=6190; 18 BP/1000C; 17% terminal olefin; GPC: $M_n$=5110; $M_w$=31,600).

Example 165

Ethylene Polymerization Using an Iron Complex of h31 Prepared in a Similar Way as That Described in Example 163

A 1000-mL Parr® reactor was charged with 300 mL toluene and 2.0 mL MAO (10 wt % in toluene). The resulting solution was heated to 60° C. and then pressurized to 200 psi with vigorous stirring. A solution of the iron complex (0.16 μmol Fe) was added under pressure through an injection loop. The temperature immediately rose to 75° C. The reaction was ran at 66° C. for 10 min and then quenched with MeOH under elevated pressure. The reactor was vented and the mixture further treated with 6M HCl. Solid material was isolated by filtration (14.45 g; 3.2M TO). $^1$H NMR: $M_n$=19 600, <1 BP/1000C, 92% terminal olefin; GPC: $M_n$=16,100, $M_w/M_n$=7.1; $T_m$=138° C.

Example 166

Ethylene Polymerization Using an Iron Complex of h29 Prepared in a Similar Way as that Described in Example 163

A 1000-mL Parr® reactor was charged with 300 mL toluene and 2.0 mL MAO (10 wt % in toluene). The resulting solution was heated to 60° C. and then pressurized to 200 psi with vigorous stirring. A solution of the iron complex (0.27 μmol Fe) was added under pressure through an injection loop. The reaction mixture was agitated for 60 min and then quenched with MeOH under elevated pressure. The reactor was vented and the mixture further treated with 6M HCl. Solid material was isolated by filtration (7.52 g; 985K TO). ($^1$H NMR: $M_n$>75K, <1 BP/1000C; GPC: $M_n$=63.9K, $M_w/M_n$=10; $T_m$=142° C.)

Example 167

Preparation of a Stock Solution of the Cobalt Complex of h31

A solution of h31 (2.8 mg; 6.7 μmol) in dichloromethane was added to Co(acac)$_2$ (1.9 mg; 7.4 μmol) and Ph$_3$CB(C$_6$F$_5$)$_4$ (6.1 mg; 6.6 μmol). The resulting solution was used in Example 168.

Example 168

Ethylene Polymerization Using the Cobalt Complex of h31 as Prepared in Example 167

A 300-mL oven-dried flask was charged with toluene (100 mL) under ethylene. MAO (Aldrich, 10 wt % in toluene; 1.0 mL) was added to the solution, followed by addition of the dichloromethane solution of the cobalt complex of prepared in Example 167. The reaction solution was stirred at room temperature for 2 min and then quenched with 6M HCl. The product was isolated by extraction with toluene (1.65 g, 8790 TO; $^1$H NMR: $M_n$>50K, <1 BP/1000 C; $T_m$=139° C.; GPC: $M_n$=99,300; $M_w$=196,000).

Example 169

Preparation of a Stock Solution of the Iron Complex of h32

A solution of ligand h32 (9.0 mg; 17 μmol) in dichloromethane was added to Fe(acac)$_2$ (4.4 mg; 17 μmol) and Ph$_3$CB(C$_6$F$_5$)$_4$ (16 mg; 17 μmol). The resulting solution was used in Example 170.

Example 170

Ethylene Polymerization Using the Iron Complex of h32 as Prepared in Example 169

A 300-mL oven-dried flask was charged with toluene (100 mL) under ethylene. MAO (Aldrich, 10 wt % in toluene; 1.0 mL) was added to the solution, followed by addition of the dichloromethane solution of the iron complex of h32 prepared in Example 169. The reaction solution was stirred at room temperature for 3 min and then quenched with 6M HCl. The product was isolated by extraction with toluene (1.05 g, 2200 TO; NMR: $M_n$>50,000, 14 BP/1000 C; GPC: $M_n$=4150, $M_w/M_n$=13; $T_m$=133° C.).

Example 171

Ethylene Polymerization Using a Cobalt Complex of h33 Prepared in a Similar Way as that Described in Example 167

A 300-mL oven-dried flask was charged with toluene (100 mL) under ethylene. MAO (Aldrich, 10 wt % in toluene; 1.0 mL) was added to the solution, followed by addition of the dichloromethane solution of the cobalt complex (5.5 μmol). The reaction solution was stirred at room temperature for 3 min and then quenched with 6M HCl. The product was isolated by filtration and further dried in a vacuum oven (1.11 g, 7000 TO; $^1$H NMR: $M_n$>50K, 1 BP/1000 C; GPC: $M_n$=134K, $M_w/M_n$=2.3; $T_m$=139° C.).

Example 172

Synthesis of b20

To a 20 mL test tube were added 500 mg (2.13 mmol) of 3,5-di-tert-butyl-2-hydroxybenzaldehyde, 218 mg (2.13 mmol) of 4-aminomorpholine, and 8 mL of CH$_2$Cl$_2$. The mixture was sonicated until a solution was obtained and 2 drops of formic acid were added. The solution was heated with a heat gun to a gentle reflux and swirled for 5 min. The solution was allowed to cool to room temperature and crystals began to form. After 1 h, the crystals were collected by vacuum filtration and washed with cold methanol to give 600 mg of b20.

Example 173

Synthesis of h32

To a flame-dried, 2 L round-bottomed flask equipped with a Dean-Stark trap were added 300 mL of o-xylene and 50 g (248.6 mmol) of chelidamic acid monohydrate. The resulting slurry was heated to reflux and stirred for 4 h then allowed to cool to room temperature. To the mixture was added 207.1 g (994.4 mmol) of $PCl_5$ in several small quantities. The resulting solution was stirred for 30 min at 25° C. then heated to reflux and stirred for an additional 1.5 h. The solution was allowed to cool to room temperature then cooled to 0° C. and quenched by adding 300 mL of anhydrous methanol slowly over 1 h. The solution was heated to reflux for 45 min and the excess methanol was removed by distillation. Once complete, the mixture was cooled to 0° C. and dimethyl-4-chloro-2,6-pyridinedicarboxylate crystallized out of solution. The product was collected by vacuum filtration and washed with 50 mL of cold methanol to give 29.9 g of dimethyl-4-chloro-2,6-pyridinedicarboxylate. $^1$H NMR ($CDCl_3$, 300 MHz) δ 4.03 (s, 6H), 8.30 (s, 2H). To a 500 mL round-bottomed flask were added 900 mg (3.9 mmol) of dimethyl-4-chloro-2,6-pyridinedicarboxylate, 1.4 mL (13.3 mmol) of N,N'-dimethylethylenediamine, and 100 mL of anhydrous toluene. The resulting solution was cooled to 0° C. and 20.0 mL of a 2 M solution of trimethylaluminum (40.0 mmol) in toluene was added dropwise. The solution was heated to reflux and stirred for 14 h then cooled to 0° C. The reaction was quenched by adding a solution of 1.65 g (11.0 mmol) of tartaric acid in 44 mL of 0.5 N NaOH. Stirring was continued for 1 h and the resulting slurry was filtered through Celite. The filtrate was transferred into a separatory funnel. Two layers formed and the organic material was collected, dried over anhydrous $K_2CO_3$, filtered, and concentrated in vacuo to an oil. Silica gel chromatography (50% methylene chloride in hexane) of the oil provided 128 mg of 4-chloro-2,6-diacetylpyridine. $^1$H NMR ($CDCl_3$, 300 MHz) δ 2.77 (s, 6H), 8.16 (s, 2H). To a 50 mL round-bottomed flask equipped with a Dean-Stark trap were added 20 mL of anhydrous toluene, 130 mg (0.66 mmol) of 4-chloro-2,6-diacetylpyridine, 235 mg (1.30 mmol) of 1-amino-2-tert-butyl-5-isopropylpyrrole, and 0.1 mg of p-toluenesulfonic acid monohydrate. The reaction mixture was stirred and heated to reflux. After 6 h, the resulting solution was allowed to cooled to room temperature and concentrated in vacuo to an oil. Silica gel chromatography (33% methylene chloride in hexane) of the oil provided 166 mg of h32. $^1$H NMR ($CDCl_3$, 300 MHz) δ 1.05 (d, J=6.5 Hz, 3H), 1.26 (d, J=6.8 Hz, 3H), 1.29 (s, 9H), 2.29 (s, 6H), 2.41 (qu, J=6.8 Hz, 2H), 5.93 (d, J=3.9 Hz, 2H), 5.98 (d, J=4 Hz, 2H), 8.53 (s, 2H).

Example 174

Synthesis of monohydrazone 1

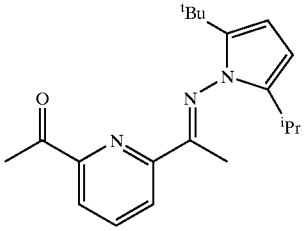

monohydrazone 1

To a 50 mL round-bottomed flask equipped with a Dean-Stark trap were added 10 mL of anhydrous toluene, 3.17 g (19.44 mmol) of 2,6-diacetylpyridine, 700 mg (3.89 mmol) of 1-amino-2-tert-butyl-5-isopropylpyrrole, and 0.1 mg of p-toluenesulfonic acid monohydrate. The reaction mixture was stirred and heated to reflux. After 30 min, the resulting solution was allowed to cool to room temperature and concentrated in vacuo to an oil. Silica gel chromatography (10% ethyl acetate in hexane) of the oil provided 959 mg of monohydrazone 1. $^1$H NMR ($CDCl_3$, 300 MHz) δ 1.03 (d, J=6.5 Hz, 3H), 1.27 (s, 9H), 1.27 (d, J=6.6 Hz, 3H), 2.30 (s, 3H), 2.44 (qu, J=6.8 Hz, 1H), 2.79 (s, 3H), 5.91 (dd, J=3.8, 0.8 Hz, 1H), 5.96 (dd, J=3.8, 1H), 7.99 (t, J=7.9 Hz, 1H), 8.18 (dd, J=7.6, 1.0 Hz, 1H), 8.58 (dd, J=7.8, 1.2 Hz, 1H).

Example 175

Synthesis of h29

To a 50 mL round-bottomed flask equipped with a Dean-Stark trap were added 10 mL of anhydrous toluene, 115 mg (0.35 mmol) of monohydrazone 1, 95 mg (0.42 mmol) of 1-amino-2-tert-butyl-4-ethoxycarbonyl-5-methylpyrrole, and 0.1 mg of p-toluenesulfonic acid monohydrate. The reaction mixture was stirred and heated to reflux. After 12 h, the resulting solution was allowed to cool to room temperature and concentrated in vacuo to an oil. Silica gel chromatography (66% methylene chloride in hexane) of the oil provided 150 mg of h29. $^1$H NMR ($CDCl_3$, 300 MHz) δ 1.03 (d, J=6.6 Hz, 3H), 1.27 (ovrlp, 3H), 1.27 (s, 9H), 1.28 (s, 9H), 1.36 (t, J=7.2 Hz, 3H), 2.28 (s, 6H), 2.32 (s, 3H), 2.43 (qu, J=6.6 Hz, 1H), 4.28 (q, J=7.2, 1.5 Hz, 2H), 5.91 (d, J=3.6 Hz, 1H), 5.96 (d, J=3.6 Hz, 1H), 6.43 (s, 1H), 8.0 (t, J=8.0 Hz, 1H), 8.49 (d, J=7.8 Hz, 1H), 8.57 (d, J=7.3 Hz, 1H).

Example 176

Synthesis of h33

To a 50 mL round-bottomed flask equipped with a Dean-Stark trap were added 20 mL of anhydrous toluene, 150 mg (0.46 mmol) of monohydrazone 1, 77 mg (0.46 mmol) of 1-amino-2-tert-butyl-4,5-dimethylpyrrole, and 2.0 mg of p-toluenesulfonic acid monohydrate. The reaction mixture was stirred and heated to reflux. After 6 h, the resulting solution was allowed to cool to room temperature and concentrated in vacuo to an oil. Silica gel chromatography (33% methylene chloride in hexane) of the oil provided 78 mg of h33. $^1$H NMR ($CDCl_3$, 300 MHz) δ 1.04 (d, J=6.5 Hz, 3H), 1.25 (d, J=6.5 Hz, 3H), 1.27 (s, 18H), 1.90 (s, 3H), 2.05 (s, 3H), 2.28 (s, 3H), 2.36 (s, 3H), 2.43 (qu, J=6.5 Hz, 1H), 5.83 (s, 1H), 5.91 (d, J=3.9 Hz, 1H), 5.96 (d, J=3.7 Hz, 1H), 7.96 (t, J=7.9 Hz, 1H), 8.47 (dd, J=7.7, 0.7 Hz, 1H), 8.52 (dd, J=8.0, 0.8 Hz, 1H).

Example 177

Synthesis of h31

To a 50 mL round-bottomed flask equipped with a Dean-Stark trap were added 10 mL of anhydrous toluene, 138 mg (0.42 mmol) of monohydrazone 1, 56 mg (0.51 mmol) of 1-amino-2,5-dimethylpyrrole, and 2.0 mg of p-toluenesulfonic acid monohydrate. The reaction mixture was stirred and heated to reflux. After 12 h, the resulting solution was allowed to cool to room temperature and concentrated in vacuo to an oil. Silica gel chromatography (5% ethyl acetate in hexane) of the oil provided 78 mg of h31. $^1$H NMR (CDCl$_3$, 300 MHz) δ 1.07 (d, J=6.7 Hz, 3H), 1.29 (d, J=6.7 Hz, 3H), 1.30 (s, 9H), 2.11 (s, 6H), 2.32 (s, 3H), 2.39 (s, 3H), 2.46 (m, 1H), 5.92 (s, 2H), 5.93 (d, J=3.7 Hz, 1H), 5.98 (d, J=3.7 Hz, 1H), 7.97 (t, J=7.7 Hz, 1H), 8.51 (dd, J=7.9, 0.8 Hz, 1H), 8.56 (dd, J=7.6, 0.9 Hz, 1H).

Example 178

Synthesis of a51

To a 50 mL round-bottomed flask equipped with a Dean-Stark trap were added 10 mL of anhydrous toluene, 400 mg (1.70 mmol) of 1-amino-2,5-di-iso-propyl-4-ethoxycarbonylpyrrole, 74 μL (0.85 mmol) of 2,3 butanedione, and 5.0 mg of p-toluenesulfonic acid monohydrate. The resulting solution was stirred at room temperature for 30 min then heated to 60° C. After 12 h, the solution was heated to reflux for 1 h, allowed to cool to room temperature, and concentrated in vacuo to an oil. Silica gel chromatography (10% ethyl acetate in hexane) of the oil provided 442 mg of a51. $^1$H NMR (CDCl$_3$, 300 MHz) δ 1.07 (d, J=4.8 Hz, 6H), 1.17 (d, J=7.1 Hz, 6H), 1.27 (d, J=6.8 Hz, 6H), 1.32 (d, J=7.2 Hz, 6H), 1.34 (t, J=7.0 Hz, 3H), 2.18 (s, 6H), 2.39 (qu, J=6.7 Hz, 2H), 3.75 (qu, J=7.3 Hz, 2H), 4.24 (q, J=7.2 Hz, 4H), 6.40 (d, J=0.5 Hz, 2H).

Example 179

Synthesis of a52

To a 50 mL round-bottomed flask equipped with a Dean-Stark trap were added 20 mL of anhydrous toluene, 330 mg (0.99 mmol) of 1-amino-2,5-di(1-naphthyl)pyrrole, 37 μL (0.42 mmol) of 2,3 butanedione, and 2.0 mg of p-toluenesulfonic acid monohydrate. The resulting solution was stirred at room temperature for 30 min then heated to 60° C. After 6 h, the solution was heated to reflux for 1 h, allowed to cool to room temperature, and concentrated in vacuo to an oil. Silica gel chromatography (10% ethyl acetate in hexane) of the oil provided 266 mg of a52. $^1$H NMR (CDCl$_3$, 300 MHz) δ 0.93 (s, 6H), 6.49 (s, 4H), 7.09 (dd, J=7.2, 1.2 Hz, 4H), 7.24 (m, 4H), 7.37 (m, 4H), 7.59 (m, 4H), 7.76 (d, J=8.1 Hz, 4H), 7.82 (d, J=8.0 Hz, 4H), 8.01 (d, J=8.5 Hz, 4H).

Example 180

Synthesis of monohydrazone 2

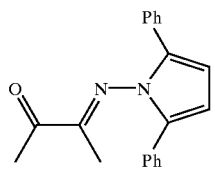

monohydrazone 2

To a 50 mL round-bottomed flask equipped with a Dean-Stark trap were added 10 mL of DMF, 5 mL of anhydrous toluene, 1.75 g (6.47 mmol) of 1-amino-2,5-diphenylpyrrole, 5.7 mL (64.7 mmol) of 2,3 butanedione, and 10.0 mg of p-toluenesulfonic acid monohydrate. The resulting solution was stirred at room temperature for 30 min then heated to 70° C. After 12 h, the solution was heated to reflux and the excess diketone and toluene were removed by distillation. Toluene (15 mL) was added to the reaction vessel and removed by distillation. The solution was allowed to cool to room temperature and concentrated in vacuo to an oil. Silica gel chromatography (10% ethyl acetate in hexane) of the oil provided 1.94 g of monohydrazone 2. $^1$H NMR (CDCl$_3$, 300 MHz) δ 1.45 (s, 3H), 2.57 (s, 3H), 6.48 (s, 2H), 7.24 (m, 2H), 7.35 (m, 4H), 7.48 (m, 4H).

Example 181

Synthesis of a53

To a 50 mL round-bottomed flask equipped with a Dean-Stark trap were added 15 mL of anhydrous toluene, 255 mg (0.84 mmol) of monohydrazone 2, 145 mg (0.84 mmol) of 1-amino-2-methyl-5-phenylpyrrole, and 5.0 mg of p-toluenesulfonic acid monohydrate. The resulting solution was heated to reflux and stirred. After 12 h, the solution was allowed to cool to room temperature and concentrated in vacuo to an oil. Silica gel chromatography (10% ethyl acetate in hexane) of the oil provided 208 mg of a53. $^1$H NMR (CDCl$_3$, 300 MHz) δ 1.72 (s, 3H), 1.86 (s, 3H), 2.05 (s, 3H), 6.01 (d, J=3.7 Hz, 1H), 6.26 (d, J=4.0 Hz, 1H), 6.47 (s, 2H), 7.26 (m, 12H), 7.44 (m, 3H).

Example 182

Synthesis of a54

To a 50 mL round-bottomed flask equipped with a Dean-Stark trap were added 7 mL of DMF, 16 mL of anhydrous toluene, 1.25 g (4.62 mmol) of 1-amino-2,5-diphenylpyrrole, 203 μL (2.31 mmol) of 2,3 butanedione, and 2.0 mg of p-toluenesulfonic acid monohydrate. The resulting solution was heated to 70° C. and stirred. After 4 h, the solution was heated to reflux for 1–24 h. The solution was allowed to cool to room temperature and concentrated in vacuo to an oil. Silica gel chromatography (10% ethyl acetate in hexane) of the oil provided a54. $^1$H NMR (CDCl$_3$, 300 MHz) δ 1.76 (s, 6H), 6.49 (s, 4H), 7.30 (m, 12H), 7.40 (m, 8H).

Example 183

Synthesis of b21

1-Amino-pyrrole (500 mg, 6.25 mmol) and salicylaldehyde (610 mg, 5 mmol) were weighed to a 50-ml round bottom flask with a septum. The flask was purged with dry argon gas. Methanol (10 ml) and 4 drops of formic acid were then added to the flask. The reaction was stirred at 50° C. for 60 minutes. After 1 hour, the mixture was cooled to 0° C. giving a crystalline solid. The crystalline product that separated was collected cold by vacuum filtration. The crystals were washed with cold methanol on the filter and then dried several hours in vacuo to yield 562 mg (68% yield). $^1$H NMR: s (OH) δ 10.75, s (N=CH) δ 8.45, m (aryl 4H) δ 6.8–7.4, s (pyrrolyl 4H) δ 6.25.

Example 184

Synthesis of b22

1-Amino-2,5-diisopropylpyrrole (693 mg, 4.2 mmol) and 3-(anthracen-9-yl)-2-hydroxybenzaldehyde (1.04 g, 3.5 mmol) were independently weighed to a 100-ml round bottom flask with a septum. 1-Amino-2,5-diisopropylpyrrole was dissolved in 2-ml of CH$_2$Cl$_2$ and 2-ml methanol and then transferred onto a suspension of compound 3-(anthracen-9-yl)-2-hydroxybenzaldehyde in methanol (10-ml). The reaction was stirred at 55° C. for 60 minutes. After 1 hour, the mixture was cooled to 0° C. giving a yellow crystalline solid. The crystalline product that separated was collected cold by vacuum filtration. The crystals were washed with cold methanol on the filter and then dried several hours in vacuo to yield 1.01 g (65% yield). $^1$H NMR: s (OH) δ 11.42, s (N=CH) δ 8.70, m (aryl 12H) δ 7.2–8.6, s (pyrrolyl 4H) δ 5.95, septet [CH(CH$_3$)$_2$] δ 3.0, [CH(CH$_3$)$_2$] δ 1.2.

Example 185

Synthesis of b23

1-Amino-pyrrole (750 mg, 9.375 mmol) was added to a 50-ml round bottom flask that contained a suspension 3-(anthracen-9-yl)-2-hydroxybenzaldehyde (1.49 g, 5 mmol) in 50-ml of methanol. The flask was sealed with a septum and purged 15–20 minutes with argon. An additional 20-ml of methanol was added and the mixture was stirred at 50° C. for 90 minutes. After 1.5 hours, the mixture was cooled to 0° C. giving a yellow crystalline solid. The crystalline product that separated was collected cold by vacuum filtration. The crystals were washed with cold methanol on the filter and then dissolved in CH$_2$Cl$_2$ and combined in a round bottom flask with 0.883 g of a trisamine scavenging resin from Argonaut Technology to remove unreacted aldehyde. The mixture was gently stirred overnight and the resin collected by suction filtration. The CH$_2$Cl$_2$ was removed in vacuo to yield 1.35 g (75% yield). $^1$H NMR: s (OH) δ 11.08, s (N=CH) δ 8.65, m (aryl 12H) δ 7.2–8.6, s (pyrrolyl 4H) δ 6.

Example 186

Synthesis of b6

1-Amino-pyrrole (990 mg, 12.4 mmol) and 3,5-di-t-butylsalicylaldehyde (2.54 g, 10.8 mmol) were weighed to a 50-ml round bottom flask and dissolved in 35-ml of warm methanol. Formic acid (4 drops) was then added to the flask. The reaction was stirred at 50° C. for 30 minutes. After 30 minutes, the mixture was cooled to 0° C. giving a crystalline solid. The crystalline product that separated was collected cold by vacuum filtration. The crystals were washed with cold methanol on the filter and then dissolved in CH$_2$Cl$_2$ and combined in a round bottom flask with 0.89 g of a trisamine scavenging resin from Argonaut Technology to remove unreacted aldehyde. The mixture was gently stirred overnight and the resin collected by suction filtration. The CH$_2$Cl$_2$ was removed in vacuo to yield 2 g of product. $^1$H NMR: s (OH) δ 10.75, s (N=CH) δ 8.45, m (aryl 4H) δ 6.8–7.4, s (pyrrolyl 4H) δ 6.25.

Example 187 to Example 197

Polymerization of Ethylene Starting from Ni(COD)$_2$/ligand/B(C$_6$F$_5$)$_3$ A Parr® stirred autoclave (600-ml) was heated to 100° C. under dynamic vacuum to completely dry the reactor. The reactor was cooled and charged with 150 ml of dry toluene. In an inert atmosphere glove box, a flame dried Schlenk flask equipped with a magnetic stir bar and a rubber septum was charged with between 0.015 mmol and 0.036 mmol of bis(1,5-cyclooctadiene)nickel(0), between 0.015 mmol and 0.036 mmol of tris(pentafluorophenyl)borane, and between 0.015 mmol and 0.036 mmol of the ligand in a 1:1:1 ratio. The flask was removed from the box and evacuated and refilled with ethylene. Toluene (25–50 ml) was added. After 5–60 minutes of premix time, the contents of the reaction flask were transferred via SS cannula to the autoclave. The reactor was sealed and pressurized up to 400-psig ethylene and left to stir at room temperature for 30–120 minutes at 25° C. After the desired reaction time, the reactor was vented and the contents poured into a beaker containing a methanol acetone/mixture. The polymer was collected by suction filtration and dried in the vacuum oven overnight at ~100° C.

| Example | Ligand | mmol cat | Rxn time/ premix time (min) | PE yield (g) | $M_w$ (× 10$^{-3}$) | Branching/ 1000 C ($^1$H NMR) | $T_m$ (° C.) |
|---|---|---|---|---|---|---|---|
| 187 | b22 | 0.036 | 120/15 | 4.0 | 422 | 7 | 131 |
| 188 | b22 | 0.036 | 60/4 | 0.8 | 213 | 13 | 128 |
| 189 | b22 | 0.036 | 120/15 | 8.7 | 798 | 2 | 133 |
| 190 | b22 | 0.036 | 90/15 | 11.5 | 352 | 3 | 139 |
| 191 | b22 | 0.036 | 90/30 | 18.8 | 380 | 4 | 131 |
| 192 | b22 | 0.036 | 60/60 | 12 | 390 | 3 | 135 |
| 193 | b22 | 0.018 | 90/30 | 9.1 | 393 | 2 | 134 |
| 194 | b24 | 0.018 | 90/15 | 5.9 | 483 | 3 | 133 |
| 195 | b24 | 0.018 | 90/30 | 4.5 | 475 | 2 | 133 |
| 196 | b25 | 0.018 | 90/15 | 3.8 | 287 | 3 | 132 |
| 197 | b25 | 0.015 | 90/30 | 1.7 | 271 | 4 | 131 |

Example 198

Polymerization of ethylene with d4

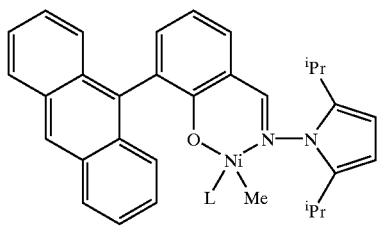

d4

L = NCMe or Et₂O

A Parr® stirred autoclave (600-ml) is heated to 100° C. under dynamic vacuum to completely dry the reactor. The reactor is cooled and charged with 150 ml of dry toluene. The reactor is pressurized to 200-psig ethylene and vented. The catalyst solution (2 mg of d4 in 2 ml of toluene) is added to the reactor and the autoclave is sealed and pressurized to 200-psig ethylene. After 30 minutes, the reactor is vented and the contents poured into a beaker containing a methanol/acetone mixture. The polymer is collected by suction filtration and dried in the vacuum oven overnight at ~100° C. giving polyethylene.

Example 199

Ethylene Polymerization with d5

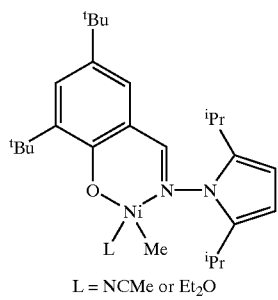

d5

L = NCMe or Et₂O

A Parr® stirred autoclave (600-ml) is heated to 100° C. under dynamic vacuum to completely dry the reactor. The reactor is cooled and charged with 150 ml of dry toluene. The reactor is pressurized to 200-psig ethylene and vented. The catalyst solution (2 mg of d5 in 2 ml of toluene) is added to the reactor and the autoclave is sealed and pressurized to 200-psig ethylene. After 30 minutes, the reactor is vented and the contents poured into a beaker containing a methanol/acetone mixture. The polymer is collected by suction filtration and dried in the vacuum oven overnight at ~100° C. giving polyethylene.

Example 200

Polymerization of Norbornene with Ni(COD)₂/b6/B(C₆F₅)₃

In an inert atmosphere glove box, a flame dried Schlenk flask equipped with a magnetic stir bar and a rubber septum was charged with 17 mg (0.062 mmol) of bis(1,5-cyclooctadiene)nickel(0), 31.6 mg (0.062 mmol) of tris(pentafluorophenyl)borane, and 18.4 mg (0.062 mmol) of the ligand of formula b6. The flask was removed from the box and evacuated and refilled with argon. Toluene (25 ml) was added, resulting in a orange solution. To the polymerization mixture was added a toluene solution containing 3 g of norbornene. In seconds, the norbornene had been converted to polynorbornene. Methanol and acetone were added to quench the reaction and a white flocculent polynorbornene precipitated. The polymer was collected by suction filtration and dried in the vacuum oven overnight at ~100° C. resulting in 2.8 grams of polynorbornene. $M_n$=127,000.

Example 201

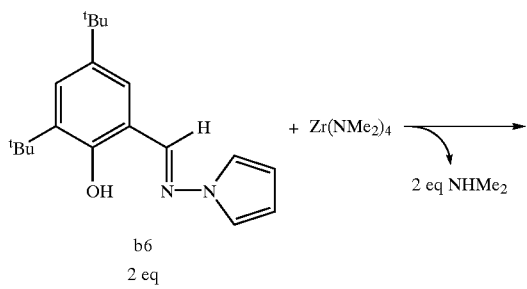

b6
2 eq

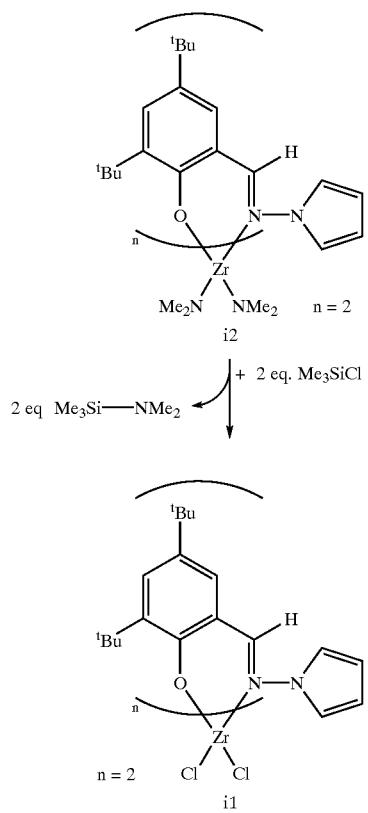

Preparation of i1 and i2

Two flame dried Schlenk flasks, each equipped with a stir bar and a rubber septum, were taken into the inert atmosphere glove box. One of the flasks was charged with 446 mg (2 eq) of b6, while to the second flask was added 200 mg of Zr(NMe$_2$)$_4$. The flasks were removed from the glove box, attached to the vacuum/argon manifold, evacuated and refilled with argon. Methylene chloride was added giving two clear solutions. While stirring the ligand solution, the methylene chloride solution of Zr(NMe$_2$)$_4$ was transferred via SS cannula onto the ligand giving a yellow/orange solution. The mixture was left to stir for 2 hours. For 5–10 minutes of that 2 hours a vent needle was place through the septum to help carry away the dimethylamine in the argon stream. After 2 hours, the solvent was removed in vacuo giving i2 as a yellow powder (498 mg isolated, 86% yield). 200 mg of i2 was added to a Schlenk flask and dissolved in toluene. While stirring, 66 μl of trimethylchlorosilane was added drop wise and the mixture left to stir for 15 hours. The solvent was removed in vacuo giving a glassy solid. The solid was dissolved in hexane, followed by removal of hexane in vacuo 3 times yielding 150 mg (78% yield) of i1 as dry yellow solid. $^1$H NMR is consistent with the desired complex.

Example 202 to Example 211

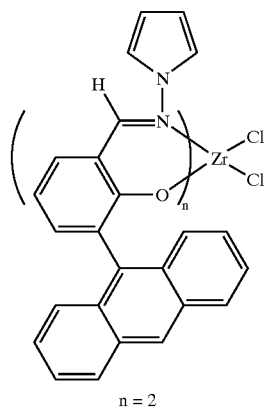

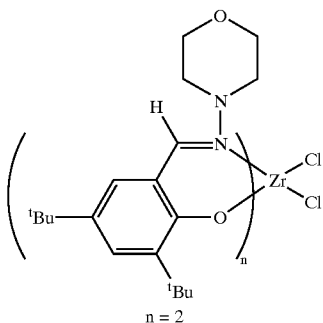

A Parr® stirred autoclave (600-ml) was heated to 100° C. under dynamic vacuum to completely dry the reactor. The reactor was cooled and charged with 150 ml of dry toluene and an appropriate amount of cocatalyst (e.g. mMAO). In an inert atmosphere glove box, a septum-capped vial was charged with the desired procatalyst. The vial was removed from the box, placed under 1 atmosphere of argon and dissolved in toluene. The reactor was sealed and pressurized up to 300–350 psig ethylene. The procatalyst was added to the reactor as a stock solution (2-ml) via the high-pressure sample loop while pressurizing the autoclave to 400 psig. After the 15 minutes of stirring at 400-psig ethylene, the reaction was quenched upon addition of 2-ml of methanol at high pressure. The reactor was vented and the contents poured into a beaker containing a methanol acetone/mixture. The polymer was collected by suction filtration and dried in vacuo at ~100° C.

| Ex | complex | cocatalyst (equiv.) | μmol catalyst | T (° C.) | PE yield (g) | kg PE/ mmol catalyst | $M_w$ ($10^{-3}$) | $T_m$ (° C.) |
|---|---|---|---|---|---|---|---|---|
| 202 | i1 | mMAO$^a$ (2000) | 0.13 | 40 | 7.0 | 53 | 4,540 | 128 |
| 203 | i1 | MMAO (10,000) | 0.33 | 70 | 6.4 | 19 | 108 | 133 |
| 204 | i3 | MMAO (10,000) | 0.28 | 70 | 0.13 | 0.46 | 781 | 134 |
| 205 | i2 | MMAO (10,000) | 0.32 | 70 | 0.27 | 0.83 | 127 | 132 |
| 206 | i2 | TMA/MAO (100/10K) | 0.32 | 70 | 0.31 | 0.98 | 320 | 136 |
| 207 | i3 | MMAO (10,000) | 0.27 | 70 | 0.14 | 0.5 | 525 | — |
| 208 | i1 | MMAO (10,000) | 0.33 | 70 | 5.8 | 18 | 81 | — |
| 209 | i1 | MMAO (2000) | 0.13 | 40 | 8.8 | 68 | 147 | — |
| 210 | i1 | MMAO (2000) | 0.13 | 70 | 4.4 | 34 | 44 | — |
| 211 | i4 | MMAO (2000) | 0.13 | 40 | 0.92 | 7 | — | — |

$^a$mMAO-3A from Akzo Nobel

Example 212

Copolymerization of Ethylene and 1-hexene with i1

A Parr® stirred autoclave (600-ml) was heated to 100° C. under dynamic vacuum to completely dry the reactor. The reactor was cooled and charged with 100 ml of dry toluene, 50 ml of deoxygenated 1-hexene and 3-ml of mMAO. In an inert atmosphere glove box, a septum-capped vial was charged with i1. The vial was removed from the glove box placed under 1 atmosphere argon and dissolved in toluene (2 mg in 16-ml). The reactor was sealed heated to 50° C. (allow 20° C. for exotherm) and pressurized up to 300–350 psig ethylene. The procatalyst was added to the reactor as a stock solution (2-ml) via the high-pressure sample loop while pressurizing the autoclave to 400 psig. After the 30 minutes of stirring at 400-psig ethylene and 70° C., the reaction was quenched by addition of 2-ml of methanol at high pressure. The reactor was vented and the contents poured into a beaker containing a methanol acetone/mixture. The polymer was collected by suction filtration and dried in the vacuum oven overnight at ~100° C. giving 1.8 grams of LLDPE. $^1$H NMR 10 branches/1000 carbon atoms; $M_w$=46,000.

Example 213

Polymerization of Ethylene with the Reaction Product of Ti(NMe$_2$)$_4$, b6, and Me$_3$SiCl A flame dried Schlenk flask equipped with a stir bar and rubber septum was taken into the inert atmosphere glove box along with a septum-capped vial. The flask was charged with 516 mg (2 eq) of b6, while 250 mg of Ti(NMe$_2$)$_4$ was added to the vial. The flask and vial were removed from the glove box, attached to the vacuum/argon manifold, and placed under an argon atmosphere. Methylene chloride (10-ml) was added to both the flask and the septum-capped vial. While stirring the ligand solution, the methylene chloride solution of Ti(NMe$_2$)$_4$ was transferred via SS cannula onto the ligand giving a deep red/orange solution. The mixture was left to stir for 1 hour. After 1 hour, the solvent was removed in vacuo giving a burgundy solid. The resulting burgundy solid was dissolved in toluene. While stirring, 109 □l of trimethylchlorosilane was added drop wise and the mixture left to stir for 15 hours. The solvent was removed in vacuo giving a glassy burgundy solid. After drying the solid in vacuo for several hours, 1 mg of the material was dissolved in 20-ml of toluene. A Parr® stirred autoclave (600-ml) was heated to 100° C. under dynamic vacuum to completely dry the reactor. The reactor was cooled and charged with 150 ml of dry toluene, 0.14-ml of mMAO. The reactor was sealed heated to 30° C. (allow 10° C. for exotherm) and pressurized up to 300–350 psig ethylene. The procatalyst was added to the reactor as a stock solution (2-ml, 0.1 mg of burgundy solid isolated above) via the high-pressure sample loop while pressurizing the autoclave to 400 psig. After the 30 minutes of stirring at 400-psig ethylene and 40° C., the reaction was quenched by addition of 2-ml of methanol at high pressure. The reactor was vented and the contents poured into a beaker containing a methanol acetone/mixture. The polymer was collected by suction filtration and dried in the vacuum oven overnight at ~100° C. giving grams of polyethylene.

Example 214

Synthesis of b3

A solution of 1-Amino-5-tert-butyl-2-methyl-1H-pyrrole-3-carboxylic acid ethyl ester (258 mg, 1.15 mmol) in toluene (20.8 mL) was treated with pyridinium p-toluenesulfonate (PPTS) (2.5 mg) and 3,5-di-t-butyl-2-hydroxybenzaldehyde (234 mg, 1.0 mmol). A Dean Stark trap and reflux condenser were attached, and the resulting solution was refluxed, with the azeotropic removal of water for ~7 h. The reaction was cooled to rt, and allowed to stand under Ar overnight. TLC indicated the reaction had not gone to completion, therefore heating was continued for an additional 2.25 h, after which a second portion of 3,5-di-t-butyl-2-hydroxybenzaldehyde (70 mg, 0.299 mmol) was added, and heating continued for another 2.5 h. The resulting solution was concentrated in vacuo. The residue was purified by flash chromatography (SiO$_2$, 2–15% EtOAC/Hexanes) to afford b3 (326 mg, 74%): $^1$H NMR (CDCl$_3$, chemical shifts in ppm relative to TMS): 1.326 (s, 9H), 1.330 (s, 9H), 1.359 (t, 3H, J=6.9 Hz), 4.286 (q, 2H, J=7.1 Hz), 7.124 (d, 1H, J=2.5 Hz), 7.552 (d, 2H, J=2.2 Hz), 8.422 (s, 1H), 11.447 (s, 1H); Field Desorption Mass Spectrometry: m/z 440.

Example 215

Synthesis of b24

3-Anthracen-9-yl-2-hydroxy-benzaldehyde (394 mg, 1.32 mmol) was treated with a solution of 1-Amino-2,5-diisopropyl-1H-pyrrole-3-carboxylic acid ethyl ester (436 mg, 1.83 mmol) in toluene, followed by MP-TsOH (Argonaut Technologies, 22 mg, 3 mol % H$^+$). The reaction was heated to 111° C. under Ar, and agitated for 1.5 h. TLC indicated that no reaction had occurred. The mixture was treated with p-TsOH (11 mg, 2.5 wt %) and heated to 111° C. for an additional 1.5 h, then treated with Trisamine resin (5 mol equiv NH$_2$) and allowed to agitate for an additional 2 h. The mixture was filtered and concentrated in vacuo. $^1$H NMR indicated that the residue contained an approximately 5:1 ratio of b24 to starting amino pyrrole. Therefore, the crude mixture was dissolved in toluene (5 mL), treated with 3-Anthracen-9-yl-2-hydroxy-benzaldehyde (106 mg, 0.355 mmol) and p-TsOH (2.8 mg) and heated to 110° C. for 1.5 h, after which the reaction was cooled to rt and treated with PS-Trisamine resin (5 equiv based on starting aldehyde). The resulting slurry was stirred at rt overnight, filtered and concentrated in vacuo. The residue was purified by crystallization (hexanes/CH$_2$Cl$_2$) to afford b24 (341 mg) contaminated with a small amount of hexanes: $^1$H NMR (CDCl$_3$, chemical shifts in ppm relative to TMS): 0.861–0.905 (m, hexanes), 1.181 (d, 6H, J=6.6 Hz), 1.26 (bs, hexanes), 1.316 (d, 6H, J=6.9 Hz), 1.350 (t, 3H, J=7.1 Hz), 2.837 (sep, 1H, J=6.9 Hz), 3.650 (sep, 1H, J=7.1 Hz), 4.265 (q, 2H, J=7.1 Hz), 6.374 (s, 1H), 7.379–7.595 (m, 7H), 7.688 (d, 2H, J=8.5 Hz), 8.082 (d, 2H, J=8.5 Hz), 8.561 (s, 1H), 8.604 (s, 1H), 11.157 (s, 1H).

Example 216

Representative Synthesis of Substituted Salicylaldehyde-derived Ligands, Synthesis of b26

A solution of 1-amino-2-methyl-5-phenyl-1H-pyrrole-3-carboxylic acid ethyl ester (238 mg, 0.975 mmol) in toluene (17.6 mL) was treated with PPTS (2.4 mg, 1 wt %) and 3,5-di-t-butyl-2-hydroxybenzaldehyde (208 mg, 0.89 mmol). A reflux condenser was attached, and the resulting solution was heated at reflux for 1.5 h. The reaction was cooled to rt, and concentrated in vacuo. The residue was flash chromatography (SiO$_2$, 30–60% CH$_2$Cl$_2$/hexanes) to afford b26 (190 mg, 46%): $^1$H NMR (DMSO): 1.231 (s, 9H), 1.284 (t, 3H, J=7.1 Hz), 1.379 (s, 9H), 2.557 (s 3H), 4.224 (q, 2H, J=6.9 Hz), 6.673 (s, 1H), 7.257–7.439 (m, 7H), 8.789 (s, 1H), 11.173 (s, 1H); Field Desorption Mass Spectrometry: m/z 460.

Example 217

Synthesis of b25 b25 was prepared from 1-Amino-5-(2,4-dimethoxyphenyl)-2-isopropyl-1H-pyrrole-3-carboxylic acid ethyl ester (1.0 equiv), 3-Anthracen-9-yl-2-hydroxybenzaldehyde (1.2 equiv), and p-TsOH (3 wt %) in toluene according to the method of Example 216. The excess aldehyde was removed by reaction with PS-Trisamine resin (Argonaut Technologies) at rt for 7 h, followed by filtration and concentration in vacuo. The residue was purified by flash chromatography ($SiO_2$, 5–25% EtOAc/hexane) to afford b25. $^1$H NMR ($CDCl_3$, chemical shifts in ppm relative to TMS): 1.298 (d, 6H, J=7.1 Hz), 1.335 (t, 3H, J=7.1 Hz), 3.601 (s, 3H), 3.856 (s, 3H), 3.953 (sep, 1H, J=7.1 Hz), 4.261 (q, 2H, J=7.1 Hz), 6.410 (d, 1H, J=2.2 Hz), 6.576 (dd, 1H, J=2.2 Hz, J=8.2 Hz), 6.606 (s, 1H), 7.025–7.107 (m, 2H), 7.333–7.394 (m, 4H), 7.441–7.495 (m, 2H), 7.607 (d, 2H, J=8.2 Hz), 8.070 (d, 2H, J=8.5 Hz), 8.142 (s, 1H), 8.542 (s, 1H), 11.229 (s, 1H).

Example 218

Synthesis of h28

A solution of 2-Isopropyl-5-o-tolyl-pyrrol-1-ylamine (60 mg, 0.279 mmol) in toluene (5.76 mL) was treated with 2,6-diacetylpyridine (21.7 mg, 0.133 mmol) and p-TsOH (1.2 mg). The resulting solution was stirred at reflux in an oil bath under Ar for 4.5 h, then cooled to rt. The solvent was removed in vacuo, and the residue was purified by flash chromatography ($SiO_2$, 5–25% EtOAc/hexanes) to afford h28 (41 mg, 56%) contaminated with a small amount of EtOAc and hexane: $^1$H NMR ($CDCl_3$, chemical shifts in ppm relative to TMS): 1.222 (d, 12H, J=6.9 Hz), 1.825 (s, 6H), 2.330 (s, 6H), 2.864 (sep, 2H, J=6.9 Hz), 6.068 (d, 2H, J=3.8 Hz), 6.146 (d, 2H, J=3.8 Hz), 7.039–7.200 (m, 8H), 7.827 (t, 1H, J=7.7 Hz), 8.26 (d, 2H, J=7.7 Hz); Field Desorption Mass Spectrometry: m/z 555.

Example 219

Representative Diketoester Synthesis, Preparation of Ethyl 2-acetyl-5,5-dimethyl-4-oxo-hexanoate Ethyl acetoacetate (1 g, 7.68 mmol) was added dropwise to a suspension of NaH (60% in mineral oil, 338 mg, 8.45 mmol) in toluene (20 mL). The resulting suspension was stirred at rt for 10 min, then treated with 1-bromopinacolone (1.3 g, 7.32 mmol). The mixture was immersed in a 75° C. oil bath, and stirred under Ar for 1 h. The reaction was cooled to rt, diluted with toluene and washed with $H_2O$ (2×50 mL). The organic layer was dried over $Na_2SO_4$, filtered and concentrated in vacuo to afford crude ethyl 2-acetyl-5,5-dimethyl-4-oxo-hexanoate (1.46 g) which was not purified: $^1$H NMR ($CDCl_3$, chemical shifts in ppm relative to TMS): 1.166 (s, 9H), 1.277 (t, 3H, J=7.1 Hz), 2.368 (s, 3H), 3.000 (dd, 1H, J=5.8 Hz, J=18.4 Hz), 3.231 (dd, 1H, J=8.2 Hz, J=18.4 Hz), 4.010 (dd, 1H, J=5.8 Hz, J=8.2 Hz), 4.191 (q, 2H, J=7.1 Hz); Field Desorption Mass Spectrometry: m/z 229 (M+1).

Example 220

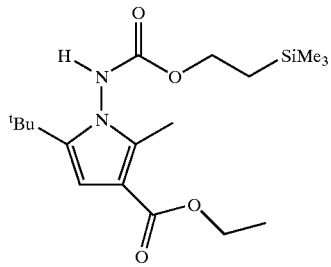

o1

A solution of 2-Acetyl-5,5-dimethyl-4-oxo-hexanoic acid ethyl ester (1.29 g, 5.65 mmol), hydrazinecarboxylic acid 2-trimethylsilanyl-ethyl ester (1 g, 5.67 mmol) and p-TsOH (21 mg) in toluene (10.2 mL) was heated to reflux with azeotropic removal of water for 2 h, then cooled to rt and concentrated in vacuo. The residue was purified by flash chromatography ($SiO_2$, $CH_2Cl_2$) to afford o1 (1.28 g, 62%) as a white solid: $^1$H NMR ($CDCl_3$, chemical shifts in ppm relative to TMS): −0.019 & 0.066 (two broad singlets, mixture of isomers, 9H), 0.913–1.094 (m, 2H), 1.297 (s, 9H), 2.375 & 2.383 (two singlets, mixture of isomers, 3H), 4.177–4.341 (m, 4H), 6.237 & 6.247 (two singlets, mixture of isomers, 1H), 7.007 & 7.060 (two singlets, mixture of isomers, 1H).

Example 221

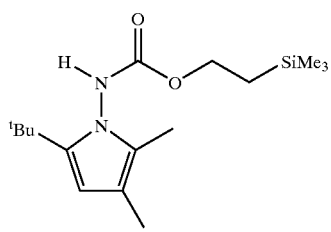

o2

A solution of o1(241.2 mg, 0.65 mmol) in anhydrous THF (1.5 mL) was treated with LAH (74 mg, 1.95 mmol). The resulting suspension was stirred at rt under Ar for 2 days, diluted with $Et_2O$ (5 mL) and quenched with $H_2O$ (74 µL), NaOH (15% w/v in $H_2O$, 74 µL) and $H_2O$ (222 µL). The resulting suspension was stirred at rt for 30 min then filtered through a polyethylene frit. The filtrate was concentrated in vacuo, and the residue was purified by flash chromatography ($SiO_2$, 5–25% EtOAc/hexane) to afford o2 (142 mg, 70%): $^1$H NMR ($CDCl_3$, chemical shifts in ppm relative to TMS): −0.003 & 0.077 (two singlets, 9H, mixture of isomers), 0.962–1.091 (m, 2H), 1.299 (s, 9H), 1.971 (s, 3H), 2.002 (s, 3H), 4.233–4.337 (m, 4H), 5.670 (s, 1H), 7.038 & 7.341 (two singlets, 1H, mixture of isomers).

Example 222

Representative Deprotection of Trimethylsilyl Ethoxycarbonyl-protected 1-aminopyrrole Derivative. Preparation of 1-amino-2-tert-butyl-4,5-dimethylpyrrole o2 (141 mg, 0.45 mmol) was treated with a solution of TBAF (where TBAF refers to tetrabutylammonium fluoride) in THF (1M solution, 0.90 mL, 0.90 mmol). The resulting solution was stirred at rt overnight, quenched with glacial acetic acid (51.5 μL) and concentrated in vacuo. The residue was dissolved in toluene (5 mL) and treated with PS-TsOH (where PS-TsOH refers to a polystyrene resin with arene sulfonic acid functionality from Argonaut Technologies, 1.45 mmol H$^+$/g, 1 g). The suspension was stirred at rt for 1 hour, then filtered through a short plug of silica gel eluting with toluene (50 mL). The filtrate was concentrated in vacuo to afford 1-amino-2-tert-butyl-4,5-dimethylpyrrole as a white solid (45 mg, 60%). $^1$H NMR (CDCl$_3$, chemical shifts in ppm relative to TMS): 1.426 (s, 9H), 2.029 (s, 3H), 2.148 (s, 3H), 4.255 (s, 2H), 5.621 (s, 1H).

Example 223

Synthesis of h30

2,6-Diacetylpyridine (79.9 mg, 0.49 mmol) and 5-tert-Butyl-2,3-dimethyl-pyrrol-1-ylamine (159 mg, 0.956 mmol) were dissolved in toluene (10.6 mL) and treated with p-TsOH (~8 mg). The resulting solution was stirred under Ar at rt for 10 min, then heated to reflux in an oil bath. The mixture was stirred at reflux, with azeotropic removal of water, for 2 h, then cooled to rt and concentrated in vacuo. The residue was purified by flash chromatography (SiO$_2$, 5% EtOAc/heptane) to afford h30 (116 mg, 51%). $^1$H NMR (CDCl$_3$, chemical shifts in ppm relative to TMS): 1.278 (s, 18H), 1.911 (s, 6H), 2.059 (s, 6H), 2.375 (s, 6H), 5.831 (s, 2H), 7.928 (t, 1H, J=8.0 Hz), 8,456 (d, 2H, J=8.0 Hz).

Example 224

Preparation of h19

2,6-diacetylpyidine (176 mg) and 1-amino-2-phenyl-5-methylpyrrole (420 mg) were dissolved in mixture of methanol (10 mL) and dichloromethane (4 drops) in a 20 mL scintillation vial. One drop of formic acid was added, then the solvent volume was reduced to 6 mL under a stream of nitrogen gas. A dark-colored oil settled. The vial was gently warmed to give a clear solution and then allowed to stand at room temperature. After 16 h, yellow crystals and a dark oil had separated. The solvent was removed in vacuo and the residue was chromatographed over silica (EtOAc/hexane) to give the product as a yellow crystalline powder (285 mg).

Example 225

Synthesis of 3-Naphthalen-1-yl-3-oxo-propionic Acid Ethyl Ester

A suspension of ethyl potassium malonate (3.4 g, 20.0 mmol) in acetonitrile (30.6 mL) was treated with Et$_3$N (3.11 mL, 22.3 mmol) and MgCl$_2$ (2.38 g, 25.0 mmol). The resulting suspension was stirred at rt for 2.5 h, then treated with 1-naphthoylchloride (1.55 mL, 10.3 mmol) and stirred under Ar at rt overnight. The acetonitrile was removed in vacuo, toluene (14 mL) was added and the suspension was concentrated again. The residue was suspended in toluene (14 mL) and washed with 12% Aq. HCl (14.1 mL). The organic layer was removed, dried over Na$_2$SO$_4$, filtered and concentrated in vacuo. The residue was purified via flash chromatography (SiO$_2$, 10% EtOAc/Heptane) to afford 3-Naphthalen-1-yl-3-oxo-propionic acid ethyl ester (1.65 g, 66%) as a 3.5:1 mixture of keto/enol isomers: 1$^1$H NMR (CDCl$_3$, chemical shifts in ppm relative to TMS): 1.21 (t, 3H, ketone isomer, J=7.1 Hz), 1.36 (3 h, enol isomer, J=7.1 Hz), 4.11 (s, 2H, ketone isomer), 4.20 (q, 2H, ketone isomer, J=7.4 Hz), 4.32 (q, 2H, enol isomer, J=7.4 Hz), 5.50 (s, 1H, enol isomer), 7.46–7.68 (m, 3H), 7.88 (d, 1H, J=8.1 Hz), 7.92 (d, 1H, J=7.3 Hz), 8.03 (d, 1H, J=8.1 Hz), 8.36 (d, 1H, enol isomer, J=8.1 Hz), 8.76 (d, 1H, J=8.1 Hz); Field Desorption Mass Spectrometry: m/z 242.

Example 226

Synthesis of 2-(Naphthalene-1-carbonyl)-4-oxo-4-phenyl-butyric acid ethyl ester

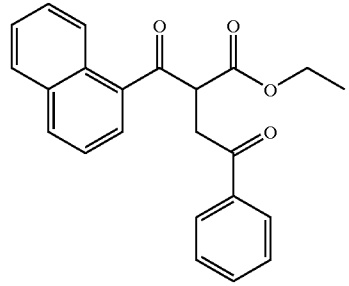

A suspension of NaH (60% in mineral oil, 323 mg, 8.07 mmol) in toluene (20 mL) was treated with 3-Naphthalen-1-yl-3-oxo-propionic acid ethyl ester (1.63 g, 6.7 mmol). The resulting suspension was stirred at rt under Ar for 1 h, then treated with 2-bromocetophenone (1.61 g, 8.07 mmol). The suspension was immersed in a 70° C. oil bath and stirred under Ar for 4 h, cooled to rt, diluted with toluene and washed with H$_2$O and brine. The organic layer was dried over Na$_2$SO$_4$, filtered and concentrated in vacuo. The residue was purified via flash chromatography (SiO$_2$, 10–20% EtOAc/Heptane) to afford 2-(Naphthalene-1-carbonyl)-4-oxo-4-phenyl-butyric acid ethyl ester (1.2 g) contaminated with a small amount of unidentified aromatic impurity: 1$^1$H NMR (CDCl$_3$, chemical shifts in ppm relative to TMS): 1.03 (t, 3H, J=7.25 Hz), 3.72 (dd, 1H, J=18.8 Hz, J=5.4 Hz), 3.96 (dd, 1H, J=18.8 Hz, J=8.05 Hz), 4.09 (m, 2H), 5.16 (m, 1H), 7.45–7.63 (m, 6H), 7.88 (d, 1H, J=7.9 Hz), 8.0–8.07 (m, 3H), 8.24 (d, 1H, J=7.2 Hz)), 8,48 (d, 1H, J=8.7 Hz).

Example 227

Synthesis of 2-Naphthalen-1-yl-5-phenyl-1-(2-trimethylsilanyl-ethoxycarbonylamino)-1H-pyrrole-3-carboxylic acid ethyl ester

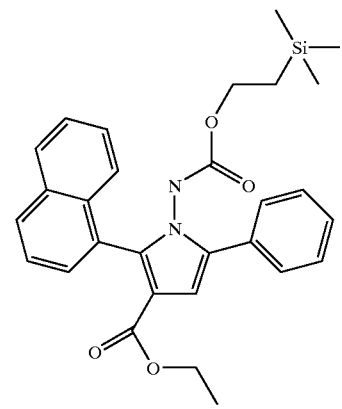

A solution of 2-(Naphthalene-1-carbonyl)-4-oxo-4-phenyl-butyric acid ethyl ester (1 g, 2.77 mmol) in toluene (6.5 mL) was treated with Hydrazinecarboxylic acid 2-trimethylsilanyl-ethyl ester (599 mg, 3.34 mmol) and p-toluene sulfonic acid (33 mg). The resulting solution was heated to reflux, with the azeotropic removal of water (Dean Stark trap), under Ar for 6 h, cooled to rt and concentrated in vacuo to afford 2-Naphthalen-1-yl-5-phenyl-1-(2-trimethylsilanyl-ethoxycarbonylamino)-1H-pyrrole-3-carboxylic acid ethyl ester (1.33 g), which was not purified, but used immediately in the next reaction.

Example 228

Synthesis of 1-Amino-2-naphthalen-1-yl-5-phenyl-1H-pyrrole-3-carboxylic acid ethyl ester

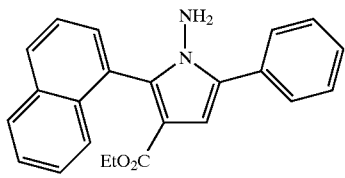

2-Naphthalen-1-yl-5-phenyl-1-(2-trimethylsilanyl-ethoxycarbonylamino)-1H-pyrrole-3-carboxylic acid ethyl ester (608 mg, 1.3 mmol) was treated with a solution of TBAF in THF (2.66 mL of a 1 M solution, 2.7 mmol). The resulting solution was stirred at rt under Ar overnight. The reaction was quenched with glacial acetic acid (145 µL, 2.5 mmol), and passed through a short plug of silica gel eluting with toluene. The filtrate was concentrated in vacuo to afford 1-Amino-2-naphthalen-1-yl-5-phenyl-1H-pyrrole-3-carboxylic acid ethyl ester (434 mg), which was not purified, but was used immediately for the next reaction.

Example 229

Synthesis of 1-[2-(2,5-Diphenyl-pyrrol-1-ylimino)-1-methyl-propylideneamino]-2-naphthalen-1-yl-5-phenyl-1H-pyrrole-3-carboxylic acid ethyl ester a66

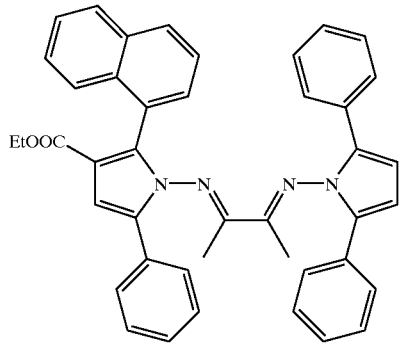

a66

A solution of 1-Amino-2-naphthalen-1-yl-5-phenyl-1H-pyrrole-3-carboxylic acid ethyl ester (434 mg, 1.22 mmol) in toluene (7.2 mL) was treated with 3-(2,5-Diphenyl-pyrrol-1-ylimino)-butan-2-one (308 mg, 1.02 mmol) and p-toluene sulfonic acid (8 mg). A Dean Stark trap was attached, and the resulting solution heated to reflux under Ar with the azeotropic removal of water for 18 h, then another portion of p-toluene sulfonic acid (8 mg) was added and the azeotropic removal of water was continued for an additional 75 min. The solution was cooled to rt and concentrated in vacuo. The residue was dissolved in THF/Acetic acid (10/1) and treated with PS-TsNHNH$_2$ resin (Argonaut Technologies, 1.039 g, 2.6 mmol). The suspension was stirred under Ar overnight, then filtered through a polyethylene frit, and concentrated in vacuo. The residue was purified by flash chromatography (SiO$_2$, 50–100% CH$_2$Cl$_2$/heptane) to afford 1-[2-(2,5-Diphenyl-pyrrol-1-ylimino)-1-methyl-propylideneamino]-2-naphthalen-1-yl-5-phenyl-1H-pyrrole-3-carboxylic acid ethyl ester a66 (240 mg, 37%): 1$^1$H NMR (DMSO, chemical shifts relative to TMS, 80° C.): 0.82 (t, 3H, J=7.3 Hz), 1.08 (s, 3H), 1.74 (s, 3H), 3.91 (q, 2H, J=6.9 Hz), 6.42 (s, 2H), 7.03 (s, 1H), 7.11 (d, 4H, J=7.3 Hz), 7.18 (t, 4H, J=7.3 Hz), 7.22–7.25 (m, 2H), 7.32–7.37 (m, 5H), 7.39–7.41 (m, 2H), 7.44–7.47 (m, 2H), 7.53 (d, 1H, J=8.2 Hz), 7.93 (t, 2H, J=8.7 Hz).

Example 230

Synthesis of 4,4''-Bis-trifluoromethyl-[1,1';3',1'']terphenyl-2'-ylamine

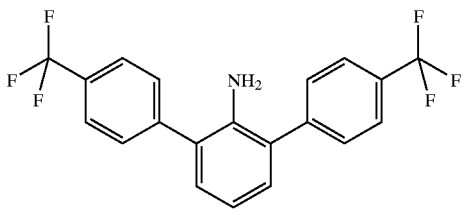

A suspension of tetrakis(triphenylphosphine) palladium (0) (66 mg, 0.06 mmol) in toluene (8 mL) was treated with 2,6-dibromoaniline (500 mg, 2.0 mmol), aqueous Na$_2$CO$_3$ (2M, 3.98 mL), and 4-trifluoromethylphenyl boronic acid (831 mg, 4.4 mmol). The resulting suspension was immersed in a 110° C. oil bath, and stirred under Ar for 22 h. The suspension was cooled to rt, and extracted with ether. The organic layer was washed with brine, dried over Na$_2$SO$_4$ and concentrated in vacuo. The residue was purified by flash chromatography (SiO$_2$, 2.5–5.0% EtOAc/Heptane) to afford 4,4''-Bis-trifluoromethyl-[1,1';3',1'']terphenyl-2'-ylamine (713 mg, 93%): $^1$H NMR (CDCl$_3$, chemical shifts in ppm relative to TMS): 6.93 (t, 1H, J=7.3 Hz), 7.14 (d, 2H, J=7.3 Hz), 7.64 (d, 4H, J=8.0 Hz), 7.74 (d, 4H, J=8.0 Hz).

Example 231

Synthesis of N, N'-Bis-(4, 4''-bis-trifluoromethyl-[1, 1'; 3', 1'']terphenyl-2'-yl)-oxalamide

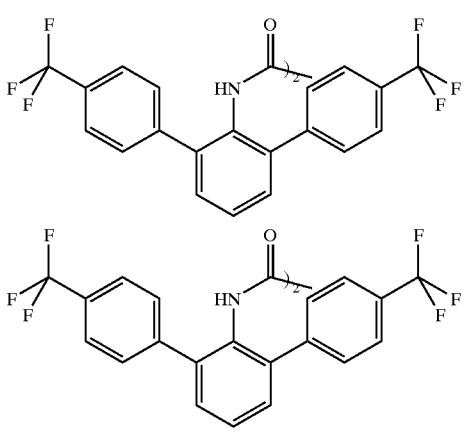

A solution of 4,4''-Bis-trifluoromethyl-[1,1';3',1''] terphenyl-2'-ylamine (700 mg, 1.84 mmol) in pyridine (5 mL) was treated with oxalyl chloride (73 µL, 0.837 mmol). The resulting suspension was stirred at rt overnight under Ar, then poured into H$_2$O. The precipitate was filtered, washed with H$_2$O and dried in vacuo. The resulting solid was crystallized from toluene/heptane, then recrystallized from toluene to afford N,N'-Bis-(4,4''-bis-trifluoromethyl-[1,1';3',1'']terphenyl-2'-yl)-oxalamide (430 mg).

Example 232

Synthesis of N¹, N²-Bis-(4, 4''-bis-trifluoromethyl-[1, 1'; 3', 1'']terphenyl-2'-yl)-oxalodiimidoyl dichloride

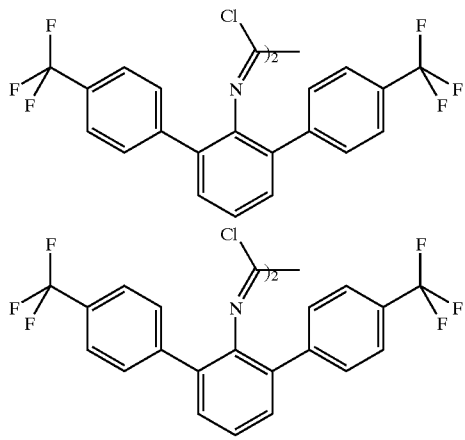

A suspension of N,N'-Bis-(4,4''-bis-trifluoromethyl-[1,1';3'1'']terphenyl-2'-yl)-oxalamide (419 mg, 0.513 mmol) in toluene (4.1 mL) was treated with PCl₅ (408 mg, 1.96 mmol) at rt. The resulting suspension was immersed in a 60° C. oil bath, and stirred under Ar for 6.5 h, then heated to 80° C. for an additional 1 h. The yellow solution was cooled to rt, diluted with ether (5 mL) and washed with H₂O (10 mL) and Aq. sat'd NaHCO₃. The organic layer was dried over Na₂SO₄, filtered and concentrated in vacuo to afford N¹,N²-Bis-(4,4''-bis-trifluoromethyl-[1,1';3',1'']terphenyl-2'-yl)-oxalodiimidoyl dichloride (401 mg, 92%) as a yellow solid: 7.33 (d, 4H, J=8.4 Hz), 7.38 (m, 3H), 7.50 (d, 4H, J=8.4 Hz); Field Desorption Mass Spectrometry: m/z 852.

Example 233

Synthesis of 2, 3-Bis-(2, 6-bis-trifluoromethylphenyl)-phenylimino)-[1, 4]dithiane V10

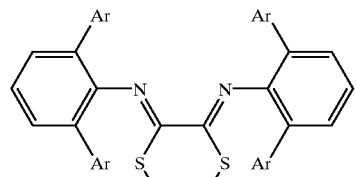

Ar = 4-trifluoromethylphenyl

Ethane dithiol (264 µL, 3.15 mmol) was added via syringe to a suspension of NaH (75.6 mg, 60% in oil, 1.89 mmol) in THF (5 mL). The resulting suspensiuon was stirred under Ar at rt for 15 min, then treated with a solution of N¹,N²-Bis-(4,4''-bis-trifluoromethyl-[1,1';3',1'']terphenyl-2'-yl)-oxalodiimidoyl dichloride (401 mg, 0.471 mmol) in THF (5 mL). The suspension was stirred overnight under Ar, then heated to 65° C. until not bis-imidoyl chloride remained (45 min) as determined by TLC. The reaction was cooled to rt, quenched with H₂O, and extracted with toluene. The organic layer was dried over Na₂SO₄, filtered and concentrated in vacuo. The residue was crystallized from heptane/CH₂Cl₂ to afford 2,3-bis-(2,6-bis-(4-trifluoromethylphenyl)-phenylimino)-[1,4]dithiane V10 (260 mg, 63%) as a yellow solid: 1¹H NMR (CDCl₃, chemical shifts in ppm relative to TMS): 2.06 (bs, 4H), 7.32–7.42 (m, 8H), 7.49 (bs, 7H); Field Desorption Mass Spectrometry: m/z 875.

Example 234

Synthesis of 2, 3-bis-(2, 6-diphenyl-phenylimino)-[1, 4]dithiane V9

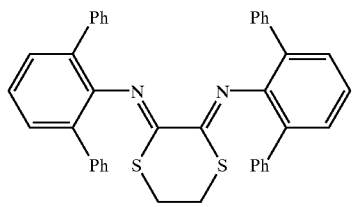

2,3-bis-(2,6-diphenyl-phenylimino)-[1,4]dithiane V9 was prepared using similar reaction conditions as described in Example 233 and was purified via washing with heptane and hot ethanol to afford 2,3-bis-(2,6-diphenyl-phenylimino)-[1,4]dithiane V9: ¹H NMR (DMSO, 80° C., chemical shifts in ppm relative to TMS): 2.21 (s, 4H), 7.21–7.39 (m, 26H).

Examples 235–241

Synthesis of ligands V1,V2, V3, V4, V5, V6, V8, and V12:

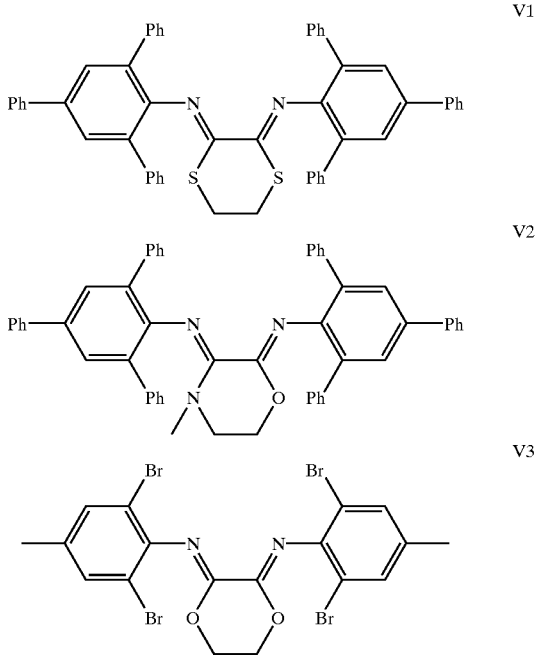

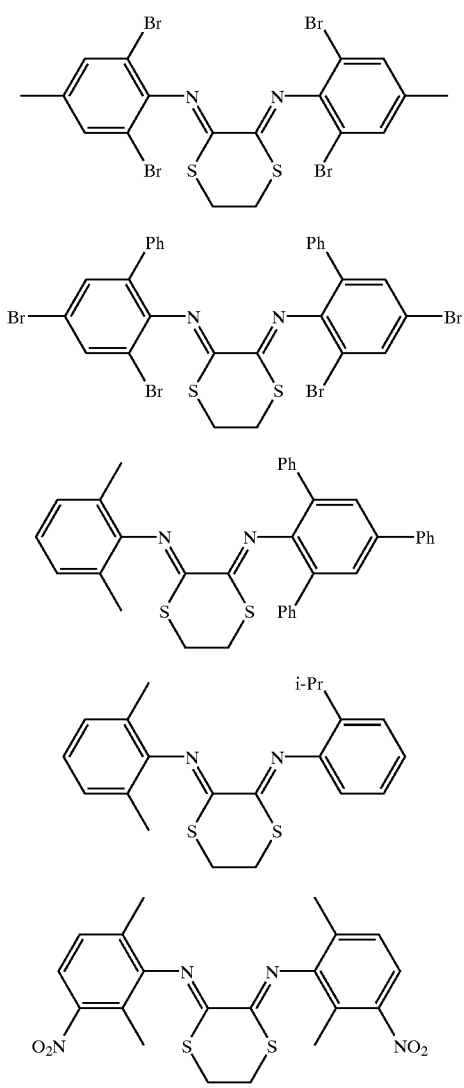

Ligands V1–V6, V8 and V12 were prepared using conditions similar to those described in Example 233.

| Example | Ligand | $^1$H NMR Data$^{a,b}$ |
|---|---|---|
| 235 | V5 | mixture of isomers, δ2.02(s, 6H), 2.54–2.62(m, 2H), 2.98–3.06(m, 2H), 6.90–7.06(m, 3H), 7.28–7.50(m, 9H), 7.60–7.76(m, 8H) |

-continued

| Example | Ligand | $^1$H NMR Data$^{a,b}$ |
|---|---|---|
| 236 | V6 | δ2.02(m, 1H), 2.47–2.64(m, 1H), 2.72–3.08(m, 2H), 7.16–7.40(m, 8H), 7.4–7.54(m, 4H), 7.68–7.82(m, 2H) |
| 237 | V2 | (CD$_2$Cl$_2$) δ1.98(m, 2H), 2.62(s, 3H), 2.98(m, 2H), 7.11–7.21(m, 10H), 7.23–7.35(m, 12H), 7.40(m, 6H), 7.49(t, J = 7.9 Hz, 3H), 7.6(d, J = 7.9 Hz, 2H), 7.78(d, J = 7.9 Hz, 2H) |
| 238 | V1 | (CD$_2$Cl$_2$) δ2.16(s, 4H), 7.25–7.41(m, 14H), 7.41–7.53(m, 12H), 7.63(s, 4H), 7.67–7.73(m, 4H) |
| 239 | V4 | δ2.32(s, 6H), 3.40(s, 4H), 7.40(s, 4H) |
| 240 | V3 | (CD$_2$Cl$_2$) δ2.30(s, 6H), 4.46(s, 4H), 7.39(s, 4H) |
| 241 | V12 | δ2.24(s, 3H), 2.25(s, 3H), 2.35(s, 3H), 2.36(s, 3H), 3.36(s, 4H), 7.22(d, J = 8.3 Hz, 2H), 7.68(d, J = 8.3 Hz, 2H) |

$^a$All Spectra Recorded in CDCl$_3$, Unless Otherwise indicated
$^b$All Chemical Shifts are Reported in ppm Relative to TMS Example 242

Preparation of a Pro-catalyst Stock Solution from Ligand V1: Ligand V1 (34.1 mg, 0.045 mmol), Ni(II) acetylacetonate (9.8 mg, 0.038 mmol) and triphenylcarbenium tetrakis (pentafluorophenyl)borate (34.8 mg, 0.038 mmol) were combined in a Schlenk Tube in an inert atmosphere dry box. The mixture was removed from the dry box and treated with CH$_2$Cl$_2$ (7.0 mL) under an inert atmosphere to provide a dark red stock solution of the pro-catalyst.

Example 243–319

Ethylene Polymerization with a Pro-Catalyst of the Type Prepared in Example 242

A Schlenk flask (200 mL, 500 mL or 1000 mL) equipped with a magnetic stir bar and capped with a septum was evacuated and refilled with ethylene, then charged with dry, deoxygenated toluene (100 mL) and a 10 wt % solution of MAO in toluene (4.0 mL). The requisite volume of pro-catalyst solution (prepared from the indicated ligand as in example 242) was added to give the amount of Ni indicated in the table below. The mixture was stirred under 1 atm ethylene at the temperature indicated in the table below and a polyethylene precipitate was observed. After the indicated reaction time, the mixture was quenched by the addition of acetone (50 mL), methanol (50 mL) and 6 N aqueous HCl (100 mL). The swollen polyethylene was isolated by vacuum filtration and washed with water, methanol and acetone, then dried under reduced pressure at 100° C. for 16 h to obtain the amount of polyethylene indicated in the table below.

| Example | Ligand | Temp (C.) | µmol Ni | Time min | g PE | $M_n$ | Branches/ 1000 C's |
|---|---|---|---|---|---|---|---|
| 243 | B8 | 23 | 0.549 | 15.00 | 0.805 | 38,200 | 21.0 |
| 244 | V1 | 23 | 0.551 | 6.00 | 0.795 | 782,700 | 4.7 |
| 245 | V1 | 23 | 0.559$^a$ | 14.00 | 1.629 | 131,500 | 1.8 |
| 246 | V1 | 23 | 0.547$^b$ | 6.00 | 0.540 | 145,300 | 2.9 |
| 247 | V7 | 23 | 0.552$^b$ | 6.00 | 0.048 | 82,800 | 22.6 |

-continued

| Example | Ligand | Temp (C.) | μmol Ni | Time min | g PE | $M_n$ | Branches/ 1000 C's |
|---|---|---|---|---|---|---|---|
| 248 | V1 | 23 | 0.276[c] | 24.00 | 0.539 | 89,000 | 3.0 |
| 249 | V1 | 23 | 0.276 | 8.00 | 0.371 | 703,700 | 4.5 |
| 250 | V1 | 23 | 0.276[c] | 24.00 | 0.934 | 87,800 | 2.7 |
| 251 | V1 | 23 | 0.276 | 8.00 | 0.529 | 540,700 | 3.6 |
| 252 | V1 | 23 | 0.276[c] | 15.00 | 0.527 | 88,500 | 3.2 |
| 253 | V2 | 23 | 2.320 | 8.00 | 0.178 | 92,900 | 11.3 |
| 254 | V3 | 23 | 1.04[d] | 8.00 | 0.351 | 77,700 | 16.2 |
| 255 | V3 | 23 | 1.040 | 8.00 | 0.776 | 46,700 | 19.9 |
| 256 | V4 | 23 | 0.21[e] | 13.66 | 0.620 | 207,000 | 11.3 |
| 257 | V4 | 23 | 0.405 | 5.33 | 0.828 | 192,200 | 12.0 |
| 258 | V4 | 23 | 0.405[d] | 6.00 | 0.324 | 177,800 | 8.4 |
| 259 | V6 | 23 | 0.418 | 56.75 | 0.611 | 97,200 | 55.4 |
| 260 | V5 | 23 | 0.380 | 6.00 | 0.333 | 103700 | 22.8 |
| 261 | V1 | 60 | 0.400 | 5.00 | | | |
| 262 | V1 | 60 | 0.400 | 30.00 | 0.219 | | |
| 263 | V1 | 60 | 0.400 | 120.00 | 0.473 | 421600 | |
| 264 | V1 | 60 | 0.400 | 15.00 | 0.104 | 112200 | 14 |
| 265 | V1 | 60 | 0.400 | 45.00 | 0.401 | 287500 | 14.7 |
| 266 | a67 | 23 | 0.366 | 14.00 | 0.446 | 115400 | 3.9 |
| 267 | a67 | 23 | 0.366 | 6.00 | 0.518 | 151100 | 3.6 |
| 268 | V12 | 23 | 0.373 | 12.00 | 0.194 | 168800 | 12.5 |
| 269 | V1 | 60 | 0.400[f,h] | 960.00 | 4.447 | | 18.5 |
| 270 | a54 | 23 | 0.392 | 2.50 | 0.762 | 132300 | 3 |
| 271 | a54 | 23 | 0.392[b] | 70.00 | 0.207 | 112500 | 1.5 |
| 272 | a54 | 23 | 0.391[i] | 8.00 | 0.596 | 115790 | 2 |
| 273 | a54 | 60 | 0.392[f,h] | 62.00 | 1.111 | 44600 | 20.2 |
| 274 | a54 | 60 | 0.196[f,h] | 62.00 | 0.711 | 82200 | 12.5 |
| 275 | V1 | 60 | 0.400 | 35.00 | 1.18 | | |
| 276 | a52 | 23 | 0.401 | 10.00 | 0.3 | 132900 | 2.3 |
| 277 | a54 | 23 | 0.402[e] | 5.00 | 2.973 | 139900 | 3.5 |
| 278 | a54 | 20 | 0.401[j,k] | 20.00 | 0.426 | 58000 | 14.3 |
| 279 | V1 | 23 | 0.384[e] | 5.00 | 0.735 | | |
| 280 | V1 | 80 | 0.384[e] | 5.00 | | | |
| 281 | V1 | 60 | 0.399[g] | 10.00 | 0.097 | 101000 | 15.1 |
| 282 | V1 | 60 | 0.200[g] | 10.00 | 0.037 | 62600 | 14.2 |
| 283 | V1 | 60 | 0.100[g] | 26.00 | 0.026 | 6390 | 64.1 |
| 284 | V1 | 80/0[l] | 0.399[g] | 20.00 | 0.728 | 368200 | 2.3 |
| 285 | V1 | 80/0/23[m] | 0.399[g] | 15.00 | 0.94 | 516200 | 4.4 |
| 286 | V1 | 80 | 0.399[g] | 45.00 | 0.253 | 97800 | 19.8 |
| 287 | a53 | 60/0/23[n] | 0.398[g] | 48.00 | 0.198 | | |
| 288 | V10 | 23 | 0.400[e] | 15.00 | 0.447 | 513800 | 5.7 |
| 289 | V10 | 23 | 0.400 | 8.00 | 0.284 | 398800 | 4.5 |
| 290 | V10 | 23 | 0.400[d] | 8.00 | 0.337 | 195200 | 2.5 |
| 291 | V10 | 23 | 0.400[c] | 8.00 | 0.233 | 109300 | 2 |
| 292 | V10 | 60 | 0.400[g] | 55.00 | 0.433 | 204300 | 13.4 |
| 293 | a59 | 23 | 0.400[g] | 6.00 | 1.054 | 98300 | |
| 294 | a59 | 23 | 0.400[d] | 6.00 | 0.768 | 77000 | |
| 295 | a59 | 60 | 0.400[g] | 60.00 | 0.236 | 28800 | |
| 296 | V11 | 23 | 0.402[g] | 20.00 | 0.623 | 302500 | |
| 297 | V11 | 23 | 0.402 | 20.00 | 0.146 | 252200 | |
| 298 | a66 | 23 | 0.398[g] | 9.00 | 0.706 | 60700 | 4.2 |
| 299 | a66 | 23 | 0.398[d] | 12.00 | 0.515 | 43600 | 3.1 |
| 300 | a66 | 60 | 0.398[g] | 60.00 | | | |
| 301 | a59 | 80/0/23 | 0.400[g] | 15.00 | | | |
| 302 | V9 | 23 | 0.400[g] | 8.00 | 0.899 | | 5.8 |
| 303 | a52 | 60 | 2.01[g] | 950.00 | 10.289 | 44300 | 18 |
| 304 | a52 | 60 | 2.01[g] | 950.00 | 10.289 | 42900 | 11 |
| 305 | a66 | 60 | 1.99[g] | 315.00 | 1.518 | | |
| 306 | a59 | 23 | 0.400[b] | 12.00 | 0.295 | 181100 | |
| 307 | a66 | 23 | 0.398[b] | 24.00 | 0.973 | 121100 | |
| 308 | a59 | 23 | 0.400[b] | 60.00 | 0.503 | 166900 | |
| 309 | a52 | 23 | 0.401[b] | 14.00 | 0.47 | 84400 | |
| 310 | a59 | 23 | 0.400[c] | 60.00 | 0.239 | 129000 | |
| 311 | a52 | 23 | 0.401[c] | 28.00 | 0.674 | 52700 | |
| 312 | a54 | 23 | 0.050 | 4.00 | 0.366 | 210200 | |
| 313 | a54 | 23 | 0.201[i] | 4.00 | 0.542 | 529800 | |
| 314 | a54 | 23 | 0.020 | 8.00 | 0.222 | 335400 | |
| 315 | a54 | 23 | 0.020 | 16.00 | 0.391 | 214500 | |
| 316 | a54 | 23 | 0.020 | 32.00 | 0.718 | | |
| 317 | a52 | 23 | 0.401 | 12.00 | 0.405 | | |

-continued

| Example | Ligand | Temp (C.) | μmol Ni | Time min | g PE | $M_n$ | Branches/ 1000 C's |
|---------|--------|-----------|---------|----------|------|-------|---------------------|
| 318 | a52 | 23 | 0.401[b] | 12.00 | 0.339 | | |
| 319 | a52 | 23 | 0.401[c] | 12.00 | 0.322 | | |

[a]60 mL of $H_2$ injected subsurface before the catalyst injection
[b]50 mL of $H_2$ injected subsurface before the catalyst injection
[c]100 mL of $H_2$ injected subsurface before the catalyst injection
[d]25 mL of $H_2$ injected subsurface before the catalyst injection
[e]600 mL of solvent
[f]DEAC used as cocatalyst
[g]300 mL of solvent
[h]Mineral spirits used as solvent
[i]10 mL of $H_2$ injected subsurface before the catalyst injection
[j]90 mL of toluene used as solvent
[k]10 mL of 1-hexene added to the polymerization
[l]5 min at 80° C., 15 min at 0° C.
[m]5 min at 80° C., 5 min at 0° C., 5 min at 23° C.
[n]25 min at 60° C., 5 min at 0° C., 18 min at 23° C.

Example 320
Synthesis of Ligand V11

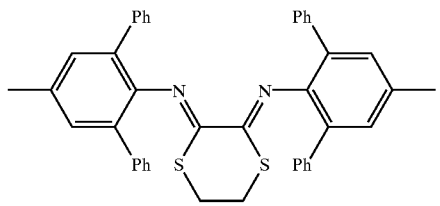

V11

2,3-bis-(2,6-diphenyl-4-methyl-phenylimino)-[1,4]dithiane V11 was prepared using similar reaction conditions as described in Example 233; $^1$H NMR (CDCl$_3$, chemical shifts in ppm relative to TMS): 2.36 (s, 4H), 2.41 (s, 6H), 7.16–7.23 (m, 24H).

Example 321

Preparation of Ligand a67

5-tert-Butyl-1-[2-(2,5-dimethyl-pyrrol-1-ylimino)-1-methyl-propylideneamine]-2-methyl-1H-pyrrole-3-carboxylic acid ethyl ester a67 was prepared using similar reaction conditions to those described in example 229; $^1$H NMR (CDCl$_3$, chemical shifts in ppm relative to TMS): 1.28 (s, 9H), 1.37 (t, 3H, J=6.9 Hz), 2.07 (s, 6H), 2.16 (s, 3H), 2.26 (s, 3H), 2.27 (s, 3H), 4.26–4.33 (m, two isomers, 2H), 5.93 (s, 2H), 6.44 (s, 3H).

Example 322
Synthesis of aa1

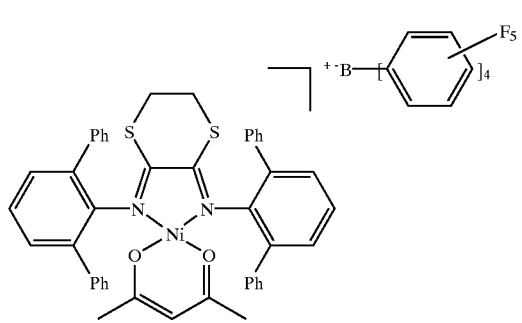

aa1

A flame dried Schlenk flask equipped with a rubber septum and a stir bar was charged with 128 mg (0.5 mmol) of nickel (II) acetylacetonate. Methylene chloride (10-ml) was added followed by the addition of a methylene chloride solution of 2,3-bis(2,6-diphenylimino)-[1,4]dithiane [300 mg (0.5 mmol) in 10-ml of CH$_2$Cl$_2$] resulting in a brown solution. After 2 minutes of stirring, a methylene chloride solution of Ph$_3$CB(C$_6$F$_5$)$_4$ was added giving a red solution. The mixture was allowed to stir for 1.5 hours. The solvent was removed in vacuo resulting in an oily solid. The oily solid was taken up in 5-ml of diethyl ether. Addition of 15-ml of hexane resulted in partial precipitation of the desired compound. The solvent was removed in vacuo giving a red powder. The red solid was washed with an Et$_2$O/hexane solution. The wash was repeated and the resulting solid taken up in a 1:1 Et$_2$O/CH$_2$Cl$_2$ solution. Hexane was layered onto the red solution and the mixture cooled to −78° C. and left to sit overnight. Upon sitting red crystals formed and the supernatent was removed via filter cannula. The resulting crystalline solid was dried under dynamic vacuum for several hours giving 374 mg of a red crystalline solid. $^1$H NMR was consistent with the desired complex.

Example 323

Polymerization of Ethylene with aa1+mMAO

A Parr® stirred autoclave (600-ml) was heated to 100° C. under dynamic vacuum to completely dry the reactor. The reactor was cooled and charged with 150 ml of dry toluene and 1-ml of mMAO (Akzo Nobel). In an inert atmosphere glove box, a septum-capped vial was charged with 3 mg of aa1. The vial was removed from the box and 20-ml of CH$_2$Cl$_2$ was added to the vial. The reactor was sealed and pressurized up to 150 psig ethylene and heated to 60° C. A 2-ml portion (0.3 mg, 2.1×10$^{-7}$ mol) of the solution of aa1 was removed from the vial and added to the autolclave via the high-pressure sample loop while pressurizing the autoclave to 200 psig. After 15 minutes of stirring at 200-psig ethylene and 60° C., the reaction was quenched upon addition of 2-ml of methanol at high pressure. The reactor was vented and the contents poured into a beaker containing a methanol acetone/mixture. The polymer was collected by suction filtration and dried in the vacuum oven overnight at ~100° C. giving 8.9 grams of polyethylene (6.1 million catalyst turnovers per hour).

Example 324

Polymerization of Ethylene with aa1+mMAO

A Parr® stirred autoclave (600-ml) was heated to 100° C. under dynamic vacuum to completely dry the reactor. The reactor was cooled and charged with 150 ml of dry toluene and 1-ml of mMAO (Akzo Nobel). In an inert atmosphere glove box, a septum-capped vial was charged with 3 mg of aa1. The vial was removed from the box and 20-ml of $CH_2Cl_2$ was added to the vial. The reactor was sealed and pressurized up to 150-psig ethylene and heated to 100° C. A 2-ml portion (0.3 mg, $2.1 \times 10^{-7}$ mol) of the solution of aa1 was removed from the vial and added to the autoclave via the high-pressure sample loop while pressurizing the autoclave to 200 psig. After 15 minutes of stirring at 200-psig ethylene and 100° C., the reaction was quenched upon addition of 2-ml of methanol at high pressure. The reactor was vented and the contents poured into a beaker containing a methanol acetone/mixture. The polymer was collected by suction filtration and dried in the vacuum oven overnight at ~100° C. giving 2.4 grams of polyethylene 1.6 million catalyst turnovers per hour). GPC analysis Mn=309,000; PDI=3.16. $^1$H NMR 13 branches/1000 carbons.

Example 325

Preparation of Silica Supported Catalyst of aa1

A flame dried Schlenk flask equipped with a stir bar and a rubber septum was charged in an inert atmosphere glove box with 14.3 mg ($9.94 \times 10^{-7}$ mol) of aa1 and 1 gram of Grace Davison 2402 silica. The flask was removed from the glove box, attached to the vacuum/argon manifold, evacuated and refilled with argon. To the solid mixture was added 5-ml of 1,2-difluorobenzene. The resulting suspension was stirred for 45 minutes at 0° C. The solvent was removed in vacuo giving 875 mg of the desired supported catalyst (catalyst loading 10 μmol/gram of silica).

Example 326

Preparation of Silica Supported Catalyst of aa1

A flame dried Schlenk flask equipped with a stir bar and a rubber septum was charged in an inert atmosphere glove box with 1 gram of Grace Davison 2402 silica. The flask was removed from the glove box, attached to the vacuum/argon manifold, evacuated and refilled with argon. To the solid was added 28.6 mg (20 μmol) of aa1 as a solution in $CH_2Cl_2$ (5-ml total). The resulting suspension was stirred for 30 minutes at room temperature. The solvent was removed in vacuo giving 889 mg of the desired supported catalyst (catalyst loading 20 μmol/gram of silica).

Example 327

Preparation of Silica Supported Catalyst of aa1

A flame dried Schlenk flask equipped with a stir bar and a rubber septum was charged in an inert atmosphere glove box with 1 gram of Grace Davison 2402 silica. The flask was removed from the glove box, attached to the vacuum/argon manifold, evacuated and refilled with argon. To the solid was added 14.3 mg (10 μmol) of aa1 as a solution in $CH_2Cl_2$ (5-ml total). The resulting suspension was stirred for 30 minutes at room temperature. The solvent was removed in vacuo giving 905 mg of the desired supported catalyst (catalyst loading 10 μmol/gram of silica).

Example 328

Preparation of Silica Supported Catalyst of aa1

A flame dried Schlenk flask equipped with a stir bar and a rubber septum was charged in an inert atmosphere glove box with 1 gram of Grace Davison 2402 silica. The flask was removed from the glove box, attached to the vacuum/argon manifold, evacuated and refilled with argon. To the solid was added 57.2 mg (40 μmol) of aa1 as a solution in $CH_2Cl_2$ (5-ml total). The resulting suspension was stirred for 30 minutes at room temperature. The solvent was removed in vacuo giving 911 mg of the desired supported catalyst (catalyst loading 40 μmol/gram of silica).

Examples 329–333

Gas Phase Polymerization of Ethylene Using in situ Activation Protocol

A Parr® stirred autoclave (600-ml) was heated to 100° C. under dynamic vacuum to completely dry the reactor. The reactor was cooled and charged with ~300 grams of NaCl and the supported procatalyst aa1 in an inert atmosphere glove box. The reactor was sealed removed from the glove box and placed under an argon atmosphere. The reactor was heated to 60° C. and trimethyl aluminum was added as a solution in toluene or hexane. The reactor is rapidly pressurized to 200-psig ethylene and left to stir. The reactor was vented and the contents poured into a beaker. The polymer was isolated by blending the salt/polymer mixture in water. The resulting polyethylene was collected dried in the vacuum oven overnight at ~100° C.

| Ex. | Conc. μmol Ni/g silica | TMA mmol | Catalyst Charged (mg) | Rxn time (min) | Yield PE (g) | TON mol $C_2H_4$/ mol Ni | Productivity g PE/g supported catalyst | $M_w$ ($\times 10^{-3}$) |
|---|---|---|---|---|---|---|---|---|
| 329 | 10 | 4 | 100 | 120 | 5.9 | 296K | 83 | 1440 |
| 330 | 10 | 4 | 100 | 50 | 4.9 | 176K | 49 | 1490 |
| 331 | 10 | 4 | 100 | 60 | 7.3 | 261K | 72 | 1660 |
| 332 | 10 | 4 | 50 | 60 | 3.5 | 254K | 70 | — |
| 333 | 40 | 8 | 50 | 60 | 17.2 | 307k | 344 | 1800 |

Examples 334–342

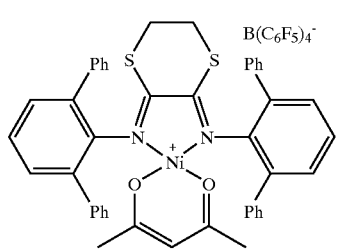

aa1

-continued

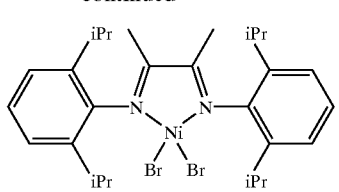
z1

Polymerization of Ethylene in the Presence of $H_2$ to Control Molecular Weight A Parr® stirred autoclave (600-ml) was heated to 100° C. under dynamic vacuum to completely dry the reactor. The reactor was cooled and charged with 150 ml of dry toluene, 1-ml of mMAO (7.14 wt % Al; Akzo Nobel) and $H_2$ gas. In an inert atmosphere glove box, a septum-capped vial was charged with $2.1 \times 10^{-6}$ mol of aa1 or z1. The vial was removed from the box and 20-ml of $CH_2Cl_2$ was added to the vial. The reactor was sealed and pressurized up to 150-psig ethylene and heated to 60° C. A 2-ml portion ($2.1 \times 10^{-7}$ mol of catalyst) of the solution of catalyst was removed from the vial and added to the autoclave via the high-pressure sample loop while pressurizing the autoclave to 200 psig. After 15 minutes of stirring at 200-psig ethylene and 60° C., the reaction was quenched upon addition of 2-ml of methanol at high pressure. The reactor was vented and the contents poured into a beaker containing a methanol acetone/mixture. The polymer was collected by suction filtration and dried in the vacuum oven overnight at ~100° C.

| Ex. | Catalyst | $H_2$ added (ml) | Yield PE (g) | TO mol $C_2H_4$/ mol Ni ($\times 10^{-3}$) | TOF mol $C_2H_4$/ mol Ni h ($\times 10^{-3}$) | $M_n$ ($\times 10^{-3}$) |
|---|---|---|---|---|---|---|
| 334 | aa1 | 0 | 8.9 | 1500 | 6100 | 1100 |
| 335 | aa1 | 25 | 6.6 | 1100 | 4500 | 1100 |
| 336 | aa1 | 50 | 7.3 | 1200 | 4900 | 524 |
| 337 | aa1 | 100 | 6.1 | 1000 | 4100 | 277 |
| 338 | aa1 | 150 | 7.7 | 1300 | 5300 | 349 |
| 339 | aa1 | 100 | 6.4 | 1100 | 4300 | 576 |
| 340 | z1 | 0 | 2.2 | 93 | 371 | 314 |
| 341 | z1 | 50 | 0.18 | 6 | 26 | 164 |
| 342 | z1 | 150 | 0.18 | 6 | 26 | 41 |

These data demonstrate that the catalysts of the present invention, especially those of the twenty-fourth and higher aspects, give rise to lower molecular weight polymer when the polymerization are conducted in the presence of hydrogen while exhibiting dramatically less inhibition or deactivation than the α-diimine catalyst z1.

Examples 343–346

Ethylene Polymerization with a Pro-Catalyst of the Type Prepared in Example 242

A Schlenk flask (200 mL, 500 mL or 1000 mL) equipped with a magnetic stir bar and capped with a septum was evacuated and refilled with ethylene, then charged with dry, deoxygenated toluene (100 mL) and a 10 wt % solution of MAO in toluene (4.0 mL). The requisite volume of pro-catalyst solution (prepared from the indicated ligand as in example 242) was added to give the amount of Ni indicated in the table below. The mixture was stirred under 1 atm ethylene at the temperature indicated in the table below and a polyethylene precipitate was observed. After the indicated reaction time, the mixture was quenched by the addition of acetone (50 mL), methanol (50 mL) and 6 N aqueous HCl (100 mL). The swollen polyethylene was isolated by vacuum filtration and washed with water, methanol and acetone, then dried under reduced pressure at 100° C. for 16 h to obtain the amount of polyethylene indicated in the table below.

| Example | Ligand | Temp (C.) | mmol Ni | Time min | g PE | $M_n$ | Branches/ 1000 C's |
|---|---|---|---|---|---|---|---|
| 343 | V3 | 60 | 1.040 | 5.00 | 0.104 | 26,000 | 21.1 |
| 344 | V4 | 60 | 0.405 | 25.00 | none | | |
| 345 | V5 | 60 | 0.380 | 25.33 | 0.492 | | |
| 346 | V5 | 23 | 0.380[a] | 6.00 | 0.175 | | |

[a] 30 mL of $H_2$ added subsurface prior to pro-catalyst injection

Example 347

Ethylene Polymerization at 57 C, 208 psig with the Catalyst Prepared from Ligand V1, Ni(acac)$_2$, Ph$_3$CB(C$_6$F$_5$)$_4$, and MAO A 1 L Parr® autoclave, Model 4520, was dried by heating under vacuum to 180° C. at 0.6 torr for 16 h, then cooled and refilled with dry nitrogen. The autoclave was charged with dry, deoxygenated toluene (450 mL) and 4.0 mL of a 10 wt % solution of MAO in toluene (Aldrich®), heated to 50° C. and pressurized to 80 psig with ethylene. A sample loop was then used to inject 2.0 mL of a stock solution of pro-catalyst prepared from 9.375 mL dry, deoxygenated $CH_2Cl_2$ and 0.625 mL of a stock solution prepared from ligand V1 (29.4 mg), Ni(acac)$_2$ (10.4 mg), Ph$_3$CB(C$_6$F$_5$)$_4$ (36.2 mg) and 5.0 mL of dry, deoxygenated $CH_2Cl_2$, and pressurized to about 200 psig with ethylene. The mixture was stirred under ethylene at an average pressure of about 208 psig and an average temperature of 57° C. for 80 min, after which the pressure was vented, the autoclave was opened, and the polymer treated with MeOH and 6 N aq HCl and isolated by filtration to obtain 60.3 g ($2.1 \times 10^6$ mol $C_2H_4$/mol Ni) of white, partially crystalline polyethylene.

Example 348

Ethylene Polymerization at 84 C, 270 psig with the Catalyst Prepared from Ligand V1, Ni(acac)$_2$, Ph$_3$CB(C$_6$F$_5$)$_4$, and MAO A procedure similar to that used in Example 347 was followed, except that the polymerization reaction temperature was 84 C, the pressure was 270 psig ethylene and the reaction was quenched by sample loop injection of 2.0 mL MeOH at 7.1 min. This gave 20.0 g polyethylene from 1.0 μmol catalyst (700,000 mol $C_2H_4$/mol Ni), corresponding to a rate of $5.9 \times 10^6$ mol $C_2H_4$/mol Ni/h. GPC: $M_n$=779,000, $M_w/M_n$=1.88.

Example 349

Ethylene Polymerization at 64 C, 260 psig with the Catalyst Prepared from Ligand a54. Ni(acac)$_2$, Ph$_3$CB(C$_6$F$_5$)$_4$, and MAO A procedure similar to that used in Example 348 was followed, except that the ligand was a54, the polymerization reaction temperature was 64 C, the pressure was 260 psig ethylene and the reaction was quenched by sample loop injection of 2.0 mL MeOH at 5.0 min. This gave 24.3 g polyethylene from 0.4 μmol catalyst ($2.2 \times 10^6$ mol $C_2H_4$/mol Ni), corresponding to a rate of $2.6 \times 10^7$ mol $C_2H_4$/mol Ni/h. GPC: $M_n$=73,000, $M_w/M_n$=1.97. $^1$H NMR: 2 branches/1000 C; 100% terminal olefin (within experimental error).

Example 350

Preparation of a Heterogeneous Catalyst Comprising Ligand V1

To a vial charged with V1 (37.8 mg; 50.0 μmol), Ni(acac)$_2$ (12.8 mg; 49.9 μmol) and Ph$_3$CB(C$_6$F$_5$)$_4$ (46.5 mg; 50.4 μmol) was added 3.0 mL 1,2-difluorobenzene. The resulting solution was stirred overnight (ca. 18 hours). This solution was then added dropwise to silica at 0° C. (1.0 g; PQ Corporation, MS-3030 dried at 600° C. under 500 SCCM helium). The flask was then warmed up to room temperature and vacuum was applied for an hour to remove volatile. The flask was then cooled back to 0° C. with an ice-water bath and diethylaluminum chloride (2.7 mL; 1.0M in hexanes) was added dropwise with proper agitation. Volatiles were removed in vacuo at 0° C. for 90 min. The resulting brown solid was stored under nitrogen at –30° C.

Example 351

Polymerization of Ethylene Using the Catalyst Prepared in Example 350

A catalyst delivery device was charged with the catalyst prepared in Example 350 (58.6 mg; 2.2 μmol Ni) and fixed to the head of a 1000-mL Parr® reactor. The device was placed under vacuum. The reactor was then charged with NaCl (325 g) that had been dried in vacuum at 120° C. for several hours, closed, evacuated and backfilled with nitrogen. The salt was subsequently treated with trimethylaluminum (10 mL; 2.0 M in toluene) and agitated at 60° C. for 30 min. The reactor was then pressurized with 200 psi ethylene and depressurized to atmospheric pressure four times. The catalyst was then introduced in the reactor with appropriate agitation. The reaction was allowed to proceed for 4 hours at 62° C. before the reactor was vented. The polymer was isolated by washing the contents of the reactor with water. The isolated polymer was further treated with 6 M HCl in methanol, rinsed with methanol and dried under vacuum to give 51.2 g (630 K TO, 875 g polymer/g silica; $^1$H NMR: $M_n$>50K, 6 BP/1000C; $T_m$=125° C.).

Example 352

Polymerization of Ethylene Using the Catalyst Prepared in Example 350 in the Presence of Hydrogen A catalyst delivery device was charged with the catalyst prepared in Example 350 (47.7 mg; 1.8 μmol Ni) and fixed to the head of a 1000-mL Parr® reactor. The device was placed under vacuum. The reactor was then charged with NaCl (348 g) that had been dried in vacuum at 120° C. for several hours, closed and evacuated. The reactor was then pressurized with 200 psi ethylene and depressurized to atmospheric pressure three times. The salt was subsequently treated with trimethylaluminum (10 mL; 2.0 M in hexanes) and agitated at 60° C. for 30 min. The reactor was again pressurized with 200 psi ethylene and depressurized to atmospheric pressure three times. Hydrogen (150 mL) was subsequently added to the reactor. The catalyst was then introduced in the reactor with appropriate agitation. The reaction was allowed to proceed for 4 hours at 56° C. before the reactor was vented. The polymer was isolated by washing the contents of the reactor with water. The isolated polymer was further treated with 6 M HCl in methanol, rinsed with methanol and dried under vacuum to give 3.41 g (67.7 K TO, 71 g polymer/g silica; GPC: $M_n$=159K, $M_w/M_n$=3.0; $T_m$=123° C.).

Example 353

Preparation of a Heterogeneous Catalyst Comprising Ligand V1

A 1,2-difluorobenzene solution (3.0 mL) containing 20.2 μmol of V1, Ni(acac)$_2$ and Ph$_3$CB(C$_6$F$_5$)$_4$ was added dropwise to silica at 0° C. (2.0 g; Grace Davison, XPO-2402). The flask was then warmed up to room temperature and vacuum was applied for an hour to remove volatile. The flask was then cooled back to 0° C. with an ice-water bath and diethylaluminum chloride (2.7 mL; 1.0M in hexanes) was added dropwise with proper agitation. Volatiles were removed in vacuo at 0° C. for 90 min. The resulting solid was stored under nitrogen at –30° C.

Example 354

Polymerization of Ethylene Using the Catalyst Prepared in Example 353

A catalyst delivery device was charged with the catalyst prepared in Example 353 (205 mg; 1.9 μmol Ni) and fixed to the head of a 1000-mL Parr® reactor. The device was placed under vacuum. The reactor was then charged with NaCl (329 g) that had been dried in vacuum at 120° C. for several hours, closed, evacuated and backfilled with nitrogen. The salt was subsequently treated with trimethylaluminum (10 mL; 2.0 M in toluene) and agitated at 60° C. for 30 min. The reactor was then pressurized with 200 psi ethylene and depressurized to atmospheric pressure four times. The catalyst was then introduced in the reactor with appropriate agitation. The reaction was allowed to proceed for 90 min at 63° C. before the reactor was vented. The polymer was isolated by washing the contents of the reactor with water. The isolated polymer was further treated with 6 M HCl in methanol, rinsed with methanol and dried under vacuum to give 45.8 g (857 K TO, 224 g polymer/g silica; $^1$H NMR: $M_n$>50K, 8 BP/1000C; $T_m$=122° C.).

Example 355

Preparation of a Heterogeneous Catalyst Comprising Ligand V1

To a vial charged with V1 (37.7 mg; 49.9 μmol), Ni(acac)$_2$ (12.8 mg; 49.9 μmol) and Ph$_3$CB(C$_6$F$_5$)$_4$ (46.1 mg; 50.0 μmol) was added 3.0 mL 1,2-difluorobenzene. The resulting solution was stirred overnight (ca. 18 hours). This solution was then added dropwise to silica at 0° C. (1.02 g; PQ Corporation, MS-3030 dried at 600° C. under 500 SCCM helium). The flask was then warmed up to room temperature and vacuum was applied for 90 min to remove volatile. The resulting brick-red solid was stored under nitrogen at –30° C.

Example 356

Polymerization of Ethylene Using the Catalyst Prepared in Example 355

A catalyst delivery device was charged with the catalyst prepared in Example 355 (44.1 mg; 2.2 μmol Ni) and fixed to the head of a 1000-mL Parr® reactor. The device was placed under vacuum. The reactor was then charged with NaCl (328 g) that had been dried in vacuum at 120° C. for several hours, closed, evacuated and backfilled with nitrogen. The salt was subsequently treated with trimethylaluminum (10 mL; 2.0 M in hexane) and agitated at 60° C. for 30 min. The reactor was then pressurized with 200 psi ethylene and depressurized to atmospheric pressure three times. The catalyst was then introduced in the reactor with appropriate agitation. The reaction was allowed to proceed for 4 hours at 86° C. before the reactor was vented. The polymer was isolated by washing the contents of the reactor with water. The isolated polymer was further treated with 6 M HCl in methanol, rinsed with methanol and dried under vacuum to give 48.0 g (777 K TO, 1100 g polymer/g silica; GPC: $M_n=1,300,000$, $M_w/M_n=2.0$; $T_m=112°$ C.).

Example 357

Preparation of a Heterogeneous Catalyst Comprising Ligand a54

To a vial charged with a54 (26.0 mg; 50.1 µmol), Ni(acac)$_2$ (12.8 mg; 49.9 µmol) and Ph$_3$CB(C$_6$F$_5$)$_4$ (46.1 mg; 50.0 µmol) was added 3.0 mL 1,2-difluorobenzene. The resulting solution was stirred overnight (ca. 18 hours). This solution was then added dropwise to silica at 0° C. (992 mg; PQ Corporation, MS-3030 dried at 600° C. under 500 SCCM helium). The flask was then warmed up to room temperature and vacuum was applied for 90 min to remove volatile. The resulting brick-red solid was stored under nitrogen at −30° C.

Example 358

Polymerization of Ethylene Using the Catalyst Prepared in Example 357

A catalyst delivery device was charged with the catalyst prepared in Example 357 (94 mg; 4.7 µmol Ni) and fixed to the head of a 1000-mL Parr® reactor. The device was placed under vacuum. The reactor was then charged with NaCl (320 g) that had been dried in vacuum a t 120° C. for several hours, closed, evacuated and backfilled with nitrogen three times. The salt was subsequently treated with trimethylaluminum (10 mL; 2.0 M in hexane) and agitated at 60° C. for 30 min. The reactor was then pressurized with 200 psi ethylene and depressurized to atmospheric pressure three times. The catalyst was then introduced in the reactor with appropriate agitation. The reaction was allowed to proceed for 3.5 hours at 58° C. before the temperature was increased to 80° C. The reaction was allowed to proceed for a total of 5.5 hours. The polymer was isolated by washing the contents of the reactor with water. The isolated polymer was further treated with 6 M HCl in methanol, rinsed with methanol and dried under vacuum to give 2.52 g (18,700 TO, 27 g polymer/g silica; GPC: $M_n=45,500$; $M_w/M_m=4.6$; $T_m=118°$ C.).

Example 359

Preparation of a Heterogeneous Catalyst Comprising Ligand V9

To a vial charged with V9 (30.1 mg; 49.9 µmol), Ni(acac)$_2$ (13.1 mg; 50.1 µmol) and Ph$_3$CB(C$_6$F$_5$)$_4$ (46.2 mg; 50.1 µmol) was added 3.0 mL 1,2-difluorobenzene. The resulting solution was stirred overnight (ca. 18 hours). This solution was then added dropwise to silica at 0° C. (996 mg; PQ Corporation, MS-3030 dried at 600° C. under 500 SCCM helium). The flask was then warmed up to room temperature and vacuum was applied for 90 min to remove volatile. The resulting solid was stored under nitrogen at −30° C.

Example 360

Polymerization of Ethylene using the Catalyst Prepared in Example 359 in the Presence of Hydrogen A catalyst delivery device was charged with the catalyst prepared in Example 359 (54.4 mg; 2.8 µmol Ni) and fixed to the head of a 1000-mL Parr® reactor. The device was placed under vacuum. The reactor was then charged with NaCl (313 g) that had been dried in vacuum at 120° C. for several hours, closed and evacuated. The reactor was then evacuated and backfilled with nitrogen (1 atm) three times. The salt was subsequently treated with trimethylaluminum (10 mL; 2.0 M in hexanes) and agitated at 80° C. for 30 min. The reactor was again pressurized with 200 psi ethylene and depressurized to atmospheric pressure three times. Hydrogen (100 mL) was subsequently added to the reactor. The catalyst was then introduced in the reactor with appropriate agitation. The reaction was allowed to proceed for 4 hours at 83° C. before the reactor was vented. The polymer was isolated by washing the contents of the reactor with water. The isolated polymer was further treated with 6 M HCl in methanol, rinsed with methanol and dried under vacuum to give 7.61 g (98 K TO, 137 g polymer/g silica; $^1$H NMR: $M_n>75K$, 12 BP/1000C; GPC: $M_n=52.5K$, $M_w/M_n=3.3$).

Example 361

Preparation of a Heterogeneous Catalyst Comprising Ligand a54

To a vial charged with a54 (7.8 mg; 15 µmol), Ni(acac)$_2$ (3.9 mg; 15 µmol) and Ph$_3$CB(C$_6$F$_5$)$_4$ (13.8 mg; 15.0 µmol) was added 0.5 mL 1,2-difluorobenzene. The resulting solution was stirred overnight (ca. 18 hours). This solution was then added dropwise to silica at 0° C. (229 mg; Grace Davison XPO-2402). The flask was then warmed up to room temperature and vacuum was applied for 90 min to remove volatile. The resulting brown solid was stored under nitrogen at −30° C.

Example 362

Polymerization of Ethylene Using the Catalyst Prepared in Example 361

A catalyst delivery device was charged with the catalyst prepared in Example 361(44 mg; 2.2 µmol Ni) and fixed to the head of a 1000-mL Parr® reactor. The device was placed under vacuum. The reactor was then charged with NaCl (348 g) that had been dried in vacuum at 120° C. for several hours, closed, evacuated and backfilled with nitrogen three times. The salt was subsequently treated with trimethylaluminum (8 mL; 2.0 M in hexane) and agitated at 60° C. for 30 min. The reactor was then pressurized with ethylene (ca. 200 psi) and depressurized to atmospheric pressure four times. The catalyst was then introduced in the reactor with appropriate agitation. The reaction was allowed to proceed for 4 hours at 60° C. The polymer was isolated by washing the contents of the reactor with water. The isolated polymer was further treated with 6 M HCl in methanol, rinsed with methanol and dried under vacuum to give 15.7 g (254 K TO, 355 g polymer/g; GPC: $M_n=110,000$, $M_w/M_n=4.2$; $^1$H NMR: $M_n>75,000$, 10 BP/1000C).

Example 363

Preparation of a Heterogeneous Catalyst Comprising Ligand V1

To a vial charged with V1 (37.9 mg; 50.2 μmol), Ni(acac)$_2$ (12.9 mg; 50.2 μmol) and Ph$_3$CBF$_4$ (16.6 mg; 50.3 μmol) was added 1.6 mL 1,2-difluorobenzene. The resulting solution was stirred overnight (ca. 18 hours). This solution was then added dropwise to silica at 0° C. (0.985 g; Grace Davison, XPO-2402). The flask was then warmed up to room temperature and vacuum was applied for 2.5 h to remove volatiles. The resulting brick-red solid was stored under nitrogen at −30° C.

Example 364

Polymerization of Ethylene Using the Catalyst Prepared in Example 363

A catalyst delivery device was charged with the catalyst prepared in Example 363 (45.4 mg; 2.3 μmol Ni) and fixed to the head of a 1000-mL Parr® reactor. The device was placed under vacuum. The reactor was then charged with NaCl (323 g), which had been dried in vacuum at 120° C. for several hours, and closed, evacuated and backfilled with nitrogen. The salt was subsequently treated with trimethylaluminum (10 mL; 2.0 M in hexane) and agitated at 80° C. for 20 min. The reactor was then pressurized with 200 psi ethylene and depressurized to atmospheric pressure three times. The catalyst was then introduced in the reactor with appropriate agitation. The reaction was allowed to proceed for 2.5 hours at 80° C. before the reactor was vented. The polymer was isolated by washing the contents of the reactor with water. The isolated polymer was further treated with 6 M HCl in methanol, rinsed with methanol and dried under vacuum to give 1.84 g of polymer (GPC: $M_n$=219,000, $M_w/M_n$=4.7).

Example 365

Polymerization of Ethylene Using the Catalyst Prepared in Example 361

A catalyst delivery device was charged with the catalyst prepared in Example 361 (74.2 mg; 3.8 μmol Ni) and fixed to the head of a 1000-mL Parr® reactor. The device was placed under vacuum. The reactor was then charged with NaCl (345 g), which had been dried in vacuum at 120° C. for several hours, and closed, evacuated and backfilled with nitrogen. The salt was subsequently treated with trimethylaluminum (10 mL; 2.0 M in hexane) and agitated at 60° C. for 30 min. The reactor was then pressurized with 200 psi ethylene and depressurized to atmospheric pressure three times. Hydrogen gas (50 mL) was then syringed in. The catalyst was then introduced in the reactor with pressure with appropriate agitation. The reaction was allowed to proceed under 200 psi C$_2$H$_4$ for 4 hours at 59° C. before the reactor was vented. The polymer was isolated by washing the contents of the reactor with water. The isolated polymer was further treated with 6 M HCl in methanol, rinsed with methanol and dried under vacuum to give 11.2 g (151 g polyethylene/g SiO$_2$; 106,000 mol C$_2$H$_4$/mol Ni; $^1$H NMR: 8 BP/1000 C; GPC: $M_n$=78,000, $M_w/M_n$=2.5).

Example 366

Polymerization of Ethylene Using a Catalyst Prepared using a Procedure Analogous to that Described in Example 361

A catalyst delivery device was charged with a 14.9 wt % dispersion in Sylopol 2100 (92.3 mg; 0.69 μmol Ni) of a catalyst prepared using a procedure analogous to that described in Example 361. In this case, Grace Davison Sylopol 2100, the actual silica used, was loaded with a solution containing the individual components, such that the concentration of nickel was 50 μmol/g silica. The catalyst delivery device was fixed to the head of a 1000-mL Parr® reactor. The device was placed under vacuum. The reactor was then charged with NaCl (278 g), which had been dried in vacuum at 120° C. for several hours, and then closed, evacuated and backfilled with nitrogen. The salt was subsequently treated with trimethylaluminum (10 mL; 2.0 M in hexane) and agitated at 60° C. for 30 min. The reactor was then pressurized with 200 psi ethylene and depressurized to atmospheric pressure three times. With appropriate agitation, the catalyst was then introduced in the reactor under ethylene pressure, which resulted in a 17° C. exotherm. The reaction was allowed to proceed under 200 psi C$_2$H$_4$ for 60 minutes at 75° C. before the reactor was vented. The polymer was isolated by washing the contents of the reactor with water. The isolated polymer was further treated with 6 M HCl in methanol, rinsed with methanol and dried under vacuum to give 19.2 g (1400 g polyethylene/g supported catalyst; 991,000 mol C$_2$H$_4$/mol Ni; $^1$H NMR: 7 BP/1000 C; GPC: $M_n$=89,900, $M_w/M_n$=3.0).

Example 367

Polymerization of Ethylene Using a Catalyst Prepared using a Procedure Analogous to that Described in Example 361

A catalyst delivery device was charged with a 3.0 wt % dispersion in Sylopol 2100 (55 mg; 82 nmol Ni) of a catalyst prepared using a procedure analogous to that described in Example 361. In this case, Grace Davison Sylopol 2100, the actual silica used, was loaded with a solution containing the individual components, such that the concentration of nickel was 50 μmol/g silica. The catalyst delivery device was fixed to the head of a 1000-mL Parr® reactor. The device was placed under vacuum. The reactor was then charged with NaCl (350 g) that had been dried in vacuum at 120° C. for several hours. The reactor was closed, and pressurized with ca. 50 psi nitrogen and depressurized to atmospheric pressure several times. The salt was subsequently treated with trimethylaluminum (10 mL; 2.0 M in hexane) and agitated at 57° C. for 30 min. The reactor was then pressurized with 200 psi ethylene and depressurized to atmospheric pressure three times. With appropriate agitation, the catalyst was then introduced in the reactor under ethylene pressure. The reaction was allowed to proceed under 100 psi C$_2$H$_4$ for 4 hours at 60° C. before the reactor was vented. The polymer was isolated by washing the contents of the reactor with water. The isolated polymer was further treated with 6 M HCl in methanol, rinsed with methanol and dried under vacuum to give 2.49 g (1500 g polyethylene/g supported catalyst; 1,100,000 mol C$_2$H$_4$/mol Ni; $^1$H NMR: 12 BP/1000 C; GPC: $M_n$=72,300, $M_w/M_n$=3.2). Example 368

Preparation of a Heterogeneous Catalyst Comprising the Nickel Complex Prepared in Example 322

A dichloromethane solution of aa1 (0.75 mL; 2.5 μmol) was added dropwise to Grace Davison XPO-2402 (5.0 g), at 0° C., with appropriate agitation. The solid was brought to room temperature and the flask placed under vacuum for 90 minutes to remove volatiles. The resulting solid was used as is in subsequent polymerization reactions.

Example 369

Polymerization of Ethylene Using the Catalyst Prepared in Example 368

A catalyst delivery device was charged with the catalyst prepared in Example 368 (1.07 g; 0.54 μmol Ni) and fixed to the head of a 1000-mL Parr® reactor. The device was placed under vacuum. The reactor was then charged with NaCl (354 g) that had been dried in vacuum at 120° C. for several hours. The reactor was closed, and pressurized with nitrogen (ca. 40 psi) and depressurized to atmospheric pressure 10 times. The salt was subsequently treated with trimethylaluminum (10 mL; 2.0 M in hexane) and agitated at 86° C. for 30 min. The reactor was then pressurized with 200 psi ethylene and depressurized to atmospheric pressure five times. The catalyst was then introduced in the reactor with appropriate agitation, leading to a 6° C. exotherm. The reaction was allowed to proceed for 60 minutes at 88° C. before the reactor was vented. The polymer was isolated by washing the contents of the reactor with water. The isolated polymer was further treated with 6 M HCl in methanol, rinsed with methanol and dried under vacuum to give 10.4 g (620,000 mol $C_2H_4$/mol Ni). $^1$H NMR (o-dichlorobenzene): 13 branch points/1000 carbons.

Example 370

Preparation of a Heterogeneous Catalyst Comprising the Nickel Complex Prepared in Example 322

A dichloromethane solution of aa1 (0.75 mL; 2.5 μmol) was added dropwise to Grace Davison XPO-2402 (5.0 g), at 0° C., with appropriate agitation. The solid was brought to room temperature and the flask placed under vacuum for ca. 60 minutes to remove volatiles. The above was repeated nine more times, leading to a final nickel loading on silica of 5.0 μmol/g. The resulting solid was used as is in subsequent polymerization reactions.

Example 371

Polymerization of Ethylene Using the Catalyst Prepared in Example 370

A catalyst delivery device was charged with the catalyst prepared in Example 370 (540 mg; 2.7 μmol Ni) and fixed to the head of a 1000-mL Parr® reactor. The device was placed under vacuum. The reactor was then charged with NaCl (281 g) that had been dried in vacuum at 120° C. for several hours. The reactor was closed, and pressurized with nitrogen (ca. 40 psi) and depressurized to atmospheric pressure 10 times. The salt was subsequently treated with trimethylaluminum (10 mL; 2.0 M in hexane) and agitated at 84° C. for 30 min. The reactor was then pressurized with 200 psi ethylene and depressurized to atmospheric pressure five times. The catalyst was then introduced in the reactor with appropriate agitation, leading to a raise in temperature to 100° C. The reaction was allowed to proceed for 30 minutes at 94° C. before the reactor was vented. The polymer was isolated by washing the contents of the reactor with water. The isolated polymer was further treated with 6 M HCl in methanol, rinsed with methanol and dried to give 24.8 g (320 K mol $C_2H_4$/mol Ni).

Example 372

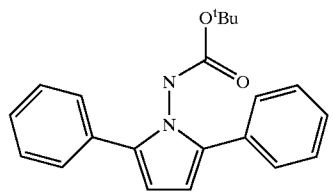

Synthesis of (2,5-Diphenyl-pyrrol-1-yl)-carbamic Acid tert-Butyl Ester

A solution of dibenzoylethane (5 g, 21.0 mmol) and t-butyl carbazate (3.98 g, 30.1 mmol) in EtOH (170 mL) and AcOH (21 mL) was heated to reflux under Ar for 4.5 h, cooled to rt and diluted with water (400 mL). The resulting suspension was stirred under Ar at rt for 3 h, and then allowed to settle overnight at rt. The solid was filtered, washed with small portions of water and dried in vacuo to afford (2,5-Diphenyl-pyrrol-1-yl)-carbamic acid tert-butyl ester (6.72 g, 96%) as a white solid: $^1$H NMR (CDCl$_3$, chemical shifts in ppm relative to TMS): 1.14 (s, 3H), 1.38 (s, 6H), 6.35 (s, 2H), 6.84 (bs, 2H), 7.29–7.53 (m, 10H).

Example 373

Synthesis of 2,5-Diphenyl-pyrrol-1-ylamine

A suspension of (2,5-Diphenyl-pyrrol-1-yl)-carbamic acid tert-butyl ester (3.7 g, 11.06 mmol) in anhydrous methanol (25 mL) was cooled to 0° C. in an ice water bath, then treated with conc. HCl (9.86 mL). The ice bath was removed, and the resulting suspension was heated to reflux in an oil bath for 1.5 h. Upon cooling to rt, a white solid precipitated, which was filtered, washed with water and dried in vacuo to afford 2,5-Diphenyl-pyrrol-1-ylamine (2.32 g, 90%): $^1$H NMR (CDCl$_3$, chemical shifts in ppm relative to TMS): 3.64 (bs, 2H), 6.28 (s, 2H), 7.28–7.33 (m, 2H), 7.42 (t, 4H, J=8.0 Hz), 7.58 (d, 4H, J=8.0 Hz).

Example 374

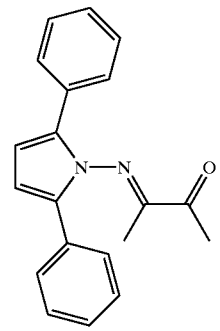

Synthesis of 3-(2,5-Diphenyl-pyrrol-1-ylimino)-butan-2-one

A suspension of 2,5-Diphenyl-pyrrol-1-ylamine (1.91 g, 8.15 mmol) in toluene (5.45 mL) was treated with 2,3-butanedione (7.15 mL, 81.5 mmol), DMF (10.9 mL) and p-toluene sulfonic acid (10.9 mg). The resulting suspension was stirred under Ar at rt for 30 min, then heated to 70° C. in an oil bath. After 2.5 h, the solutions cooled to rt and concentrated in vacuo. The oily solid was dissolved in toluene and concentrated in vacuo to remove excess 2,3-butanedione. The residue was purified by flash chromatography (SiO$_2$, 10% EtOAc/heptane) to afford 3-(2,5-Diphenyl-pyrrol-1-ylimino)-butan-2-one: $^1$H NMR (CDCl$_3$, chemical shifts in ppm relative to TMS): 1.44 (s, 3H), 2.56 (s, 3H), 6.47 (s, 2H), 7.20–7.26 (m, 2H), 7.34 (t, 4H, J=8.0 Hz), 7.47 (d, 4H, J=8.0 Hz).

Example 375

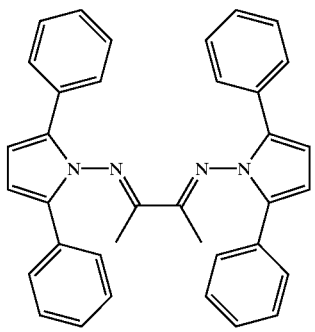

Synthesis of 2,3-bis(2,5-Diphenyl-pyrrol-1-ylimino)-butane

A suspension of 3-(2,5-Diphenyl-pyrrol-1-ylimino)-butan-2-one (2.45 g, 8.1 mmol) in toluene (28 mL) was treated with DMF (14 mL), 2,5-diphenyl-pyrrol-1-ylamine (1.99 g, 8.5 mmol) and p-toluene sulfonic acid (73 mg). The resulting suspension was fitted with a Dean Stark trap and heated to reflux in an oil bath for 21 h, then cooled to rt and allowed to stand under Ar for 4 days. The desired compound did not crystallize, therefore the solution was concentrated in vacuo. Approximately half of the residue was purified by flash chromatography (SiO$_2$, 5–100% EtOAc/heptane) to afford some pure desired 2,3-bis(2,5-Diphenyl-pyrrol-1-ylimino)-butane (780 mg) and some desired contaminated with starting 2,5-diphenyl-pyrrol-1-ylamine. The remaining crude residue was flash chromatographed (SiO$_2$, 33–50% CH$_2$Cl$_2$/heptane) in an attempt to remove excess amino pyrrole. No separation was achieved, therefore all of the fractions were combined, together with the impure material from the first column and concentrated in vacuo. This mixture was suspended in toluene (15 mL) and treated with DMF (5 mL), 2,3-butanedione (0.81 mL, 9.24 mmol) and p-toluene sulfonic acid (7 mg). The resulting suspension was heated to 70° C. in an oil bath, and stirred under Ar for 3 h, then cooled to rt and concentrated in vacuo. The resulting solid was washed with water, heptane and toluene (to remove 3-(2,5-Diphenyl-pyrrol-1-ylimino)-butan-2-one and 2,3-butanedione) and dried in vacuo to afford 2,3-bis(2,5-Diphenyl-pyrrol-1-ylimino)-butane (1.42 g) as a yellow solid. Overall, 2.2 g (52% based on 3-(2,5-Diphenyl-pyrrol-1-ylimino)-butan-2-one) of 2,3-bis(2,5-Diphenyl-pyrrol-1-ylimino)-butane was isolated as a yellow solid: $^1$H NMR (CDCl$_3$, chemical shifts in ppm relative to TMS): 1.71 (s, 6H), 6.44 (s, 4H), 7.22–7.36 (m, 20H).

Example 376

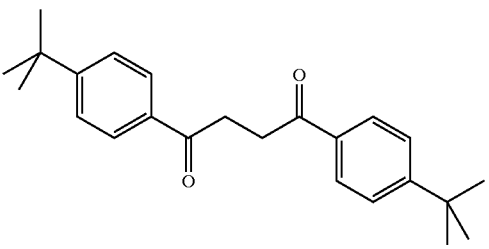

Synthesis of 1,4-bis-(4-tert-Butyl-phenyl)-butane-1,4-dione

A solution of lithium diisopropyl amide (LDA) in THF was prepared by adding 2.5 M in hexanes n-butyl lithium (6.3 mL, 15.7 mmol) dropwise to a solution of diisopropyl amine (2.2 mL, 15.7 mmol) in THF (16.32 mL) at −78° C. To this solution was added 4'-t-butyl acetophenone (2.5 g, 14.2 mmol) as a solution in THF (3 mL) via dropping funnel at −78° C. The resulting solution was stirred at −78° C. under Ar for 1 h, then treated with a solution of anhydrous CuCl$_2$ (2.11 g, 15.7 mmol) in DMF (15.84 mL). After the completion of the addition, the dry ice bath was removed, and the reaction allowed to warm to rt over 1 h, then poured into a 0.5 M solution of HCl (120 mL). The aqueous suspension was extracted with Et$_2$O. The organic layers were dried over Na$_2$SO$_4$, filtered and concentrated in vacuo. The residue was crystallized from EtOH, to afford 1,4-bis-(4-tert-butyl-phenyl)-butane-1,4-dione (377 mg, 16%) as white crystals. A second crop of crystals (253 mg, 10%) was recovered by concentration of the filtrate: $^1$H NMR (CDCl$_3$, chemical shifts in ppm relative to TMS): 1.35 (s, 18H), 3.44 (s, 4H), 7.50 (d, 4H, J=8.3 Hz), 7.98 (d, 4H, J=8.3 Hz).

Example 377

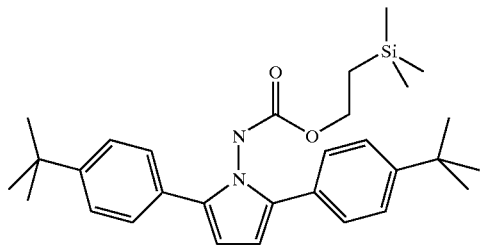

Synthesis of [2,5-bis-(4-tert-Butyl-phenyl)-pyrrol-1-yl]-carbamic Acid 2-Trimethylsilanyl-ethyl Ester A solution of 1,4-bis-(4-tert-butyl-phenyl)-butane-1,4-dione (377 mg, 1.08 mmol) in toluene (3 mL) was treated with hydrazinecarboxylic acid 2-trimethylsilanyl-ethyl ester (212 mg, 1.18 mmol) and p-toluene sulfonic acid (11.3 mg). The resulting solution was heated to reflux under Ar for 1.5 h, then cooled to rt and concentrated in vacuo to provide crude [2,5-Bis-(4-tert-butyl-phenyl)-pyrrol-1-yl]-carbamic acid 2-trimethylsilanyl-ethyl ester. The residue was not purified, but was deprotected immediately as follows.

Example 378

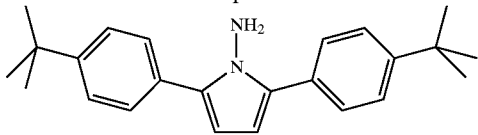

Synthesis of 2,5-bis-(4-tert-Butyl-phenyl)-pyrrol-1-ylamine

[2,5-Bis-(4-tert-butyl-phenyl)-pyrrol-1-yl]-carbamic acid 2-trimethylsilanyl-ethyl ester (681 mg, 1.39 mmol) was treated with a 1 M solution of TBAF in THF (2.78 mL). The resulting solution was stirred at rt overnight, then quenched with glacial acetic acid (0.155 mL). The solution was passed through a short plug of silica gel, eluting with toluene and concentrated in vacuo to afford 2,5-Bis-(4-tert-butyl-phenyl)-pyrrol-1-ylamine (299 mg, 80% for two steps) as a creamy white solid: $^1$H NMR (CDCl$_3$, chemical shifts in ppm relative to TMS): 1.36 (s, 18H), 4.60 (s, 2H), 6.24 (s, 2H), 7.46 (d, 4H, J=8.7 Hz), 7.52 (d, 4H, J=8.7 Hz).

Example 379

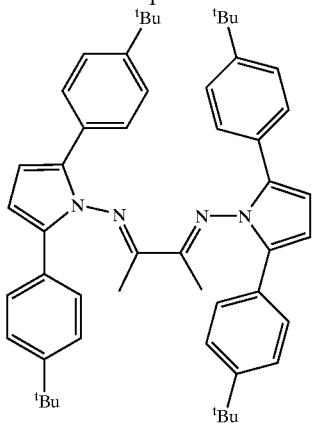

Synthesis of 2,3-bis(2,5-bis(4-tert-Butylphenyl)-pyrrol-1-ylimino)-butane

A solution of 2,5-bis-(4-tert-butyl-phenyl)-pyrrol-1-ylamine (174 mg, 0.502 mmol) in toluene (4.5 mL) was treated with butanedione (19.7 μL, 0.225 mmol) and p-toluene sulfonic acid (5.2 mg). The resulting solution was heated to 80° C. in an oil bath under Ar overnight. The solution was cooled to rt and concentrated in vacuo. The residue was purified by flash chromatography (SiO$_2$, 33% CH$_2$Cl$_2$/heptane) to afford 2,3-bis(2,5-bis(4-tert-butylphenyl)-pyrrol-1-ylimino)-butane (121 mg, 72%): $^1$H NMR (CDCl$_3$, chemical shifts in ppm relative to TMS): 1.33 (s, 36H), 1.69 (s, 6H), 6.39 (s, 4H), 7.33–7.39 (m, 16H).

Example 380 to Example 389

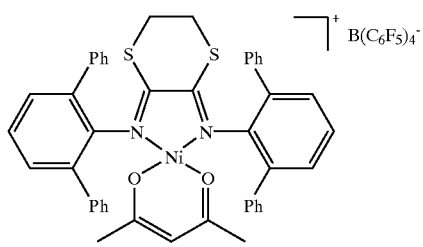

aa1

Ethylene Polymerization in the Presence of Hydrogen as a Chain Transfer Agent A stock solution of aa1 containing 0.75 mg of aa1/ml of solvent was prepared by dissolving 6 mg of aa1 in 40-ml of CH$_2$CL$_2$ or toluene and then diluting 2-ml of that solution to 4-ml. A Parr® stirred autoclave (600-ml) was heated to 100° C. under dynamic vacuum to completely dry the reactor. The reactor was cooled and charged with 150 ml of dry toluene, 1-ml of mMAO (7.14 wt % Al; Akzo Nobel) and optionally H$_2$ gas (0, 50, 150, 300 or 450-ml of H$_2$ gas added to the reactor head space via syringe). The reactor was sealed and pressurized up to 150-psig ethylene and heated to 60° C. A 2-ml portion (1.04×10$^{-7}$ mol of catalyst) of the catalyst stock solution of aa1 was added to the autoclave via the high-pressure sample loop while pressurizing the autoclave to 200 psig. After 15 minutes of stirring at 200-psig ethylene and 60° C., the reaction was quenched upon addition of 2-ml of methanol at high pressure. The reactor was vented and the contents poured into a beaker containing a methanol/acetone mixture. The polymer was collected by suction filtration and dried in the vacuum oven overnight at ~100° C.

| Example | H$_2$ added (ml) | Yield PE (g) | TO mol C$_2$H$_4$/mol Ni (×10$^{-3}$) | TOF mol C$_2$H$_4$/ mol Ni h (×10$^{-3}$) | M$_n$ (×10$^{-3}$) |
|---|---|---|---|---|---|
| 380 | 0 | 46 | 1600 | 6200 | 790 |
| 381 | 0 | 4.6 | 1600 | 6400 | — |
| 382 | 50 | 4.8 | 1600 | 6500 | 171 |
| 383 | 50 | 4.0 | 1400 | 5500 | — |
| 384 | 150 | 4.9 | 1700 | 6700 | 166 |
| 385 | 150 | 4.8 | 1600 | 6500 | — |
| 386 | 300 | 4.5 | 1500 | 6200 | 146 |
| 387 | 300 | 5.0 | 1700 | 6900 | — |
| 388 | 300 | 4.7 | 1600 | 6500 | 126 |
| 389 | 450 | 5.2 | 1800 | 7100 | 108 |

Example 390 to Example 394

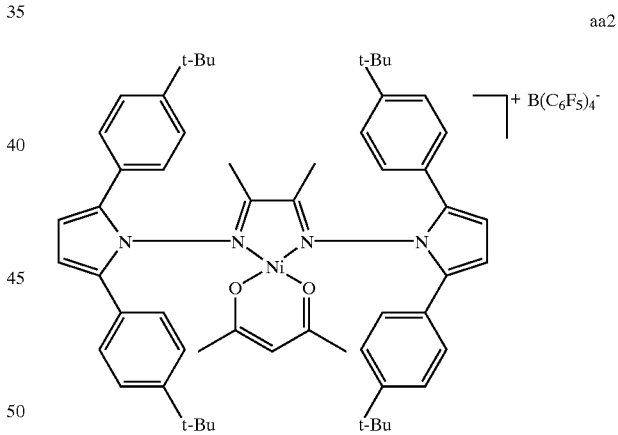

aa2

Ethylene Polymerization with aa2

A stock solution was prepared by combining 3.3 mg (12.7 μmol) of Ni(acac)$_2$, 11.7 mg (12.7 μmol) Ph$_3$C—B(C$_6$F$_5$)$_4$ and 9.3 mg (12.7 μmol) of the requisite osazone in 5-ml of methylene chloride. The mixture was allowed to sit for 30 minutes. After 30 minutes, an additional 10-ml of methylene chloride was added followed by removal of 5-ml (1/3) of the resulting solution. The 5-ml of the solution removed was diluted to 40-ml with toluene giving a stock solution with 0.0825 mg of aa2/ml solvent. Subsequently, a Parr® stirred autoclave (600-ml) was heated to 100° C. under dynamic vacuum to completely dry the reactor. The reactor was cooled and charged with 150 ml of dry toluene, 1-ml of mMAO (7.14 wt % Al; Akzo Nobel) and optionally H$_2$ gas (0, 50, 150 or 300-ml of $H_2$ gas added to the reactor head space via syringe). The reactor was sealed and pressurized up to 150 psig ethylene and heated to 60° C. A 2-ml portion ($1.04 \times 10^{-7}$ mol of catalyst) of the catalyst stock solution of aa2 was added to the autoclave via the high-pressure sample loop while pressurizing the autoclave to 200 psig. After 15 minutes of stirring at 200-psig ethylene and 60° C., the reaction was quenched upon addition of 2-ml of methanol at high pressure. The reactor was vented and the contents poured into a beaker containing a methanol/acetone mixture. The polymer was collected by suction filtration and dried in the vacuum oven overnight at ~100° C.

| Example | $H_2$ added (ml) | Yield PE (g) | TO mol $C_2H_4$/mol Ni ($\times 10^{-3}$) | TOF mol $C_2H_4$/ mol Ni h ($\times 10^{-3}$) |
|---|---|---|---|---|
| 390 | 0 | 3.6 | 1200 | 4900 |
| 391 | 0 | 4.6 | 1600 | 6400 |
| 392 | 50 | 1.9 | 667 | 2700 |
| 393 | 150 | 1.6 | 545 | 2200 |
| 394 | 300 | 1.8 | 608 | 2400 |

Example 395

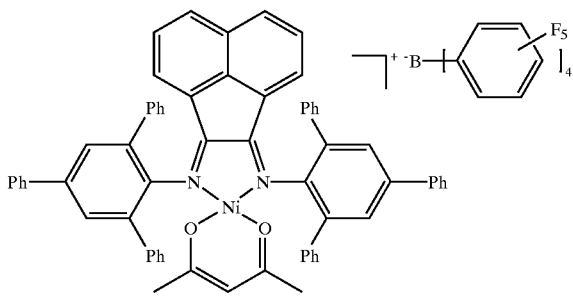

Preparation of z2

A flame dried Schlenk flask equipped with a rubber septum and a stir bar was charged with 100 mg (0.39 mmol) of nickel (II) acetylacetonate, 308 mg (0.39 mmol) of the appropriate α-diimine ligand and 360 mg (0.39 mmol) $Ph_3CB(C_6F_5)_4$. Methylene chloride 20-ml was added to the solid mixture giving a homogeneous blood red solution within seconds. The solution was left to stir at room temperature for 60 minutes. After 60 minutes, the solution was concentrated to 5-ml and 20-ml of dry degassed hexane was added resulting in the formation of a red precipitate. The supernate was removed via filter cannula. The resulting solid was then dissolved in 5-ml of methylene chloride and re-precipitated upon addition of 20-ml of hexanes. The supernatent was again removed via filter cannula. The wash procedure was repeated one additional time. The red powder that resulted was dried in vacuo overnight resulting in 546 mg (86% yield) of the desired complex. $^1H$ NMR was consistent with the desired complex.

Example 396

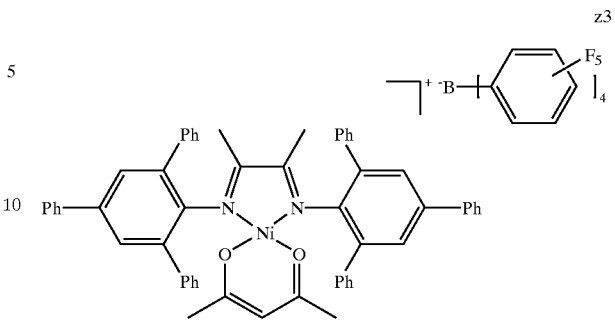

Preparation of z3

A flame dried Schlenk flask equipped with a rubber septum and a stir bar was charged with 100 mg (0.39 mmol) of nickel (II) acetylacetonate, 270 mg (0.39 mmol) of the appropriate α-diimine ligand and 360 mg (0.39 mmol) $Ph_3C\text{—}B(C_6F_5)_4$. Methylene chloride 20-ml was added to the solid mixture giving a homogeneous blood red solution within seconds. The solution was left to stir at room temperature for 60 minutes. After 60 minutes, the solvent was removed in vacuo giving a red glassy solid. The resulting solid was washed 4 times with a 1-part ether and 4-part hexane solution. The supernatent was removed via filter cannula. The red powder that resulted was dried in vacuo overnight resulting in 413 mg (69% yield) of the desired complex. $^1H$ NMR was consistent with the desired complex.

Example 397 to Example 400

Polymerization with z2 or z3

A Parr® stirred autoclave (600-ml) was heated to 100° C. under dynamic vacuum to completely dry the reactor. The reactor was cooled and charged with 150 ml of dry toluene, 1-ml of mMAO (7.14 wt % Al; Akzo Nobel) and optionally $H_2$ gas (0, 50, 150 or 300-ml of $H_2$ gas added to the reactor head space via syringe). The reactor was seated and pressurized up to 150-psig ethylene and heated to 60° C. A 2-ml portion ($1.04 \times 10^{-7}$ mol of catalyst) of a catalyst stock solution of z2 or z3 was added to the autoclave via the high-pressure sample loop while pressurizing the autoclave to 200 psig. After 15 minutes of stirring at 200-psig ethylene and 60° C., the reaction was quenched upon addition of 2 ml of methanol at high pressure. The reactor was vented and the contents poured into a beaker containing a methanol/acetone mixture. The polymer was collected by suction filtration and dried in the vacuum oven overnight at ~100° C.

| Example | Catalyst | $H_2$ added (ml) | Yield PE (g) | TO mol $C_2H_4$/mol Ni ($\times 10^{-3}$) | TOF mol $C_2H_4$/ mol Ni h ($\times 10^{-3}$) |
|---|---|---|---|---|---|
| 397 | z2 | 0 | 0.53 | 180 | 720 |
| 398 | z3 | 0 | 3.2 | 1100 | 4300 |
| 399 | z3 | 150 | 4.2 | 1400 | 5800 |
| 400 | z3 | 300 | 4.5 | 1600 | 6400 |

Example 401

Preparation of v20

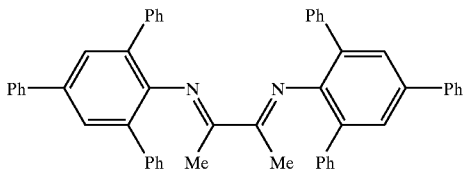

A 50 mL round bottom flask was charged with 2,4,6-triphenylaniline (762 mg, 1 eq), 2,3-butanedione (2 mL, 10 eq), p-toluenesulfonic acid hydrate(15 mg), and dry toluene (10 mL). The mixture was heated at 60 C for 10 h under a nitrogen atmosphere, then allowed to cool to rt overnight. Most of the solvent and excess butanedione were removed in vacuo to leave the crude mono imine-mono ketone as an amber oil (Field desorption mass spectronomy: m/z 389). Toluene (23 mL), sufuric acid (1 drop), and 2,4,6-triphenylaniline (1 g) were added. The solution was refluxed for 10 h using a Dean-Stark trap (ca. 13 mL capacity) to collect the water eliminated. After standing at rt for 1 d, some methanol was added and a light-colored precipitate separated from the dark solution. After standing 11 d more the yellow crystalline product was isolated by vacuum filtration, and washed with toluene and methanol. Yield of v20=1.4 g (85% based on initial charge of the aniline). $^1$H NMR (300 MHz, CDCl$_3$, 295 K): δ 7.64 (apparent d, 4H), 7.54(apparent s, 4H), 7.43 (apparent t, 4H), 7.34 (apparent d, 2H), 7.31–7.15 (m,

Example 402

Preparation of v21

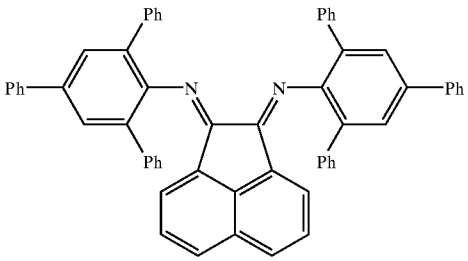

A 50 mL round bottom flask was charged with 2,4,6-triphenylaniline (1.295 g, 1 eq), acenaphthenequinone (0.294 g, eq), sulfuric acid(1 drop), and dry toluene (20 mL). The solution was refluxed for 10 h using a Dean-Stark trap (ca. 13 mL capacity) to collect the water eliminated, then allowed to cool to rt overnight. After standing at rt 12 d, the orange crystalline product that had separated from solution was isolated by vacuum filtration, and washed with toluene and methanol. Yield of v21=0.9 g (71%). $^1$H NMR (300 MHz, CDCl$_3$, 295 K): δ 7.75 (apparent d, 4H), 7.68 (apparent t, 2H), 7.64 (apparent s, 4H), 7.47 (apparent t, 4H), 7.40–7.32 (apparent t, 2H), 7.11–7.04 (m, 4H), 7.01–6.92 (m, 8H), 6.89 (apparent d, 2H). Field desorption mass spectroscopy: m/z=789.

Example 403

Preparation of v22

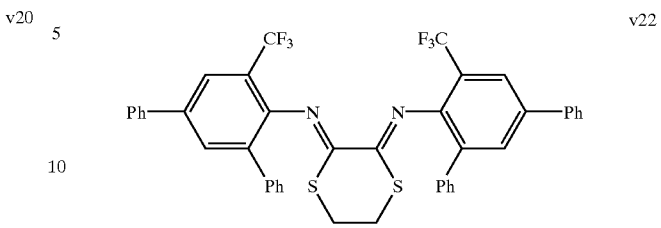

Compound v22 was prepared by a procedure similar to that described in Example 233. 1H NMR (300 MHz, CDCl$_3$, 295 K), mixture of isomers: δ 7.9 (s, 2H), 7.79 (d, J=7.45 Hz, 2H), 7.65 (d, J=7.45 Hz, 4H), 7.57 (d, J=7.45 Hz, 2H), 7.52–7.28(m, 14H), 2.88–2.64 (m, 2H), 2.34–2.00(m, 2H). The requisite aniline was prepared by phenylation of the corresponding bromo-substituted aniline under Suzuki conditions (see Y. Miura et al., *Synthesis*, 1995, 1419–1422 for a convenient procedure). Ortho-trifluromethylaniline was dibrominated with bromine in acetic acid to give the required bromo-substituted aniline (see, for example, R. G. Pews, et al., *Tetrahedron*, 1993, 49(22), 4809–4820 for a general procedure for bromination of anilines).

Example 404

Preparation of v23

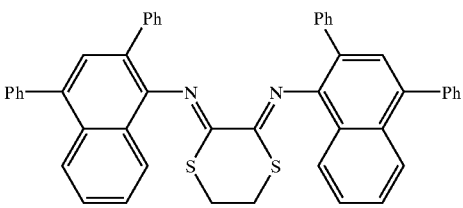

Compound v23 was prepared by a procedure similar to that described in Example 233. $^1$H NMR (300 MHz, CDCl$_3$, 295 K), mixture of isomers: δ 8.19–8.10 (m, 1H), 8.03–7.89 (m, 3H), 7.84–7.75 (m, 2H), 7.68–7.39 (m, 20H), 7.39–7.27 (m, 4H), 2.85–2.73 (m, 2H), 2.53–2.44 (m, 1H), 2.32–2.19 (m, 1H). The requisite amine was prepared starting from 1-naphthylamine similar to the procedure described in Example 403.

Example 405 to Example 407

Ethylene Polymerization with a Pro-Catalyst of the Type Prepared in Example 242

A Schlenk flask (200 mL, 500 mL or 1000 mL) equipped with a magnetic stir bar and capped with a septum was evacuated and refilled with ethylene, then charged with dry, deoxygenated toluene (100 mL) and a 10 wt % solution of MAO in toluene (4.0 mL). The requisite volume of pro-catalyst solution (prepared from the indicated ligand as in example 242) was added to give the amount of Ni indicated in the table below. The mixture was stirred under 1 atm ethylene at the temperature indicated in the table below and a polyethylene precipitate was observed. After the indicated reaction time, the mixture was quenched by the addition of acetone (50 mL), methanol (50 mL) and 6 N aqueous HCl (100 mL). The swollen polyethylene was isolated by vacuum filtration and washed with water, methanol and acetone, then dried under reduced pressure at 100° C. for 16 h to obtain the amount of polyethylene indicated in the table below ($M_n$ determined in this case by $^1$H NMR).

| Example | Ligand | Temp (C.) | µmol Ni | Time min | g PE | $M_n$ | Branches/ 1000 C's |
|---|---|---|---|---|---|---|---|
| 405 | V22 | 23 | 0.352 | 215.00 | 1.42 | 93,000 | 51.5 |
| 406 | V22 | 60 | 0.352 | 35.00 | 2.3 | 26,000 | 96.4 |
| 407 | V23 | 23 | 0.407 | 10.17 | .456 | 21,000 | 20.3 |

Example 408 and Example 409

A stock procatalyst solution of the type prepared in Example 242 was prepared from ligand v22 at the concentration of 0.51 µmol/mL. Subsequently, a Parr® stirred autoclave (600-ml) was heated to 100° C. under dynamic vacuum to completely dry the reactor. The reactor was cooled and charged with 150 ml of dry toluene, 1-ml of mMAO (7.14 wt % Al; Akzo Nobel) and optionally H$_2$ gas (0, 50, 150 or 300-ml of H$_2$ gas added to the reactor head space via syringe). The reactor was sealed and pressurized up to 150 psig ethylene and heated to 60° C. A 2-ml portion (1.02×10$^{-6}$ mol of catalyst) of the catalyst stock solution from ligand v22 was added to the autoclave via the high-pressure sample loop while pressurizing the autoclave to 200 psig. After 15 minutes of stirring at 200-psig ethylene and 60° C., the reaction was quenched upon addition of 2-ml of methanol at high pressure. The reactor was vented and the contents poured into a beaker containing a methanol/acetone mixture. The polymer was collected by suction filtration and dried in the vacuum oven overnight at ~100° C.

| Example | H$_2$ added (ml) | Yield PE (g) | TO mol C$_2$H$_4$/mol Ni (×10$^{-3}$) | TOF mol C$_2$H$_4$/ mol Ni h (×10$^{-3}$) |
|---|---|---|---|---|
| 408 | 0 | 6.4 | 234 | 938 |
| 409 | 50 | .096 | 3.5 | 14 |

Example 410

Synthesis of (2,5-di-Pyridin-3-yl-pyrrol-1-yl)-carbamic Acid 2-Trimethylsilanyl-ethyl Ester A solution of 1,4-di-Pyridin-3-yl-butane-1,4-dione (1 g, 4.2 mmol) in toluene (40 mL) is treated with hydrazinecarboxylic acid 2-trimethylsilanyl-ethyl ester (888 mg, 5.0 mmol) and p-toluenesulfonic acid (30 mg). The reaction vessel is fitted with a Dean Stark trap, and the resulting solution is heated to reflux, with azeotropic removal of water until no starting materials are detected by TLC. The solution is cooled to rt, and washed with water. The organic layer is dried over Na$_2$SO$_4$, filtered and concentrated to afford (2,5-di-pyridin-3-yl-pyrrol-1-yl)-carbamic acid 2-trimethylsilanyl-ethyl ester, which is not purified further.

Example 411

Synthesis of 2,5-di-Pyridin-3-yl-pyrrol-1-ylamine (2,5-di-pyridin-3-yl-pyrrol-1-yl)-carbamic acid 2-trimethylsilanyl-ethyl ester (1 g, 2.6 mmol) is treated with a 1M solution of TBAF in THF (5.2 ml, 5.2 mmol). The resulting solution is stirred overnight under Ar at rt, then quenched with glacial acetic acid (0.3 ml, 5.2 mmol) and diluted with toluene. The resulting solution is passed through a short plug of silica gel and concentrated in vacuo to afford 2,5-Di-pyridin-3-yl-pyrrol-1-ylamine.

Example 412

Synthesis of 2-(2,5-Diphenyl-pyrrol-1-ylimino)-3-(2,5-dipyridine-3-yl-pyrrol-1-ylimino)-butane A suspension of 3-(2,5-Diphenyl-pyrrol-1-ylimino)-butan-2-one (1.0 g, 3.4 mmol) in toluene (12 ml) is treated with DMF (6 ml), 2,5-di-pyridin-3-yl-pyrrol-1-ylamine (850 mg, 3.6 mmol) and p-toluene sulfonic acid (30 mg). The resulting suspension is fitted with a Dean Stark trap and heated to reflux with azeotropic removal of water in an oil bath until no starting materials remain by TLC. The solution is cooled to rt and concentrated in vacuo. The residue is purified by flash chromatography to afford 2-(2,5-diphenyl-pyrrol-1-ylimino)-3-(2,5-dipyridine-3-yl-pyrrol-1-ylimino)-butane.

Example 413

Preparation of z4

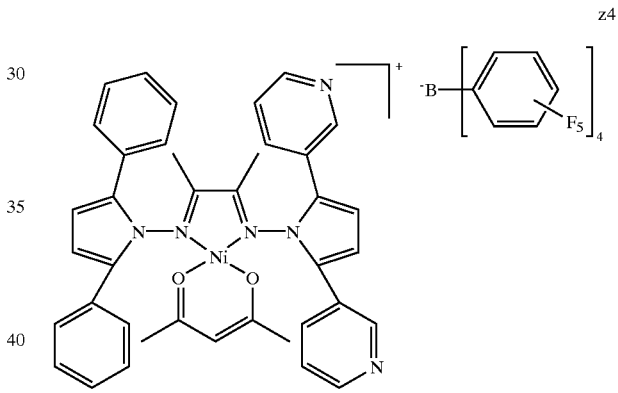

A flame dried Schlenk flask equipped with a rubber septum and a stir bar is charged with 100 mg (0.39 mmol) of nickel (II) acetylacetonate, 203 mg (0.39 mmol) of 2-(2,5-diphenyl-pyrrol-1-ylimino)-3-(2,5-dipyridine-3-yl-pyrrol-1-ylimino)-butane and 360 mg (0.39 mmol) Ph$_3$C—B(C$_6$F$_5$)$_4$. Methylene chloride (20 ml) is added to the solid mixture giving a homogeneous blood red solution within seconds. The solution is left to stir at room temperature for 60 minutes. After 60 minutes, the solvent is removed in vacuo giving a red glassy solid. The resulting solid is washed 4 times with a 1-part ether and 4-part hexane solution. The supernatent is removed via filter cannula. The red powder is dried in vacuo overnight to afford z4.

Example 414

Ethylene Polymerization with z4

A Parr® stirred autoclave (600-ml) is heated to 100° C. under dynamic vacuum to completely dry the reactor. The reactor is cooled and charged with 150 ml of dry toluene and 1-ml of mMAO (7.14 wt % Al; Akzo Nobel). The reactor is sealed and pressurized up to 150-psig ethylene and heated to 60° C. A 2-ml portion (1.04×10$^{-7}$ mol of catalyst) of a

Example 415

Polymerization of Ethylene Using a Catalyst Prepared as in Example 368

A catalyst delivery device was charged with a catalyst prepared as in Example 368, wherein aa1 (73.8 mg) was dissolved in 1.5 mL dichloromethane and added to Grace Davison XPO-2402 (1.0 g). The device containing 10.2 mg of the catalyst dispersed in 200 mg XPO-2402 was then fixed to the head of a 1000-mL Parr® reactor. The device was placed under vacuum. The reactor was then charged with NaCl (304 g) that had been dried in vacuum at 120° C. for several hours. The reactor was closed, and pressurized with nitrogen (ca. 40 psi) and depressurized to atmospheric pressure 10 times. The salt was subsequently treated with trimethylaluminum (10 mL; 2.0 M in hexane) and agitated at 86° C. for 30 min. The reactor was then pressurized with 200 psi ethylene and depressurized to atmospheric pressure five times. The catalyst was then introduced in the reactor with appropriate agitation. The reaction was allowed to proceed for 60 minutes at 86° C. before the reactor was vented. The polymer was isolated by washing the content of the reactor with water. The isolated polymer was further treated with 6 M HCl in methanol, rinsed with methanol and dried under vacuum to give 7.4 g (520,000 mol $C_2H_4$/mol Ni).

Example 416

Polymerization of Ethylene Using a Catalyst Prepared from a54, Co(acac)$_2$ and Ph$_3$CB(C$_6$F$_5$)$_4$ A mixture of prepared a54 (20.2 mg), Co(acac)$_2$ (10.1 mg) and Ph$_3$CB(C$_6$F$_5$)$_4$ (36.1 mg) was dissolved in 5.0 mL dry, deoxygenated methylene chloride to afford a deep reddish-brown catalyst stock solution. A portion of this solution (54 µL) was added to a vigorously stirred mixture of 300 mL dry, deoxygenated toluene and 4.0 mL of a 10 wt % solution of MAO in toluene (Aldrich) under 1 atm ethylene at 23° C., resulting in weak ethylene uptake. After 9.5 min, an additional 0.46 mL of the stock solution was added, leading to an increase in ethylene uptake. After a total of 39 min, the reaction was quenched by addition of MeOH and 6 N aq HCl. The polymer was recovered by filtration and dried in vacuo to afford 0.250 g white powdery polyethylene. GPC: $M_n$ 99,000; $M_w$ 265,800. DSC ($2^{nd}$ heat from melt, endothermic maximum): 135.1° C. $^1$H NMR (o-dichlorobenzene): 4.4 branch points/1000 carbons.

While the invention has been described with reference to preferred embodiments and working examples, it is to be understood that variations and modifications may be resorted to as will be apparent to those skilled in the art. Such variations and modifications are to be considered within the purview and scope of the invention as defined by the claims appended hereto.

We claim:

1. A process for the polymerization of olefins, which comprises contacting one or more olefins with a catalyst composition comprising (a) a Ti, Zr, or Hf complex of a dianionic bidentate ligand, wherein at least one of the donor atoms of the ligand is a nitrogen atom substituted by a 1-pyrrolyl or substituted 1-pyrrolyl group and the remaining donor atoms of the ligand are selected from the group consisting of N, P, As, O, S, and Se, and optionally (b) an aluminum or boron-containing Lewis acid.

2. A process for the polymerization of olefins, which comprises contacting one or more olefins with a catalyst composition comprising (a) a Ti, Zr, or Hf complex of a monoanionic bidentate ligand, wherein at least one of the donor atoms of the ligand is a nitrogen atom substituted by a 1-pyrrolyl or substituted 1-pyrrolyl group and the remaining donor atoms of the ligand are selected from the group consisting of N, P, As, O, S, and Se, and optionally (b) a second compound $Y^2$, wherein $Y^2$ is selected from the group consisting of (i) a neutral Lewis acid which is capable of reacting with said Ti, Zr, or Hf complex to form a salt comprising a weakly coordinating anion, (ii) a cationic Lewis acid whose counterion is a weakly coordinating anion, and (iii) a Bronsted acid whose conjugate base is a weakly coordinating anion.

3. A process for the polymerization of olefins, which comprises contacting one or more olefins with a catalyst composition comprising (a) a Cr, Mo, or W complex of a monodentate dianionic ligand, wherein at least one of the donor atoms of the ligand is a nitrogen atom substituted by a 1-pyrrolyl or substituted 1-pyrrolyl group and the remaining donor atoms of the ligand are selected from the group consisting of N, P, As, O, S, and Se, and optionally (b) a second compound $Y^2$, wherein $Y^2$ is selected from the group consisting of (i) a neutral Lewis acid which is capable of reacting with said Cr, Mo, or W complex to form a salt comprising a weakly coordinating anion, (ii) a cationic Lewis acid whose counterion is a weakly coordinating anion, and (iii) a Bronsted acid whose conjugate base is a weakly coordinating anion.

4. A process for the polymerization of olefins, which comprises contacting one or more olefins with a catalyst composition comprising (a) a V, Nb, or Ta complex of a monodentate dianionic ligand, wherein at least one of the donor atoms of the ligand is a nitrogen atom substituted by a 1-pyrrolyl or substituted 1-pyrrolyl group and the remaining donor atoms of the ligand are selected from the group consisting of N, P, As, O, S, and Se, and optionally (b) a second compound $Y^2$, wherein $Y^2$ is selected from the group consisting of (i) a neutral Lewis acid which is capable of reacting with said V, Nb, or Ta complex to form a salt comprising a weakly coordinating anion, (ii) a cationic Lewis acid whose counterion is a weakly coordinating anion, and (iii) a Bronsted acid whose conjugate base is a weakly coordinating anion.

5. A process for the polymerization olefins, which comprises contacting one or more olefins with a catalyst composition comprising (a) a cationic Ti, Zr or Hf complex of a mono- or dianionic, nitrogen donor ligand, wherein said nitrogen donor is substituted by a 1-pyrrolyl or substituted 1-pyrrolyl group and is linked by a bridging group to a cyclopentadienyl, phosphacyclopentadienyl, pentadienyl, 6-oxacyclohexadienyl, or borataaryl group which is also bonded to said metal, and optionally (b) an aluminum or boron-containing Lewis acid.

* * * * *